US012692498B2

(12) United States Patent
Khvorova et al.

(10) Patent No.: US 12,692,498 B2
(45) Date of Patent: Jul. 28, 2026

(54) MODIFIED OLIGONUCLEOTIDES TARGETING SNPs

(71) Applicant: UNIVERSITY OF MASSACHUSETTS, Boston, MA (US)

(72) Inventors: Anastasia Khvorova, Westborough, MA (US); Julia Alterman, Worcester, MA (US); Faith Conroy, Worcester, MA (US); Edith Pfister, Boxborough, MA (US); Neil Aronin, Newtonville, MA (US); Ken Yamada, Boston, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 265 days.

(21) Appl. No.: 18/446,929

(22) Filed: Aug. 9, 2023

(65) Prior Publication Data

US 2024/0132888 A1 Apr. 25, 2024

Related U.S. Application Data

(62) Division of application No. 16/537,374, filed on Aug. 9, 2019, now Pat. No. 11,827,882.

(60) Provisional application No. 62/825,429, filed on Mar. 28, 2019, provisional application No. 62/717,287, filed on Aug. 10, 2018.

(51) Int. Cl.
*C12N 15/113* (2010.01)
*C12N 15/85* (2006.01)

(52) U.S. Cl.
CPC ............ *C12N 15/113* (2013.01); *C12N 15/85* (2013.01); *C12N 2310/14* (2013.01); *C12N 2310/312* (2013.01); *C12N 2310/351* (2013.01)

(58) Field of Classification Search
CPC ...... C12N 15/113; C12N 15/85; C12N 15/63; C12N 2310/14; C12N 2320/11; C12N 2320/34
USPC ..................... 435/6.1, 91.1, 91.31, 455, 458; 514/44 A; 536/23.1, 24.5
See application file for complete search history.

(56) References Cited

U.S. PATENT DOCUMENTS

| | | | |
|---|---|---|---|
| 4,522,811 | A | 6/1985 | Khvorova et al. |
| 5,194,596 | A | 3/1993 | Tischer et al. |
| 5,219,739 | A | 6/1993 | Tischer et al. |
| 5,240,848 | A | 8/1993 | Keck et al. |
| 5,328,470 | A | 7/1994 | Nabel et al. |
| 5,332,671 | A | 7/1994 | Ferrara et al. |
| 5,684,143 | A | 11/1997 | Grayaznov et al. |
| 5,814,014 | A | 9/1998 | Elsberry et al. |
| 5,858,988 | A | 1/1999 | Wang |
| 5,939,402 | A | 8/1999 | Weis et al. |
| 6,025,335 | A | 2/2000 | Weis et al. |
| 6,093,180 | A | 7/2000 | Elsberry et al. |
| 6,107,094 | A | 8/2000 | Crooke |
| 6,168,587 | B1 | 1/2001 | Bellhouse et al. |
| 6,177,403 | B1 | 1/2001 | Stedman |
| 6,194,389 | B1 | 2/2001 | Johnston et al. |
| 6,291,438 | B1 | 9/2001 | Wang |
| 6,312,900 | B1 | 11/2001 | Dean et al. |
| 6,383,814 | B1 | 5/2002 | Lee et al. |
| 6,447,768 | B1 | 9/2002 | Van Zonneveld et al. |
| 6,471,996 | B1 | 10/2002 | Sokoll et al. |
| 6,472,375 | B1 | 10/2002 | Hoon et al. |
| 6,489,464 | B1 | 12/2002 | Agrawal et al. |
| 7,250,496 | B2 | 7/2007 | Bentwich |
| 7,459,547 | B2 | 12/2008 | Zamore et al. |
| 7,691,997 | B2 | 4/2010 | Khvorova et al. |
| 7,723,512 | B2 | 5/2010 | Manoharan et al. |
| 7,732,593 | B2 | 6/2010 | Zamore et al. |
| 7,750,144 | B2 | 7/2010 | Zamore et al. |
| 7,772,203 | B2 | 8/2010 | Zamore et al. |
| 7,790,867 | B2 | 9/2010 | Bentwich |
| 7,820,809 | B2 | 10/2010 | Khvorova et al. |
| 7,834,171 | B2 | 11/2010 | Leake et al. |
| 8,013,136 | B2 | 9/2011 | Manoharan et al. |
| 8,097,752 | B2 | 1/2012 | Calogeropolou et al. |
| 8,304,530 | B2 | 11/2012 | Zamore et al. |
| 8,309,704 | B2 | 11/2012 | Zamore et al. |
| 8,309,705 | B2 | 11/2012 | Zamore et al. |
| 8,329,892 | B2 | 12/2012 | Zamore et al. |
| 8,431,544 | B1 | 4/2013 | Agrawal et al. |
| 8,501,706 | B2 | 8/2013 | Yamada et al. |

(Continued)

FOREIGN PATENT DOCUMENTS

| | | |
|---|---|---|
| CN | 101199858 A | 6/2008 |
| CN | 101365801 A | 2/2009 |

(Continued)

OTHER PUBLICATIONS

Pfister et al (Curr. Biol. vol. 19, No. 9, pp. 774-778 (2009)) (Year: 2009).*

(Continued)

*Primary Examiner* — Jane J Zara

(74) *Attorney, Agent, or Firm* — LATHROP GPM LLP; James H. Velema, Esq.

(57) ABSTRACT

Novel oligonucleotides that enhance silencing of the expression of a gene containing a single nucleotide polymorphism (SNP) relative to the expression of the corresponding wild-type gene are provided. Methods of using novel oligonucleotides that enhance silencing of the expression of a gene containing a SNP relative to the expression of the corresponding wild-type gene are provided.

12 Claims, 53 Drawing Sheets

Specification includes a Sequence Listing.

(56) References Cited

U.S. PATENT DOCUMENTS 8,507,661 B2 8/2013 Manoharan et al.
8,664,189 B2 3/2014 Khvorova et al.
8,703,731 B2 4/2014 Jimenez et al.
8,796,443 B2 8/2014 Khvorova et al.
8,815,818 B2 8/2014 Samarsky et al.
8,871,774 B2 10/2014 Charifson et al.
8,877,439 B2 11/2014 Butora et al.
8,906,874 B2 12/2014 Rao et al.
8,993,738 B2 3/2015 Prakash et al.
9,029,389 B2 5/2015 No et al.
9,074,211 B2 7/2015 Woolf et al.
9,080,171 B2 7/2015 Khvorova et al.
9,095,504 B2 8/2015 Libertine et al.
9,175,289 B2 11/2015 Khvorova et al.
9,198,981 B2 12/2015 Ambati et al.
9,303,259 B2 4/2016 Khvorova et al.
9,340,786 B2 5/2016 Khvorova et al.
9,493,774 B2 11/2016 Kamens et al.
9,695,206 B2 7/2017 Minomi et al.
9,745,574 B2 8/2017 Woolf et al.
9,796,756 B2 10/2017 Hadwiger et al.
9,809,817 B2 11/2017 Khvorova et al.
9,862,350 B2 1/2018 Guerrero et al.
9,862,952 B2 1/2018 Khvorova et al.
9,867,882 B2 1/2018 Manoharan et al.
10,087,210 B2 10/2018 Prakash et al.
10,435,688 B2 10/2019 Khvorova et al.
10,478,503 B2 11/2019 Khvorova et al.
10,479,992 B2 11/2019 Woolf et al.
10,519,451 B2 12/2019 Khvorova et al.
10,548,914 B2 2/2020 Lai et al.
10,633,653 B2 4/2020 Khvorova et al.
10,774,327 B2 9/2020 Khvorova et al.
10,799,591 B2 10/2020 Khvorova et al.
10,844,377 B2 11/2020 Khvorova et al.
11,230,713 B2 1/2022 Khvorova et al.
11,279,930 B2 3/2022 Khvorova et al.
11,345,917 B2 5/2022 Khvorova et al.
11,492,619 B2 11/2022 Khvorova et al.
11,667,915 B2 6/2023 Woolf et al.
11,702,659 B2 7/2023 Khvorova et al.
11,753,638 B2 9/2023 Khvorova et al.
11,827,882 B2 * 11/2023 Khvorova .............. C12N 15/85
11,896,669 B2 2/2024 Khvorova et al.
12,024,706 B2 7/2024 Khvorova et al.
12,173,286 B2 12/2024 Khvorova et al.
12,180,477 B2 12/2024 Khvorova et al.
12,297,430 B2 5/2025 Khvorova et al.
12,365,894 B2 7/2025 Khvorova et al.
2001/0027251 A1 10/2001 Cook et al.
2003/0045705 A1 3/2003 Cook
2003/0143732 A1 7/2003 Fosnaugh et al.
2004/0121426 A1 6/2004 Hsieh
2004/0198640 A1 10/2004 Leake et al.
2004/0205839 A1 10/2004 Doutriaux et al.
2005/0096284 A1 5/2005 Mcswiggen
2005/0220766 A1 10/2005 Amalfitano et al.
2005/0255487 A1 11/2005 Khvorova et al.
2006/0003322 A1 1/2006 Bentwich et al.
2006/0009409 A1 1/2006 Woolf
2006/0024715 A1 2/2006 Liu et al.
2006/0078542 A1 4/2006 Mah et al.
2006/0094032 A1 5/2006 Fougerolles et al.
2006/0105998 A1 5/2006 Calogeropoulou et al.
2007/0004664 A1 1/2007 Mcswiggen et al.
2007/0004665 A1 1/2007 Mcswiggen et al.
2007/0015722 A1 1/2007 Kraynack et al.
2007/0099860 A1 5/2007 Sah et al.
2007/0135372 A1 6/2007 Maclachlan et al.
2007/0160534 A1 7/2007 Dennis et al.
2007/0191273 A1 8/2007 Ambat et al.
2007/0259827 A1 11/2007 Aronin et al.
2008/0039415 A1 2/2008 Stewart et al.
2008/0108583 A1 5/2008 Feinstein
2008/0108801 A1 5/2008 Manoharan
2008/0113369 A1 5/2008 Khvorova et al.
2008/0119427 A1 5/2008 Bhat et al.
2008/0188429 A1 8/2008 Iyer
2008/0269149 A1 10/2008 Bowles et al.
2009/0143322 A1 6/2009 Burkoth et al.
2009/0234109 A1 9/2009 Han et al.
2009/0269332 A1 10/2009 Gimeno et al.
2009/0281299 A1 11/2009 Manorahan et al.
2009/0306178 A1 12/2009 Bhat et al.
2009/0318676 A1 12/2009 Manoharan et al.
2010/0003258 A1 1/2010 Weng et al.
2010/0015706 A1 1/2010 Quay et al.
2010/0093085 A1 4/2010 Yamada et al.
2010/0184209 A1 7/2010 Vermeulen et al.
2010/0186103 A1 7/2010 Gao et al.
2010/0209487 A1 8/2010 Quay et al.
2010/0240730 A1 9/2010 Beigelman et al.
2011/0039914 A1 2/2011 Pavco et al.
2011/0046206 A1 2/2011 Bhat et al.
2011/0086905 A1 4/2011 Glazer
2011/0097716 A1 4/2011 Natt et al.
2011/0201006 A1 8/2011 Roehl et al.
2011/0237522 A1 9/2011 Khvorova et al.
2011/0237648 A1 9/2011 Khvorova et al.
2011/0251258 A1 10/2011 Samarsky et al.
2011/0263680 A1 10/2011 Khvorova et al.
2012/0016005 A1 1/2012 Samarsky et al.
2012/0040459 A1 2/2012 Khvorova et al.
2012/0052487 A9 3/2012 Khvorova et al.
2012/0059046 A1 3/2012 Woolf et al.
2012/0065243 A1 3/2012 Woolf et al.
2012/0136039 A1 * 5/2012 Aronin ................ A61K 31/713
536/24.5
2013/0065298 A1 3/2013 Davidson et al.
2013/0131141 A1 5/2013 Khvorova et al.
2013/0131142 A1 5/2013 Libertine et al.
2013/0178513 A1 7/2013 Dobie et al.
2013/0196434 A1 8/2013 Maier et al.
2013/0197055 A1 8/2013 Kamens et al.
2013/0345218 A1 12/2013 Charifson et al.
2014/0005192 A1 1/2014 Charifson et al.
2014/0005197 A1 1/2014 Charifson et al.
2014/0113950 A1 4/2014 Khvorova et al.
2014/0155387 A1 6/2014 No et al.
2014/0288148 A1 9/2014 Biegelman et al.
2014/0296486 A1 10/2014 Gao et al.
2014/0315974 A1 10/2014 Khvorova et al.
2014/0364482 A1 12/2014 Khvorova et al.
2015/0025122 A1 1/2015 Smith
2015/0190525 A1 7/2015 Tatro
2015/0209441 A1 7/2015 Carell
2015/0232840 A1 8/2015 Aronin et al.
2015/0247142 A1 9/2015 Esau et al.
2015/0267200 A1 9/2015 Mcswiggen et al.
2015/0307542 A1 10/2015 Roy et al.
2015/0315584 A1 11/2015 Macdonald et al.
2016/0017323 A1 1/2016 Prakash et al.
2016/0115482 A1 4/2016 Libertine et al.
2016/0115484 A1 4/2016 Woolf et al.
2016/0130578 A1 5/2016 Khvorova et al.
2016/0130583 A1 5/2016 Yokota et al.
2016/0244765 A1 8/2016 Khvorova et al.
2016/0281148 A1 9/2016 Greenlee et al.
2016/0319278 A1 11/2016 Khvorova et al.
2016/0348103 A1 12/2016 Wheeler et al.
2016/0355808 A1 12/2016 Khvorova et al.
2016/0355826 A1 12/2016 Khvorova et al.
2016/0376598 A1 12/2016 Lee et al.
2017/0009239 A1 1/2017 Khvorova et al.
2017/0009304 A1 1/2017 Zhou
2017/0037456 A1 2/2017 Kokoris et al.
2017/0043024 A1 2/2017 Khvorova et al.
2017/0043204 A1 2/2017 James
2017/0051283 A1 2/2017 Khvorova
2017/0051286 A1 2/2017 Smith
2017/0067056 A1 3/2017 Khvorova et al.
2017/0183655 A1 6/2017 Grabcysk et al.
2017/0189541 A1 7/2017 Foster
2017/0281795 A1 10/2017 Geall

(56) References Cited

U.S. PATENT DOCUMENTS

| | | | |
|---|---|---|---|
| 2017/0312367 | A1 | 11/2017 | Khvorova et al. |
| 2017/0327524 | A1 | 11/2017 | Nanna et al. |
| 2017/0349903 | A1 | 12/2017 | Wanqing et al. |
| 2017/0369882 | A1 | 12/2017 | Khvorova et al. |
| 2018/0023082 | A1 | 1/2018 | Stanek et al. |
| 2018/0087052 | A1 | 3/2018 | Hung et al. |
| 2018/0094263 | A1 | 4/2018 | Khvorova et al. |
| 2018/0179546 | A1 | 6/2018 | Khvorova et al. |
| 2018/0251764 | A1 | 9/2018 | Albaek et al. |
| 2019/0002880 | A1 | 1/2019 | Woolf et al. |
| 2019/0024082 | A1 | 1/2019 | Khvorova et al. |
| 2019/0144860 | A1 | 5/2019 | Konstantinova et al. |
| 2019/0185855 | A1 | 6/2019 | Khvorova et al. |
| 2019/0211341 | A1 | 7/2019 | Butler et al. |
| 2019/0225965 | A1 | 7/2019 | Khvorova et al. |
| 2019/0247414 | A1 | 8/2019 | Yakota et al. |
| 2019/0247507 | A1 | 8/2019 | Khvorova et al. |
| 2020/0087663 | A1 | 3/2020 | Aronin |
| 2020/0095580 | A1 | 3/2020 | Hauptmann et al. |
| 2020/0123543 | A1 | 4/2020 | Khvorova et al. |
| 2020/0165618 | A1 | 5/2020 | Khvorova et al. |
| 2020/0270605 | A1 | 8/2020 | Khvorova et al. |
| 2020/0308578 | A1 | 10/2020 | Woolf et al. |
| 2020/0308584 | A1 | 10/2020 | Khvorova et al. |
| 2020/0339983 | A1 | 10/2020 | Khvorova et al. |
| 2020/0362341 | A1 | 11/2020 | Khvorova |
| 2020/0385737 | A1 | 12/2020 | Khvorova |
| 2020/0385740 | A1 | 12/2020 | Khvorova et al. |
| 2021/0024926 | A1 | 1/2021 | Khvorova et al. |
| 2021/0071177 | A1 | 3/2021 | Khvorova |
| 2021/0085793 | A1 | 3/2021 | Khvorova et al. |
| 2021/0115442 | A1 | 4/2021 | Khvorova et al. |
| 2021/0139901 | A1 | 5/2021 | Khvorova et al. |
| 2021/0317460 | A1 | 10/2021 | Khvorova et al. |
| 2021/0340535 | A1 | 11/2021 | Khvorova |
| 2021/0355491 | A1 | 11/2021 | Khvorova et al. |
| 2021/0363523 | A1 | 11/2021 | Khvorova et al. |
| 2022/0002724 | A1 | 1/2022 | Milstein et al. |
| 2022/0010309 | A1 | 1/2022 | Khvorova et al. |
| 2022/0042015 | A1 | 2/2022 | Khvorova et al. |
| 2022/0090069 | A1 | 3/2022 | Khvorova et al. |
| 2022/0228141 | A1 | 7/2022 | Khvorova et al. |
| 2022/0251554 | A1 | 8/2022 | Khvorova et al. |
| 2022/0251555 | A1 | 8/2022 | Khvorova et al. |
| 2022/0364100 | A1 | 11/2022 | Khvorova et al. |
| 2023/0021431 | A1 | 1/2023 | Khvorova |
| 2023/0061751 | A1 | 3/2023 | Khvorova et al. |
| 2023/0078622 | A1 | 3/2023 | Khvorova et al. |
| 2023/0193281 | A1 | 6/2023 | Khvorova et al. |
| 2023/0313198 | A1 | 10/2023 | Khvorova et al. |
| 2023/0340475 | A1 | 10/2023 | Khvorova et al. |
| 2023/0348907 | A1 | 11/2023 | Khvorova et al. |
| 2023/0392146 | A1 | 12/2023 | Khvorova et al. |
| 2023/0416735 | A1 | 12/2023 | Khvorova et al. |
| 2024/0067967 | A1 | 2/2024 | Khvorova et al. |
| 2024/0084297 | A1 | 3/2024 | Khvorova et al. |
| 2024/0132888 | A1 | 4/2024 | Khvorova et al. |
| 2024/0132892 | A1 | 4/2024 | Khvorova et al. |
| 2024/0173420 | A1 | 5/2024 | Khvorova et al. |
| 2024/0287514 | A1 | 8/2024 | Khvorova et al. |
| 2024/0293550 | A1 | 9/2024 | Khvorova et al. |
| 2024/0301410 | A1 | 9/2024 | Khvorova et al. |
| 2024/0325546 | A1 | 10/2024 | Khvorova et al. |
| 2024/0327836 | A1 | 10/2024 | Khvorova et al. |
| 2025/0059533 | A1 | 2/2025 | Khvorova et al. |
| 2025/0188458 | A1 | 6/2025 | Khvorova et al. |
| 2026/0015614 | A1 | 1/2026 | Khvorova et al. |

FOREIGN PATENT DOCUMENTS

| | | | |
|---|---|---|---|
| CN | 104884618 | A | 11/2015 |
| CN | 105194689 | A | 12/2015 |
| CN | 107980062 | A | 5/2018 |
| EP | 1423428 | A2 | 6/2004 |
| EP | 1752536 | A1 | 2/2007 |
| EP | 2407539 | A1 | 1/2012 |
| EP | 2601204 | A2 | 6/2013 |
| EP | 2679600 | A1 | 1/2014 |
| EP | 2853597 | A1 | 4/2015 |
| EP | 3277811 | A1 | 2/2018 |
| EP | 3277814 | A1 | 2/2018 |
| EP | 3277815 | A1 | 2/2018 |
| EP | 3408391 | A1 | 12/2018 |
| EP | 3550021 | A1 | 10/2019 |
| EP | 3642341 | A1 | 4/2020 |
| EP | 3929293 | A2 | 12/2021 |
| EP | 3946369 | A2 | 2/2022 |
| EP | 4126040 | A2 | 2/2023 |
| JP | H06-41183 | A | 2/1994 |
| JP | H6-504680 | A | 6/1994 |
| JP | 2001-501614 | A | 2/2001 |
| JP | 2009-504782 | A | 2/2009 |
| JP | 2009-513144 | A | 4/2009 |
| JP | 2010-506598 | A | 3/2010 |
| JP | 2012-502657 | A | 2/2012 |
| JP | 2013-049714 | A | 3/2013 |
| JP | 2014-526882 | A | 10/2014 |
| JP | 2015-061534 | A | 4/2015 |
| JP | 2016-103986 | A | 6/2016 |
| JP | 2016-171815 | A | 9/2016 |
| JP | 2016-526529 | A | 9/2016 |
| JP | 2017-534290 | A | 11/2017 |
| JP | 2017-538679 | A | 12/2017 |
| JP | 2018-516091 | A | 6/2018 |
| RU | 2568066 | C2 | 11/2015 |
| TW | 201038283 | A | 11/2010 |
| WO | WO 1992/013869 | A1 | 8/1992 |
| WO | WO 1993/009239 | A1 | 5/1993 |
| WO | WO 1993/024641 | A2 | 12/1993 |
| WO | WO 1994/022890 | A1 | 10/1994 |
| WO | WO 1996/003500 | A1 | 2/1996 |
| WO | WO 1998/013526 | A1 | 4/1998 |
| WO | WO 2003/029459 | A2 | 4/2003 |
| WO | WO 2004/008946 | A2 | 1/2004 |
| WO | WO 2004/013280 | A2 | 2/2004 |
| WO | WO 2004/044136 | A2 | 5/2004 |
| WO | WO 2004/061081 | A2 | 7/2004 |
| WO | WO 2004/108956 | A1 | 12/2004 |
| WO | WO 2005/078095 | A1 | 8/2005 |
| WO | WO 2006/019430 | A2 | 2/2006 |
| WO | WO 2007/022470 | A2 | 2/2007 |
| WO | WO 2007/022506 | A2 | 2/2007 |
| WO | WO 2007/051045 | A2 | 5/2007 |
| WO | WO 2007/056153 | A2 | 5/2007 |
| WO | WO 2007/091269 | A2 | 8/2007 |
| WO | WO 2007/094218 | A1 | 8/2007 |
| WO | WO 2007/112414 | A2 | 10/2007 |
| WO | WO 2008/005562 | A2 | 1/2008 |
| WO | WO 2008/036841 | A2 | 3/2008 |
| WO | WO 2008/049078 | A1 | 4/2008 |
| WO | WO 2008/070477 | A2 | 6/2008 |
| WO | WO 2008/154482 | A2 | 12/2008 |
| WO | WO 2008/154482 | A3 | 12/2008 |
| WO | WO 2009/002944 | A1 | 12/2008 |
| WO | WO 2009/054551 | A2 | 4/2009 |
| WO | WO 2009/099991 | A2 | 8/2009 |
| WO | WO 2009/102427 | A2 | 8/2009 |
| WO | WO 2010/008582 | A2 | 1/2010 |
| WO | WO 2010/011346 | A1 | 1/2010 |
| WO | WO 2010/033246 | A1 | 3/2010 |
| WO | WO 2010/033247 | A2 | 3/2010 |
| WO | WO 2010/033248 | A2 | 3/2010 |
| WO | WO 2010/048352 | A2 | 4/2010 |
| WO | WO 2010/048585 | A2 | 4/2010 |
| WO | WO 2010/059226 | A2 | 5/2010 |
| WO | WO 2010/078536 | A1 | 7/2010 |
| WO | WO 2010/090762 | A1 | 8/2010 |
| WO | WO 2010/111367 | A1 | 9/2010 |
| WO | WO 2010/111503 | A2 | 9/2010 |
| WO | WO 2010/118263 | A1 | 10/2010 |
| WO | WO 2011/097643 | A1 | 8/2011 |
| WO | WO 2011/109698 | A1 | 9/2011 |
| WO | WO 2011/119852 | A1 | 9/2011 |
| WO | WO 2011/119871 | A1 | 9/2011 |

(56) References Cited

FOREIGN PATENT DOCUMENTS

| | | |
|---|---|---|
| WO | WO 2011/119887 A1 | 9/2011 |
| WO | WO 2011/125943 A1 | 10/2011 |
| WO | WO 2011/139702 A2 | 11/2011 |
| WO | WO 2011/158924 A1 | 12/2011 |
| WO | WO 2012/005898 A2 | 1/2012 |
| WO | WO 2012/037254 A1 | 3/2012 |
| WO | WO 2012/058210 A1 | 5/2012 |
| WO | WO 2012/078637 A2 | 6/2012 |
| WO | WO 2012/118911 A1 | 9/2012 |
| WO | WO 2012/131365 A1 | 10/2012 |
| WO | WO 2012/177906 A1 | 12/2012 |
| WO | WO 2013/165816 A2 | 11/2013 |
| WO | WO 2014/009429 A1 | 1/2014 |
| WO | WO 2014/043544 A1 | 3/2014 |
| WO | WO 2014/076195 A1 | 5/2014 |
| WO | WO 2014/089313 A1 | 6/2014 |
| WO | WO 2014/201306 A1 | 12/2014 |
| WO | WO 2014/203518 A1 | 12/2014 |
| WO | WO 2015/025122 A1 | 2/2015 |
| WO | WO 2015/057847 A1 | 4/2015 |
| WO | WO 2015/113004 A2 | 7/2015 |
| WO | WO 2015/161184 A1 | 10/2015 |
| WO | WO 2015/171918 A2 | 11/2015 |
| WO | WO 2015/200078 A1 | 12/2015 |
| WO | WO 2016/028649 A1 | 2/2016 |
| WO | WO 2016/077321 A1 | 5/2016 |
| WO | WO 2016/077349 A1 | 5/2016 |
| WO | WO 2016/083623 A1 | 6/2016 |
| WO | WO 2016/149331 A2 | 9/2016 |
| WO | WO 2016/161374 A1 | 10/2016 |
| WO | WO 2016/161378 A1 | 10/2016 |
| WO | WO 2016/161388 A1 | 10/2016 |
| WO | WO 2016/164866 A1 | 10/2016 |
| WO | WO 2016/205410 A2 | 12/2016 |
| WO | WO 2017/015555 A1 | 1/2017 |
| WO | WO 2017/024239 A1 | 2/2017 |
| WO | WO 2017/030973 A1 | 2/2017 |
| WO | WO 2017/062862 A2 | 4/2017 |
| WO | WO 2017/132669 A1 | 8/2017 |
| WO | WO 2017/174572 A1 | 10/2017 |
| WO | WO 2018/031933 A2 | 2/2018 |
| WO | WO 2018/041973 A1 | 3/2018 |
| WO | WO 2018/056442 A1 | 3/2018 |
| WO | WO 2018/185241 A1 | 10/2018 |
| WO | WO 2018/223056 A1 | 12/2018 |
| WO | WO 2018/237245 A1 | 12/2018 |
| WO | WO 2019/075418 A1 | 4/2019 |
| WO | WO 2019/075419 A1 | 4/2019 |
| WO | WO 2019/099949 A1 | 5/2019 |
| WO | WO 2019/217459 A1 | 11/2019 |
| WO | WO 2019/232255 A1 | 12/2019 |
| WO | WO 2020/033899 A1 | 2/2020 |
| WO | WO 2020/041769 A1 | 2/2020 |
| WO | WO 2020/150636 A1 | 7/2020 |
| WO | WO 2020/198509 A2 | 10/2020 |
| WO | WO 2021/216556 A2 | 10/2021 |
| WO | WO 2021/195533 A2 | 11/2021 |
| WO | WO 2021/242883 A1 | 12/2021 |
| WO | WO 2023/173061 A2 | 9/2023 |

OTHER PUBLICATIONS

Ohnishi et al (Plos One, vol. 3, No. 5, e2248 (2008)) (Year: 2008).*
Ostergaard et al (Molecular Therapy Nucleic acids, vol. 7, pp. 20-30 (2017)) (Year: 2017).*
U.S. Appl. No. 15/089,319 2016/0355808 U.S. Pat. No. 9,809,817, filed Apr. 1, 2016 Dec. 8, 2016 Nov. 7, 2017, Anastasia Khvorova, Oligonucleotide Compounds for Targeting Huntingtin mRNA.
U.S. Appl. No. 15/697,120 2018/0094263 U.S. Pat. No. 10,435,688, filed Sep. 6, 2017 Apr. 5, 2018 Oct 8, 2019, Anastasia Khvorova, Oligonucleotide Compounds for Targeting Huntingtin mRNA.
U.S. Appl. No. 16/263,200 2019/0225965 U.S. Pat. No. 10,744,327, filed Jan. 31, 2019 Jul. 25, 2019 Sep. 15, 2020, Anastasia Khvorova, Oligonucleotide Compounds for Targeting Huntingtin mRNA.
U.S. Appl. No. 16/811,580 2020/0308584 U.S. Pat. No. 11,230,713, filed Mar. 6, 2020 Oct. 1, 2020 Jan. 5, 2022, Anastasia Khvorova, Oligonucleotide Compounds for Targeting Huntingtin mRNA.
U.S. Appl. No. 17/536,647 2022/0251554, filed Nov. 29, 2021 Aug. 11 2022, Anastasia Khvorova, Oligonucleotide Compounds for Targeting Huntingtin mRNA.
U.S. Appl. No. 15/089,437 2016/0355826 U.S. Pat. No. 9,862,952, filed Apr. 1, 2016 Dec. 8, 2016 Jan. 9, 2018, Anastasia Khvorova, Oligonucleotide Compounds For Treatment of Preeclampsia And Other Angiogenic Disorders.
U.S. Appl. No. 15/814,350 2018/0179546 U.S. Pat. No. 10,519,451, filed Nov. 15, 2017 Jun. 28, 2018 Dec. 31, 2019, Anastasia Khvorova, Oligonucleotide Compounds For Treatment of Preeclampsia And Other Angiogenic Disorders.
U.S. Appl. No. 16/675,369 2020/0165618 U.S. Pat. No. 11,345,917, filed Nov. 6, 2019 May 28, 2020 May 11, 2022, Anastasia Khvorova, Oligonucleotide Compounds For Treatment of Preeclampsia And Other Angiogenic Disorders.
U.S. Appl. No. 17/718,918 2022/0364100, filed Apr. 12, 2022 Nov. 17, 2022, Anastasia Khvorova, Oligonucleotide Compounds For Treatment of Preeclampsia And Other Angiogenic Disorders.
U.S. Appl. No. 15/089,423 2016/0319278, filed Apr. 1, 2016 Nov. 3, 2016, Anastasia Khvorova, Fully Stabilized Asymmetric siRNA.
U.S. Appl. No. 15/691,120 2017/0396882, filed Aug. 30, 2017 Dec. 28, 2017, Anastasia Khvorova, Fully Stabilized Asymmetric siRNA.
U.S. Appl. No. 16/927,543 2021/0024926 U.S. Pat. No. 12,173,286, filed Jul. 13, 2020 Jan. 28, 2021 Dec. 24, 2024, Anastasia Khvorova, Fully Stabilized Asymmetric siRNA.
U.S. Appl. No. 18/939,685, filed Nov. 7, 2024, Anastasia Khvorova, Fully Stabilized Asymmetric siRNA.
U.S. Appl. No. 15/236,051 2017/0043024 U.S. Pat. No. 10,633,653, filed Aug. 12, 2016 Feb. 16, 2017 Apr. 28, 2020, Anastasia Khvorova, Bioactive Conjugates For Oligonucleotide Delivery.
U.S. Appl. No. 16/812,714 2020/0339983, filed Mar. 9, 2020 Oct. 29, 2020, Anastasia Khvorova, Bioactive Conjugates For Oligonucleotide Delivery.
U.S. Appl. No. 18/769,546, filed Jul. 11, 2024, Anastasia Khvorova, Bioactive Conjugates For Oligonucleotide Delivery.
U.S. Appl. No. 15/419,593 2017/0312367 U.S. Pat. No. 10,478,503, filed Jan. 30, 2017 Nov. 2, 2017 Nov. 19, 2019, Anastasia Khvorova, Branched Oligonucleotides.
U.S. Appl. No. 16/390,712 2019/0247507 U.S. Pat. No. 10,799,591, filed Apr. 22, 2019 Aug. 15, 2019 Oct. 13, 2020, Anastasia Khvorova, Branched Oligonucleotides.
U.S. Appl. No. 17/012,787 2021/0085793 U.S. Pat. No. 11,896,669, filed Sep. 4, 2020 Mar. 25, 2021 Feb. 13, 2024, Anastasia Khvorova, Branched Oligonucleotides.
U.S. Appl. No. 18/396,613 2024/0293550, filed Dec. 26, 2023 Sep. 5, 2024, Anastasia Khvorova, Branched Oligonucleotides.
U.S. Appl. No. 16/322,212 2019/0185855 U.S. Pat. No. 11,753,638, filed Jan. 31, 2019 Jun. 20, 2019 Sep. 12, 2023, Anastasia Khvorova, Conjugated Oligonucleotides.
U.S. Appl. No. 18/170,167 2024/0084297, filed Feb. 16, 2023 Mar. 14, 2024, Anastasia Khvorova, Conjugated Oligonucleotides.
U.S. Appl. No. 16/015,440 2019/0024082 U.S. Pat. No. 10,844,377, filed Jun. 22, 2018 Jan. 24, 2019 Nov. 24, 2020, Anastasia Khvorova, Two-Tailed Self-Delivering siRNA.
U.S. Appl. No. 17/071,473 2021/0139901, filed Oct. 15, 2020 May 13, 2021, Anastasia Khvorova, Two-Tailed Self-Delivering siRNA.
U.S. Appl. No. 16/537,374 2020/0123543 U.S. Pat. No. 11,827,882, filed Aug. 9, 2019 Apr. 23, 2020 Nov. 28, 2023, Anastasia Khvorova, Modified Oligonucleotides Targeting SNPs.
U.S. Appl. No. 16/988,391 2021/0071177 U.S. Pat. No. 12,024,706, filed Aug. 7, 2020 Mar. 11, 2021 Jul. 2, 2024, Anastasia Khvorova, Modified Oligonucleotides Targeting SNPs.
U.S. Appl. No. 18/421,647 2024/0327836, filed Jan. 24, 2024 Oct. 3, 2024, Anastasia Khvorova, Modified Oligonucleotides Targetting SNPs.
U.S. Appl. No. 16/746,555 2020/0270605 U.S. Pat. No. 11,492,619, filed Jan. 17, 2020 Aug. 27, 2020 Nov. 8, 2022, Anastasia Khvorova, Dynamic Pharmacokinetic-Modifying Anchors.

(56) References Cited

OTHER PUBLICATIONS

U.S. Appl. No. 17/725,102 2022/0372476, filed Apr. 20, 2022 Nov. 24, 2022, Anastasia Khvorova, Dynamic Pharmacokinetic-Modifying Anchors.
U.S. Appl. No. 17/792,705 2023/0061751, filed Jul. 13, 2022 Mar. 2, 2023, Anastasia Khvorova, Universal Dynamic Pharmacokinetic-Modifying Anchors.
U.S. Appl. No. 16/550,076 2020/0087663 U.S. Pat. No. 11,279,930, filed Aug. 23, 2019 Mar. 19, 2020 Mar. 22, 2022, Anastasia Khvorova, O-Methyl Rich Fully Stabilized Oligonucleotides.
U.S. Appl. No. 16/999,759 2021/0115442, filed Aug. 21, 2020 Apr. 22, 2021, Anastasia Khvorova, O-Methyl Rich Fully Stabilized Oligonucleotides.
U.S. Appl. No. 17/580,269 2022/0251555, filed Jan. 20, 2022 Aug. 11, 2022, Anastasia Khvorova, O-Methyl Rich Fully Stabilized Oligonucleotides.
U.S. Appl. No. 17/022,678 2021/0108200, filed Sep. 16, 2020 Apr. 15, 2021, Anastasia Khvorova, Branched Lipid Conjugates Of siRNA For Specific Tissue Delivery.
U.S. Appl. No. 17/235,153 2021/0355491, filed Apr. 20, 2021 Nov. 18, 2021, Anastasia Khvorova, Oligonucleotides For MSH3 Modulation.
U.S. Appl. No. 17/331,146 2021/0395739, filed May 26, 2021 Dec. 23, 2021, Anastasia Khvorova, Synthetic Oligonucleotides Having Regions Of Block And Cluster Modifications.
U.S. Appl. No. 17/391,475 2022/0090069, filed Aug. 2, 2021 Mar. 24, 2022, Anastasia Khvorova, Oligonucleotides For HTT-1A Modulation.
U.S. Appl. No. 18/430,581 2024/0301410, filed Feb. 1, 2024 Sep. 12, 2024, Anastasia Khvorova, Oligonucleotides For HTT-1A Modulation.
U.S. Appl. No. 17/377,632 2022/0042015, filed Jul. 16, 2021 Feb. 10, 2022, Anastasia Khvorova, Conjugated Oligonucleotides for Tissue Specific Delivery.
U.S. Appl. No. 17/846,526 2023/0078622 U.S. Pat. No. 11,702,659, filed Jun. 22, 2022 Mar. 16, 2023 Jul. 18, 2023, Anastasia Khvorova, Optimized ANTI-FLT1 Oligonucleotide Compounds for Treatment of Preeclampsia and Other Angiogenic Disorders.
U.S. Appl. No. 18/321,971 2024/0067967, filed May 23, 2023 Feb. 29, 2024, Anastasia Khvorova, Optimized ANTI-FLTI Oligonucleotide Compounds for Treatment of Preeclampsia and Other Angiogenic Disorders.
Aguiar et al., "RNAi mechanisms in Huntington's disease therapy: siRNA versus shRNA", Transl Neurodegener., Nov. 27, 2017, 6:30, eCollection 2017.
Bioinformatics.org (Oct. 1, 2023) DNA Molecular Weight Calculator, Available online at: bioinformatics.org/sms2/dna_mw.html.
Biosyn, (2006) Oligonucleotide Properties Calculator., Available online at: biosyn.com/gizmo/tools/oligo/oligonucleotide%20properties %20calculator.htm.
Charoenphol et al. (Apr. 16, 2014), "Aptamer-Targeted DNA Nanostructures for Therapeutic Delivery", Molec. Pharmaceut., 11(5): 1721-1725.
Cleveland Clinic (2022) "Peripheral Neuropathy" and "Personality disorders", Available online at: my.clevelandclinic.org.
Espe et al. (Jan. 2018) "Malacards", J. Med. Libr. Assoc., 106(1): 140-141.
Extended European Search Report for European Application No. 21843183.1, mailed Jun. 17, 2025.
Gannon et al., "MutSβ and histone deacetylase complexes promote expansions of trinucleotide repeats in human cells", Nucleic Acids Research, Nov. 1, 2012, 40(20): 10324-10333. Epub Aug. 31, 2012.
Greco et al., "Soluble Fms-Like Tyrosine Kinase-1 Is A Marker of Endothelial Dysfunction During Sepsis", J. Clin. Med. Res., Sep. 2018, 10(9): 700-706. Epub Jul. 31, 2018.
Hastie et al., "EGFR (Epidermal Growth Factor Receptor) Signaling and the Mitochondria Regulate sFlt-1 (Soluble FMS-Like Tyrosine Kinase-1) Secretion", Hypertension, Mar. 2019, 73(3): 659-670.
Hu et al. (Jan. 22, 2018) "DNA Nanostructure-Based Systems for Intelligent Delivery of Therapeutic Oligonucleotides", Adv. Healthcare Mater., 7: 1701153.
Hu et al., "Therapeutic siRNA: State of the Art", Signal Transduct. Target Ther., Jun. 19, 2020, 5(1):101.
International Preliminary Report on Patentability (Chapter II) for PCT International Patent Application No. PCT/US2019/046013, mailed Apr. 10, 2020.
Lee et al. (Jun. 3, 2012) "Molecularly self-assembled nucleic acid nanoparticles for targeted in vivo siRNA delivery", Nat. Nanotechnol., 7: 389-393.
Bosco et al., "VEGFR-1/Flt-1 inhibition increases angiogenesis and improves muscle function in a mouse model of Duchenne muscular dystrophy", Mol. Ther. Methods Clin. Dev., Mar. 23, 2021, 21: 369-381. eCollection Jun. 11, 2021.
Chakraborty et al., "Nucleic Acid-Based Nanodevices in Biological Imaging", Annu. Rev. Biochem., Jun. 2, 2016, 85: 349-373.
Holman, "Protein Similarity Score: A Simplified Version of the Blast Score as a Superior Alternative to Percent Identity for Claiming Genuses of Related Protein Sequences", Santa Clara High Tech. L.J., Jan. 2004, 21(1): 55-99. Published online Oct. 2006.
Ikeda et al., "Impacts of PEGylation on the Gene and Oligonucleotide Delivery System", J. Appl. Polymer Sci., 2014, 131(9): 40293, Epublished Dec. 31, 2013.
International Search Report & Written Opinion for PCT International Patent Application No. PCT/US2023/064096, dated Jan. 31, 2024.
Myatt et al., "Preeclampsia: Syndrome or Disease?", Curr. Hypertens Rep., Nov. 2015, 17(11): 83.
Rana et al., "Preeclampsia: Pathophysiology, Challenges, and Perspectives", Circ. Res., Mar. 29, 2019, 124(7): 1094-1112.
Rouzina et al., "Heat Capacity Effects on the Melting of DNA. 1. General Aspects", Biophys. J., Dec. 1999, 77(6): 3242-3251.
Thermofisher, "Polyethylene Glycol [PEG] and Pegylation of Proteins", Available online at The Wayback Machine web.archive.org, Page archived on Jul. 25, 2017.
Verma et al., "Inhibition of FLT1 ameliorates muscular dystrophy phenotype by increased vasculature in a mouse model of Duchenne muscular dystrophy", PLoS Genet., Dec. 26, 2019, 15(12): e1008468.
Wilson et al., "Targeting the Dysfunctional Placenta to Improve Pregnancy Outcomes Based on Lessons Learned in Cancer", Clin Ther., Jan. 11, 2021, 43(2): 246-264.
Akinc et al., A Combinatorial Library of Lipid-like Materials for Delivery of RNAi Therapeutics, Nature Biotechnology, vol. 26, No. 5, 20 Pages, May 2008.
Alagia, et al., Exploring PAZ/3'-overhang Interaction to Improve siRNA Specificity. A Combined Experimental and Modeling Study, Chemical Science, vol. 9, No. 8, pp. 2074-2086, 2018.
Alexopoulou, et al., Recognition of Double-Stranded RNA and Activation of NF-κB by Toll-like receptor 3, Nature, vol. 413, No. 6857, pp. 732-738, Oct. 18, 2001.
Alisky, et al., "Gene Therapy for Amyotrophic Lateral Sclerosis and Other Motor Neuron Diseases", Human Gene Therapy, vol. 11, Issue 17, pp. 2315-2329, Nov. 20, 2000.
Allerson et al., "Fully 2'-modified oligonucleotide duplexes with improved in vitro potency and stability compared to unmodified small interfering RNA", J Med Chem., Feb. 24, 2005, 48(4): 901-904.
Alterman et al., "A divalent siRNA chemical scaffold for potent and sustained modulation of gene expression throughout the central nervous system", Nat Biotechnol., Aug. 2019, 37(8): 884-894.
Alterman, et al., Hydrophobically Modified siRNAs Silence Huntingtin mRNA in Primary Neurons and Mouse Brain, Molecular Therapy—Nucleic Acids, vol. 4, pp. e266, Dec. 1, 2015.
Alvarez-Erviti, et al., "Delivery of siRNA To The Mouse Brain By Systemic Injection Of Targeted Exosomes", Nature Biotechnology, vol. 29, No. 4, pp. 341-345, Apr. 2011.
Alves, et al., Selectivity, Cooperativity, and Reciprocity in the Interactions between the δ-Opioid Receptor, Its Ligands, and G-proteins, Journal of Biological Chemistry, vol. 279 No. 43, pp. 4673-44682, Aug. 17, 2004.

(56) References Cited

OTHER PUBLICATIONS

Amarzguioui, et al., "Tolerance for Mutations And Chemical Modifications in a siRNA", Nucleic Acids Research, Jan. 15, 2003, 31(2): 589-595.
Ambardekar et al., "The modification of siRNA with 3' cholesterol to increase nuclease protection and suppression of native mRNA by select siRNA polyplexes", Biomaterials, Elsevier, Amsterdam, NL, vol. 32, No. 5, pp. 1404-1411. (Nov. 2, 2010).
Ambros, et al., MicroRNAs and Other Tiny Endogenous RNAs in C. elegans, Current Biology, vol. 13, Issue 10, pp. 807-818, May 13, 2003.
Ameres, et al., Molecular Basis for Target RNA Recognition and Cleavage by Human RISC, Cell, vol. 130, Issue 1, pp. 101-112, Jul. 13, 2007.
Ämmälä, et al., Targeted Delivery of Antisense Oligonucleotides to Pancreatic β-cells, Science Advances, vol. 4, No. 10, eaat3386, pp. 1-11, Oct. 17, 2018.
Anderson, et al., Experimental Validation Of The Importance Of Seed Complement Frequency To siRNA Specificity, RNA, vol. 14, No. 5, pp. 853-861, Mar. 26, 2008.
Anderson, et al., Identifying siRNA-Induced Off-Targets by Microarray Analysis, Methods in Molecular Biology, vol. 442, pp. 45-63, 2008.
Atwell, et al., Stable Heterodimers From Remodeling The Domain Interface Of A Homodimer Using A Phage Display Library, Journal Of Molecular Biology, vol. 270, Issue 1, pp. 26-35, Jul. 4, 1997.
Aubuchon, et al., "Preeclampsia: Animal Models for a Human Cure", Proceedings of the National Academy of Sciences, vol. 108, No. 4, pp. 1197-1198, Jan. 25, 2011.
Aureli, et al., GM1 Ganglioside: Past Studies and Future Potential, Molecular Neurobiology, vol. 53, Issue 3, pp. 1824-1842, Apr. 2016.
Avino, et al., Branched RNA: A New Architecture for RNA Interference, Journal of Nucleic Acids, Article ID 586935, 7 pages, Mar. 6, 2011.
Bagella, et al., Cloning Of Murine CDK9/PITALRE And Its Tissue-Specific Expression In Development, Journal of cellular physiology, vol. 177, No. 2, pp. 206-213, Dec. 7, 1998.
Bartlett, et al., Can Metastatic Colorectal Cancer Be Cured?, Journal Oncology, Cancer Network, vol. 26, No. 3, pp. 266-275, Mar. 15, 2012.
Bartlett, et al., Insights Into The Kinetics of siRNA-Mediated Gene Silencing From Live-Cell And Live-Animal Bioluminescent Imaging, Nucleic Acids Research, vol. 34, Issue 1, pp. 322-333, Jan. 1, 2006.
Behlke, et al., Chemical Modification of siRNAs for In Vivo Use, Oligonucleotides, vol. 18, No. 4, pp. 305-320, Nov. 29, 2008.
Bell, et al., Liposomal Transfection Efficiency And Toxicity On Glioma Cell Lines: In Vitro And In Vitro Studies, Neuroreport, vol. 9, Issue 5, pp. 793-798, Mar. 30, 1998.
Bertram et al., "Vinylphosphonate Internucleotide Linkages Inhibit the Activity of PcrA DNA Helicase", Biochemistry, Jun. 18, 2002, 41(24): 7725-7731.
Betkekar, et al., A Tandem Enyne/Ring Closing Metathesis Approach to 4-Methylene-2-cyclohexenols: An Efficient Entry to Otteliones and Loloanolides, Organic Letters, Dec. 6, 2011, vol. 14, No. 1, pp. 198-201.
Billy, et al., Specific Interference With Gene Expression Induced By Long, Double-Stranded RNA In Mouse Embryonal Teratocarcinoma Cell Lines, Proceedings of the National Academy of Sciences, vol. 98, No. 25, pp. 14428-14433, Dec. 4, 2001.
Birmingham, et al., 3' UTR Seed Matches, But Not Overall Identity, Are Associated With RNAi Off-Targets, Nature Methods, vol. 3, No. 3, pp. 199-204, Feb. 17, 2006.
Birmingham, et al., A Protocol For Designing siRNAs With High Functionality And Specificity, Nature Protocols, vol. 2, No. 9, pp. 2068-2078, Aug. 23, 2007.
Biscans et al., "Docosanoic acid conjugation to siRNA enables functional and safe delivery to skeletal and cardiac muscles", Molecular Therapy, Apr. 2021, vol. 29, No. 4, pp. 1382-1394.
Biscans et al., "Hydrophobicity of Lipid-Conjugated siRNAs Predicts Productive Loading to Small Extracellular Vesicles", Molecular Therapy, Jun. 2018, vol. 26, No. 6, pp. 1520-1528.
Biscans et al., "The Chemical Structure and Phosphorothioate content of hydrophobically modified siRNAs impact extrahepatic distribution and efficacy", Nucleic Acids Research, 2020, vol. 48, No. 14, pp. 7665-7680.
Biscans et al., Diverse Lipid Conjugates for Functional Extra-Hepatic siRNA Delivery in Vivo, Nucleic Acids Research, vol. 47, No. 3, pp. 1082-1096, Dec. 14, 2018.
Biscans, et al., The Valency of Fatty Acid Conjugates Impacts siRNA Pharmacokinetics, Distribution, and Efficacy in Vivo, Journal of Controlled Release, vol. 302, pp. 116-125, Mar. 2019.
Boutla et al., "Short 5'-phosphorylated double-stranded RNAs induce RNA interference in *Drosophila*", Biology, 2001, 11: 1776-1780.
Braasch, et al., "RNA Interference in Mammalian Cells by Chemically-Modified RNA", Biochemistry, vol. 42, No. 26, pp. 7967-7975, Jun. 11, 2003.
Brennecke, et al., Towards A Complete Description Of The microRNA Complement Of Animal Genomes, Genome Biology, vol. 4, No. 9, 3 Pages, Aug. 21, 2003.
Brown, et al., Effect of Phosphorothioate Modification of Oligodeoxynucleotides on Specific Protein Binding, Journal of Biological Chemistry, vol. 269, No. 43, pp. 26801-26805, 1994.
Brummelkamp, et al., A System for Stable Expression of Short Interfering RNAs in Mammalian Cells, Science, vol. 296, Issue 5567, pp. 550-553, Apr. 19, 2002.
Burchard, et al., MicroRNA-Like Off-Target Transcript Regulation By siRNAs is Species Specific, RNA, vol. 15, No. 2, pp. 308-315, 2009.
Burke, et al., "Spiral Arterial Remodeling Is Not Essential for Normal Blood Pressure Regulation in Pregnant Mice", Hypertension, vol. 55, No. 3, pp. 729-737, Jan. 25, 2010.
Byrne, et al., Novel Hydrophobically Modified Asymmetric RNAi Compounds (sd-rxRNA) Demonstrate Robust Efficacy in the Eye, Journal of Ocular Pharmacology and Therapeutics, vol. 29, Issue 10, pp. 855-864, Dec. 3, 2013.
Calegari, et al., Tissue-Specific RNA Interference In Postimplantation Mouse Embryos With Endoribonuclease-Prepared Short Interfering RNA, Proceedings of the National Academy of Sciences, vol. 99, No. 22, pp. 14236-14240, Oct. 29, 2002.
Carter, "Handbook of Parvoviruses", ed., P. Tijsser, CRC Press, pp. 155-168, 1990.
Chang, et al., Asymmetric Shorter-duplex siRNA Structures Trigger Efficient Gene Silencing With Reduced Nonspecific Effects, Molecular Therapy, vol. 17, Issue 4, pp. 725-732, Apr. 2009.
Chang, et al., Enhanced intracellular delivery and multi-target gene silencing triggered by tripodal RNA Structure, The journal of gene Medicine, vol. 14, No. 2, pp. 138-146, Feb. 2012.
Chang, et al., Transgenic Animal Models For Study of The Pathogenesis Of Huntington's Disease And Therapy, Drug design, development and therapy, vol. 9, pp. 2179-2188, Apr. 2015.
Chappell, et al., Mechanisms of Palmitic Acid-conjugated Antisense Oligonucleotide Distribution in Mice, Nucleic Acids Research, vol. 48, Issue 8, „ pp. 4382-4395, May 7, 2020.
Charnock-Jones, et al., "Identification and Localization of Alternately Spliced mRNAs for Vascular Endothelial Growth Factor in Human Uterus and Estrogen Regulation in Endometrial Carcinoma Cell Lines", Biology of Reproduction, vol. 48, pp. 1120-1128, 1993.
Charrier, et al., Inhibition of SRGAP2 Function by Its Human-Specific Paralogs Induces Neoteny during Spine Maturation, Cell, vol. 149, Issue 4, pp. 923-935, May 11, 2012.
Chatterjee et al., "Mechanisms of DNA damage, repair, and mutagenesis", DNA Repair, Apr. 16, 2016, 42: 26-32.
Chen et al., "Lipophilic siRNAs mediate efficient gene silencing in oligodendrocytes with direct CNC delivery", Journal Of Controlled Release, Elsevier, vol. 144, pp. 227-232. (Feb. 17, 2010).
Chen et al., "Thermoresponsive polypeptides from pegylated poly-L-glutamates", Biomacromolecules 2011, 12: 2859-2863.
Chen et al., Influence of Particle Size on the in Vivo Potency of Lipid Nanoparticle Formulations of siRNA, Journal of Controlled Release, vol. 235, pp. 236-244, Aug. 10, 2016.

(56) References Cited

OTHER PUBLICATIONS

Chen, et al., "Gene Therapy For Brain Tumors: Regression Of Experimental Gliomas By Adenovirus-Mediated Gene Transfer In Vivo", Proceedings of the National Academy of Sciences, vol. 91, No. 8, pp. 3054-3057, 1994.
Cheng, et al., Enhanced Hepatic Uptake and Bioactivity of Type α1 (I) Collagen Gene Promoter-Specific Triplex-Forming Oligonucleotides after Conjugation with Cholesterol, Journal of Pharmacology and Experimental Therapeutics, vol. 370, Issue 2, pp. 797-805, Aug. 1, 2019.
Cheung, et al., Effects of All-Trans-Retinoic Acid on Human SH-SYSY Neuroblastoma as in Vitro Model in Neurotoxicity Research, Neurotoxicology, vol. 30, No. 1, pp. 127-135, Jan. 1, 2009.
Cho, et al., Vascular Endothelial Growth Factor Receptor 1 Morpholino Decreases Angiogenesis in a Murine Corneal Suture Model, Investigative ophthalmology & visual science, vol. 53, Issue 2, pp. 685-692, Feb. 2012.
Choe, et al., Crystal Structure of Human Toll-Like Receptor 3 (TLR3) Ectodomain, Science, vol. 309, Issue 5734, pp. 581-585, Jun. 16, 2005.
Choi et al., Suppression of diacylglycerol acyltransferase-2 (DGAT2), but not DGAT1, with antisense oligonucleotides reverses diet-induced hepatic steatosis and insulin resistance, J Biol Chem., Aug. 3, 2007, 282(31): 22678-22688.
Chu, et al., Potent RNAi by Short RNA Triggers, RNA, vol. 14, pp. 1714-1719, 2008.
Chung et al., "Reducible siRNA Dimeric Conjugates for Efficient Cellular Uptake and Gene Silencing", Bioconjugate Chem., 2011, 22(2): 299-306.
Coelho, et al., Safety and Efficacy of RNAi Therapy for Transthyretin Amyloidosis, New England Journal of Medicine, vol. 369, No. 9, pp. 819-829, Aug. 29, 2013.
Coles, et al., A High-Throughput Method for Direct Detection of Therapeutic Oligonucleotide-Induced Gene Silencing In Vivo, Nucleic Acid Therapeutics, vol. 26, Issue 2, pp. 86-92, Apr. 11, 2016.
Collis, "The synthesis of vinylphosphonate-linked RNA", Ph.D. Thesis, University of Nottingham, Feb. 2008.
Crooke, et al., Cellular Uptake and Trafficking of Antisense Oligonucleotides, Nature Biotechnology, vol. 35, No. 3, pp. 230-237, Mar. 2017.
Crooke, et al., Phosphorothioate Modified Oligonucleotide—Protein Interactions, Nucleic Acids Research, May 1, 2020, 48(10): 5235-5253.
Cui, et al., "Role of Corin in Trophoblast Invasion and Uterine Spiral Artery Remodelling in Pregnancy", Nature, vol. 484, No. 7393, pp. 246-250, Mar. 21, 2012.
Czauderna, et al., Structural Variations and Stabilising Modifications of Synthetic siRNAs in Mammalian Cells, Nucleic Acids Research, vol. 31, Issue 11, pp. 2705-2716, Jun. 2003.
Dahlman et al., In Vivo Endothelial siRNA Delivery using Polymeric Nanoparticles with Low Molecular Weight, Nature Nanotechnology, vol. 9, No. 8, 17 Pages, Aug. 2014.
Damha et al. (1990) "An improved procedure for derivatization of controlled-pore glass beads for solid-phase oligonucleotide synthesis," Nucleic Acids Research, 18(13):3813-3821.
Dass, Crispin R., Cytotoxicity Issues Pertinent To Lipoplex-Mediated Gene Therapy In-Vivo, Journal of Pharmacy and Pharmacology, vol. 54, Issue 5, pp. 593-601, Feb. 18, 2010.
Davidson, et al., A Model System For In Vivo Gene Transfer Into The Central Nervous System Using An Adenoviral Vector, Nature Genetics, vol. 3, No. 3, pp. 219-223, Mar. 1, 1993.
Davidson, et al., Recombinant Adeno-Associated Virus Type 2, 4, and 5 Vectors: Transduction of Variant Cell Types And Regions In The Mammalian Central Nervous System, Proceedings of the National Academy of Sciences, vol. 97, No. 7, pp. 3428-3432, Mar. 28, 2000.
De Fougerolles, et al., "Interfering With Disease: a Progress Report on siRNA-based Therapeutics", Nature Reviews Drug Discovery, vol. 6, pp. 443-453, Jun. 2007.
De Marre et al., "Synthesis, characterization, and in vitro biodegradation of poly(ethylene glycol) modified poly[5N-(2-hydroxyethyl-L-glutamine]", J Bioact Compat Polym, 1996, 11: 85-99.
De Paula et al., "Hydrophobization and bioconjugation for enhanced siRNA delivery and targeting", RNA, Feb. 28, 2007, vol. 13, No. 4, pp. 431-456.
Deleavey, et al., The 5' Binding MID Domain of Human Argonaute2 Tolerates Chemically Modified Nucleotide Analogues, Nucleic acid therapeutics, vol. 23, No. 1, pp. 81-87, Feb. 7, 2013.
Difiglia, et al., Therapeutic Silencing Of Mutant Huntingtin With siRNA Attenuates Striatal And Cortical Neuropathology And Behavioral Deficits, Proceedings of the National Academy of Sciences, vol. 104, No. 43, pp. 17204-17209, Oct. 23, 2007.
Dinusha, Differnce Between Sterol and Steroid, Home / Health / Medicine / Nutrients & Drugs, Aug. 4, 2011.
Doddridge et al., Effects of Vinylphosphonate Internucleotide Linkages on the Cleavage Specificity of Exonuclease III and on the Activity of DNA Polymerase I, Biochemistry, Mar. 25, 2003, 42(11): 3239-3246.
Doench, et al., siRNAs Can Function As miRNAs, Genes & Development, vol. 17, pp. 438-442, 2003.
Dohmen et al., "Defined Folate-PEG-siRNA Conjugates for Receptor-specific Gene Slicing", Molecular Therapy—Nucleic Acids, 2012, 1(1): e7.
Dowdy, Overcoming Cellular Barriers for RNA Therapeutics, Nature Biotechnology, vol. 35, pp. 222-229, Feb. 27, 2017.
Dua et al., "Modified siRNA Structure With a Single Nucleotide Bulge Overcomes Conventional siRNA-mediated Off-target Silencing", Molecular Therapy, Jun. 2011, 16(9): 1676-1687.
Ducruix, et al., Crystallization of Nucleic Acids and Proteins: A Practical Approach, Second Edition, 1999, pp. 201-216.
Dufour, et al., Intrajugular Vein Delivery of AAV9-RNAi Prevents Neuropathological Changes and Weight Loss in Huntington's Disease Mice, Molecular Therapy, vol. 22, No. 4, pp. 797-810, Jan. 6, 2014.
Dyall, et al., Long-chain omega-3 fatty acids and the brain: a review of the independent and shared effects of EPA, DPA and DHA, Frontiers in Aging Neuroscience, vol. 7, p. 52, Apr. 21, 2015.
Echevarría, et al., Evaluating the Impact of Variable Phosphorothioate Content in Tricyclo-DNA Antisense Oligonucleotides in a Duchenne Muscular Dystrophy Mouse Model, Nucleic Acid Therapeutics, vol. 29, No. 3, pp. 148-160, May 30, 2019.
Eckstein, Developments in RNA Chemistry, A Personal View, Biochimie, vol. 84, No. 9, pp. 841-848, Sep. 2002.
Eckstein, Phosphorothioate Oligodeoxynucleotides: What Is Their Origin and What Is Unique About Them?, Antisense and Nucleic Acid Drug Development, vol. 10, Issue 2, pp. 117-121, Jan. 30, 2009.
Egli, et al., Re-engineering RNA Molecules Into Therapeutic Agents, Accounts of Chemical Research, vol. 52, pp. 1036-1047, 2019.
Egusquiaguirre, et al., "Nanoparticle Delivery Systems For Cancer Therapy: Advances In Clinical And Preclinical Research", Clinical and Translational Oncology, vol. 14, pp. 83-93, 2012.
El Andaloussi, et al., "Exosome-Mediated Delivery of siRNA In Vitro And In Vivo", Nature Protocols, vol. 7, No. 12, pp. 2112-2126, Nov. 15, 2012.
El Andaloussi, et al., "Exosomes For Targeted siRNA Delivery Across Biological Barriers", Advanced Drug Delivery Reviews, vol. 65, pp. 391-397, 2013.
El Andaloussi, et al., "Extracellular Vesicles: Biology And Emerging Therapeutic Opportunities", Nature Reviews Drug Discovery, vol. 12, pp. 347-357, May 2013.
Elbashir, et al., RNA Interference Is Mediated By 21- and 22-Nucleotide RNAs, Genes & Development, vol. 15, No. 2, pp. 188-200, 2001.
Elmen, et al., Locked Nucleic Acid (LNA) Mediated Improvements in siRNA Stability And Functionality, Nucleic Acids Research, vol. 33, Issue 1, pp. 439-447, Jan. 14, 2005.
EMBL Database, WO 2005116204-A/113070: Double Strand Polynucleotides Generating RNA Interference, EBI Accession No. EM PAT:FW706544, XP055753619, , Apr. 18, 2011.

(56) References Cited

OTHER PUBLICATIONS

Eremina, et al., "Glomerular-Specific Alterations of VEGF-A Expression Lead to Distinct Congenital and Acquired Renal Diseases", Journal of Clinical Investigation, vol. 111, No. 5, pp. 707-716, Mar. 2003.
Eremina, et al., "VEGF Inhibition and Renal Thrombotic Microangiopathy", New England Journal of Medicine, vol. 358, No. 11, pp. 1129-1136, Mar. 13, 2008.
Etzold et al., "The extension of the sugar chain of thymidine: a new route to 5'-deoxyhexose nucleosides", Chemical Communications (London), 1968, Issue 7.
Evers, et al., Antisense Oligonucleotides In Therapy For Neurodegenerative Disorders, Advanced Drug Delivery Reviews, vol. 87, pp. 90-103, Jun. 29, 2015.
Extended European Search Report for European Patent Application No. 16837593.9, dated Mar. 20, 2019.
Extended European Search Report for European Patent Application No. 17745083.0, dated on Jul. 31, 2019.
Extended European Search Report for European Patent Application No. 17840367.1, dated Oct. 14, 2020.
Extended European Search Report for European Patent Application No. 18819571.3, dated May 14, 2021.
Extended European Search Report for European Patent Application No. 19847586.5, dated Jun. 21, 2023.
Extended European Search Report for European Patent Application No. 19852320.1, dated May 2, 2022.
Extended European Search Report for European Patent Application No. 20164108.1, dated on Dec. 3, 2020.
Extended European Search Report for European Patent Application No. 20216265.7, dated Feb. 10, 2022.
Extended European Search Report for European Patent Application No. 20741865.8, dated Apr. 26, 2023.
Extended European Search Report for European Patent Application No. 20856904.6, mailed Jan. 2, 2024.
Extended European Search Report for European Patent Application No. 21197881.2, dated Oct. 31, 2022.
Extended European Search Report for European Patent Application No. 21741867.2, mailed Mar. 12, 2024.
Extended European Search Report for European Patent Application No. 21792058.6, dated Jul. 8, 2024.
Extended Supplementary European Search Report for European Patent Application No. 20777915.8, mailed Sep. 15, 2023.
Extended Supplementary European Search Report for European Patent Application No. 21814030.9, mailed May 24, 2024.
Fan, et al., Endometrial VEGF Induces Placental sFLT1 And Leads To Pregnancy Complications, The Journal of clinical investigation, vol. 124, No. 11, pp. 4941-4952, Oct. 20, 2014.
Fattal, et al., Biodegradable Polyalkylcyanoacrylate Nanoparticles For The Delivery Of Oligonucleotides, Journal of Controlled Release, vol. 53, pp. 137-143, May 1998.
Fedorov, et al., Off-Target Effects By siRNA Can Induce Toxic Phenotype, RNA, vol. 12, No. 7, pp. 1188-1196, May 2006.
Felber, et al., The Interactions of Amphiphilic Antisense Oligonucleotides With Serum Proteins And Their Effects on In Vitro Silencing Activity, Biomaterials, vol. 33, Issue 25, pp. 5955-5965, Sep. 2012.
Figueroa, et al., Neurorestorative Targets of Dietary Long-Chain Omega-3 Fatty Acids in Neurological Injury, Molecular Neurobiology, vol. 50, Issue 1, pp. 197-213, Aug. 2014.
Fisher, et al., Transduction With Recombinant Adeno-Associated Virus For Gene Therapy Is Limited By Leading-Strand Synthesis, Journal of virology, vol. 70, No. 1, pp. 520-532, Jan. 1996.
Fitzgerald, et al., A Highly Durable RNAi Therapeutic Inhibitor of PCSK9, New England Journal of Medicine, vol. 376, No. 1, pp. 41-51, Jan. 5, 2017.
Flower et al., MSH3 Modifies Somatic instability and Disease Severity in Huntington's and Myotonic Dystrophy Type 1, Brain, A Journal of Neurology, Jul. 2019, 142(7): 1876-1886.
Foster et al., "Advanced siRNA Designs Further Improve In Vivo Performance of GalNAc-siRNA Conjugates", Molecular Therapy, vol. 26, No. 3, pp. 709-717, Mar. 2018.
Franich, et al., AAV Vector—Mediated RNAi of Mutant Huntingtin Expression is Neuroprotective in a Novel Genetic Rat Model of Huntington's Disease, Molecular Therapy, vol. 16, Issue 5, pp. 947-956, Mar. 25, 2008.
Frank et al., Structural Basis for 5'-Nucleotide Base-specific Recognition of Guide RNA by Human AGO2, Nature, vol. 465, pp. 818-822, Jun. 2010.
Frazier, Antisense Oligonucleotide Therapies: The Promise and the Challenges from a Toxicologic Pathologist's Perspective, Toxicologic pathology, vol. 43, Issue 1, pp. 78-89, Nov. 9, 2014.
Frigg et al., Relationships between vitamin A and vitamin E in the chick, Int J Vitam Nutr Res., 1984, 54(2-3): 125-133.
Furuhashi et al., Expression of Low Density Lipoprotein Receptor Gene in Hjuman Placenta during Pregnancy, Molecular Endocrinology, 1989, 3: 1252-1256.
Gaglione, et al., Recent Progress in Chemically Modified siRNAs, Mini Reviews in Medicinal Chemistry, vol. 10, No. 7, pp. pp. 578-595, 2010.
Gaus, et al., Characterization of the Interactions of Chemically-modified Therapeutic Nucleic Acids With Plasma Proteins Using a Fluorescence Polarization Assay, Nucleic Acids Research, vol. 47, No. 3, pp. 1110-1122, 2019.
Gavrilov et al. (Jun. 2012) "Therapeutic siRNA: principles, challenges, and strategies", Yale Journal of Biology and Medicine, 85:187-200.
Geary, Antisense Oligonucleotide Pharmacokinetics and Metabolism, Expert Opinion on Drug Metabolism & Toxicology, vol. 5, pp. 381-391, Apr. 1, 2009.
Geary, et al., Pharmacokinetics, Biodistribution And Cell Uptake of Antisense Oligonucleotides, Advanced Drug Delivery Reviews, vol. 87, pp. 46-51, Jun. 29, 2015.
GenBank, "*Homo sapiens* RNA polymerase II subunit M (POLR2M), transcript variant 1, mRNA", NCBI Reference Sequence: NM_015532.5, Apr. 4, 2024.
GenBank, Mus Musculus Non-Coding RNA, Oocyte_Clustered_Small_RNA6599, Complete Sequence, GenBank Accession No. AB341398.1, May 24, 2008, 1 page.
GenBank, Rattus Norvegicus piRNA piR-182271, Complete Sequence, GenBank Accession No. DQ766949.1, Jul. 12, 2006, 1 Page.
GenBank, Signal Recognition Particle 54 kDa protein 2 [Perkinsus marinus ATCC 50983], NCBI Reference Sequence: XP_002784438.1, Apr. 30, 2010.
Ghidini et al., "An RNA modification with remarkable resistance to RNase A", Chemical Communications, Aug. 8, 2013, 49(79): 9036-9038.
Ghosh et al., "Comparing 2-nt 3' overhangs against blunt-ended siRNAs: a systems biology based study", BMC Genomics, 2009, 10(Suppl. 1):S17.
Gilany, et al., The Proteome of The Human Neuroblastoma Cell Line SH-SY5Y: An Enlarged Proteome, Biochimica et Biophysica Acta (BBA)—Proteins and Proteomics, vol. 1784, Issues 7-8, pp. 983-985, Jul.-Aug. 2008.
Gilbert, et al., "Hypertension Produced by Reduced Uterine Perfusion in Pregnant Rats Is Associated With Increased Soluble fms-like Tyrosine Kinase-1 Expression", Hypertension, vol. 50, No. 6, pp. 1142-1147, Oct. 8, 2007.
Gille, et al., "Analysis of Biological Effects and Signaling Properties of Flt-1 (VEGFR-1) and KDR (VEGFR-2)", Mechanisms of Signal Transduction, vol. 276, Issue 5, pp. 3222-3230, Feb. 2001.
Godard, et al., "Antisense Effects of Cholesterol-Oligodeoxynucleotide Conjugates Associated with Poly(alkylcyanoacrylate) Nanoparticles", European Journal of Biochemistry banner, vol. 232, pp. 404-410, 1995.
Godinho et al., "PK-modifying anchors significantly alter clearance kinetics, tissue distribution, and efficacy of therapeutics siRNAs", Mol Ther Nucleic Acids, Jun. 13, 2022,29: 116-132, ePublished Sep. 13, 2022.
Godinho et al., Pharmacokinetic Profiling of Conjugated Therapeutic Oligonucleotides: A High-Throughput Method based upon Serial

(56) References Cited

OTHER PUBLICATIONS

Blood Microsampling Coupled to Peptide Nucleic Acid Hybridization Assay, Nucleic Acid Therapeutics, vol. 27, pp. 323-334, Dec. 1, 2017.
Goodson et al., Dental Applications, Medical Applications of Controlled Release, vol. 2, pp. 115-138, 1984.
Grad, et al., Computational and Experimental Identification of C. elegans microRNAs, Molecular Cell, vol. 11, Issue 5, pp. 1253-1263, May 2003.
Gray, et al., Human Mutant Huntingtin with a Stable Polyglutamine Repeat Can Elicit Progressive and Selective Neuropathogenesis in BACHD Mice, Journal of Neuroscience, vol. 28, Issue 24, pp. 6182-6195, Jun. 11, 2008.
Griffiths-Jones, San, The microRNA Registry, Nucleic Acids Research, vol. 32, Issue Supplement 1, pp. D109-D111, Jan. 1, 2004.
Grimm, D, Asymmetry in siRNA Design, Gene Therapy, vol. 16, No. 7, pp. 827-829, Apr. 30, 2009.
Grimm, et al., Fatality In Mice Due To Oversaturation Of Cellular MicroRNA/short Hairpin RNA Pathways, Nature, vol. 441, No. 7092, pp. 537-541, May 25, 2006.
Gvozdeva et al., "Noncanonical Synthetic RNAi Inducers InL RNA Interference", InTech, Apr. 6, 2016.
Haly et al., "An extended phosphate linkage: Synthesis, hybridization and modeling studies of modified oligonucleotides", Nucleosides and Nucleotides, 1996, 15(7-8): 1383-1395.
Hamajima, et al., Intranasal Administration of HIV-DNA Vaccine Formulated with a Polymer, Carboxymethylcellulose, Augments Mucosal Antibody Production and Cell-Mediated Immune Response, Clinical Immunology and Immunopathology, vol. 88, Issue 2, pp. 205-210, Aug. 1998.
Hammerling et al., Monoclonal Antibodies and T-Cell Hybridomas, Research Monographs in Immunology, vol. 3, pp. 563-681, 1981.
Hanuš et al., "-CH2-lengthening of the internucleotide linkage in the ApA dimer can improve its conformational compatibility with its natural polynucleotide counterpart", Nucleic Acids Research, Dec. 15, 2001, 29(24): 5182-5194.
Haraszti, et al., "5'-Vinylphosphonate improves tissue accumulation and efficacy of conjugated siRNAs in vivo", Nucleic Acids Research, Jul. 27, 2017, 45(13): 7581-7592.
Harborth et al., Sequence, Chemical, and Structural Variation of Small Interfering RNAs and Short Hairpin RNAs and the Effect on Mammalian Gene Silencing, Antisense and Nucleic Acid Drug Development, vol. 13, pp. 83-105, Apr. 1, 2003.
Harlow et al., "Antibodies: A Laboratory Manual", Cold Spring Harbor Laboratory Chapter 14, Second Edition, 2013.
Hassler et al., Comparison of Partially and Fully Chemically-Modified siRNA in Conjugate-Mediated Delivery in Vivo, Nucleic Acids Research, vol. 46, No. 5, pp. 2185-2196, Mar. 16, 2018.
Herdewijn, Piet, Heterocyclic Modifications of Oligonucleotides and Antisense Technology, Antisense and Nucleic Acid Drug Development, vol. 10, Issue 4, pp. 297-310, Jul. 8, 2004.
Heydarian, et al., Novel Splice Variants of sFlt1 are Upregulated in Preeclampsia, Placenta, vol. 30, Issue 3, pp. 250-255, Mar. 2009, Epub Jan. 14, 2009.
Heyer, et al., An Optimized Kit-Free Method For Making Strand-Specific Deep Sequencing Libraries From RNA Fragments, Nucleic Acids Research, vol. 43, Issue 1, pp. 1-14, Jan. 9, 2015.
Hillier et al., yw97a12.r1 Soares_placenta_8to9weeks_2NbHP8to9W *Homo sapiens* cDNA clone Image:260158 5' similar to gb:X51602_cds1 Vascular Endothelial Growth Factor Receptor 1 (Human);contains element OFR repetitive element, mRNA sequence, NIH, Genbank Accession No. N47911.1, Feb. 14, 1996.
Hirashima, et al., "Trophoblast Expression of Fms-like Tyrosine Kinase 1 Is Not Required for the Establishment of the Maternal—fetal Interface in the Mouse Placenta", Proceedings of the National Academy of Sciences of the United States of America, vol. 100, No. 26, pp. 15637-15642, Dec. 23, 2003.
Hodgson, et al., A YAC Mouse Model for Huntington's Disease with Full-Length Mutant Huntingtin, Cytoplasmic Toxicity, and Selective Striatal Neurodegeneration, Neuron, vol. 23, Issue 1, pp. 181-192, May 1999.
Hong et al., "Effect of the guide strand 3'-end structure on the gene-silencing potency of asymmetric siRNA", Biochem J., Aug. 1, 2014, 461(3): 427-434.
Hong et al., "Reducible Dimeric Conjugates of Small Internally Segment Interfering RNA for Efficient Gene Silencing", Macromolecular Bioscience, Jun. 2016, vol. 16, No. 10, pp. 1442-1449.
Huang et al., "Effects of Conformational Alteration Induced by d-/l-Isonucleoside Incorporation in siRNA on Their Stability in Serum and Silencing Activity" Effects of Conformational Alteration Induced by d-/l-Isonucleoside Incorporation in siRNA on Their Stability in Serum and Silencing Activity, Bioconjugate Chemistry, May 17, 2013, 24(6): 951-959.
Huang, Preclinical and Clinical Advances of GalNAc-Decorated Nucleic Acid Therapeutics, Molecular Therapy—Nucleic Acids, vol. 6,, pp. 116-132, Mar. 17, 2017.
Hult, et al., Mutant Huntingtin Causes Metabolic Imbalance by Disruption of Hypothalamic Neurocircuits, Cell Metabolism, vol. 13, Issue 4, pp. 428-439, Apr. 6, 2011.
Hutvagner, et al., A microRNA in a Multiple-Turnover RNAi Enzyme Complex, Science, vol. 297, Issue 5589, pp. 2056-2060, Sep. 20, 2002.
Intapad, et al., "Reduced Uterine Perfusion Pressure Induces Hypertension in the Pregnant Mouse", American Journal of Physiology-Regulatory, Integrative and Comparative Physiology, vol. 307, Issue 11, pp. R1353-R1357, Dec. 2014.
International Search Report & Written Opinion Received for PCT Application No. PCT/US2019/046013, mailed on Jan. 9, 2020.
International Search Report & Written Opinion Received for PCT Application No. PCT/US2020/014181, mailed on Jun. 2, 2020.
International Search Report & Written Opinion Received for PCT Application No. PCT/US2021/028166, mailed on Nov. 26, 2021.
International Search Report & Written Opinion Received for PCT Application No. PCT/US2021/044158, dated Jan. 31, 2022.
International Search Report & Written Opinion Received for PCT Application No. PCT/US2022/039047, dated Mar. 3, 2023.
International Search Report and Written Opinion for PCT International Patent Application No. PCT/US2019/048027 mailed Nov. 15, 2019.
International Search Report and Written Opinion for PCT International Patent Application No. PCT/US2020/025017, mailed Sep. 18, 2020.
International Search Report and Written Opinion for PCT International Patent Application No. PCT/US2020/047492, mailed Feb. 17, 2022.
International Search Report and Written Opinion in related PCT Application No. PCT/US2020/014146, mailed May 22, 2020.
International Search Report and Written Opinion in related PCT Application No. PCT/US2021/024425, mailed Oct. 15, 2021.
International Search Report and Written Opinion received for PCT Patent Application No. PCT/US2016/025722, mailed on Aug. 12, 2016.
International Search Report and Written Opinion received for PCT Patent Application No. PCT/US2016/025731, mailed on Sep. 9, 2016.
International Search Report and Written Opinion received for PCT Patent Application No. PCT/US2016/025753, mailed on Sep. 14, 2016.
International Search Report and Written Opinion received for PCT Patent Application No. PCT/US2016/046810, mailed on Nov. 29, 2016.
International Search Report and Written Opinion received for PCT Patent Application No. PCT/US2017/015633, mailed on May 11, 2017.
International Search Report and Written Opinion received for PCT Patent Application No. PCT/US2018/038952, mailed on Sep. 24, 2018.
International Search Report and Written Opinion received for PCT Patent Application No. PCT/US2020/045487, mailed on Dec. 31, 2020.

(56) References Cited

OTHER PUBLICATIONS

International Search Report and Written Opinion received for PCT Patent Application No. PCT/US2021/013620, mailed on Apr. 26, 2021.
International Search Report and Written Opinion received for PCT Patent Application No. PCT/US2021/034290, mailed on Nov. 4, 2021.
International Search Report and Written Opinion received for PCT Patent Application No. PCT/US2021/041946, mailed on Oct. 29, 2021.
International Search Report and Written Opinion received for PCT Patent Application No. PCT/US2021/060356, mailed on Apr. 13, 2022.
Iriyama et al., Hypoxia-independent up-regulation of placental HIF-1α gene expression contributes to the pathogenesis of preeclampsia, Hypertension, Jun. 2015, 65(6): 1307-1315, Supplemental Data.
Iversen et al., "Optimized siRNA-PEG Conjugates for Extended Blood Circulation and Reduced Urine Excretion in Mice", Feb. 25, 2013, Theranostics 2013, vol. 3, Issue 3, pp. 201-209.
Jackson et al., Position-Specific Chemical Modification Of siRNAs Reduces "Off-Target" Transcript Silencing, RNA, vol. 12, No. 7, pp. 1197-1205, May 8, 2006.
Jackson, et al., Recognizing And Avoiding siRNA Off-Target Effects For Target Identification And Therapeutic Application, Nature Reviews Drug Discovery, vol. 9, No. 1, pp. 57-67, Jan. 1, 2010.
Jacque, et al., Modulation of HIV-1 replication by RNA interference, Nature, vol. 418, No. 6896, pp. 435-438, Jun. 26, 2002.
Janssen, et al., Long-Chain Polyunsaturated Fatty Acids (LCPUFA) From Genesis To Senescence: The Influence of LCPUFA On Neural Development, Aging, And Neurodegeneration, Progress in Lipid Research, vol. 53, pp. 1-17, Jan. 2014.
Jebbink et al., "Expression of Placental FLT1 Transcript Variants Relates to Both Gestational Hypertensive Disease and Fetal Growth", Hypertension, Apr. 25, 2011, 58(1): 70-76.
Jeong et al., "Synthesis and Hybridization Property of Sugar and Phosphate Linkage Modified Oligonucleotides", Bioorganic & Medicinal Chemistry, 1999, 7: 1467-1473.
Jin, et al., DARPP-32 to Quantify Intracerebral Hemorrhage-induced Neuronal Death in Basal Ganglia, Translational Stroke Research, vol. 4, No. 1, pp. 130-134, Feb. 1, 2013.
Jo et al., "Small Interfering RNA Nunchucks with a Hydrophobic Linker for Efficient Intracellular Delivery", Macromol Biosci., 2014, 14: 195-201.
Jo, et al., Selection and Optimization of Asymmetric siRNA Targeting the Human c-MET Gene, Molecules and cells, vol. 32, No. 6, pp. 543-548, Dec. 31, 2011.
Judge, et al., Design of Noninflammatory Synthetic siRNA Mediating Potent Gene Silencing in Vivo, Molecular Therapy, vol. 13, Issue 3, pp. 494-505, Mar. 2006.
Jung et al., "Gene silencing efficiency of siRNA-PEG conjugates: Effect of PEGylation site and PEG molecular weight", Journal of Controlled Release, Mar. 4, 2010, vol. 144, No. 3, pp. 306-313.
Kachare et al., "Phospho-carboxylic anhydride of a homologated nucleoside leads to primer degradation in the presence of a polymerase", Bioorg Med Chem Letters, Jun. 15, 2014, 24(12): 2720-2723.
Kamba, et al., "VEGF-dependent Plasticity of Fenestrated Capillaries in the Normal Adult Microvasculature", American Journal of Physiology—Heart and Circulatory Physiology, vol. 29, pp. H560-H576, Feb. 1, 2006.
Karaki et al., Lipid-Oligonucleotide Conjugates Improve Cellular Uptake and Efficiency of TCTP-Antisense in Castration-Resistant Prostate Cancer, Journal of Controlled Release, vol. 258, pp. 1-9, Jul. 28, 2017.
Karlin, et al., Applications And Statistics For Multiple High-Scoring Segments In Molecular Sequences, Proceedings of the National Academy of Sciences of the USA, vol. 90, pp. 5873-5877, Jun. 1993.
Karlin, et al., Methods For Assessing The Statistical Significance Of Molecular Sequence Features By Using General Scoring Schemes, Proceedings of the National Academy of science of the USA, vol. 87, No. 6, pp. 2264-2268, Mar. 1990.
Karra, et al., Transfection Techniques for Neuronal Cells, Journal of Neuroscience, vol. 30, No. 18, pp. 6171-6177, May 5, 2010.
Kaura, et al., Synthesis, Hybridization Characteristics, and Fluorescence Properties of Oligonucleotides Modified with Nucleobase-Functionalized Locked Nucleic Acid Adenosine and Cytidine Monomers, The Journal of Organic Chemistry, Jun. 16, 2014, 79: 6256-6268.
Kenski et al. (2012) "siRNA-optimized Modifications for Enhanced In Vivo Activity," Mol. Ther. Nucleic Acids. 1:e5. pp. 1-8.
Kent et al., "The 5' external transcribed spacer in mouse ribosomal RNA contains two cleavage sites", RNA, Jan. 2009, 15(1): 14-20, Epublished Nov. 24, 2008.
Khan et al., Silencing Myostatin using Cholesterol-Conjugated siRNAs Induces Muscle Growth, Molecular Therapy, Nucleic Acids, vol. 5, 9 Pages, Jan. 1, 2016.
Khankin, et al., "Intravital High-frequency Ultrasonography to Evaluate Cardiovascular and Uteroplacental Blood Flow in Mouse Pregnancy", Pregnancy Hypertension: An International Journal of Women's Cardiovascular Health, vol. 2, pp. 84-92, 2012.
Khorev et al., Trivalent, Gal//GalNAc-containing ligands designed for the asialoglycoprotein receptor, Bioorgan. & Medicin. Chem., 2008, 16: 5216-5231.
Khvorova, et al., Abstract IA27: Advances In Oligonucleotide Chemistry For The Treatment Of Neurodegenerative Disorders And Brain Tumors, Cancer Research, vol. 76, Issue 6, Abstract IA27, Mar. 2016.
Khvorova, et al., Functional siRNAs and miRNAs Exhibit Strand Bias, Cell, vol. 115, Issue 2, pp. 209-216, Oct. 17, 2003.
Khvorova, Oligonucleotide Therapeutics—A New Class of Cholesterol-Lowering Drugs, The New England Journal of Medicine, vol. 376, No. 1, pp. 4-7, Jan. 5, 2017.
Kim et al., "LHRH Receptor-Mediated Delivery of siRNA Using Polyelectrolyte Complex Micelles Self-Assembled from siRNA-PEG-LHRH Conjugate and PEI", Bioconjugate Chemistry, Oct. 14, 2008, vol. 19, No. 11, pp. 2156-2162.
Kim et al., "PEG conjugated VEGF siRNA for anti-angiogenic gene therapy", Journal of Controlled Release, Jun. 3, 2006, vol. 116, No. 2, pp. 123-129.
Kofoed et al., "Oligodeoxynucleotides with Extended 3'- and 5'-Homologous Internucleotide Linkages", Acta Chemica Scandanavia, 1997, 51: 318-324.
Kordasiewicz, et al., Sustained Therapeutic Reversal of Huntington's Disease by Transient Repression of Huntingtin Synthesis, Neuron, vol. 74, Issue 6, pp. 1031-1044, Jun. 21, 2012.
Kubo et al., "Lipid-Conjugated 27-Nucleotide Double-Stranded RNAs with Dicer-Substrate Potency enhance RNAi-Mediated Gene Silencing", Molecular Pharmaceutics, American Chemical Society, US, vol. 9, No. 5, pp. 1374-1382, DOI: 10.1021/MP2006278. (Apr. 11, 2012).
Kubo et al., "Palmitic Acid-Conjugated 21-Nucleotide siRNA Enhances Gene-Silencing Activity", Molecular Pharmaceutics, vol. 8, No. 6, pp. 2193-2203, DOI: 10.1021/mp200250f. (Oct. 10, 2011).
Kubo, et al., Modified 27-nt dsRNAs With Dramatically Enhanced Stability in Serum and Long-term RNAi Activity, Oligonucleotides, vol. 17, No. 4, pp. 445-464, 2007.
Kumar, et al., "Shielding of Lipid Nanoparticles for siRNA Delivery: Impact on Physicochemical Properties", Cytokine Induction, and Efficacy, Molecular Therapy—Nucleic Acids, vol. 3, e210, pp. 1-7, Nov. 18, 2014.
Lagos-Quintana, et al., Identification of Novel Genes Coding for Small Expressed RNAs, Science, vol. 294, Issue 5543, pp. 853-858, Oct. 26, 2001.
Lagos-Quintana, et al., Identification of Tissue-Specific MicroRNAs from Mouse, Current Biology, vol. 12, Issue 9, pp. 735-739, Apr. 30, 2002.
Lagos-Quintana, et al., New microRNAs From Mouse And Human, RNA, vol. 9, No. 2, pp. 175-179, 2003.
Lai, et al., Computational Identification of *Drosophila* microRNA Genes, Genome Biology, vol. 4, No. 7, pp. 1-20, Jun. 30, 2003.

(56) References Cited

OTHER PUBLICATIONS

Lam, et al., "A New Type of Synthetic Peptide Library For Identifying Ligand-Binding Activity", Nature, vol. 354, pp. 82-84, Nov. 7, 1991.
Lambert, et al., "Nanoparticulate Systems For The Delivery Of Antisense Oligonucleotides", Advanced Drug Delivery Reviews, vol. 47, pp. 99-112, 2001.
Lan, et al., Neuroactive Steroid Actions at the GABAA Receptor, Hormones and Behavior, vol. 28, Issue 4, pp. 537-544, Dec. 1994.
Landis, et al., "A Call for Transparent Reporting to Optimize the Predictive Value of Preclinical Research", Nature, vol. 490, pp. 187-191, Oct. 10, 2012.
Lau, et al., An Abundant Class of Tiny RNAs with Probable Regulatory Roles in Caenorhabditis elegans, Science, vol. 294, Issue 5543, pp. 858-862, Oct. 26, 2001.
Lau, et al., Characterization of the piRNA Complex from Rat Testes, Science, vol. 313, Issue 5785, pp. 363-367, Jul. 21, 2006.
Laufer, et al., "Selected Strategies for the Delivery of siRNA In Vitro and In Vivo", RNA Technologies and Their Applications, 2010, pp. 29-58.
Lebedeva et al., "Phosphorothioate oligodeoxynucleotides as inhibitors of gene expression: antisense and non-antisense effects", Applications of Antisense therapies to restenosis, 1999, p. 101.
Lee et al., A Novel Approach to Investigate Tissue-specific Trinucleotide Repeat Instability, BMC Systems Biology, Mar. 19, 2010, 4(29): 1-16.
Lee et al., Adeno-associated virus (AAV) vectors: Rational design strategies for capsid engineering, Current Opinion in Biomed. Eng., 2018, 58-63.
Lee et al., "Current preclinical small interfering RNA (siRNA)-based conjugate systems for RNA therapeutics", Advanced Drug Delivery Reviews, Oct. 27, 2015, vol. 104, pp. 78-92.
Lee, et al., "Recent Developments In Nanoparticle-Based siRNA Delivery For Cancer Therapy", BioMed Research International, vol. 2013, Article ID 782041, 10 Pages, Jun. 2013.
Lee, et al., An Extensive Class of Small RNAs in Caenorhabditis elegans, Science, vol. 294, Issue 5543, pp. 862-864, Oct. 26, 2001.
Lee, et al., Expression of Small Interfering RNAs Targeted Against HIV-1 rev Transcripts in Human Cells, Nature Biotechnology, vol. 20, No. 5, pp. 500-505, May 1, 2002.
Lee, et al., RNA Interference-Mediated Simultaneous Silencing of Four Genes Using Cross-Shaped RNA, Molecules and Cells, vol. 35, No. 4, pp. 320-326, Apr. 4, 2013.
Lee, et al., Small-interfering RNA (siRNA)-based functional micro- and nanostructures for efficient and selective gene silencing, Accounts of Chemical Research, vol. 45, No. 7, pp. 1014-1025, Jul. 17, 2012.
Levine, et al., "Circulating Angiogenic Factors and the Risk of Preeclampsia", The New England Journal of Medicine, vol. 350, pp. 672-683, 2004.
Li, et al., "Recombinant Vascular Endothelial Growth Factor 121 Attenuates Hypertension and Improves Kidney Damage in a Rat Model of Preeclampsia", Hypertension, vol. 50, pp. 686-692, 2007.
Li, et al., Distribution of 5-Hydroxymethylcytosine in Different Human Tissues, "SAGE—Hindawi Access to Research, Journal of Nucleic Acids, vol. 2011", pp. 1-7, 2011.
Li, et al., Huntington's Disease Gene (IT15) Is Widely Expressed In Human And Rat Tissues, Neuron, vol. 11, No. 5, pp. 985-993, Nov. 1993.
Liang, et al., Identification and Characterization of Intracellular Proteins That Bind Oligonucleotides With Phosphorothioate Linkages, Nucleic Acids Research, vol. 43, Issue 5, pp. 2927-2945, Mar. 11, 2015.
Lim, et al., The microRNAs of Caenorhabditis elegans, Genes & Development, vol. 17, No. 8, pp. 991-1008, 2003.
Lim, et al., Vertebrate MicroRNA Genes, Science, vol. 299, Issue 5612, p. 1540, Mar. 7, 2003.
Lima, et al., Single-Stranded siRNAs Activate RNAi in Animals, Cell, vol. 150, Issue 5, pp. 883-894, Aug. 31, 2012.
Liu et al., Snapshot PK: A Rapid Rodent in Vivo Preclinical Screening Approach, Drug Discovery Today, vol. 13, No. 7-8, pp. 360-367, Apr. 1, 2008.
Lopes, et al., Comparison Between Proliferative And Neuron-Like SH-SY5Y Cells As An In Vitro Model For Parkinson Disease Studies, Brain Research, vol. 1337, pp. 85-94, Jun. 14, 2010.
Lorenz, et al., Steroid And Lipid Conjugates of siRNAs To Enhance Cellular Uptake And Gene Silencing In Liver Cells, Bioorganic & Medicinal Chemistry Letters, vol. 14, Issue 19, pp. 4975-4977, Oct. 4, 2004.
Lorenzer et al., Going beyond the liver: Progress and challenges of targeted delivery of siRNA therapeutics, Journ Controlled Release, Apr. 10, 2015, 203: 1-15.
Loy et al., "Allele-Specific Gene Silencing in Two Mouse Models of Autosomal Dominant Skeletal Myopathy", PLoS One, Nov. 2012, 7(11): e49757, 11 pages.
Lundh, et al., Hypothalamic Expression Of Mutant Huntingtin Contributes To The Development Of Depressive-Like Behavior In The Bac Transgenic Mouse Model Of Huntington's Disease, Human Molecular Genetics, vol. 22, Issue 17, pp. 3485-3497, Sep. 1, 2013.
Luo, et al., Photoreceptor Avascular Privilege Is Shielded By Soluble VEGF Receptor-1, Elife, vol. 2, pp. 1-22, Jun. 18, 2013.
Ly et al., Visualization of Self-Delivering Hydrophobically Modified siRNA Cellular Internalization, Nucleic Acids Research, vol. 45, pp. 15-25, Nov. 29, 2016.
Ma et al., Structural Basis For 5'-End-Specific Recognition Of Guide RNA By The A. Fulgidus Piwi Protein, Nature, vol. 434, No. 7033, pp. 666-670, Mar. 31, 2005.
Ma, et al., Structural Basis For Overhang-Specific Small Interfering RNA Recognition By The PAZ Domain, Nature, vol. 429, No. 6989, pp. 318-322, May 20, 2004.
Magner et al., "Influence of mismatched and bulged nucleotides on SNP-preferential RNase H cleavage of RNA-antisense gapmer heteroduplexes", Scientific Reports, Oct. 2017, 7(12532): 1-16.
Makris, et al., "Uteroplacental Ischemia Results in Proteinuric Hypertension and Elevated sFLT-1", Kidney International, vol. 71, Issue 1, pp. 977-984, May 2, 2007.
Maltepe, et al., "The Placenta: Transcriptional, Epigenetic, and Physiological Integration During Development", The Journal of Clinical Investigation, vol. 120, No. 4, pp. 1016-1025, Apr. 1, 2010.
Mangiarini, et al., Exon 1 of the HD Gene with an Expanded CAG Repeat Is Sufficient to Cause a Progressive Neurological Phenotype in Transgenic Mice, Cell, vol. 87, Issue 3, pp. 493-506, Nov. 1, 1996.
Mantha, et al., Rnai-Based Therapies For Huntington's Disease: Delivery Challenges And Opportunities, Therapeutic Delivery, vol. 3, No. 9, pp. 1061-1076, Aug. 29, 2012.
Marcus, et al., FedExosomes: Engineering Therapeutic Biological Nanoparticles that Truly Deliver, Pharmaceuticals, vol. 6, No. 5, pp. 659-680, Apr. 29, 2013.
Marques, et al., A Structural Basis For Discriminating Between Self And Nonself Double-Stranded Rnas In Mammalian Cells, Nature biotechnology, vol. 23, No. 11, pp. 1399-1405, 2005.
Masotti, et al., Comparison of Different Commercially Available Cationic Liposome—DNA Lipoplexes: Parameters Influencing Toxicity And Transfection Efficiency, Colloids and Surfaces B: Biointerfaces, vol. 68, Issue 2, pp. 136-144, Feb. 1, 2009.
Matsuda et al., siRNA Conjugates Carrying Sequentially Assembled Trivalent N-Acetylgalactosamine Linked Through Nucleosides Elicit Robust Gene Silencing In Vivo in Hepatocytes, ACS Chemical Biology, vol. 10, No. 5, pp. 1181-1187, Mar. 2, 2015.
Maynard, et al., "Excess Placental Soluble fms-like Tyrosine Kinase 1 (sFltl) may Contribute to Endothelial Dysfunction", Hypertension, and Proteinuria in Preeclampsia, The Journal of Clinical Investigation, vol. 111, pp. 649-658, 2003.
Mazur et al., "Isosteres of natural phosphates. 11. Synthesis of a phosphonic acid analogue of an oligonucleotide", Tetrahedron, 1984, 40(20): 3949-3956.
Mccaffrey, et al., Gene Expression: RNA Interference in Adult Mice, Nature, vol. 418, No. 6893, pp. 38-39, Jul. 4, 2002.
Mcmanus, et al., Gene Silencing Using Micro-RNA Designed Hairpins, RNA, vol. 8, Issue 6, pp. 842-850, Aug. 20, 2002.

(56) References Cited

OTHER PUBLICATIONS

Mikhailov et al., "Use of 5-deoxy-ribo-hexofuranose derivatives for the preparation of 5'-nucleotide phosphonates and homoribonucleosides", Collect Czech Chem Commun., 1989, 54(4): 1055-1066.

Miller et al., Adaptable Synthesis of C-Glycosidic Multivalent Carbohydrates and Succinamide-Linked Derivization, Org. Letter., 2010, 12(22): 5262-5265.

Miller, et al., Receptor-mediated Uptake of Phosphorothioate Antisense Oligonucleotides in Different Cell Types of the Liver, Nucleic Acid Therapeutics, vol. 28, No. 3, pp. 119-127, 2018.

Miyagishi, et al., U6 promoter-driven siRNAs With Four Uridine 3' Overhangs Efficiently Suppress Targeted Gene Expression In Mammalian Cells, Nature Biotechnology, vol. 20, No. 5, pp. 497-500, May 1, 2002.

Mok, et al., Multimeric small interfering ribonucleic acid for highly efficient sequence-specific gene silencing~, Nature Materials, vol. 9, pp. 272-278, Jan. 24, 2010.

Molitoris, et al., siRNA Targeted to p53 Attenuates Ischemic and Cisplatin-Induced Acute Kidney Injury, Journal of the American Society of Nephrology, vol. 20, Issue 8, pp. 1754-1764, Aug. 1, 2009.

Monteys et al., "Artificial miRNAs Targeting Mutant Huntingtin Show Preferential Silencing In Vitro and In Vivo", Molecular Therapy, Nucleic Acids, 2015, 4: E234, 11 pages.

Morrissey et al., "Activity of stabilized short interfering RNA in a mouse model of hepatitis B virus replication", Hepatology, 2005, 41: 1349-1356.

Moss et al., Identification of Genetic Variants Associated with Huntington's Disease Progression: A Genome-wide Association Study, The Lancet, Neurology, Sep. 2017, 16(9): 701-711.

Mourelatos, et al., miRNPs: A Novel Class Of Ribonucleoproteins Containing Numerous microRNAs, Genes & Development, vol. 16, No. 6, pp. 720-728, 2002.

Mullen, et al., NeuN, A Neuronal Specific Nuclear Protein In Vertebrates, Development, vol. 116, No. 1, pp. 201-211, 1992.

Myers, et al., Optimal Alignments In Linear Space, Computer Applications in the Biosciences, vol. 4, No. 1, pp. 11-17, Mar. 1988.

Nagamatsu, et al., "Cytotrophoblasts Up-Regulate Soluble Fms-Like Tyrosine Kinase-1 Expression under Reduced Oxygen: An Implication for the Placental Vascular Development and the Pathophysiology of Preeclampsia", Endocrinology, vol. 145, Issue 11, pp. 4838-484, Nov. 1, 2004.

Nair, et al., Impact of Enhanced Metabolic Stability on Pharmacokinetics and Pharmacodynamics of GalNAc-siRNA Conjugates, Nucleic Acids Research, vol. 45, Issue 19, pp. 10969-10977, Nov. 2, 2017.

Nair, et al., Multivalent N-Acetylgalactosamine-Conjugated siRNA Localizes in Hepatocytes and Elicits Robust RNAi-Mediated Gene Silencing, Journal of the American Chemical Society, vol. 136, No. 49, pp. 16958-16961, Dec. 10, 2014.

Nallagatla et al., Nucleoside Modifications Modulate Activation of the Protein Kinase PKR in an RNA Structure-Specific Manner, RNA, vol. 14, pp. 1201-1213, Jun. 1, 2008.

Namjou et al., "GWAS and enrichment analyses of non-alcoholic fatty liver disease identify new trait-associated genes and pathways across eMERGE Network", BMC Medicine, Jul. 2019, 17: 135, 19 pages.

NCBI, "EXOSC10 exosome component 10 [ *Homo sapiens* (human) ]", Jun. 17, 2024, Retrieved from url: <https://www.ncbi.nlm.nih.gov/gene?Db=gene&Cmd=DetailsSearch&Term=5394>.

Nelson et al. (1992) "Oligonucleotide labeling methods 3. Direct labeling of oligonucleotides employing a novel, non-nucleosidic, 2-aminobutyl-1 ,3-propanediol backbone," 20(23):6253-6259.

Neufeld, et al., "Similarities and Differences Between the Vascular Endothelial Growth Factor (VEGF) Splice Variants", Cancer and Metastasis Reviews, vol. 15, pp. 153-158, Jun. 1996.

Nielsen, et al., Sequence-Selective Recognition of DNA by Strand Displacement With A Thymine-Substituted Polyamide, Science, vol. 254, Issue 5037, pp. 1497-1500, Dec. 6, 1991.

Nikan et al., Synthesis and Evaluation of Parenchymal Retention and Efficacy of a Metabolically Stable, O-Phosphocholine-N-Docosahexaenoyl-L-serine siRNA Conjugate in Mouse Brain, Bioconjugate Chemistry, vol. 28, No. 6, 21 Pages, Jun. 21, 2017.

Nikan, et al., Docosahexaenoic Acid Conjugation Enhances Distribution and Safety of siRNA upon Local Administration in Mouse Brain, Molecular Therapy—Nucleic Acids, vol. 5, No. 8, pp. 1-11, Aug. 9, 2016, with Supplement.

Nishina et al., "Efficient In Vivo Delivery of siRNA to the Liver by Conjugation of α-Tocopherol", Mol Ther., Apr. 2008, 16(4): 734-740.

Noguchi et al., "Allele-specific Gene Silencing of Mutant mRNA Restores Cellular Function in Ullrich Congenital Muscular Dystrophy Fibroblasts", Molecular Therapy—Nucleic Acids, Jun. 2014, 3: e171.

Oberbauer et al., Renal Uptake of an 18-mer Phosphorothioate Oligonucleotide, Kidney International, vol. 48, pp. 1226-1232, 1995.

Ohnishi, et al., "Enhancement of Allele Discrimination by Introduction of Nucleotide Mismatches into siRNA in Allele-Specific Gene Silencing by RNAi", Plos One, vol. 3, Issue 5, e2248, 9 Pages, May 2008.

Ohtsuka et al., "Joining of synthetic ribotrinucleotides with defined catalyzed by T4 RNA ligase", European Journal of Biochemistry, 1977, 81(2): 285-291.

Oishi et al., "Lactosylated Poly(ethylene glycol)-siRNA Conjugate through Acid-Labile B-Thiopropionate Linkage to Construct pH-Sensitive Polyion Complex Micelles Achieving Enhanced Gene Silencing in Hepatoma Cells", J. Am. Chem. Soc., 2005, 127: 1624-1625.

Old et al., "Cloning in Yeast and Microbial Eukaryotes", Principles of Gene Manipulation: An Introduction to Genetic Engineering, Studies in Microbiology, 1989, 2(11): 199-221.

Osborn et al., Hydrophobicity Drives the Systemic Distribution of Lipid-Conjugated siRNAs Via Lipid Transport Pathways, Nucleic Acids Research, vol. 47, No. 3, pp. 1070-1081, Dec. 8, 2018.

Osborn, et al., "Improving siRNA Delivery In Vivo Through Lipid Conjugation", Nucleic Acid Therapeutics, vol. 28, No. 3, pp. 128-136, May 10, 2018.

Østergaard et al., "Conjugation of hydrophobic moieties enhances potency of antisense oligonucleotides in the muscle of rodents and non-human primates", Nucleic Acids Research, 2019, 47(12): 6045-6058.

Østergaard, et al., "Fluorinated Nucleotide Modifications Modulate Allele Selectivity of SNP-Targeting Antisense Oligonucleotides", Molecular Therapy Nucleic Acids, vol. 7, pp. 20-30, Jun. 2017.

Ouimet, et al., DARPP-32, A Dopamine- And Adenosine 3':5'-Monophosphate-Regulated Phosphoprotein Enriched In Dopamine-Innervated Brain Regions. III. Immunocytochemical Localization, Journal of Neuroscience, vol. 4, No. 1, pp. 111-124, Jan. 1, 1984.

Overhoff, et al., "Quantitative Detection of siRNA and Single-stranded Oligonucleotides: Relationship Between Uptake and Biological Activity of siRNA", Nucleic Acids Research, vol. 32, Issue 21, pp. 1-5, Dec. 2, 2004.

Owen, Morpholino-Mediated Increase in Soluble Flt-1 Expression Results in Decreased Ocular and Tumor Neovascularization, PLoS One, vol. 7, No. 3, pp. e33576, Mar. 15, 2012.

Paddison, et al., Short Hairpin RNAs (shRNAs) Induce Sequence-Specific Silencing In Mammalian Cells, Genes & Development, vol. 16, No. 8, pp. 948-958, 2002.

Padiukova et al., "Synthesis of 5'-derivatives of thymidine", Bioorg Khim., 1990, 16(5): 668-673 [Article in Russian—no abstract available].

Parmar, et al., 5'-(E)-Vinylphosphonate: A Stable Phosphate Mimic can Improve the RNAi Activity of siRNA-GalNAc Conjugates, ChemBioChem, vol. 17, pp. 985-989, Jun. 2, 2016.

Partial European Search Report for European Patent Application No. 20216265.7, dated Nov. 10, 2021.

Partial European Search Report for European Patent Application No. 21197881.2, mailed Mar. 14, 2022.

Partial European Search Report for European Patent Application No. 21792058.6, dated Apr. 17, 2024.

Partial Supplementary European Search Report for European Patent Application No. 20741865.8, mailed Dec. 20, 2022.

(56) References Cited

OTHER PUBLICATIONS

Partial Supplementary European Search Report for European Patent Application No. 20777915.8, mailed Apr. 5, 2023.
Partial Supplementary European Search Report for European Patent Application No. 20852443.9, mailed Aug. 25, 2023.
Partial Supplementary European Search Report for European Patent Application No. 20856904.6, mailed Sep. 13, 2023.
Pasquinelli, et al., Conservation of The Sequence And Temporal Expression of let-7 Heterochronic Regulatory RNA, Nature, vol. 408, No. 6808, pp. 86-89., Nov. 2, 2000.
Paul, et al., Effective Expression of Small Interfering RNA In Human Cells, Nature Biotechnology, vol. 20, No. 5, pp. 505-508, May 1, 2002.
Peel, et al., Conjugation and Evaluation of Small Hydrophobic Molecules to Triazole-Linked siRNAs, ACS medicinal chemistry letters, vol. 6, No. 2, pp. 117-122, Dec. 4, 2014.
Pei, et al., Quantitative Evaluation of siRNA Delivery in Vivo, RNA, vol. 16, No. 12, pp. 2553-2563, Oct. 12, 2010.
Petersen, et al., LNA: A Versatile Tool for Therapeutics and Genomics, Trends in Biotechnology, vol. 21, Issue 2, pp. 74-81, Feb. 2003.
Pfister, et al., “Five siRNAs Targeting Three SNPs in Huntingtin May Provide Therapy for Three-Quarters of Huntington’s Disease Patients”, Current Biology, vol. 19, No. 9, pp. 774-778., May 12, 2009.
Podbevsek et al., “Solution-state structure of a fully alternately 2'-F/2'-OMe modified 42-nt dimeric siRNA construct”, Nucleic Acids Research, vol. 38, No. 20, pp. 7298-7307, DOI: 10.1093/nar/gkq621. (Jul. 12, 2010).
Pokholenko et al., Lipid Oligonucleotide Conjugates as Responsive Nanomaterials for Drug Delivery, Journal of Materials Chemistry B, vol. 1, 6 Pages, 2013.
Posocco, et al., “Impact of siRNA Overhangs for Dendrimer-mediated siRNA Delivery and Gene Silencing”, Molecular Pharmaceutics, Aug. 5, 2013, 10(8): 3262-3273.
Powe, et al., “Preeclampsia, a Disease of the Maternal Endothelium: the Role of Antiangiogenic Factors and Implications for Later Cardiovascular Disease”, Circulation, vol. 123, No. 24, pp. 2856-2869, Jun. 11, 2011.
Prakash et al., Targeted Delivery Of Antisense Oligonucleotides To Hepatocytes Using Triantennary N-Acetyl Galactosamine Improves Potency 10-Fold In Mice, Nucleic Acids Research, vol. 42, Issue 13, pp. 8796-8807, Jul. 29, 2014.
Prakash, et al., Identification of Metabolically Stable 5'-Phosphate Analogs That Support Single-Stranded siRNA Activity, Nucleic Acids Research, Mar. 9, 2015, 43(6): 2993-3011.
PubChem Database, Amino-Teg-Diol, National Institute or Biotechnology Information, PubChem Accession No. 22136768, 2003.
PubChem Database, SCHEMBL867745, National Institute for Biotechnology Information, PubChem Accession No. 12454428, 12 pages, 2005.
PubChem Detabase, CID-16131506, Compund Summary: dGTGGGTGGGT, Jul. 3, 2007, Retrieved from url: https://pubchem.ncbi.nlm.nih.gov/compound/16131506.
Putnam, David A., Antisense Strategies and Therapeutic Applications, American Journal of Health System Pharmacy, vol. 53, No. 2, pp. 151-160, Jan. 15, 1996.
Raal, et al., Inclisiran for the Treatment of Heterozygous Familial Hypercholesterolemia, New England Journal of Medicine, vol. 382, No. 16, pp. 1520-1530, Apr. 16, 2020.
Rajeev et al., Hepatocyte-Specific Delivery of Sirnas Conjugated to Novel Non-Nucleosidic Trivalent N-Acetylgalactosamine Elicits Robust Gene Silencing in Vivo, ChemBioChem, vol. 16, pp. 903-908, Apr. 13, 2015.
Raouane et al., “Lipid Conjugated Oligonucleotides: A Useful Strategy for Delivery”, Chem., 2012, 23: 1091-1104.
Reed et al., Forty Mouse Strain Survey of Body Composition, Physiology & Behavior, vol. 91, No. 5, 15 Pages, Aug. 15, 2007.
Reinhart, et al., Small RNAs Correspond to Centromere Heterochromatic Repeats, Science, vol. 297, No. 5588, 1 Page, Sep. 13, 2002.
Reynolds, A, et al., Rational siRNA Design for RNA Interference, Nature Biotechnology, vol. 22, No. 3, pp. 326-330, Apr. 2004.
Rigo, et al., Pharmacology of a Central Nervous System Delivered 2'-O-Methoxyethyl-Modified Survival of Motor Neuron Splicing Oligonucleotide in Mice and Nonhuman Primates, Journal of Pharmacology and Experimental Therapeutics, vol. 350, Issue 1, pp. 46-55, Jul. 1, 2014.
Rodriguez-Lebron, et al., Intrastriatal rAAV-Mediated Delivery of Anti-Huntingtin shRNAs Induces Partial Reversal Of Disease Progression In R6/1 Huntington’s Disease Transgenic Mice, Molecular Therapy, vol. 12, Issue 4, pp. 618-633, Oct. 2005.
Roy et al., “Synthesis of DNA/RNA and Their Analogs via Phosphoramidite and H-Phosphonate Chemistries”, Molecules, 2013, 18(11): 14268-14284.
Rozners et al., “Synthesis and Properties of RNA Analogues Having Amides as Interuridine Linkages at Selected Positions”, JACS Articles, Sep. 6, 2003, 125: 12125-12136.
Rupprecht, et al., Neuroactive Steroids: Mechanisms Of Action And Neuropsychopharmacological Properties, Psychoneuroendocrinology, vol. 28, Issue 2, pp. 139-168, Feb. 2003.
Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345, Jan. 30, 2009.
Sah, et al., Oligonucleotide Therapeutic Approaches for Huntington disease, The Journal of Clinical Investigation, vol. 121, No. 2, pp. 500-507, Feb. 1, 2011.
Samuelson, Kristin W., Post-Traumatic Stress Disorder And Declarative Memory Functioning: A Review, Dialogues In Clinical Neuroscience, vol. 13, No. 3, pp. 346-351, Sep. 2011.
Sarett et al., Lipophilic siRNA Targets Albumin in Situ and Promotes Bioavailability, tumor Penetration, and Carrier-Free Gene Silencing, Proceedings of the National Academy of Sciences, vol. 114, pp. E6490-E6497, Jul. 24, 2017.
Scherman et al., Genetic Pharmacology: Progresses in siRNA Delivery and Therapeutic Applications, Gene Therapy, vol. 24, pp. 151-156, Mar. 2017.
Schirle, et al., Structural Basis for MicroRNA Targeting, Science, vol. 346, Issue 6209, pp. 608-613, Oct. 31, 2014.
Schlegal et al., “Chirality Dependent Potency Enhancement and Structural Impact of Glycol Nucleic Acid Modification on siRNA”, JACS, Jun. 1, 2017, pp. 1-28.
Schoch, et al., Antisense Oligonucleotides: Translation From Mouse Models to Human Neurodegenerative Diseases, Neuron, vol. 94, Issue 6, pp. 1056-1070, Jun. 21, 2017.
Schwab, et al., An Approach For New Anticancer Drugs:Oncogene-Targeted Antisense DNA, Annals of Oncology, vol. 5, Issue 4, pp. 55-58, 1994.
Schwarz et al., “Designing siRNA that distinguish between genes that differ by a single nucleotide”, Plos Genetics, Sep. 2006, 2(9): e140.
Schwarz, et al., Asymmetry in the Assembly of the RNAi Enzyme Complex, Cell, vol. 115, Issue 2, pp. 199-208, Oct. 17, 2003.
Seq Id No. 1112 from U.S. Pat. No. 7,790,867. [Accessed Nov. 28, 2018].
Setten, et al., The Current State and Future Directions of RNAi-based Therapeutics, Nature Reviews Drug Discovery, vol. 18, pp. 421-446, Mar. 7, 2019.
Shen, et al., 2'-fluoro-modified Phosphorothioate Oligonucleotide Can Cause Rapid Degradation of P54nrb and PSF, Nucleic Acids Research, vol. 43, Issue 9, pp. 4569-4578, May 19, 2015.
Shen, et al., Acute Hepatotoxicity of 2' Fluoro-modified 5-10-5 Gapmer Phosphorothioate Oligonucleotides in Mice Correlates With Intracellular Protein Binding and the Loss of DBHS Proteins, Nucleic Acids Research, vol. 46, Issue 5, pp. 2204-2217, Mar. 16, 2018.
Shen, et al., Chemical Modification of PS-ASO Therapeutics Reduces Cellular Protein-binding and Improves the Therapeutic Index, Nature Biotechnology, vol. 37, pp. 640-650, Apr. 29, 2019.
Shukla et al., “Exploring Chemical Modifications for siRNA Therapeutics: A Structural and Functional Outlook”, ChemMedChem, Feb. 19, 2010, 5(3): 328-349.

(56) References Cited

OTHER PUBLICATIONS

Sibley et al., "Identification of Allele-Specific RNAi Effectors Targeting Genetic Forms of Parkinson's Disease", Plos One, Oct. 2011, 6(10): e26194.
SiPova et al., "5'-O-Methylphosphonate nucleic acids—new modified DNAs that increase the *Escherichia coli* RNase H cleavage rate of hybrid duplexes", Nucleic Acids Research, 2014, 42(8): 5378-5389.
Smith et al., "RNA Nanotherapeutics for the Amelioration of Astroglial Reactivity", Mol Ther Nucleic Acids, Mar. 2, 2018, 10: 103-121, ePublished Nov. 24, 2017.
Smith et al., Reversed-Phase High Performance Liquid Chromatography of Phosphatidylcholine: A Simple Method for Determining Relative Hydrophobic Interaction of Various Molecular Species, Journal of Lipid Research, vol. 22, pp. 697-704, May 1, 1981.
Solano et al., Toxicological and Pharmacokinetic Properties of QPI-1007, a Chemically Modified Synthetic siRNA Targeting Caspase 2 mRNA, Following Intravitreal Injection, Nucleic Acid Therapeutics, vol. 24, pp. 258-266, Aug. 1, 2014.
Song, et al., Sustained Small Interfering RNA-Mediated Human Immunodeficiency Virus Type 1 Inhibition in Primary Macrophages, Journal of Virology, vol. 77, No. 13, pp. 7174-7181, 2003.
Soutschek, et al., Therapeutic Silencing of An Endogenous Gene By Systemic Administration Of Modified siRNAs, Nature, vol. 432, No. 7014, pp. 173-178, Nov. 11, 2004.
Stalder, et al., The Rough Endoplasmatic Reticulum Is A Central Nucleation Site of siRNA-Mediated RNA Silencing, The EMBO Journal, vol. 32, Issue 8, pp. 1115-1127, Mar. 19, 2013.
Stein, et al., Inhibition of Vesivirus Infections in Mammalian Tissue Culture with Antisense Morpholino Oligomers, Antisense and Nucleic Acid Drug Development, vol. 11, Issue 5, pp. 317-325, Oct. 2001.
Stein, et al., Physicochemical Properties Of Phosphorothioate Oligodeoxynucleotides, Nucleic Acids Research, vol. 16, No. 8, pp. 3209-3221, Apr. 25, 1988.
Stein, et al., Systemic and Central Nervous System Correction of Lysosomal Storage in Mucopolysaccharidosis Type VII Mice, Journal of Virology, vol. 73, No. 4, pp. 3424-3429, Apr. 1999.
Stokman, et al., Application of siRNA In Targeting Protein Expression In Kidney Disease, Advanced Drug Delivery Reviews, vol. 62, Issue 14, pp. 1378-1389, Nov. 30, 2010.
Sugo et al., "Development of antibody-siRNA conjugate targeted to cardiac and skeletal muscles", Journal of Controlled Release, Jun. 29, 2016, vol. 237, pp. 1-13.
Suhr et al., Efficacy and Safety of Patisiran for Familial Amyloidotic Polyneuropathy: A Phase II Multi-Dose Study, Orphanet Journal of Rare Diseases, vol. 10, pp. 1-9, Dec. 1, 2015.
Sui, et al., A DNA Vector-Based RNAi Technology To Suppress Gene Expression In Mammalian Cells, Proceedings of the National Academy of Sciences, vol. 99, No. 8, pp. 5515-5520, Apr. 16, 2002.
Sun, et al., Asymmetric RNA Duplexes Mediate RNA Interference in Mammalian Cells, Nature Biotechnology, vol. 26, pp. 1379-1382, Dec. 2008.
Svendsen et al., "Oligodeoxynucleotide analogues containing 3'-deoxy-3'-C-threo-hydroxymethylthymidine: Synthesis, hybridization properties and enzymatic stability", Tetrahedron, 1993, 49(48): 11341-11352.
Tabernero, et al., First-in-Humans Trial of an RNA Interference Therapeutic Targeting VEGF and KSP in Cancer Patients with Liver Involvement, vol. 3, Issue 4, pp. 406-417, Apr. 2013.
Tai et al., "Current Aspects of siRNA Bioconjugate for In Vitro and In Vivo Delivery", Molecules, Jun. 2019, 24(12): 2211, ePublished Jun. 13, 2019.
Tan et al., "Allele-Specific Targeting of microRNAs to HLA-G and Risk of Asthma", American Journal of Human Genetics, Oct. 2007, 81(4): 829-834.
Tang, et al., "Excess Soluble Vascular Endothelial Growth Factor Receptor-1 in Amniotic Fluid Impairs Lung Growth in Rats: Linking Preeclampsia With Bronchopulmonary Dysplasia", American Journal of Physiology-Lung Cellular and Molecular Physiology, vol. 302, No. 1, pp. L36-L46, Jan. 1, 2012.
Taniguchi et al., Plasmodium Berghei ANKA Causes Intestinal Malaria Associated with Dysbiosis, Scientific Reports, vol. 5, pp. 1-12, Oct. 27, 2015.
Tanowitz et al., Asialoglycoprotein Receptor 1 Mediates Productive Uptake of N-Acetylgalactosamine-Conjugated and Unconjugated Phosphorothioate Antisense Oligonucleotides into Liver Hepatocytes, Nucleic Acids Research, vol. 45, No. 21, pp. 12388-12400, Dec. 1, 2017.
Teng et al., "A GDF15 3' UTR variant, rs1054564, results in allele-specific translational repression of GDF15 by hsa-miR-1233-3p", PLoS One, Aug. 2017, 12(8): e0183187, 15 pages.
Thadani, et al., "Pilot Study of Extracorporeal Removal of Soluble fms-like Tyrosine kinase 1 in Preeclampsia", Circulation, vol. 124, No. 8, pp. 940-950, Aug. 1, 2011.
Thomas et al. (2007) "Intronic polyadenylation signal sequences and alternate splicing generate human soluble F1t1 variants and regulate the abundance of soluble F1t1 in the placenta," The FASEB Journal, 21(14):3885-3895.
Thomas, et al., A Recently Evolved Novel Trophoblast-Enriched Secreted Form of fms-Like Tyrosine Kinase-1 Variant Is Up-Regulated in Hypoxia and Preeclampsia, The Journal of Clinical Endocrinology & Metabolism, vol. 94, Issue 7, pp. 2524-2530, Jul. 1, 2009.
Thompson et al., Toxicological and Pharmacokinetic Properties of Chemically Modified siRNAs Targeting p53 RNA Following Intravenous Administration, Nucleic Acid Therapeutics, vol. 22, No. 4, pp. 255-264, Aug. 1, 2012.
Tischer, et al., "The Human Gene for Vascular Endothelial Growth Factor. Multiple Protein Forms are Encoded Through Alternative Exon Splicing", The Journal of Biological Chemistry, vol. 266, pp. 11947-11954, Jun. 25, 1991.
Tome et al., MSH3 Polymorphisms and Protein Levels Affect CAG Repeat Instability in Huntington's Disease Mice, Plos Genetics, Feb. 28, 2013, 9(2): el003280, 1-16.
Turanov et al., "RNAi Modulation of Placental sFLT1 for the Treatment of Preeclampsia", Nature Biotechnology, Nov. 19, 2018, 36: 1164-1173.
Tuschl et al. (May 6, 2004) "The siRNA User Guide," Accessible on the Internet at URL: http://diyhpl.us/~bryan/irc/protocol-online/protocol-cache/sirna.html. [Last Accessed Aug. 11, 2016].
Tuschl, et al., Expanding small RNA interference, Nature Biotechnology, vol. 20, No. 5, pp. 446-448, 2002.
Uchida, et al., "An Integrated Approach for the Systematic Identification and Characterization of Heart-enriched Genes With Unknown Functions", BMC Genomics, vol. 10, No. 100, pp. 1-12, Mar. 2009.
Ueno et al., "Synthesis and silencing properties of siRNAs possessing lipophilic groups at their 3'-termini", Nucleic Acids Symposium Series, vol. 52, Issue 1, pp. 503-504, https://doi.org/10.1093/nass/nrn255. (Sep. 2008).
Vaught, et al., T7 RNA Polymerase Transcription with 5-Position Modified UTP Derivatives, Journal of the American Chemical Society, vol. 126, No. 36, pp. 11231-11237, Aug. 19, 2004.
Vickers, et al., Development of a Quantitative BRET Affinity Assay for Nucleic Acid-protein Interactions, PloS One, vol. 11, No. 8, p.e0161930, pp. 1-17, Aug. 29, 2016.
Videira, et al., "Preclinical Development of siRNA Therapeutics: Towards the Match Between Fundamental Science and Engineered Systems", Nanomedicine: Nanotechnology, Biology and Medicine, vol. 10, No. 4, pp. 689-702, 2014.
Vorlová, et al., "Induction of Antagonistic Soluble Decoy Receptor Tyrosine Kinases by Intronic polyA Activation", Molecular Cell, vol. 43, Issue 6, pp. 927-939, Sep. 16, 2011.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.
Wada et al., "Evaluation of the effects of chemically different linkers on hepatic accumulations, cell tropism and gene silencing ability of cholesterol-conjugated antisense oligonucleotides", Journal Of Controlled Release, Elsevier, vol. 226, pp. 57-65, DOI: 10.1016/J.JCONREL.2016.02.007. (Feb. 5, 2016).

(56) References Cited

OTHER PUBLICATIONS

Wang, et al., Nanoparticle-Based Delivery System for Application of siRNA In Vivo, Current Drug Metabolism, vol. 11, No. 2, pp. 182-196, 2010.
Wanke et al., Overgrowth of Skin in Growth Hormone Transgenic Mice Depends on the Presence of Male Gonads, Journal of Investigative Dermatology, vol. 113, pp. 967-971, Dec. 1, 1999.
Watanabe, et al., Endogenous siRNAs From Naturally Formed dsRNAs Regulate Transcripts In Mouse Oocytes, Nature, vol. 453, No. 7194, pp. 539-543, Apr. 10, 2008.
Watts et al., "Chemically modified siRNA: tools and applications", Drug Discov. Today, Oct. 2008, 13(19-20): 842-855.
Weyer, et al., Developmental And Cell Type-Specific Expression Of The Neuronal Marker NeuN In The Murine Cerebellum, Journal of Neuroscience Research, vol. 73, Issue 3, pp. 400-409, May 23, 2003.
Whitehead et al., Degradable Lipid Nanoparticles with Predictable in Vivo siRNA Delivery Activity, Nature Communications, vol. 5, pp. 1-10, Jun. 27, 2014.
Whitehead, et al., "Knocking Down Barriers: Advances in siRNA Delivery", Nature Reviews Drug Discovery, vol. 8, No. 2, pp. 129-138, Feb. 2009.
Wickstrom, Oligodeoxynucleotide Stability in Subcellular Extracts and Culture Media, Journal of Biochemical and Biophysical Methods, vol. 13, Issue 2, pp. 97-102, Sep. 1986.
Wolfrum et al., "Mechanisms and optimization of in vivo delivery of lipophilic siRNAs", Nature Biotechnology, Oct. 2007, 25(10): 1149-1157.
Wong, et al., Co-Injection of a Targeted, Reversibly Masked Endosomolytic Polymer Dramatically Improves the Efficacy of Cholesterol-Conjugated Small Interfering RNAs In Vivo, Nucleic Acid Therapeutics, vol. 22, No. 6, pp. 380-390, Nov. 26, 2012.
Wooddell, et al., Hepatocyte-targeted RNAi Therapeutics for the Treatment of Chronic Hepatitis B Virus Infection, Molecular Therapy, vol. 21, Issue 5, pp. 973-985, May 2013.
Wright, et al., Identification Of Factors That Contribute To Recombinant AAV2 Particle Aggregation And Methods To Prevent Its Occurrence During Vector Purification And Formulation, Molecular Therapy, vol. 12, Issue 1,, pp. 171-178, Jul. 2005.
Xia, et al., siRNA-Mediated Gene Silencing in Vitroand In Vivo, Nature Biotechnology, vol. 20, No. 10, pp. 1006-1010, Sep. 16, 2002.
Yamana, et al., 2'-Pyrene Modified Oligonucleotide Provides a Highly Sensitive Fluorescent Probe of RNA, Nucleic Acids Research, 1999, 27(11): 2387-2392.
Yekta, et al., MicroRNA-Directed Cleavage of HOXB8 mRNA, Science, Apr. 23, 2004, 304(5670): 594-596.
You et al., "Design of LNA probes that improve mismatch discrimination", Nucleic Acids Research, May 2006, 34(8): e60, 11 pages.
Young, et al., Pathogenesis of Preeclampsia, Annual Review of Pathology: Mechanisms of Disease, vol. 5, pp. 173-192, Feb. 2, 2010.
Younis, et al., Overview of the Nonclinical Development Strategies and Class-Effects of Oligonucleotide-Based Therapeutics, A Comprehensive Guide to Toxicology in Preclinical Drug Development, Chapter 26, pp. 647-664, 2013.
Yu, et al., RNA Interference by Expression Of Short-Interfering RNAs And Hairpin Rnas In Mammalian Cells, Proceedings of the National Academy of Sciences, vol. 99, No. 9, pp. 6047-6052., Apr. 30, 2002.
Yu, et al., Single-Stranded RNAs Use RNAi to Potently and Allele-Selectively Inhibit Mutant Huntingtin Expression, Cell, vol. 150, Issue 5, pp. 895-908, Aug. 31, 2012.
Yuan, et al., Recent Advances of siRNA Delivery By Nanoparticles, Expert Opinion on Drug Delivery vol. 8, Issue 4, pp. 521-536, 2011.
Zamore, et al., Ancient Pathways Programmed by Small RNAs, Science, May 17, 2002, 296(5571): 1265-1269.
Zeng et al., "RNA Interference in human cells is restricted to the cytoplasm", RNA, Jul. 1, 2002, 8(7): 855-860.
Zeng, et al., Both Natural and Designed Micro RNAs Can Inhibit the Expression of Cognate mRNAs When Expressed in Human Cells, Molecular Cell, vol. 9, pp. 1327-1333, Jun. 2002.
Zeng, et al., Sequence Requirements for Micro RNA Processing and Function in Human Cells, RNA, vol. 9, pp. 112-123, 2003.
Zhang, et al., "Birth-weight-for-gestational-age Patterns by Race, Sex, and Parity in the United States Population", Obstetrics & Gynecology, vol. 86, No. 2, pp. 200-208, 1995.
Zhang, et al., "Several rAAV Vectors Efficiently Cross the Blood-brain Barrier and Transduce Neurons and Astrocytes in the Neonatal Mouse Central Nervous System", Molecular Therapy, vol. 19, Issue 8, pp. 1440-1448, Aug. 1, 2011.
Zhang, et al., Cyclohexane 1,3-Diones And Their Inhibition Of Mutant SOD1-Dependent Protein Aggregation And Toxicity In PC12 Cells, Bioorganic & Medicinal Chemistry, vol. 20, Issue 2, pp. 1029-1045, Jan. 15, 2012.
Zhou et al., "Functional In Vivo Delivery of Multiplexed Anti-HIV-1 siRNAs via a Chemically Synthesized Aptamer With a Sticky Bridge", Mol Ther., Jan. 2013, 21(1): 192-200.
Zhou et al., Nanoparticle-based Delivery of RNAi Therapeutics: Progress and Challenges, Pharmaceuticals, vol. 6, pp. 85-107, Jan. 2013.
Zimmermann et al., Clinical Proof of Concept for a Novel Hepatocyte-Targeting GalNAc-siRNA Conjugate, Molecular Therapy, vol. 25, Issue 1, pp. 71-78, Jan. 4, 2017.
Zlatev, et al., Reversal of siRNA-mediated Gene Silencing in Vivo, Nature Biotechnology, vol. 36, No. 6, pp. 509-511, 2018.
Zou, et al., Liposome-Mediated NGF Gene Transfection Following Neuronal Injury: Potential Therapeutic Applications, Gene Therapy, vol. 6, No. 6, pp. 994-1005, Jun. 25, 1999.
Zuccato, et al., Molecular Mechanisms and Potential Therapeutical Targets in Huntington's Disease, Physiological Reviews, vol. 90, No. 3, pp. 905-981, Jul. 1, 2010.

* cited by examiner

SNP site psiCHECK 2273-1 (A) {match}
5'-tcgaAGCCACGAGAAGCTGCTGCTACAGATCAACCCCGAGCGGGA-3'
3'-TCGGTGCTCTTCGACGACGATGTCTAGTTGGGGCTCGCCCTccgg-5' psiCHECK 2273-2 (G) {mismatch}
5'-tcgaAGCCACGAGAAGCTGCTGCTGCAGATCAACCCCGAGCGGGA-3'
3'-TCGGTGCTCTTCGACGACGACGTCTAGTTGGGGCTCGCCCTccgg-5' psiCHECK 2273-1 (A)

psiCHECK 2273-2 (G)

FIG. 12A

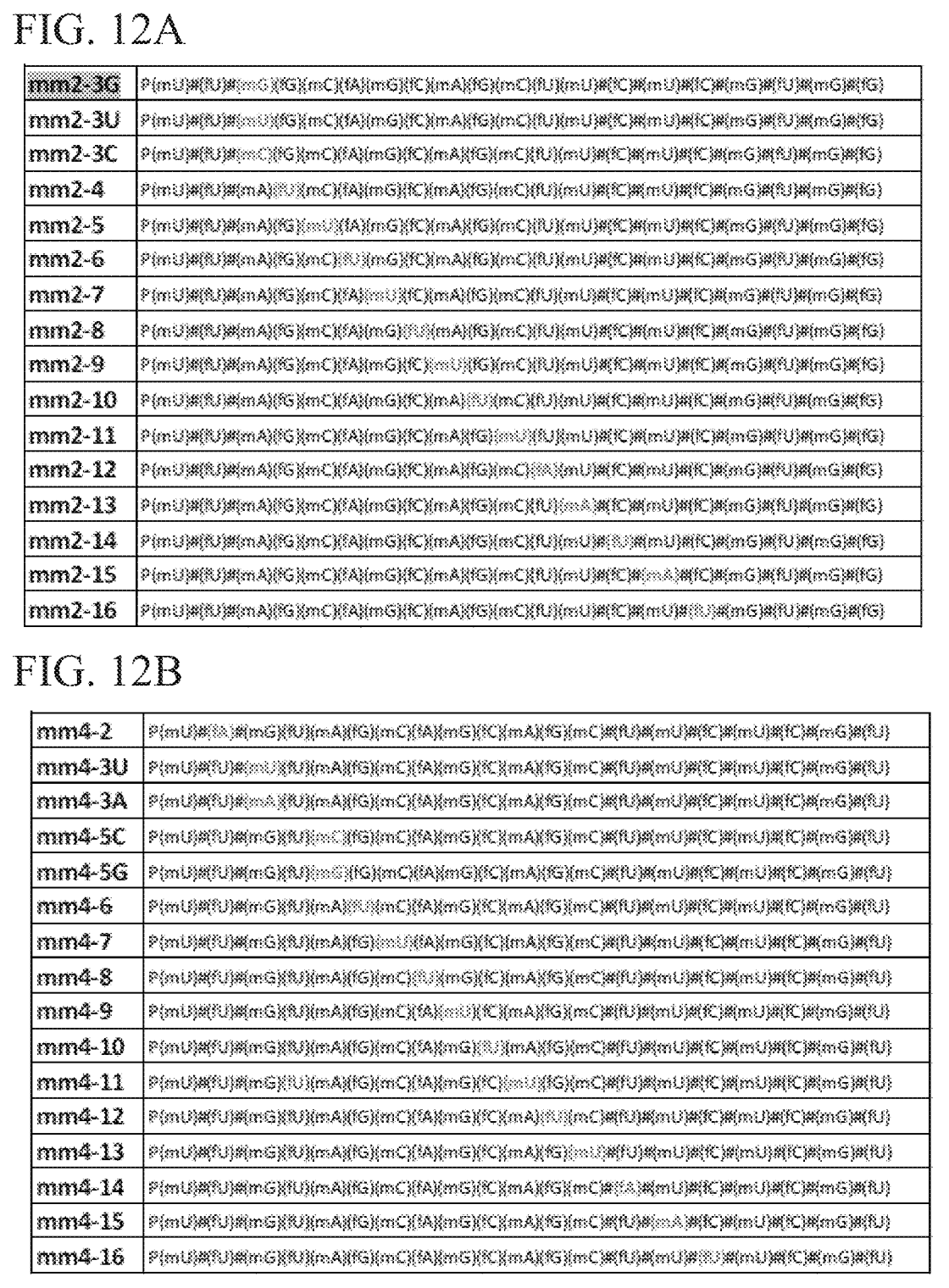

| | |
|---|---|
| mm2-3G | P{mU}#{fU}#{mG}{fG}{mC}{fA}{mG}{fC}{mA}{fG}{mC}{fU}{mU}#{fC}#{mU}#{fC}#{mG}#{fU}#{mG}#{fG} |
| mm2-3U | P{mU}#{fU}#{mU}{fG}{mC}{fA}{mG}{fC}{mA}{fG}{mC}{fU}{mU}#{fC}#{mU}#{fC}#{mG}#{fU}#{mG}#{fG} |
| mm2-3C | P{mU}#{fU}#{mC}{fG}{mC}{fA}{mG}{fC}{mA}{fG}{mC}{fU}{mU}#{fC}#{mU}#{fC}#{mG}#{fU}#{mG}#{fG} |
| mm2-4 | P{mU}#{fU}#{mA}{fU}{mC}{fA}{mG}{fC}{mA}{fG}{mC}{fU}{mU}#{fC}#{mU}#{fC}#{mG}#{fU}#{mG}#{fG} |
| mm2-5 | P{mU}#{fU}#{mA}{fG}{mU}{fA}{mG}{fC}{mA}{fG}{mC}{fU}{mU}#{fC}#{mU}#{fC}#{mG}#{fU}#{mG}#{fG} |
| mm2-6 | P{mU}#{fU}#{mA}{fG}{mC}{fU}{mG}{fC}{mA}{fG}{mC}{fU}{mU}#{fC}#{mU}#{fC}#{mG}#{fU}#{mG}#{fG} |
| mm2-7 | P{mU}#{fU}#{mA}{fG}{mC}{fA}{mU}{fC}{mA}{fG}{mC}{fU}{mU}#{fC}#{mU}#{fC}#{mG}#{fU}#{mG}#{fG} |
| mm2-8 | P{mU}#{fU}#{mA}{fG}{mC}{fA}{mG}{fU}{mA}{fG}{mC}{fU}{mU}#{fC}#{mU}#{fC}#{mG}#{fU}#{mG}#{fG} |
| mm2-9 | P{mU}#{fU}#{mA}{fG}{mC}{fA}{mG}{fC}{mU}{fG}{mC}{fU}{mU}#{fC}#{mU}#{fC}#{mG}#{fU}#{mG}#{fG} |
| mm2-10 | P{mU}#{fU}#{mA}{fG}{mC}{fA}{mG}{fC}{mA}{fU}{mC}{fU}{mU}#{fC}#{mU}#{fC}#{mG}#{fU}#{mG}#{fG} |
| mm2-11 | P{mU}#{fU}#{mA}{fG}{mC}{fA}{mG}{fC}{mA}{fG}{mU}{fU}{mU}#{fC}#{mU}#{fC}#{mG}#{fU}#{mG}#{fG} |
| mm2-12 | P{mU}#{fU}#{mA}{fG}{mC}{fA}{mG}{fC}{mA}{fG}{mC}{fA}{mU}#{fC}#{mU}#{fC}#{mG}#{fU}#{mG}#{fG} |
| mm2-13 | P{mU}#{fU}#{mA}{fG}{mC}{fA}{mG}{fC}{mA}{fG}{mC}{fU}{mA}#{fC}#{mU}#{fC}#{mG}#{fU}#{mG}#{fG} |
| mm2-14 | P{mU}#{fU}#{mA}{fG}{mC}{fA}{mG}{fC}{mA}{fG}{mC}{fU}{mU}#{fU}#{mU}#{fC}#{mG}#{fU}#{mG}#{fG} |
| mm2-15 | P{mU}#{fU}#{mA}{fG}{mC}{fA}{mG}{fC}{mA}{fG}{mC}{fU}{mU}#{fC}#{mA}#{fC}#{mG}#{fU}#{mG}#{fG} |
| mm2-16 | P{mU}#{fU}#{mA}{fG}{mC}{fA}{mG}{fC}{mA}{fG}{mC}{fU}{mU}#{fC}#{mU}#{fU}#{mG}#{fU}#{mG}#{fG} |

FIG. 12B

| | |
|---|---|
| mm4-2 | P{mU}#{fA}#{mG}{fU}{mA}{fG}{mC}{fA}{mG}{fC}{mA}{fG}{mC}#{fU}#{mU}#{fC}#{mU}#{fC}#{mG}#{fU} |
| mm4-3U | P{mU}#{fU}#{mU}{fU}{mA}{fG}{mC}{fA}{mG}{fC}{mA}{fG}{mC}#{fU}#{mU}#{fC}#{mU}#{fC}#{mG}#{fU} |
| mm4-3A | P{mU}#{fU}#{mA}{fU}{mA}{fG}{mC}{fA}{mG}{fC}{mA}{fG}{mC}#{fU}#{mU}#{fC}#{mU}#{fC}#{mG}#{fU} |
| mm4-5C | P{mU}#{fU}#{mG}{fU}{mC}{fG}{mC}{fA}{mG}{fC}{mA}{fG}{mC}#{fU}#{mU}#{fC}#{mU}#{fC}#{mG}#{fU} |
| mm4-5G | P{mU}#{fU}#{mG}{fU}{mG}{fG}{mC}{fA}{mG}{fC}{mA}{fG}{mC}#{fU}#{mU}#{fC}#{mU}#{fC}#{mG}#{fU} |
| mm4-6 | P{mU}#{fU}#{mG}{fU}{mA}{fU}{mC}{fA}{mG}{fC}{mA}{fG}{mC}#{fU}#{mU}#{fC}#{mU}#{fC}#{mG}#{fU} |
| mm4-7 | P{mU}#{fU}#{mG}{fU}{mA}{fG}{mU}{fA}{mG}{fC}{mA}{fG}{mC}#{fU}#{mU}#{fC}#{mU}#{fC}#{mG}#{fU} |
| mm4-8 | P{mU}#{fU}#{mG}{fU}{mA}{fG}{mC}{fU}{mG}{fC}{mA}{fG}{mC}#{fU}#{mU}#{fC}#{mU}#{fC}#{mG}#{fU} |
| mm4-9 | P{mU}#{fU}#{mG}{fU}{mA}{fG}{mC}{fA}{mU}{fC}{mA}{fG}{mC}#{fU}#{mU}#{fC}#{mU}#{fC}#{mG}#{fU} |
| mm4-10 | P{mU}#{fU}#{mG}{fU}{mA}{fG}{mC}{fA}{mG}{fU}{mA}{fG}{mC}#{fU}#{mU}#{fC}#{mU}#{fC}#{mG}#{fU} |
| mm4-11 | P{mU}#{fU}#{mG}{fU}{mA}{fG}{mC}{fA}{mG}{fC}{mU}{fG}{mC}#{fU}#{mU}#{fC}#{mU}#{fC}#{mG}#{fU} |
| mm4-12 | P{mU}#{fU}#{mG}{fU}{mA}{fG}{mC}{fA}{mG}{fC}{mA}{fU}{mC}#{fU}#{mU}#{fC}#{mU}#{fC}#{mG}#{fU} |
| mm4-13 | P{mU}#{fU}#{mG}{fU}{mA}{fG}{mC}{fA}{mG}{fC}{mA}{fG}{mU}#{fU}#{mU}#{fC}#{mU}#{fC}#{mG}#{fU} |
| mm4-14 | P{mU}#{fU}#{mG}{fU}{mA}{fG}{mC}{fA}{mG}{fC}{mA}{fG}{mC}#{fA}#{mU}#{fC}#{mU}#{fC}#{mG}#{fU} |
| mm4-15 | P{mU}#{fU}#{mG}{fU}{mA}{fG}{mC}{fA}{mG}{fC}{mA}{fG}{mC}#{fU}#{mA}#{fC}#{mU}#{fC}#{mG}#{fU} |
| mm4-16 | P{mU}#{fU}#{mG}{fU}{mA}{fG}{mC}{fA}{mG}{fC}{mA}{fG}{mC}#{fU}#{mU}#{fU}#{mU}#{fC}#{mG}#{fU} |

FIG. 12C

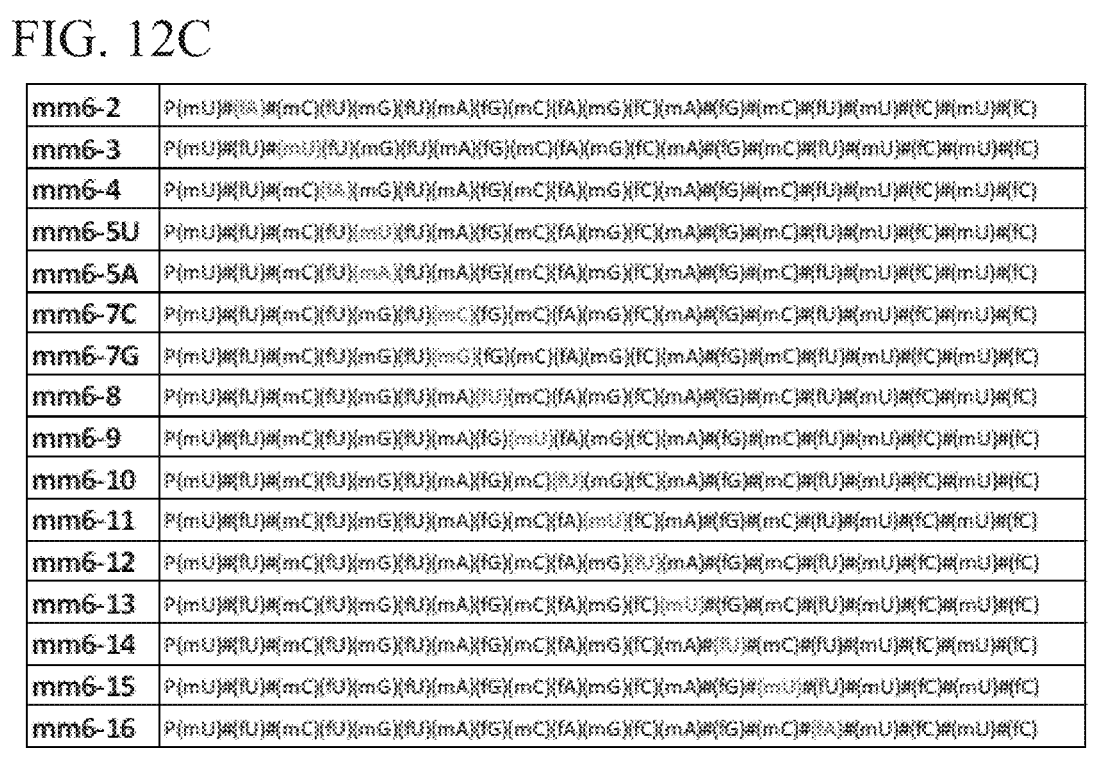

| | |
|---|---|
| mm6-2 | P{mU}#{fA}#{mC}{fU}{mG}{fU}{mA}{fG}{mC}{fA}{mG}{fC}{mA}#{fG}#{mC}#{fU}#{mU}#{fC}#{mU}#{fC} |
| mm6-3 | P{mU}#{fU}#{mU}{fU}{mG}{fU}{mA}{fG}{mC}{fA}{mG}{fC}{mA}#{fG}#{mC}#{fU}#{mU}#{fC}#{mU}#{fC} |
| mm6-4 | P{mU}#{fU}#{mC}{fA}{mG}{fU}{mA}{fG}{mC}{fA}{mG}{fC}{mA}#{fG}#{mC}#{fU}#{mU}#{fC}#{mU}#{fC} |
| mm6-5U | P{mU}#{fU}#{mC}{fU}{mU}{fU}{mA}{fG}{mC}{fA}{mG}{fC}{mA}#{fG}#{mC}#{fU}#{mU}#{fC}#{mU}#{fC} |
| mm6-5A | P{mU}#{fU}#{mC}{fU}{mA}{fU}{mA}{fG}{mC}{fA}{mG}{fC}{mA}#{fG}#{mC}#{fU}#{mU}#{fC}#{mU}#{fC} |
| mm6-7C | P{mU}#{fU}#{mC}{fU}{mG}{fU}{mC}{fG}{mC}{fA}{mG}{fC}{mA}#{fG}#{mC}#{fU}#{mU}#{fC}#{mU}#{fC} |
| mm6-7G | P{mU}#{fU}#{mC}{fU}{mG}{fU}{mG}{fG}{mC}{fA}{mG}{fC}{mA}#{fG}#{mC}#{fU}#{mU}#{fC}#{mU}#{fC} |
| mm6-8 | P{mU}#{fU}#{mC}{fU}{mG}{fU}{mA}{fU}{mC}{fA}{mG}{fC}{mA}#{fG}#{mC}#{fU}#{mU}#{fC}#{mU}#{fC} |
| mm6-9 | P{mU}#{fU}#{mC}{fU}{mG}{fU}{mA}{fG}{mU}{fA}{mG}{fC}{mA}#{fG}#{mC}#{fU}#{mU}#{fC}#{mU}#{fC} |
| mm6-10 | P{mU}#{fU}#{mC}{fU}{mG}{fU}{mA}{fG}{mC}{fU}{mG}{fC}{mA}#{fG}#{mC}#{fU}#{mU}#{fC}#{mU}#{fC} |
| mm6-11 | P{mU}#{fU}#{mC}{fU}{mG}{fU}{mA}{fG}{mC}{fA}{mU}{fC}{mA}#{fG}#{mC}#{fU}#{mU}#{fC}#{mU}#{fC} |
| mm6-12 | P{mU}#{fU}#{mC}{fU}{mG}{fU}{mA}{fG}{mC}{fA}{mG}{fU}{mA}#{fG}#{mC}#{fU}#{mU}#{fC}#{mU}#{fC} |
| mm6-13 | P{mU}#{fU}#{mC}{fU}{mG}{fU}{mA}{fG}{mC}{fA}{mG}{fC}{mU}#{fG}#{mC}#{fU}#{mU}#{fC}#{mU}#{fC} |
| mm6-14 | P{mU}#{fU}#{mC}{fU}{mG}{fU}{mA}{fG}{mC}{fA}{mG}{fC}{mA}#{fU}#{mC}#{fU}#{mU}#{fC}#{mU}#{fC} |
| mm6-15 | P{mU}#{fU}#{mC}{fU}{mG}{fU}{mA}{fG}{mC}{fA}{mG}{fC}{mA}#{fG}#{mU}#{fU}#{mU}#{fC}#{mU}#{fC} |
| mm6-16 | P{mU}#{fU}#{mC}{fU}{mG}{fU}{mA}{fG}{mC}{fA}{mG}{fC}{mA}#{fG}#{mC}#{fA}#{mU}#{fC}#{mU}#{fC} |

FIG. 13

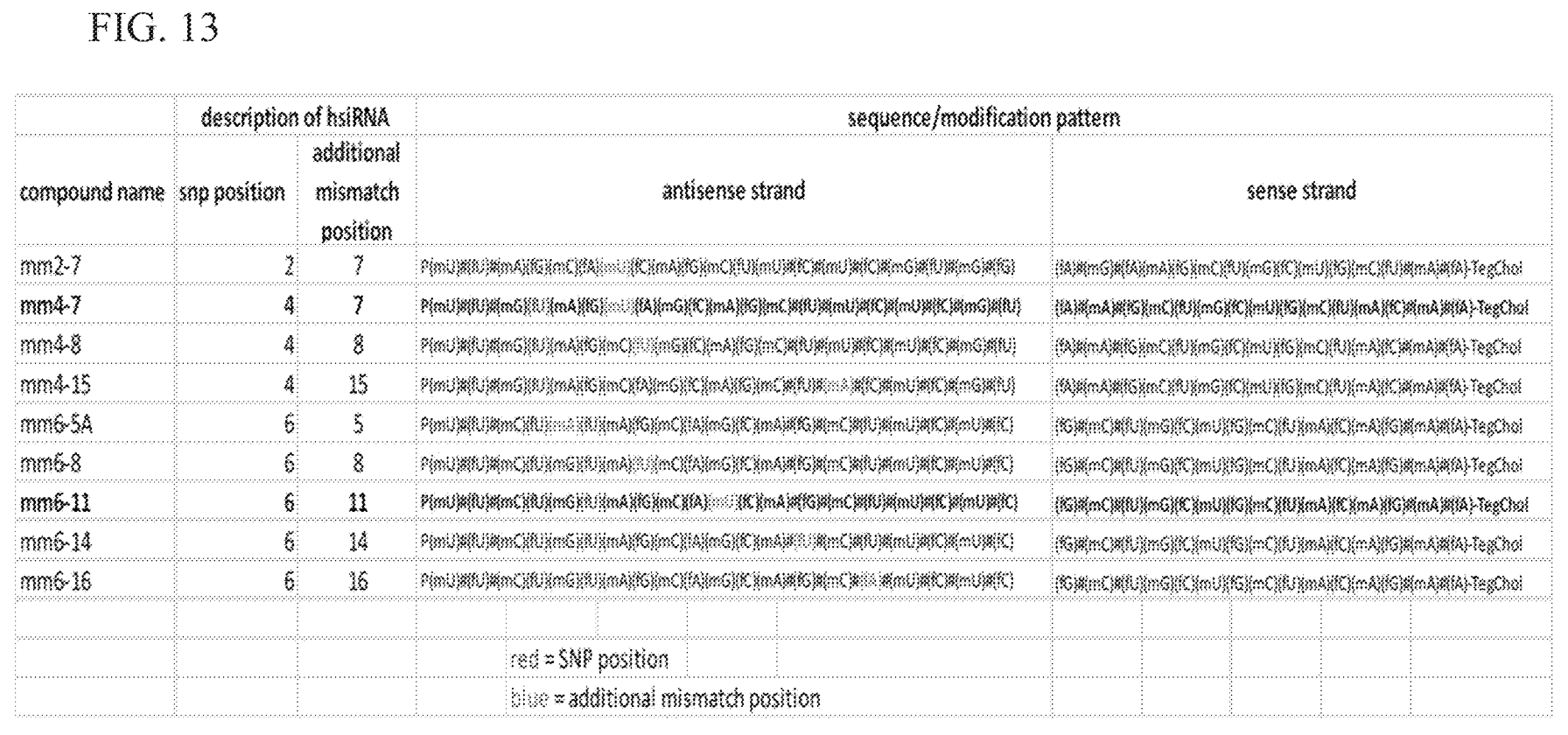

| | description of hsiRNA | | sequence/modification pattern | |
|---|---|---|---|---|
| compound name | snp position | additional mismatch position | antisense strand | sense strand |
| mm2-7 | 2 | 7 | P(mU)#(fU)#(mA)(fG)(mC)(fA)[illegible](fC)(mA)(fG)(mC)(fU)(mU)#(fC)#(mU)#(fC)#(mG)#(fU)#(mG)#(fG) | (A)#(mG)#(fA)(mA)(fG)(mC)(fU)(mG)(fC)(mU)(fG)(mC)(fU)#(mA)#(fA)-TegChol |
| mm4-7 | 4 | 7 | P(mU)#(fU)#(mG)(fU)(mA)(fG)[illegible](fA)(mG)(fC)(mA)(fG)(mC)#(fU)#(mU)#(fC)#(mU)#(fC)#(mG)#(fU) | (A)#(mA)#(fG)(mC)(fU)(mG)(fC)(mU)(fG)(mC)(fU)(mA)(fC)#(mA)#(fA)-TegChol |
| mm4-8 | 4 | 8 | P(mU)#(fU)#(mG)(fU)(mA)(fG)(mC)[illegible](mG)(fC)(mA)(fG)(mC)#(fU)#(mU)#(fC)#(mU)#(fC)#(mG)#(fU) | (A)#(mA)#(fG)(mC)(fU)(mG)(fC)(mU)(fG)(mC)(fU)(mA)(fC)#(mA)#(fA)-TegChol |
| mm4-15 | 4 | 15 | P(mU)#(fU)#(mG)(fU)(mA)(fG)(mC)(fA)(mG)(fC)(mA)(fG)(mC)#(fU)#[illegible]#(fC)#(mU)#(fC)#(mG)#(fU) | (A)#(mA)#(fG)(mC)(fU)(mG)(fC)(mU)(fG)(mC)(fU)(mA)(fC)#(mA)#(fA)-TegChol |
| mm6-5A | 6 | 5 | P(mU)#(fU)#(mC)(fU)[illegible](fU)(mA)(fG)(mC)(fA)(mG)(fC)(mA)#(fG)#(mC)#(fU)#(mU)#(fC)#(mU)#(fC) | (fG)#(mC)#(fU)(mG)(fC)(mU)(fG)(mC)(fU)(mA)(fC)(mA)(fG)#(mA)#(fA)-TegChol |
| mm6-8 | 6 | 8 | P(mU)#(fU)#(mC)(fU)(mG)(fU)(mA)[illegible](mC)(fA)(mG)(fC)(mA)#(fG)#(mC)#(fU)#(mU)#(fC)#(mU)#(fC) | (fG)#(mC)#(fU)(mG)(fC)(mU)(fG)(mC)(fU)(mA)(fC)(mA)(fG)#(mA)#(fA)-TegChol |
| mm6-11 | 6 | 11 | P(mU)#(fU)#(mC)(fU)(mG)(fU)(mA)(fG)(mC)(fA)[illegible](fC)(mA)#(fG)#(mC)#(fU)#(mU)#(fC)#(mU)#(fC) | (fG)#(mC)#(fU)(mG)(fC)(mU)(fG)(mC)(fU)(mA)(fC)(mA)(fG)#(mA)#(fA)-TegChol |
| mm6-14 | 6 | 14 | P(mU)#(fU)#(mC)(fU)(mG)(fU)(mA)(fG)(mC)(fA)(mG)(fC)(mA)#[illegible]#(mC)#(fU)#(mU)#(fC)#(mU)#(fC) | (fG)#(mC)#(fU)(mG)(fC)(mU)(fG)(mC)(fU)(mA)(fC)(mA)(fG)#(mA)#(fA)-TegChol |
| mm6-16 | 6 | 16 | P(mU)#(fU)#(mC)(fU)(mG)(fU)(mA)(fG)(mC)(fA)(mG)(fC)(mA)#(fG)#(mC)#[illegible]#(mU)#(fC)#(mU)#(fC) | (fG)#(mC)#(fU)(mG)(fC)(mU)(fG)(mC)(fU)(mA)(fC)(mA)(fG)#(mA)#(fA)-TegChol |

red = SNP position blue = additional mismatch position

FIG. 14
SNP selective compound designed as Di-siRNA
```
        R3                                       R3
      R1=U=U-C-U-G-U-A-G-C-A-U-C-A=G=C=U=U=C=U=C  (5'-3')
          . . . . . . . . . . . . . . .
          A=A=G-A-C-A-U-C-G-U-C-G-U=C=G            (3'-5')
        R3                            R3
L
      R1=U=U-C-U-G-U-A-G-C-A-U-C-A=G=C=U=U=C=U=C  (5'-3')
          . . . . . . . . . . . . . . .
          A=A=G-A-C-A-U-C-G-U-C-G-U=C=G            (3'-5')
```
SNP site
Secondary mismatch
*Legend*
X- *2'-deoxy-2'-fluoro*
X- *2'-O-methyl*
=
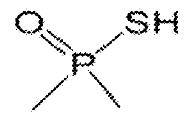
–
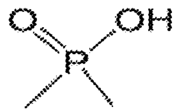
R1=5'-*E*-*VP*-mU
$C_{12}H_{18}N_2O_8P_2S$, Molecular Weight: 428.29
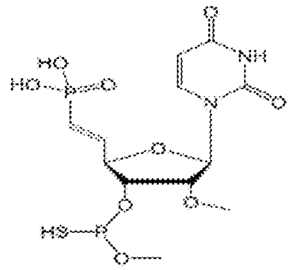
L=3'- *TEG phosphoramidate*
$C_{13}H_{29}NO_{10}P_2^{2-}$, Molecular Weight: 405.28
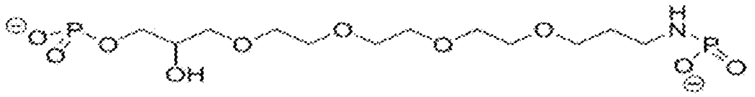

Phosphodiester

Phosphorothioate

Phosphoramidate

Boranophosphate

2',5'-Phosphodiester

Amide-linked

Phosphonoacetate

Morpholino

Peptide Nucleic Acid

RNA, DNA, 2'-O-Me, 2'F-RNA, 2'F-ANA, 4'S-RNA

LNA, 4'S-FANA, MOE, 2'-O-Allyl, 2'-O-Ethylamine, CNEt-RNA

Tricyclo-DNA, CeNA, ANA, HNA

1a R = F
1b R = OMe
2a
2b
3a
3b
4a
4b
5a
5b
6a
6b
7a-E 7a-Z
7b-E 7b-Z
8a R' = F
8b R' = OMe
9a-E
9b-E
10a-E
10b-E
11a-E
11b-E

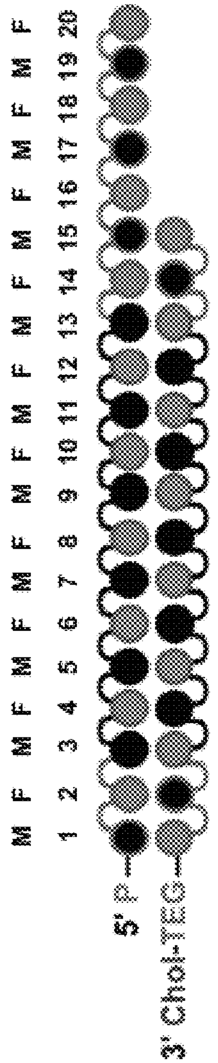
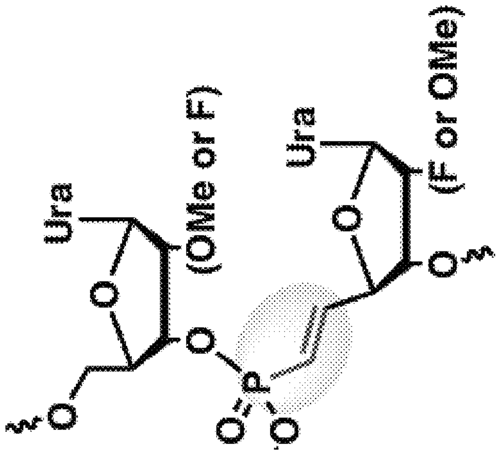
FIG. 23

FIG. 24

Vinyl phosphonate walk on Guide strand

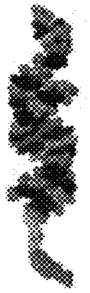

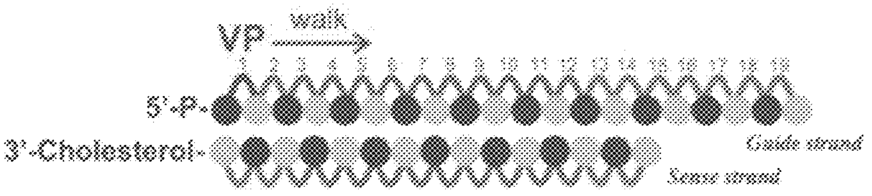

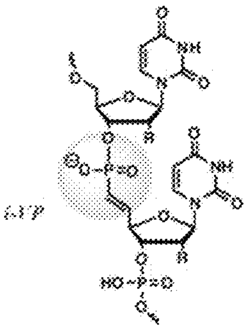

(R = OMe or F)

| # | Name | Sequence | Calcd (M-H) | Found |
|---|---|---|---|---|
| 2615 | HTT10150_1/2 | [illegible] | 6599.4 | 6599.7 |
| 2720 | HTT_10125_2/3 | [illegible] | 6724.5 | 6724.8 |
| 2616 | HTT10125_3/4 | [illegible] | 6739.6 | 6740.7 |
| 2721 | HTT_10125_4/5 | [illegible] | 6740.6 | 6740.7 |
| 2617 | HTT10146_5/6 | [illegible] | 6614.4 | 6615.7 |
| 2722 | HTT_462_6/7 | [illegible] | 6631.4 | 6631.7 |
| 2618 | HTT8603_7/8 | [illegible] | 6801.6 | 6802.7 |
| 2723 | HTT_exon1_150-P2-as_s_8/9 | [illegible] | 6700.5 | 6700.7 |
| 2619 | HTT10150_9/10 | [illegible] | 6615.4 | 6615.6 |
| 2724 | HTT_10150_10/11 | [illegible] | 6615.4 | 6615.6 |
| 2620 | HTT1219_11/12 | [illegible] | 6675.5 | 6675.7 |
| 2725 | HTT_467_12/13 | [illegible] | 6590.4 | 6590.7 |
| 2621 | HTT1907_13/14 | [illegible] | 6708.6 | 6708.7 |
| 2726 | HTT_1257_14/15 | [illegible] | 6707.6 | 6707.7 |
| 2622 | HTT462_15/16 | [illegible] | 6615.4 | 6615.7 |
| 2727 | HTT_420_16/17 | [illegible] | 6710.4 | 6710.7 |
| 2623 | HTT10150-mod_17/18 | [illegible] | 6576.3 | 6576.7 |
| 2728 | HTT_10146_18/19 | [illegible] | 6599.4 | 6599.7 |
| 2624 | HTT10150-mod_19/20 | [illegible] | 6576.3 | 6576.7 |
| 2625 | HTT10150-mod_1/2_17/18_19/20 | [illegible] | 6513.2 | 6513.7 |

FIG. 28A

SNPs mRNA Cleavage site m f m f m f m f m f m f m f m f m f m f

[Match_G11] #3195 5'-P-UUCUGvpUAGCAGCAGCUUCUC-3'

GvpU =

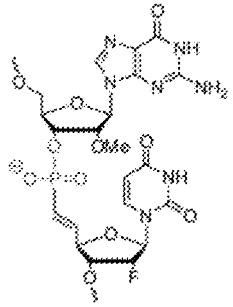

Mut-HTT mRNA 3'-...AAGAC AUCGUCGUCGUCGAAGAG...5' On-target

WT-HTT mRNA 3'-...AAGAC GUCGUCGUCGUCGAAGAG...5' OFF-target

Sequence inputted to the synthesizer

| | | | |
|---|---|---|---|
| **3195** | KEN | HTT_SNPs_vpGU_matchG | [illegible] |
| **3196** | KEN | HTT_SNPs_vpGU_mismatchU | [illegible] |
| **3197** | KEN | HTT_SNPs_vpGU_mismatchA | [illegible] |
| **3198** | KEN | HTT_SNPs_vpGU_mismatchC | [illegible] |

P : Phosphate, #: Phosphorothioate, (mN): 2'-OMe, (fN): 2'-F, [mG-fU]: E-VP-linked mG/fU dimer

FIG. 28B

SNPs
mRNA Cleavage site m f m f m f m f m f m f m f m f m f m f

[Match_$G_{11}$] #3195 5'-P-UUCUGvpUAGCAGCAGCUUCUC-3'

[Mismatch_$U_{11}$] #3196 5'-P-UUCUGvpUAGCAUCAGCUUCUC-3'

[Mismatch_$A_{11}$] #3197 5'-P-UUCUGvpUAGCAACAGCUUCUC-3'

[Mismatch_$C_{11}$] #3198 5'-P-UUCUGvpUAGCACCAGCUUCUC-3'

GvpU =

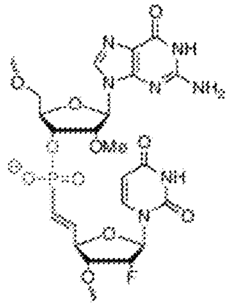

Mut-HTT mRNA 3'-...AAGAC AUCGUCGUCGUCGAAGAG...5' On-target

WT-HTT mRNA 3'-...AAGAC GUCGUCGUCGUCGAAGAG...5' OFF-target

Sequence inputted to the synthesizer

| | | | |
|---|---|---|---|
| 3195 | KEN | HTT_SNPs_vpGU_matchG | [illegible] |
| 3196 | KEN | HTT_SNPs_vpGU_mismatchU | [illegible] |
| 3197 | KEN | HTT_SNPs_vpGU_mismatchA | [illegible] |
| 3198 | KEN | HTT_SNPs_vpGU_mismatchC | [illegible] |

P : Phosphate, #: Phosphorothioate, (mN): 2'-OMe, (fN): 2'-F, [mG-fU]: E-VP-linked mG/fU dimer

FIG. 35

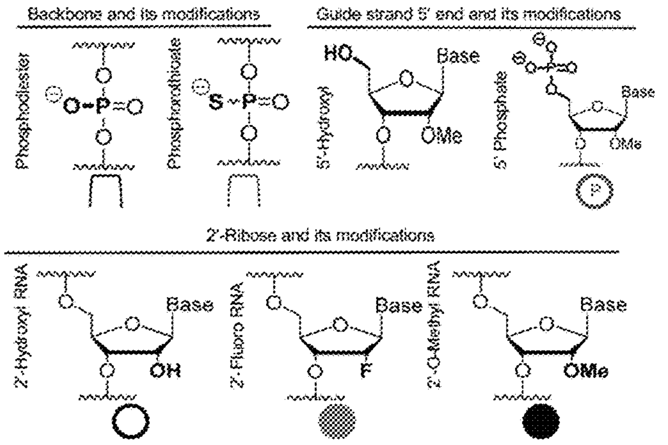

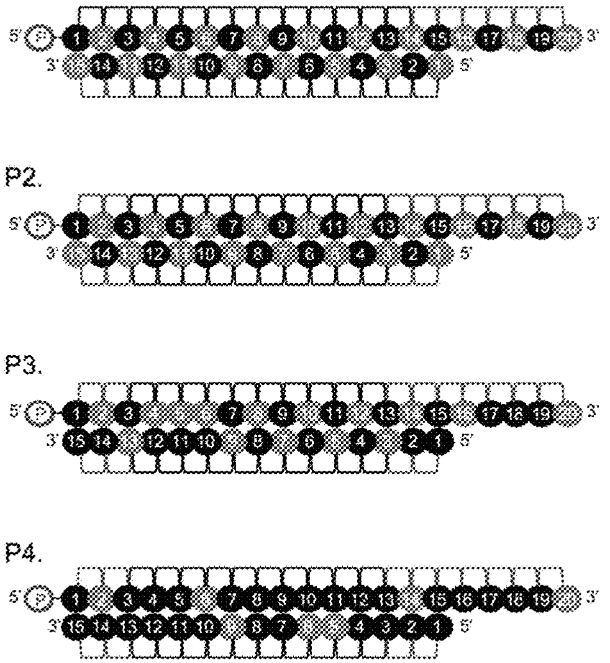

P5.

V(mU)#(fU)#(mA)(mA)(mU)(fC)(mU)(mC)(mU)(mU)(mU)(mA)(mC)#(fU)#(mG)#(fA)#(mU)#(mA)#(mU)#(fA)
(mC)#(mA)#(mG)(mU)(fA)(fA)(fA)(mG)(fA)(mG)(mA)(mU)(mU)#(mA)#(mA)-DIO

| Pattern | AS | Sense | Notes | | |
|---|---|---|---|---|---|
| P1 | mf pattern, 6PS at 3' | fm pattern, 2PS at 3' | 5'P(mU) | [illegible] | [illegible]-TegChol |
| P2 | mf pattern, 2PS at 5' and 7PS at 3' | fm pattern, 2PS at 5' and 3' | 5'P(mU) | [illegible] | [illegible]-TegChol |
| P3 | P2 with (f5, m12) | P2 with (m1, m11, m15) | 5'P(mU) | [illegible] | [illegible]-TegChol |
| P4 (methyl Rich) | P2 with (f1, f5, f14, f20) | all methyls except f5, f?, f? and P2 PS pattern | 5'P(mU) | [illegible] | [illegible]-TegChol |

Where X is and alkyl: $(C)_n$ or polyether: $(CH_2OCH_2)_n$ Polyethylene: $(-CH_2CH_2O-)_n$ etc. Or any block copolymer, peptide or poly peptide, or any mixture of thereof.
Where Y is spacer or divider, cleavable or not. Of similar compositions as above.
Where Z is a branch point moiety Where X is (C)n or (CO)n or (COC)n or (CONH)n or mixture of therein
Where Y is (C)n or (CO)n or (COC)n or (CONH)n or mixture of therein or spacer or divider, cleavable or not
Where W is a bioactive conjugate (right)

Linkers and Spacers

Branching Moieties

Polypeptides

Canonical Phosphodiester (oPo)

Phosphinate (cPc)

3'-C-Phosphonate (cPo)

5'-C-Phosphonate (oPc)

(E)-Vinyl phosphonate (E-VP)

Extended Nucleic Acid (ex-NA)

(E)-Vinyl phosphinate 1 2 3 4 5 6 7 8 9

10 11 12 13 14 15 16 17 18

18, 19, 20, 21, 22

SEQUENCE LISTING

```
Sequence total quantity: 386
SEQ ID NO: 1            moltype = DNA  length = 41
FEATURE                 Location/Qualifiers
source                  1..41
                        mol_type = other DNA
                        organism = Homo sapiens
SEQUENCE: 1
gttaagagat ggggacagta mttcaacgct agaagaacac a                        41

SEQ ID NO: 2            moltype = DNA  length = 41
FEATURE                 Location/Qualifiers
source                  1..41
                        mol_type = other DNA
                        organism = Homo sapiens
SEQUENCE: 2
agccacgaga agctgctgct rcagatcaac cccgagcggg a                        41

SEQ ID NO: 3            moltype = DNA  length = 41
FEATURE                 Location/Qualifiers
source                  1..41
                        mol_type = other DNA
                        organism = Homo sapiens
SEQUENCE: 3
ccggagcctt tggaagtctg ygcccttgtg ccctgcctcc a                        41

SEQ ID NO: 4            moltype = DNA  length = 41
FEATURE                 Location/Qualifiers
source                  1..41
                        mol_type = other DNA
                        organism = Homo sapiens
SEQUENCE: 4
cagcccgagc tgcctgcaga rccggcggcc tactggagca a                        41

SEQ ID NO: 5            moltype = DNA  length = 41
FEATURE                 Location/Qualifiers
source                  1..41
                        mol_type = other DNA
                        organism = Homo sapiens
SEQUENCE: 5
cccacgcctg ctccctcatc yactgtgtgc acttcatcct g                        41

SEQ ID NO: 6            moltype = DNA  length = 41
FEATURE                 Location/Qualifiers
source                  1..41
                        mol_type = other DNA
                        organism = Homo sapiens
SEQUENCE: 6
gggttggagc cctgcacggc rtcctctatg tgctggagtg c                        41

SEQ ID NO: 7            moltype = DNA  length = 41
FEATURE                 Location/Qualifiers
source                  1..41
                        mol_type = other DNA
                        organism = Homo sapiens
SEQUENCE: 7
ctgctggttg ttgccaggtt rcagctgctc ttgcatctgg g                        41

SEQ ID NO: 8            moltype = DNA  length = 41
FEATURE                 Location/Qualifiers
source                  1..41
                        mol_type = other DNA
                        organism = Homo sapiens
SEQUENCE: 8
tcctccctcc tgcaggctgg stgttggccc ctstgctgtc c                        41

SEQ ID NO: 9            moltype = DNA  length = 41
FEATURE                 Location/Qualifiers
source                  1..41
                        mol_type = other DNA
                        organism = Homo sapiens
SEQUENCE: 9
gatttgggag ctctgcttgc ygactggctg tgagacgagg c                        41

SEQ ID NO: 10           moltype = DNA  length = 41
FEATURE                 Location/Qualifiers
source                  1..41
                        mol_type = other DNA
                        organism = Homo sapiens
```

-continued

```
SEQUENCE: 10
gaaaagtttg gagggtttct ycgctcagcc ttggatgttc t                    41

SEQ ID NO: 11          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 11
ttctgtagca tcagcttctc                                            20

SEQ ID NO: 12          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 12
ttagcatcag cttctcgtgg                                            20

SEQ ID NO: 13          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 13
ttgtagtagc agcttctcgt                                            20

SEQ ID NO: 14          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 14
ttgtagctgc agcttctcgt                                            20

SEQ ID NO: 15          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 15
ttgtagcagc agctactcgt                                            20

SEQ ID NO: 16          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 16
ttctatagca gcagcttctc                                            20

SEQ ID NO: 17          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 17
ttctgtatca gcagcttctc                                            20
```

```
SEQ ID NO: 18          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 18
ttctgtagca tcagcttctc                                              20

SEQ ID NO: 19          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 19
ttctgtagca gcatcttctc                                              20

SEQ ID NO: 20          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 20
ttctgtagca gcagcatctc                                              20

SEQ ID NO: 21          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 21
tcgcggactt ccaaaggctc                                              20

SEQ ID NO: 22          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 22
tcgcaggctt ccaaaggctc                                              20

SEQ ID NO: 23          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 23
tcgcagattt ccaaaggctc                                              20

SEQ ID NO: 24          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 24
agaagctgct gctaa                                                   15

SEQ ID NO: 25          moltype = RNA  length = 15
```

-continued

```
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 25
aagctgctgc tacaa                                                   15

SEQ ID NO: 26           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 26
aagctgctgc tacaa                                                   15

SEQ ID NO: 27           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 27
aagctgctgc tacaa                                                   15

SEQ ID NO: 28           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 28
gctgctgcta cagaa                                                   15

SEQ ID NO: 29           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 29
gctgctgcta cagaa                                                   15

SEQ ID NO: 30           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 30
gctgctgcta cagaa                                                   15

SEQ ID NO: 31           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 31
gctgctgcta cagaa                                                   15

SEQ ID NO: 32           moltype = RNA  length = 15
FEATURE                 Location/Qualifiers
misc_feature            1..15
```

-continued

```
                        note = Description of Artificial Sequence: Synthetic
                         oligonucleotide
source                  1..15
                        mol_type = other RNA
                        organism = synthetic construct
SEQUENCE: 32
gctgctgcta cagaa                                                    15

SEQ ID NO: 33           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 33
tttggaagtc cgcga                                                    15

SEQ ID NO: 34           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 34
tttggaagcc tgcga                                                    15

SEQ ID NO: 35           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 35
tttggaaatc tgcga                                                    15

SEQ ID NO: 36           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 36
ttagcatcag cttctcgtgg                                               20

SEQ ID NO: 37           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 37
ttgtagtagc agcttctcgt                                               20

SEQ ID NO: 38           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 38
ttgtagctgc agcttctcgt                                               20

SEQ ID NO: 39           moltype = RNA  length = 20
FEATURE                 Location/Qualifiers
misc_feature            1..20
                        note = Description of Artificial Sequence: Synthetic
                         oligonucleotide
```

-continued

```
source                1..20
                      mol_type = other RNA
                      organism = synthetic construct
SEQUENCE: 39
ttgtagcagc agctactcgt                                              20

SEQ ID NO: 40         moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 40
ttctatagca gcagcttctc                                              20

SEQ ID NO: 41         moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 41
ttctgtatca gcagcttctc                                              20

SEQ ID NO: 42         moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 42
ttctgtagca tcagcttctc                                              20

SEQ ID NO: 43         moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 43
ttctgtagca gcatcttctc                                              20

SEQ ID NO: 44         moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 44
ttctgtagca gcagcatctc                                              20

SEQ ID NO: 45         moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 45
tcgcggactt ccaaaggctc                                              20

SEQ ID NO: 46         moltype = RNA  length = 20
FEATURE               Location/Qualifiers
misc_feature          1..20
                      note = Description of Artificial Sequence: Synthetic
                       oligonucleotide
source                1..20
                      mol_type = other RNA
```

-continued

```
                       organism = synthetic construct
SEQUENCE: 46
tcgcaggctt ccaaaggctc                                              20

SEQ ID NO: 47          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 47
tcgcagattt ccaaaggctc                                              20

SEQ ID NO: 48          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 48
agaagctgct gctaa                                                   15

SEQ ID NO: 49          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 49
aagctgctgc tacaa                                                   15

SEQ ID NO: 50          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 50
aagctgctgc tacaa                                                   15

SEQ ID NO: 51          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 51
aagctgctgc tacaa                                                   15

SEQ ID NO: 52          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 52
gctgctgcta cagaa                                                   15

SEQ ID NO: 53          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 53
```

-continued

```
gctgctgcta cagaa                                                   15

SEQ ID NO: 54          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 54
gctgctgcta cagaa                                                   15

SEQ ID NO: 55          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 55
gctgctgcta cagaa                                                   15

SEQ ID NO: 56          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 56
gctgctgcta cagaa                                                   15

SEQ ID NO: 57          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 57
tttggaagtc cgcga                                                   15

SEQ ID NO: 58          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 58
tttggaagcc tgcga                                                   15

SEQ ID NO: 59          moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 59
tttggaaatc tgcga                                                   15

SEQ ID NO: 60          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 60
tcagcatcag cttctcgtgg                                              20
```

-continued

```
SEQ ID NO: 61            moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 61
ttgcagtagc agcttctcgt                                              20

SEQ ID NO: 62            moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 62
ttgcagctgc agcttctcgt                                              20

SEQ ID NO: 63            moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 63
ttgcagcagc agctactcgt                                              20

SEQ ID NO: 64            moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 64
ttctacagca gcagcttctc                                              20

SEQ ID NO: 65            moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 65
ttctgcatca gcagcttctc                                              20

SEQ ID NO: 66            moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 66
ttctgcagca tcagcttctc                                              20

SEQ ID NO: 67            moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 67
ttctgcagca gcatcttctc                                              20

SEQ ID NO: 68            moltype = RNA  length = 20
FEATURE                  Location/Qualifiers
```

-continued

```
misc_feature          1..20
                      note = Description of Artificial Sequence: Synthetic
                       oligonucleotide
source                1..20
                      mol_type = other RNA
                      organism = synthetic construct
SEQUENCE: 68
tcacggactt ccaaaggctc                                              20

SEQ ID NO: 69         moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 69
tcacaggctt ccaaaggctc                                              20

SEQ ID NO: 70         moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 70
tcacagattt ccaaaggctc                                              20

SEQ ID NO: 71         moltype = RNA  length = 15
FEATURE               Location/Qualifiers
misc_feature          1..15
                      note = Description of Artificial Sequence: Synthetic
                       oligonucleotide
source                1..15
                      mol_type = other RNA
                      organism = synthetic construct
SEQUENCE: 71
agaagctgct gctga                                                   15

SEQ ID NO: 72         moltype = RNA  length = 15
FEATURE               Location/Qualifiers
misc_feature          1..15
                      note = Description of Artificial Sequence: Synthetic
                       oligonucleotide
source                1..15
                      mol_type = other RNA
                      organism = synthetic construct
SEQUENCE: 72
aagctgctgc tgcaa                                                   15

SEQ ID NO: 73         moltype = RNA  length = 15
FEATURE               Location/Qualifiers
misc_feature          1..15
                      note = Description of Artificial Sequence: Synthetic
                       oligonucleotide
source                1..15
                      mol_type = other RNA
                      organism = synthetic construct
SEQUENCE: 73
aagctgctgc tgcaa                                                   15

SEQ ID NO: 74         moltype = RNA  length = 15
FEATURE               Location/Qualifiers
misc_feature          1..15
                      note = Description of Artificial Sequence: Synthetic
                       oligonucleotide
source                1..15
                      mol_type = other RNA
                      organism = synthetic construct
SEQUENCE: 74
aagctgctgc tgcaa                                                   15

SEQ ID NO: 75         moltype = RNA  length = 15
FEATURE               Location/Qualifiers
misc_feature          1..15
                      note = Description of Artificial Sequence: Synthetic
```

```
                        oligonucleotide
source                  1..15
                        mol_type = other RNA
                        organism = synthetic construct
SEQUENCE: 75
gctgctgctg cagaa                                                    15

SEQ ID NO: 76           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 76
gctgctgctg cagaa                                                    15

SEQ ID NO: 77           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 77
gctgctgctg cagaa                                                    15

SEQ ID NO: 78           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 78
gctgctgctg cagaa                                                    15

SEQ ID NO: 79           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 79
tttggaagtc cgtga                                                    15

SEQ ID NO: 80           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 80
tttggaagcc tgtga                                                    15

SEQ ID NO: 81           moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 81
tttggaaatc tgtga                                                    15

SEQ ID NO: 82           moltype = DNA  length = 45
FEATURE                 Location/Qualifiers
misc_feature            1..45
                        note = Description of Artificial Sequence: Synthetic
                         oligonucleotide
source                  1..45
```

-continued

```
                        mol_type = other DNA
                        organism = synthetic construct
SEQUENCE: 82
tcgaagccac gagaagctgc tgctacagat caaccccgag cggga                   45

SEQ ID NO: 83           moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 83
ggcctcccgc tcggggttga tctgtagcag cagcttctcg tggct                   45

SEQ ID NO: 84           moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 84
tcgaagccac gagaagctgc tgctgcagat caaccccgag cggga                   45

SEQ ID NO: 85           moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 85
ggcctcccgc tcggggttga tctgcagcag cagcttctcg tggct                   45

SEQ ID NO: 86           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 86
ttggcagcag cttctcgtgg                                               20

SEQ ID NO: 87           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 87
tttgcagcag cttctcgtgg                                               20

SEQ ID NO: 88           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 88
ttcgcagcag cttctcgtgg                                               20

SEQ ID NO: 89           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
```

```
SEQUENCE: 89
ttatcagcag cttctcgtgg                                              20

SEQ ID NO: 90          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 90
ttagtagcag cttctcgtgg                                              20

SEQ ID NO: 91          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 91
ttagctgcag cttctcgtgg                                              20

SEQ ID NO: 92          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 92
ttagcatcag cttctcgtgg                                              20

SEQ ID NO: 93          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 93
ttagcagtag cttctcgtgg                                              20

SEQ ID NO: 94          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 94
ttagcagctg cttctcgtgg                                              20

SEQ ID NO: 95          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 95
ttagcagcat cttctcgtgg                                              20

SEQ ID NO: 96          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 96
ttagcagcag tttctcgtgg                                              20
```

```
SEQ ID NO: 97           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 97
ttagcagcag catctcgtgg                                              20

SEQ ID NO: 98           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 98
ttagcagcag ctactcgtgg                                              20

SEQ ID NO: 99           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 99
ttagcagcag cttttcgtgg                                              20

SEQ ID NO: 100          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 100
ttagcagcag cttcacgtgg                                              20

SEQ ID NO: 101          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 101
ttagcagcag cttcttgtgg                                              20

SEQ ID NO: 102          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 102
tagtagcagc agcttctcgt                                              20

SEQ ID NO: 103          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 103
ttttagcagc agcttctcgt                                              20

SEQ ID NO: 104          moltype = RNA  length = 20
```

```
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 104
ttatagcagc agcttctcgt                                              20

SEQ ID NO: 105          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 105
ttgtcgcagc agcttctcgt                                              20

SEQ ID NO: 106          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 106
ttgtggcagc agcttctcgt                                              20

SEQ ID NO: 107          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 107
ttgtatcagc agcttctcgt                                              20

SEQ ID NO: 108          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 108
ttgtagtagc agcttctcgt                                              20

SEQ ID NO: 109          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 109
ttgtagctgc agcttctcgt                                              20

SEQ ID NO: 110          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 110
ttgtagcatc agcttctcgt                                              20

SEQ ID NO: 111          moltype = RNA  length = 20
FEATURE                 Location/Qualifiers
misc_feature            1..20
```

```
                        note = Description of Artificial Sequence: Synthetic
                         oligonucleotide
source                  1..20
                        mol_type = other RNA
                        organism = synthetic construct
SEQUENCE: 111
ttgtagcagt agcttctcgt                                                    20

SEQ ID NO: 112          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 112
ttgtagcagc tgcttctcgt                                                    20

SEQ ID NO: 113          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 113
ttgtagcagc atcttctcgt                                                    20

SEQ ID NO: 114          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 114
ttgtagcagc agtttctcgt                                                    20

SEQ ID NO: 115          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 115
ttgtagcagc agcatctcgt                                                    20

SEQ ID NO: 116          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 116
ttgtagcagc agctactcgt                                                    20

SEQ ID NO: 117          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 117
ttgtagcagc agcttttcgt                                                    20

SEQ ID NO: 118          moltype = RNA  length = 20
FEATURE                 Location/Qualifiers
misc_feature            1..20
                        note = Description of Artificial Sequence: Synthetic
                         oligonucleotide
```

-continued

```
source                  1..20
                        mol_type = other RNA
                        organism = synthetic construct
SEQUENCE: 118
tactgtagca gcagcttctc                                                20

SEQ ID NO: 119          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 119
ttttgtagca gcagcttctc                                                20

SEQ ID NO: 120          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 120
ttcagtagca gcagcttctc                                                20

SEQ ID NO: 121          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 121
ttctttagca gcagcttctc                                                20

SEQ ID NO: 122          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 122
ttctatagca gcagcttctc                                                20

SEQ ID NO: 123          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 123
ttctgtcgca gcagcttctc                                                20

SEQ ID NO: 124          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 124
ttctgtggca gcagcttctc                                                20

SEQ ID NO: 125          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
```

-continued

```
                       organism = synthetic construct
SEQUENCE: 125
ttctgtatca gcagcttctc                                              20

SEQ ID NO: 126         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 126
ttctgtagta gcagcttctc                                              20

SEQ ID NO: 127         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 127
ttctgtagct gcagcttctc                                              20

SEQ ID NO: 128         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 128
ttctgtagca tcagcttctc                                              20

SEQ ID NO: 129         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 129
ttctgtagca gtagcttctc                                              20

SEQ ID NO: 130         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 130
ttctgtagca gctgcttctc                                              20

SEQ ID NO: 131         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 131
ttctgtagca gcatcttctc                                              20

SEQ ID NO: 132         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 132
```

-continued

```
ttctgtagca gcagtttctc                                              20

SEQ ID NO: 133          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 133
ttctgtagca gcagcatctc                                              20

SEQ ID NO: 134          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 134
ttagcatcag cttctcgtgg                                              20

SEQ ID NO: 135          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 135
ttgtagtagc agcttctcgt                                              20

SEQ ID NO: 136          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 136
ttgtagctgc agcttctcgt                                              20

SEQ ID NO: 137          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 137
ttgtagcagc agctactcgt                                              20

SEQ ID NO: 138          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 138
ttctatagca gcagcttctc                                              20

SEQ ID NO: 139          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 139
ttctgtatca gcagcttctc                                              20
```

-continued

```
SEQ ID NO: 140          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 140
ttctgtagca tcagcttctc                                                   20

SEQ ID NO: 141          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 141
ttctgtagca gcatcttctc                                                   20

SEQ ID NO: 142          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 142
ttctgtagca gcagcatctc                                                   20

SEQ ID NO: 143          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 143
agaagctgct gctaa                                                        15

SEQ ID NO: 144          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 144
aagctgctgc tacaa                                                        15

SEQ ID NO: 145          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 145
aagctgctgc tacaa                                                        15

SEQ ID NO: 146          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 146
aagctgctgc tacaa                                                        15

SEQ ID NO: 147          moltype = RNA  length = 15
FEATURE                 Location/Qualifiers
```

-continued

```
misc_feature          1..15
                      note = Description of Artificial Sequence: Synthetic
                       oligonucleotide
source                1..15
                      mol_type = other RNA
                      organism = synthetic construct
SEQUENCE: 147
gctgctgcta cagaa                                                          15

SEQ ID NO: 148        moltype = RNA  length = 15
FEATURE               Location/Qualifiers
misc_feature          1..15
                      note = Description of Artificial Sequence: Synthetic
                       oligonucleotide
source                1..15
                      mol_type = other RNA
                      organism = synthetic construct
SEQUENCE: 148
gctgctgcta cagaa                                                          15

SEQ ID NO: 149        moltype = RNA  length = 15
FEATURE               Location/Qualifiers
misc_feature          1..15
                      note = Description of Artificial Sequence: Synthetic
                       oligonucleotide
source                1..15
                      mol_type = other RNA
                      organism = synthetic construct
SEQUENCE: 149
gctgctgcta cagaa                                                          15

SEQ ID NO: 150        moltype = RNA  length = 15
FEATURE               Location/Qualifiers
misc_feature          1..15
                      note = Description of Artificial Sequence: Synthetic
                       oligonucleotide
source                1..15
                      mol_type = other RNA
                      organism = synthetic construct
SEQUENCE: 150
gctgctgcta cagaa                                                          15

SEQ ID NO: 151        moltype = RNA  length = 15
FEATURE               Location/Qualifiers
misc_feature          1..15
                      note = Description of Artificial Sequence: Synthetic
                       oligonucleotide
source                1..15
                      mol_type = other RNA
                      organism = synthetic construct
SEQUENCE: 151
gctgctgcta cagaa                                                          15

SEQ ID NO: 152        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 152
ttctgtagca tcagcttctc                                                     20

SEQ ID NO: 153        moltype = RNA  length = 15
FEATURE               Location/Qualifiers
misc_feature          1..15
                      note = Description of Artificial Sequence: Synthetic
                       oligonucleotide
source                1..15
                      mol_type = other RNA
                      organism = synthetic construct
SEQUENCE: 153
gctgctgcta cagaa                                                          15

SEQ ID NO: 154        moltype = RNA  length = 20
FEATURE               Location/Qualifiers
misc_feature          1..20
                      note = Description of Artificial Sequence: Synthetic
```

```
                         oligonucleotide
source                  1..20
                        mol_type = other RNA
                        organism = synthetic construct
SEQUENCE: 154
ttaatctctt tactgatata                                                  20

SEQ ID NO: 155          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 155
tttttaaatc ctgagaagaa                                                  20

SEQ ID NO: 156          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 156
tttttaaatc ctgagaagaa                                                  20

SEQ ID NO: 157          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 157
tttttaaatc ctgagaagaa                                                  20

SEQ ID NO: 158          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 158
tctctttact gatataatta                                                  20

SEQ ID NO: 159          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 159
tatgttttca catattgtca                                                  20

SEQ ID NO: 160          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 160
tgaatgttca cgcagtgggc                                                  20

SEQ ID NO: 161          moltype = RNA  length = 20
FEATURE                 Location/Qualifiers
misc_feature            1..20
                        note = Description of Artificial Sequence: Synthetic
                         oligonucleotide
source                  1..20
```

```
                         mol_type = other RNA
                         organism = synthetic construct
SEQUENCE: 161
tatcagcttt tccagggtcg                                                 20

SEQ ID NO: 162           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 162
ttaatctctt tactgatata                                                 20

SEQ ID NO: 163           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 163
ttaatctctt tactgatata                                                 20

SEQ ID NO: 164           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 164
ttaacgtcag ttcataaacc                                                 20

SEQ ID NO: 165           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 165
tccactatgt tttcacatat                                                 20

SEQ ID NO: 166           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 166
tccaaatact ggttgtcggt                                                 20

SEQ ID NO: 167           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 167
tccggtcaca acattgtggt                                                 20

SEQ ID NO: 168           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
```

```
SEQUENCE: 168
tatgttttca catattgtca                                              20

SEQ ID NO: 169          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 169
tttggtagct gaaagttctt                                              20

SEQ ID NO: 170          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 170
ttaatctctt tactgattta                                              20

SEQ ID NO: 171          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 171
tctctttact gatataatta                                              20

SEQ ID NO: 172          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 172
ttaatctctt tactgatatt                                              20

SEQ ID NO: 173          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 173
ttaatctctt tactgatttt                                              20

SEQ ID NO: 174          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 174
tactgtagca gcagcttctc                                              20

SEQ ID NO: 175          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 175
ttttgtagca gcagcttctc                                              20
```

```
SEQ ID NO: 176          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 176
ttcagtagca gcagcttctc                                                20

SEQ ID NO: 177          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 177
ttctttagca gcagcttctc                                                20

SEQ ID NO: 178          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 178
ttctatagca gcagcttctc                                                20

SEQ ID NO: 179          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 179
ttctgtcgca gcagcttctc                                                20

SEQ ID NO: 180          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 180
ttctgtggca gcagcttctc                                                20

SEQ ID NO: 181          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 181
ttctgtatca gcagcttctc                                                20

SEQ ID NO: 182          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 182
ttctgtagta gcagcttctc                                                20

SEQ ID NO: 183          moltype = RNA  length = 20
```

-continued

```
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 183
ttctgtagct gcagcttctc                                              20

SEQ ID NO: 184          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 184
ttctgtagca tcagcttctc                                              20

SEQ ID NO: 185          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 185
ttctgtagca gtagcttctc                                              20

SEQ ID NO: 186          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 186
ttctgtagca gctgcttctc                                              20

SEQ ID NO: 187          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 187
ttctgtagca gcatcttctc                                              20

SEQ ID NO: 188          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 188
ttctgtagca gcagtttctc                                              20

SEQ ID NO: 189          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 189
ttctgtagca gcagcatctc                                              20

SEQ ID NO: 190          moltype = RNA  length = 20
FEATURE                 Location/Qualifiers
misc_feature            1..20
```

```
                         note = Description of Artificial Sequence: Synthetic
                          oligonucleotide
source                   1..20
                         mol_type = other RNA
                         organism = synthetic construct
SEQUENCE: 190
ttctgtagca gcagcttctc                                                  20

SEQ ID NO: 191           moltype = RNA  length = 23
FEATURE                  Location/Qualifiers
misc_feature             1..23
                         note = Description of Artificial Sequence: Synthetic
                          oligonucleotide
source                   1..23
                         mol_type = other RNA
                         organism = synthetic construct
SEQUENCE: 191
gagaagctgc tgctgctaca gaa                                              23

SEQ ID NO: 192           moltype = RNA  length = 23
FEATURE                  Location/Qualifiers
misc_feature             1..23
                         note = Description of Artificial Sequence: Synthetic
                          oligonucleotide
source                   1..23
                         mol_type = other RNA
                         organism = synthetic construct
SEQUENCE: 192
gagaagctgc tgctgctgca gaa                                              23

SEQ ID NO: 193           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 193
ttctgtagca gcagcttctc                                                  20

SEQ ID NO: 194           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 194
ttctgtagca tcagcttctc                                                  20

SEQ ID NO: 195           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 195
ttctgtagca acagcttctc                                                  20

SEQ ID NO: 196           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 196
ttctgtagca ccagcttctc                                                  20

SEQ ID NO: 197           moltype = RNA  length = 20
FEATURE                  Location/Qualifiers
misc_feature             1..20
                         note = Description of Artificial Sequence: Synthetic
                          oligonucleotide
```

-continued

```
source                  1..20
                        mol_type = other RNA
                        organism = synthetic construct
SEQUENCE: 197
ttctgtagca gcagcttctc                                              20

SEQ ID NO: 198          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 198
ttctgtagca tcagcttctc                                              20

SEQ ID NO: 199          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 199
ttctgtagca acagcttctc                                              20

SEQ ID NO: 200          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 200
ttctgtagca ccagcttctc                                              20

SEQ ID NO: 201          moltype = RNA  length = 23
FEATURE                 Location/Qualifiers
misc_feature            1..23
                        note = Description of Artificial Sequence: Synthetic
                         oligonucleotide
source                  1..23
                        mol_type = other RNA
                        organism = synthetic construct
SEQUENCE: 201
gagaagctgc tgctgctaca gaa                                          23

SEQ ID NO: 202          moltype = RNA  length = 23
FEATURE                 Location/Qualifiers
misc_feature            1..23
                        note = Description of Artificial Sequence: Synthetic
                         oligonucleotide
source                  1..23
                        mol_type = other RNA
                        organism = synthetic construct
SEQUENCE: 202
gagaagctgc tgctgctgca gaa                                          23

SEQ ID NO: 203          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 203
ttctgtagca gcagcttctc                                              20

SEQ ID NO: 204          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
```

-continued

```
                        organism = synthetic construct
SEQUENCE: 204
ttctgtagca tcagcttctc                                              20

SEQ ID NO: 205          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 205
ttctgtagca acagcttctc                                              20

SEQ ID NO: 206          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 206
ttctgtagca ccagcttctc                                              20

SEQ ID NO: 207          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 207
ttaatctctt tactgatata                                              20

SEQ ID NO: 208          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 208
aattagagaa atgac                                                   15

SEQ ID NO: 209          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 209
ttttggataa actggtagcc                                              20

SEQ ID NO: 210          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 210
ttttggataa actggtagcc                                              20

SEQ ID NO: 211          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 211
```

```
ttttggataa actggtagcc                                              20

SEQ ID NO: 212          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 212
ttttggataa actggtagcc                                              20

SEQ ID NO: 213          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 213
ccagtttatc caaaa                                                   15

SEQ ID NO: 214          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 214
ccagtttatc caaaa                                                   15

SEQ ID NO: 215          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 215
ccagtttatc caaaa                                                   15

SEQ ID NO: 216          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 216
ccagtttatc caaaa                                                   15

SEQ ID NO: 217          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 217
ttagcagcag cttctcgtgg                                              20

SEQ ID NO: 218          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 218
tgtagcagca gcttctcgtg                                              20
```

-continued

```
SEQ ID NO: 219          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 219
ttgtagcagc agcttctcgt                                              20

SEQ ID NO: 220          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 220
tctgtagcag cagcttctcg                                              20

SEQ ID NO: 221          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 221
ttctgtagca gcagcttctc                                              20

SEQ ID NO: 222          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 222
tatctgtagc agcagcttct                                              20

SEQ ID NO: 223          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 223
tgatctgtag cagcagcttc                                              20

SEQ ID NO: 224          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 224
ttgatctgta gcagcagctt                                              20

SEQ ID NO: 225          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 225
tttgatctgt agcagcagct                                              20

SEQ ID NO: 226          moltype = RNA  length = 20
FEATURE                 Location/Qualifiers
```

```
misc_feature          1..20
                      note = Description of Artificial Sequence: Synthetic
                       oligonucleotide
source                1..20
                      mol_type = other RNA
                      organism = synthetic construct
SEQUENCE: 226
tgttgatctg tagcagcagc                                            20

SEQ ID NO: 227        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 227
tggttgatct gtagcagcag                                            20

SEQ ID NO: 228        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 228
tgggttgatc tgtagcagca                                            20

SEQ ID NO: 229        moltype = DNA  length = 105
FEATURE               Location/Qualifiers
misc_feature          1..105
                      note = This sequence may encompass 8-35 'cag' repeating
                       units
source                1..105
                      mol_type = other DNA
                      organism = Homo sapiens
SEQUENCE: 229
cagcagcagc agcagcagca gcagcagcag cagcagcagc agcagcagca gcagcagcag  60
cagcagcagc agcagcagca gcagcagcag cagcagcagc agcag                  105

SEQ ID NO: 230        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 230
ttagcatcag cttctcgtgg                                            20

SEQ ID NO: 231        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 231
ttgtagtagc agcttctcgt                                            20

SEQ ID NO: 232        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 232
ttgtagctgc agcttctcgt                                            20

SEQ ID NO: 233        moltype = RNA  length = 20
FEATURE               Location/Qualifiers
misc_feature          1..20
```

-continued

```
                        note = Description of Artificial Sequence: Synthetic
                         oligonucleotide
source                  1..20
                        mol_type = other RNA
                        organism = synthetic construct
SEQUENCE: 233
ttgtagcagc agctactcgt                                                    20

SEQ ID NO: 234          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 234
ttctatagca gcagcttctc                                                    20

SEQ ID NO: 235          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 235
ttctgtatca gcagcttctc                                                    20

SEQ ID NO: 236          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 236
ttctgtagca tcagcttctc                                                    20

SEQ ID NO: 237          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 237
ttctgtagca gcatcttctc                                                    20

SEQ ID NO: 238          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 238
ttctgtagca gcagcatctc                                                    20

SEQ ID NO: 239          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 239
tcgcggactt ccaaaggctc                                                    20

SEQ ID NO: 240          moltype = RNA  length = 20
FEATURE                 Location/Qualifiers
misc_feature            1..20
                        note = Description of Artificial Sequence: Synthetic
                         oligonucleotide
```

-continued

```
source                  1..20
                        mol_type = other RNA
                        organism = synthetic construct
SEQUENCE: 240
tcgcaggctt ccaaaggctc                                             20

SEQ ID NO: 241          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 241
tcgcagattt ccaaaggctc                                             20

SEQ ID NO: 242          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 242
agaagctgct gctaa                                                  15

SEQ ID NO: 243          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 243
aagctgctgc tacaa                                                  15

SEQ ID NO: 244          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 244
gctgctgcta cagaa                                                  15

SEQ ID NO: 245          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 245
tttggaagtc cgcga                                                  15

SEQ ID NO: 246          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 246
tttggaagcc tgcga                                                  15

SEQ ID NO: 247          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
```

```
                        organism = synthetic construct
SEQUENCE: 247
tttggaaatc tgcga                                                15

SEQ ID NO: 248          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 248
tcagcatcag cttctcgtgg                                           20

SEQ ID NO: 249          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 249
ttgcagtagc agcttctcgt                                           20

SEQ ID NO: 250          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 250
ttgcagctgc agcttctcgt                                           20

SEQ ID NO: 251          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 251
ttgcagcagc agctactcgt                                           20

SEQ ID NO: 252          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 252
ttctacagca gcagcttctc                                           20

SEQ ID NO: 253          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 253
ttctgcatca gcagcttctc                                           20

SEQ ID NO: 254          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 254
```

-continued

```
ttctgcagca tcagcttctc                                          20

SEQ ID NO: 255         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 255
ttctgcagca gcatcttctc                                          20

SEQ ID NO: 256         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 256
tcacggactt ccaaaggctc                                          20

SEQ ID NO: 257         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 257
tcacaggctt ccaaaggctc                                          20

SEQ ID NO: 258         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 258
tcacagattt ccaaaggctc                                          20

SEQ ID NO: 259         moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 259
agaagctgct gctga                                               15

SEQ ID NO: 260         moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 260
aagctgctgc tgcaa                                               15

SEQ ID NO: 261         moltype = RNA  length = 15
FEATURE                Location/Qualifiers
misc_feature           1..15
                       note = Description of Artificial Sequence: Synthetic
                        oligonucleotide
source                 1..15
                       mol_type = other RNA
                       organism = synthetic construct
SEQUENCE: 261
gctgctgctg cagaa                                               15
```

-continued

```
SEQ ID NO: 262          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 262
tttggaagtc cgtga                                                   15

SEQ ID NO: 263          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 263
tttggaagcc tgtga                                                   15

SEQ ID NO: 264          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 264
tttggaaatc tgtga                                                   15

SEQ ID NO: 265          moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 265
tcgaagccac gagaagctgc tgctacagat caaccccgag cggga                  45

SEQ ID NO: 266          moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 266
ggcctcccgc tcggggttga tctgtagcag cagcttctcg tggct                  45

SEQ ID NO: 267          moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 267
tcgaagccac gagaagctgc tgctgcagat caaccccgag cggga                  45

SEQ ID NO: 268          moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 268
ggcctcccgc tcggggttga tctgcagcag cagcttctcg tggct                  45

SEQ ID NO: 269          moltype = RNA  length = 20
FEATURE                 Location/Qualifiers
```

-continued

```
misc_feature           1..20
                       note = Description of Artificial Sequence: Synthetic
                        oligonucleotide
source                 1..20
                       mol_type = other RNA
                       organism = synthetic construct
SEQUENCE: 269
ttggcagcag cttctcgtgg                                                  20

SEQ ID NO: 270         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 270
tttgcagcag cttctcgtgg                                                  20

SEQ ID NO: 271         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 271
ttcgcagcag cttctcgtgg                                                  20

SEQ ID NO: 272         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 272
ttgtcagcag cttctcgtgg                                                  20

SEQ ID NO: 273         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 273
ttggtagcag cttctcgtgg                                                  20

SEQ ID NO: 274         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 274
ttggctgcag cttctcgtgg                                                  20

SEQ ID NO: 275         moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 275
ttggtatcag cttctcgtgg                                                  20

SEQ ID NO: 276         moltype = RNA  length = 20
FEATURE                Location/Qualifiers
misc_feature           1..20
                       note = Description of Artificial Sequence: Synthetic
```

-continued

```
                        oligonucleotide
source                  1..20
                        mol_type = other RNA
                        organism = synthetic construct
SEQUENCE: 276
ttggcagtag cttctcgtgg                                            20

SEQ ID NO: 277          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 277
ttggccgctg cttctcgtgg                                            20

SEQ ID NO: 278          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 278
ttggccgcat cttctcgtgg                                            20

SEQ ID NO: 279          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 279
ttggccgcag tttctcgtgg                                            20

SEQ ID NO: 280          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 280
ttggccgcag catctcgtgg                                            20

SEQ ID NO: 281          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 281
ttggccgcag ctactcgtgg                                            20

SEQ ID NO: 282          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 282
ttggccgcag cttttcgtgg                                            20

SEQ ID NO: 283          moltype = RNA  length = 20
FEATURE                 Location/Qualifiers
misc_feature            1..20
                        note = Description of Artificial Sequence: Synthetic
                         oligonucleotide
source                  1..20
```

-continued

```
                        mol_type = other RNA
                        organism = synthetic construct
SEQUENCE: 283
ttggccgcag cttcacgtgg                                                20

SEQ ID NO: 284          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 284
ttggccgcag cttcttgtgg                                                20

SEQ ID NO: 285          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 285
tagtagcagc agcttctcgt                                                20

SEQ ID NO: 286          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 286
ttttagcagc agcttctcgt                                                20

SEQ ID NO: 287          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 287
ttatagcagc agcttctcgt                                                20

SEQ ID NO: 288          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 288
ttgtcgcagc agcttctcgt                                                20

SEQ ID NO: 289          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 289
ttgtggcagc agcttctcgt                                                20

SEQ ID NO: 290          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
```

```
SEQUENCE: 290
ttgtatcagc agcttctcgt                                        20

SEQ ID NO: 291          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 291
ttgtagtagc agcttctcgt                                        20

SEQ ID NO: 292          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 292
ttgtagctgc agcttctcgt                                        20

SEQ ID NO: 293          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 293
ttgtagcatc agcttctcgt                                        20

SEQ ID NO: 294          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 294
ttgtagcagt agcttctcgt                                        20

SEQ ID NO: 295          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 295
ttgtagcagc tgcttctcgt                                        20

SEQ ID NO: 296          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 296
ttgtagcagc atcttctcgt                                        20

SEQ ID NO: 297          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 297
ttgtagcagc agtttctcgt                                        20
```

-continued

```
SEQ ID NO: 298          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 298
ttgtagcagc agcatctcgt                                              20

SEQ ID NO: 299          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 299
ttgtagcagc agctactcgt                                              20

SEQ ID NO: 300          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 300
ttgtagcagc agcttttcgt                                              20

SEQ ID NO: 301          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 301
tactgtagca gcagcttctc                                              20

SEQ ID NO: 302          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 302
ttttgtagca gcagcttctc                                              20

SEQ ID NO: 303          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 303
ttcagtagca gcagcttctc                                              20

SEQ ID NO: 304          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 304
ttctttagca gcagcttctc                                              20

SEQ ID NO: 305          moltype = RNA  length = 20
```

-continued

```
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 305
ttctatagca gcagcttctc                                              20

SEQ ID NO: 306        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 306
ttctgtcgca gcagcttctc                                              20

SEQ ID NO: 307        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 307
ttctgtggca gcagcttctc                                              20

SEQ ID NO: 308        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 308
ttctgtatca gcagcttctc                                              20

SEQ ID NO: 309        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 309
ttctgtagta gcagcttctc                                              20

SEQ ID NO: 310        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 310
ttctgtagct gcagcttctc                                              20

SEQ ID NO: 311        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 311
ttctgtagca tcagcttctc                                              20

SEQ ID NO: 312        moltype = RNA  length = 20
FEATURE               Location/Qualifiers
misc_feature          1..20
```

-continued

```
                         note = Description of Artificial Sequence: Synthetic
                          oligonucleotide
source                   1..20
                         mol_type = other RNA
                         organism = synthetic construct
SEQUENCE: 312
ttctgtagca gtagcttctc                                                   20

SEQ ID NO: 313           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 313
ttctgtagca gctgcttctc                                                   20

SEQ ID NO: 314           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 314
ttctgtagca gcatcttctc                                                   20

SEQ ID NO: 315           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 315
ttctgtagca gcagtttctc                                                   20

SEQ ID NO: 316           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 316
ttctgtagca gcagcatctc                                                   20

SEQ ID NO: 317           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 317
ttagcatcag cttctcgtgg                                                   20

SEQ ID NO: 318           moltype = RNA  length = 15
FEATURE                  Location/Qualifiers
misc_feature             1..15
                         note = Description of Artificial Sequence: Synthetic
                          oligonucleotide
source                   1..15
                         mol_type = other RNA
                         organism = synthetic construct
SEQUENCE: 318
agaagctgct gctaa                                                        15

SEQ ID NO: 319           moltype = RNA  length = 15
FEATURE                  Location/Qualifiers
misc_feature             1..15
                         note = Description of Artificial Sequence: Synthetic
                          oligonucleotide
```

```
source                  1..15
                        mol_type = other RNA
                        organism = synthetic construct
SEQUENCE: 319
aagctgctgc tacaa                                                          15

SEQ ID NO: 320          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 320
gctgctgcta cagaa                                                          15

SEQ ID NO: 321          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 321
ttctgtagca tcagcttctc                                                     20

SEQ ID NO: 322          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 322
gctgctgcta cagaa                                                          15

SEQ ID NO: 323          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 323
ttaatctctt tactgatata                                                     20

SEQ ID NO: 324          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 324
tttttaaatc ctgagaagaa                                                     20

SEQ ID NO: 325          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 325
tttttaaatc ctgagaagaa                                                     20

SEQ ID NO: 326          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
```

```
                         organism = synthetic construct
SEQUENCE: 326
tttttaaatc ctgagaagaa                                                20

SEQ ID NO: 327           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 327
tctctttact gatataatta                                                20

SEQ ID NO: 328           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 328
tatcttttca catattgtca                                                20

SEQ ID NO: 329           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 329
tgaatgttca cgcagtgggc                                                20

SEQ ID NO: 330           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 330
tatcagcttt tccagggtcg                                                20

SEQ ID NO: 331           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 331
ttaatctctt tactgatata                                                20

SEQ ID NO: 332           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 332
ttaatctctt tactgatata                                                20

SEQ ID NO: 333           moltype = RNA  length = 20
FEATURE                  Location/Qualifiers
misc_feature             1..20
                         note = Description of Artificial Sequence: Synthetic
                          oligonucleotide
source                   1..20
                         mol_type = other RNA
                         organism = synthetic construct
SEQUENCE: 333
```

-continued

```
ttaacgtcag ttcataaacc                                            20

SEQ ID NO: 334          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 334
tccactatgt tttcacatat                                            20

SEQ ID NO: 335          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 335
tccaaatact ggttgtcggt                                            20

SEQ ID NO: 336          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 336
tccggtcaca acattgtggt                                            20

SEQ ID NO: 337          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 337
tatgttttca catattgtca                                            20

SEQ ID NO: 338          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 338
tttggtagct gaaagttctt                                            20

SEQ ID NO: 339          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 339
ttaatctctt tactgattta                                            20

SEQ ID NO: 340          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 340
tctctttact gatataatta                                            20
```

```
SEQ ID NO: 341          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 341
ttaatctctt tactgatatt                                                20

SEQ ID NO: 342          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 342
ttaatctctt tactgatttt                                                20

SEQ ID NO: 343          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 343
tactgtagca gcagcttctc                                                20

SEQ ID NO: 344          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 344
ttttgtagca gcagcttctc                                                20

SEQ ID NO: 345          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 345
ttcagtagca gcagcttctc                                                20

SEQ ID NO: 346          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 346
ttctttagca gcagcttctc                                                20

SEQ ID NO: 347          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 347
ttctgtcgca gcagcttctc                                                20

SEQ ID NO: 348          moltype = RNA  length = 20
FEATURE                 Location/Qualifiers
```

```
misc_feature          1..20
                      note = Description of Artificial Sequence: Synthetic
                       oligonucleotide
source                1..20
                      mol_type = other RNA
                      organism = synthetic construct
SEQUENCE: 348
ttctgtggca gcagcttctc                                              20

SEQ ID NO: 349        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 349
ttctgtagta gcagcttctc                                              20

SEQ ID NO: 350        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 350
ttctgtagct gcagcttctc                                              20

SEQ ID NO: 351        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 351
ttctgtcgca gtagcttctc                                              20

SEQ ID NO: 352        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 352
ttctgtagca gctgcttctc                                              20

SEQ ID NO: 353        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 353
ttctgtagca gcagtttctc                                              20

SEQ ID NO: 354        moltype = RNA  length = 20
FEATURE               Location/Qualifiers
misc_feature          1..20
                      note = Description of Artificial Sequence: Synthetic
                       oligonucleotide
source                1..20
                      mol_type = other RNA
                      organism = synthetic construct
SEQUENCE: 354
ttctgtagca gcagcttctc                                              20

SEQ ID NO: 355        moltype = RNA  length = 23
FEATURE               Location/Qualifiers
misc_feature          1..23
                      note = Description of Artificial Sequence: Synthetic
```

```
                         oligonucleotide
source                  1..23
                        mol_type = other RNA
                        organism = synthetic construct
SEQUENCE: 355
gagaagctgc tgctgctaca gaa                                            23

SEQ ID NO: 356          moltype = RNA  length = 23
FEATURE                 Location/Qualifiers
misc_feature            1..23
                        note = Description of Artificial Sequence: Synthetic
                         oligonucleotide
source                  1..23
                        mol_type = other RNA
                        organism = synthetic construct
SEQUENCE: 356
gagaagctgc tgctgctgca gaa                                            23

SEQ ID NO: 357          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 357
ttctgtagca gcagcttctc                                                20

SEQ ID NO: 358          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 358
ttctgtagca tcagcttctc                                                20

SEQ ID NO: 359          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 359
ttctgtagca acagcttctc                                                20

SEQ ID NO: 360          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 360
ttctgtagca ccagcttctc                                                20

SEQ ID NO: 361          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 361
ttctgtagca gcagcttctc                                                20

SEQ ID NO: 362          moltype = RNA  length = 20
FEATURE                 Location/Qualifiers
misc_feature            1..20
                        note = Description of Artificial Sequence: Synthetic
                         oligonucleotide
source                  1..20
```

```
                        mol_type = other RNA
                        organism = synthetic construct
SEQUENCE: 362
ttctgtagca tcagcttctc                                              20

SEQ ID NO: 363          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 363
ttctgtagca acagcttctc                                              20

SEQ ID NO: 364          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 364
ttctgtagca ccagcttctc                                              20

SEQ ID NO: 365          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 365
ttaatctctt tactgatata                                              20

SEQ ID NO: 366          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 366
ttttggataa actggtagcc                                              20

SEQ ID NO: 367          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 367
ttttggataa actggtagcc                                              20

SEQ ID NO: 368          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 368
ttttggataa actggtagcc                                              20

SEQ ID NO: 369          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
```

```
SEQUENCE: 369
ttttggataa actggtagcc                                              20

SEQ ID NO: 370          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 370
ccagtttatc caaaa                                                   15

SEQ ID NO: 371          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 371
ccagtttatc caaaa                                                   15

SEQ ID NO: 372          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 372
ccagtttatc caaaa                                                   15

SEQ ID NO: 373          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 373
ccagtttatc caaaa                                                   15

SEQ ID NO: 374          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 374
ttagcagcag cttctcgtgg                                              20

SEQ ID NO: 375          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 375
tgtagcagca gcttctcgtg                                              20

SEQ ID NO: 376          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 376
ttgtagcagc agcttctcgt                                              20
```

```
SEQ ID NO: 377          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 377
tctgtagcag cagcttctcg                                            20

SEQ ID NO: 378          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 378
ttctgtagca gcagcttctc                                            20

SEQ ID NO: 379          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 379
tatctgtagc agcagcttct                                            20

SEQ ID NO: 380          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 380
tgatctgtag cagcagcttc                                            20

SEQ ID NO: 381          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 381
ttgatctgta gcagcagctt                                            20

SEQ ID NO: 382          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 382
tttgatctgt agcagcagct                                            20

SEQ ID NO: 383          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 383
tgttgatctg tagcagcagc                                            20

SEQ ID NO: 384          moltype = RNA  length = 20
```

-continued

```
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 384
tggttgatct gtagcagcag                                                20

SEQ ID NO: 385          moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 385
tgggttgatc tgtagcagca                                                20

SEQ ID NO: 386          moltype = RNA  length = 15
FEATURE                 Location/Qualifiers
misc_feature            1..15
                        note = Description of Artificial Sequence: Synthetic
                         oligonucleotide
source                  1..15
                        mol_type = other RNA
                        organism = synthetic construct
SEQUENCE: 386
cagtaaagag attaa                                                     15
```

MODIFIED OLIGONUCLEOTIDES TARGETING SNPs

RELATED APPLICATIONS

This application is a division of U.S. patent application Ser. No. 16/537,374, filed Aug. 9, 2019, which claims priority to U.S. Provisional Patent Application Nos. 62/717,287, filed Aug. 10, 2018, and 62/825,429, filed Mar. 28, 2019. The entire contents of these applications are incorporated herein by reference.

STATEMENT OF FEDERALLY SPONSORED RESEARCH

This invention was made with government support under grant numbers NS104022 and GM108803 awarded by the National Institutes of Health. The Government has certain rights in the invention.

SEQUENCE LISTING

The instant application contains a Sequence Listing which has been submitted electronically in XML format and is hereby incorporated by reference in its entirety. Said XML file, created on Aug. 9, 2023, is named 745353_UM9-227DIV_ST26.xml and is 501,544 bytes in size.

BACKGROUND

RNA interference represents a simple and effective tool for inhibiting the function of genes. RNA silencing agents have received particular interest as research tools and therapeutic agents for their ability to knock down expression of a particular protein with a high degree of sequence specificity. The sequence specificity of RNA silencing agents is particularly useful for the treatment of diseases caused by dominant mutations in heterozygotes bearing one mutant and one wild-type copy of a particular gene. However, there remains a need for RNA silencing agents that can preferentially silence mutant, disease-causing allele expression while not or only minimally effecting expression of the wild-type allele.

SUMMARY

The present invention is based on the surprising discovery of novel oligonucleotides that enhance silencing of the expression of a gene containing a single nucleotide polymorphism (SNP) (e.g., a heterozygous SNP) relative to the expression of the corresponding wild-type gene in a heterozygote, e.g., by up to more than 100 times. In certain aspects, an oligonucleotide (e.g., a dsRNA) is provided that preferentially targets a SNP-containing nucleic acid for degradation, wherein the oligonucleotide (e.g., a double-stranded RNA (dsRNA)) does not target, or targets to a lesser degree, the corresponding wild-type (non-SNP-containing) nucleic acid for degradation. In certain aspects, an oligonucleotide (e.g., a dsRNA) of the invention is: 1) complementary to a SNP position in a target nucleic acid; and 2) contains a mismatch at a particular position of the target nucleic acid relative to the SNP. In certain embodiments, an oligonucleotide (e.g., a dsRNA) of the invention also contains a two mismatches relative to the corresponding wild-type target nucleic acid sequence: 1) at the wild-type SNP position; and 2) at the particular position of the target nucleic acid sequence relative to the wild-type SNP position.

Accordingly, an exemplary oligonucleotide (e.g., dsRNA) contains one mismatch relative to a SNP-containing target and two mismatches relative to the corresponding wild-type sequence, thus resulting in preferential cleavage of the SNP-containing target relative to the corresponding wild-type sequence.

In one aspect, an oligonucleotide having a 5' end, a 3' end and a seed region, wherein the RNA is complementary to a region of a gene comprising an allelic polymorphism, and wherein the RNA comprises a SNP position nucleotide at a position within the seed region, wherein the SNP position nucleotide is complementary to the allelic polymorphism; and a mismatch (MM) position nucleotide located 2-11 nucleotides from the SNP position nucleotide that is a mismatch with a nucleotide in the gene is provided. In some cases, the oligonucleotide is complementary to a region of a gene comprising an allelic polymorphism, wherein the oligonucleotide comprises an SNP position nucleotide at any one of positions 2 to 6 from the 5' end; and a mismatch position nucleotide located 2-11 nucleotides from the SNP position nucleotide that is a mismatch with a nucleotide in the gene.

In certain exemplary embodiments, the oligonucleotide is RNA.

In certain exemplary embodiments, the RNA further comprises at least one vinyl phosphonate (VP) modification in an intersubunit linkage having the formula:

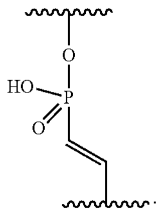 [SMILES: */C=C/P(=O)(O)O*]

In certain exemplary embodiments, a VP motif is inserted next to the SNP position nucleotide or next to the MM position nucleotide.

In certain exemplary embodiments, oligonucleotide is selected from the group consisting of siRNA, miRNA, shRNA, CRISPR guide, DNA, antisense oligonucleotide (ASO), gapmer, mixmer, miRNA inhibitor, splice-switching oligonucleotide (SSO), phosphorodiamidate morpholino oligomer (PMO), and peptide nucleic acid (PNA).

In certain exemplary embodiments, the RNA is an antisense oligonucleotide (ASO) or a dsRNA.

In certain exemplary embodiments, the dsRNA comprises a first strand of about 15-35 nucleotides that is complementary to the region of the gene comprising an allelic polymorphism, and a second strand of about 15-35 nucleotides that is complementary to at least a portion of the first strand, wherein the first strand comprises the SNP position nucleotide in a seed region (e.g., at position 2-6 from the 5' end) that is complementary to the allelic polymorphism, and wherein the first strand comprises the MM position nucleotide located 2-6 nucleotides from the SNP position nucleotide that is a mismatch with a nucleotide in the gene.

In certain exemplary embodiments, the SNP position nucleotide is located at position 2, 4 or 6 from the 5' end of the RNA, and the MM position nucleotide is located 2-6 nucleotides from the SNP position nucleotide.

In certain exemplary embodiments, the MM position nucleotide is located within 2, 3, 4 or 6 nucleotides of the SNP position nucleotide. In certain exemplary embodiments, the MM position nucleotide is located within 5 nucleotides of the SNP position nucleotide.

In certain exemplary embodiments, the dsRNA is blunt-ended. In certain exemplary embodiments, the dsRNA comprises at least one single-stranded nucleotide overhang. In certain exemplary embodiments, the dsRNA comprises naturally occurring nucleotides. In certain exemplary embodiments, the dsRNA comprises at least one modified nucleotide. In certain exemplary embodiments, each nucleotide of the dsRNA is modified.

In certain exemplary embodiments, the at least one modified nucleotide is selected from the group consisting of a 2'-O-methyl modified nucleotide, a nucleotide comprising a 5'-phosphorothioate group, a terminal nucleotide linked to a cholesteryl derivative and a terminal nucleotide linked to a dodecanoic acid bisdecylamide group.

In certain exemplary embodiments, the modified nucleotide is selected from the group consisting of a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

In certain exemplary embodiments, the dsRNA comprises at least one 2'-O-methyl modified nucleotide and a 5'-phosphorothioate group.

In certain exemplary embodiments, the first strand comprises at least three 2'-O-methyl modified nucleotides. In certain exemplary embodiments, the first strand comprises a 2'-O-methyl modified nucleotide on either side of the SNP position nucleotide.

In certain exemplary embodiments, the dsRNA comprises a hydrophobic moiety.

In certain exemplary embodiments, the region of a gene comprising the allelic polymorphism comprises a nucleic acid sequence selected from the group consisting of SEQ ID NOs: 1-10. In certain exemplary embodiments, the first strand comprises UUCUGUAGCAUCAGCUUCUC.

In certain exemplary embodiments, an RNA described herein (e.g., the first strand of a dsRNA) comprises a SNP position nucleotide (referenced from the 5' end)—MM position nucleotide (referenced from the 5' end) combination selected from the group consisting of 2-7, 4-7, 4-8, 4-15, 6-5, 6-8, 6-11, 6-14, 6-16, 3-5, 3-7 and 3-8.

In certain exemplary embodiments, the SNP position nucleotide is complementary to an allelic polymorphism of an htt SNP selected from the group consisting of rs363125, rs362273, rs362307, rs362336, rs362331, rs362272, rs362306, rs362268, rs362267, and rs363099.

In certain exemplary embodiments, the RNA further comprises a 5' stabilizing moiety selected from the group consisting of phosphate, vinyl phosphonate, C5-methyl (R or S or racemic), C5-methyl on vinyl, and reduced vinyl.

In certain exemplary embodiments, the RNA further comprises a conjugate moiety selected from the group consisting of alkyl chain, vitamin, peptide, glycosphingolipid, polyunsaturated fatty acid, secosteroid, steroid hormone, and steroid lipid.

In one aspect, a dsRNA comprising a first strand of about 15-35 nucleotides that is complementary to a region of a gene comprising an allelic polymorphism, and a second strand of about 15-35 nucleotides that is complementary to at least a portion of the first strand, wherein the first strand comprises a SNP position nucleotide at any one of positions in the seed region (e.g., one of positions 2 to 6 from the 5' end) that is complementary to the allelic polymorphism, and wherein the first strand comprises a MM position nucleotide located 2-6 nucleotides from the SNP position nucleotide that is a mismatch with a nucleotide in the gene, is provided.

In certain exemplary embodiments, a dsRNA comprising a first strand of about 15-35 nucleotides that is complementary to a region of a gene comprising an allelic polymorphism, and a second strand of about 15-35 nucleotides that is complementary to at least a portion of the first strand, wherein the first strand comprises a SNP position nucleotide at position 2, 4 or 6 from the 5' end that is complementary to the allelic polymorphism, and wherein the first strand comprises a MM position nucleotide located 2-6 nucleotides from the SNP position nucleotide that is a mismatch with a nucleotide in the gene, is provided.

In certain exemplary embodiments, the RNA further comprises at least one vinyl phosphonate modification in an intersubunit linkage having the formula:

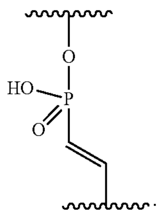 [SMILES: */C=C/P(=O)(O)O*]

In certain exemplary embodiments, a VP motif is inserted next to the SNP position nucleotide or next to the MM position nucleotide.

In certain exemplary embodiments, the SNP position nucleotide is at position 2 from the 5' end, at position 4 from the 5' end, or at position 6 from the 5' end of the first strand. In other exemplary embodiments, the MM position nucleotide is located within 2 nucleotides of the SNP position nucleotide, is located within 3 nucleotides of the SNP position nucleotide, is located within 4 nucleotides of the SNP position nucleotide, is located within 5 nucleotides of the SNP position nucleotide, or is located within 6 nucleotides of the SNP position nucleotide. In certain exemplary embodiments, the SNP position nucleotide is located 4 nucleotides from the 5' end, and the MM position nucleotide is located 7 nucleotides from the 5' end. In other exemplary embodiments, the SNP position nucleotide is located 6 nucleotides from the 5' end, and the MM position nucleotide is located 11 nucleotides from the 5' end.

In another aspect, a dsRNA comprising a first strand of about 15-35 nucleotides that is complementary to a region of a gene comprising an allelic polymorphism, and a second strand of about 15-35 nucleotides that is complementary to at least a portion of the first strand, wherein the first strand comprises a SNP position nucleotide at a position 6 from the 5' end that is complementary to the allelic polymorphism, and wherein the first strand comprises a MM position nucleotide located at position 11 from the 5' end is a mismatch with a nucleotide in the gene, is provided.

In certain exemplary embodiments, the RNA further comprises at least one vinyl phosphonate modification in an intersubunit linkage having the formula:

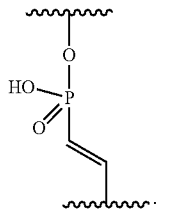

In certain exemplary embodiments, a VP motif is inserted next to the SNP position nucleotide or next to the MM position nucleotide.

In certain exemplary embodiments, the first strand comprises a 2'-O-methyl modified nucleotide on either side of the SNP position nucleotide. In certain exemplary embodiments, the first strand comprises at least three 2'-O-methyl modified nucleotides.

In certain exemplary embodiments, the dsRNA comprises a 5'-phosphorothioate group.

In certain exemplary embodiments, the gene comprising an allelic polymorphism is the Huntingtin (htt) gene.

In certain exemplary embodiments, the region of a gene comprising the allelic polymorphism comprises a nucleic acid sequence selected from the group consisting of SEQ ID NOs: 1-10. In certain exemplary embodiments, the first strand comprises UUCUGUAGCAUCAGCUUCUC.

In certain aspects, a pharmaceutical composition comprising the RNA described herein and a pharmaceutically acceptable carrier is provided.

In certain aspects, a method of inhibiting expression of a gene comprising an allelic polymorphism in a cell, the method comprising contacting the cell with the described herein is provided.

In another aspect, a method of treating a disease or disorder characterized or caused by a gene comprising an allelic polymorphism in a subject in need thereof, comprising administering to a subject a therapeutically effective amount of an RNA having a 5' end, a 3' end, and a seed region, that is complementary to a region of a gene comprising an allelic polymorphism, wherein the RNA comprises a SNP position nucleotide at position in the seed region that is complementary to the allelic polymorphism, and a MM position nucleotide located 2-11 nucleotides from the SNP position nucleotide that is a mismatch with a nucleotide in the gene, provided.

In certain exemplary embodiments, the RNA further comprises at least one vinyl phosphonate modification in an intersubunit linkage having the formula:

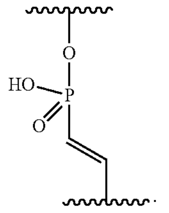

In certain exemplary embodiments, a VP motif is inserted next to the SNP position nucleotide or next to the MM position nucleotide.

In certain exemplary embodiments, the RNA is an ASO or a dsRNA.

In certain exemplary embodiments, the dsRNA comprises a first strand of about 15-35 nucleotides that is complementary to the region of the gene comprising an allelic polymorphism, and a second strand of about 15-35 nucleotides that is complementary to at least a portion of the first strand, wherein the first strand comprises the SNP position nucleotide within the seed region (e.g, any one of positions 2 to 6 from the 5' end, such as position 2, 4 or 6 from the 5' end) that is complementary to the allelic polymorphism, and wherein the first strand comprises the MM position nucleotide located 2-6 nucleotides from the SNP position nucleotide that is a mismatch with a nucleotide in the gene.

In certain exemplary embodiments, said dsRNA is administered to the brain of the subject. In certain exemplary embodiments, said dsRNA is administered by intrastriatal infusion. In certain exemplary embodiments, a decrease in expression of the gene in the striatum is achieved. In certain exemplary embodiments, a decrease in expression of the gene in the cortex is achieved.

In certain exemplary embodiments, the gene comprising an allelic polymorphism is the Huntingtin (htt) gene. In certain exemplary embodiments, the disease is Huntington's disease.

In certain exemplary embodiments, the SNP position nucleotide is located at position 2, 4 or 6 from the 5' end of the RNA, and the MM position nucleotide is located 2-6 nucleotides from the SNP position nucleotide.

In another aspect, a di-branched oligonucleotide compound comprising two RNAs, wherein the RNAs are connected to one another by one or more moieties selected from a linker, a spacer and a branching point, wherein each RNA has a 5' end, a 3' end and a seed region, wherein each RNA is complementary to a region of a gene comprising an allelic polymorphism, and wherein each RNA comprises a SNP position nucleotide at a position within the seed region, the SNP position nucleotide being complementary to the allelic polymorphism, and a MM position nucleotide located 2-11 nucleotides from the SNP position nucleotide that is a mismatch with a nucleotide in the gene, is provided.

In certain exemplary embodiments, the RNA further comprises at least one vinyl phosphonate modification in an intersubunit linkage having the formula:

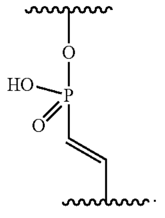 [SMILES: */C=C/P(=O)(O)O*]

In certain exemplary embodiments, a VP motif is inserted next to the SNP position nucleotide or next to the MM position nucleotide.

In certain exemplary embodiments, the di-branched oligonucleotide compound has an hsi-RNA structure.

In certain exemplary embodiments, the SNP position nucleotide is complementary to an allelic polymorphism of an htt SNP selected from the group consisting of rs363125, rs362273, rs362307, rs362336, rs362331, rs362272, rs362306, rs362268, rs362267, and rs363099.

In another aspect, a di-branched oligonucleotide compound comprising two or more nucleic acid sequences, wherein the nucleic acid sequences (N) are connected to one another by one or more moieties selected from a linker (L), a spacer (S) and optionally a branching point (B), wherein each nucleic acid sequence is double-stranded and comprises a sense strand and an antisense strand, wherein the sense strand and the antisense strand each have a 5' end and a 3' end, wherein the sense strand and the antisense strand each comprises one or more chemically-modified nucleotides, wherein each antisense strand has a seed region, wherein each antisense strand is complementary to a region of a gene comprising an allelic polymorphism, and wherein each antisense strand comprises a SNP position nucleotide at a position within the seed region, the SNP position nucleotide being complementary to the allelic polymorphism, and a mismatch (MM) position nucleotide located 2-11 nucleotides from the SNP position nucleotide that is a mismatch with a nucleotide in the gene, is provided.

In certain exemplary embodiments, the RNA further comprises at least one vinyl phosphonate modification in an intersubunit linkage having the formula:

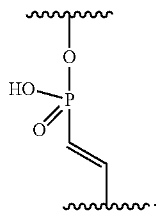

In certain exemplary embodiments, a VP motif is inserted next to the SNP position nucleotide or next to the MM position nucleotide.

In certain exemplary embodiments, the sense strands and the antisense strands each comprise >80% chemically-modified nucleotides.

In certain exemplary embodiments, the nucleotides at positions 1 and 2 from the 5' end of the sense and antisense strands are connected to adjacent nucleotides via phosphorothioate linkages.

In certain exemplary embodiments, each antisense strand comprises at least 15 contiguous nucleotides, and wherein each sense strand comprises at least 15 contiguous nucleotides and has complementarity to the antisense strand.

In certain exemplary embodiments, the compound further comprises a hydrophobic moiety attached to the terminal 5' position of the branched oligonucleotide compound.

In certain exemplary embodiments, each double-stranded nucleic acid sequence is independently connected to a linker, spacer or branching point at the 3' end or at the 5' end of the sense strand or the antisense strand.

In certain exemplary embodiments, the SNP position nucleotide is complementary to an allelic polymorphism of an htt SNP selected from the group consisting of rs363125, rs362273, rs362307, rs362336, rs362331, rs362272, rs362306, rs362268, rs362267, and rs363099.

In another aspect, a nucleic acid having a 5' end, a 3' end and a seed region, that is complementary to a region of a gene comprising an allelic polymorphism, wherein the nucleic acid comprises a SNP position nucleotide at a position within the seed region, wherein the SNP position nucleotide is complementary to the allelic polymorphism, a MM position that is a mismatch with a nucleotide in the gene, and at least one modified nucleotide (X) on either side of the SNP position nucleotide, wherein each X is located within four, three or two nucleotides from the SNP position nucleotide, is provided.

In certain exemplary embodiments, the RNA further comprises at least one vinyl phosphonate modification in an intersubunit linkage having the formula:

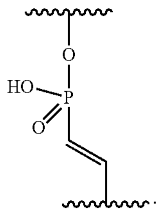 [SMILES: */C=C/P(=O)(O)O*]

In certain exemplary embodiments, a VP motif is inserted next to the SNP position nucleotide or next to the MM position nucleotide.

In certain exemplary embodiments, X comprises a sugar modification selected from the group consisting of 2'-O-methyl (2'-OMe), 2'-fluoro (2'-F), 2'-ribo, 2'-deoxyribo, 2'-F-4'-thioarabino (2'-F-ANA), 2-O-(2-methoxyethyl) (2'-MOE), 4'-S-RNA, locked nucleic acid (LNA), 4'-S—F-ANA, 2'-O-allyl, 2'-O-ethylamine, 2-cyanoethyl-RNA (CNet-RNA), tricyclo-DNA, cyclohexenyl nucleic acid (CeNA), arabino nucleic acid (ANA), and hexitol nucleic acid (HNA).

In certain exemplary embodiments, an X is positioned immediately 5' to the SNP position nucleotide or immediately 3' to the SNP position nucleotide. In certain exemplary embodiments, an X is positioned immediately 5' to the SNP position nucleotide and immediately 3' to the SNP position nucleotide.

In certain exemplary embodiments, the SNP position nucleotide is present from position 2 to position 6 from the 5' end. In certain exemplary embodiments, the MM position nucleotide is located 2-11 nucleotides from the SNP position nucleotide. In certain exemplary embodiments, the MM position nucleotide is located 2-6 nucleotides from the SNP position nucleotide.

In another aspect, a nucleic acid having a 5' end, a 3' end and a seed region, that is complementary to a region of a gene comprising an allelic polymorphism, wherein the nucleic acid comprises a SNP position nucleotide at a position within the seed region, wherein the SNP position nucleotide is complementary to the allelic polymorphism, a MM position that is a mismatch with a nucleotide in the gene, and at least one modified nucleotide (Y) on either side of the MM position nucleotide, wherein each Y is located within four, three or two nucleotides from the MM position nucleotide, is provided.

In certain exemplary embodiments, the RNA further comprises at least one vinyl phosphonate modification in an intersubunit linkage having the formula:

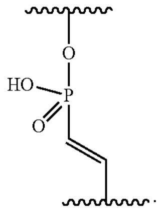 [SMILES: */C=C/P(=O)(O)O*]

In certain exemplary embodiments, a VP motif is inserted next to the SNP position nucleotide or next to the MM position nucleotide.

In certain exemplary embodiments, a Y is positioned immediately 5' to the MM position nucleotide or immediately 3' to the MM position nucleotide. In certain exemplary embodiments, a Y is positioned immediately 5' to the MM position nucleotide and immediately 3' to the MM position nucleotide.

In certain exemplary embodiments, the SNP position nucleotide is present from position 2 to position 6 from the 5' end. In certain exemplary embodiments, the MM position nucleotide is located 2-11 nucleotides from the SNP position nucleotide. In certain exemplary embodiments, the MM position nucleotide is located 2-6 nucleotides from the SNP position nucleotide.

In another aspect, a nucleic acid having a 5' end, a 3' end and a seed region, that is complementary to a region of a gene comprising an allelic polymorphism, wherein the nucleic acid comprises a SNP position nucleotide at a position within the seed region, wherein the SNP position nucleotide is complementary to the allelic polymorphism, a MM position that is a mismatch with a nucleotide in the gene, and at least one modified nucleotide (X) on either side of the SNP position nucleotide, wherein each X is located within four, three or two nucleotides from the SNP position nucleotide, and at least one modified nucleotide (Y) on either side of the MM position nucleotide, wherein each Y is located within four, three or two nucleotides from the MM position nucleotide, is provided.

In certain exemplary embodiments, the RNA further comprises at least one vinyl phosphonate modification in an intersubunit linkage having the formula:

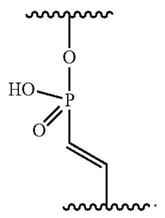

In certain exemplary embodiments, a VP motif is inserted next to the SNP position nucleotide or next to the MM position nucleotide.

In certain exemplary embodiments, X comprises a sugar modification selected from the group consisting of 2'-OMe, 2'-F, 2'-ribo, 2'-deoxyribo, 2'-F-ANA, 2'-MOE, 4'-S-RNA, LNA, 4'-S—F-ANA, 2'-O-allyl, 2'-O-ethylamine, CNet-RNA, tricyclo-DNA, CeNA, ANA, and HNA. In certain exemplary embodiments, Y comprises a sugar modification selected from the group consisting of 2'-OMe, 2'-F, 2'-ribo, 2'-deoxyribo, 2'-F-ANA, 2'-MOE, 4'-S-RNA, LNA, 4'-S—F-ANA, 2'-O-allyl, 2'-O-ethylamine, CNet-RNA, tricyclo-DNA, CeNA, ANA, and HNA.

In certain exemplary embodiments, an X is positioned immediately 5' to the SNP position nucleotide or immediately 3' to the SNP position nucleotide. In certain exemplary embodiments, an X is positioned immediately 5' to the SNP position nucleotide and immediately 3' to the SNP position nucleotide.

In certain exemplary embodiments, a Y is positioned immediately 5' to the MM position nucleotide or immediately 3' to the MM position nucleotide. In certain exemplary embodiments, a Y is positioned immediately 5' to the MM position nucleotide and immediately 3' to the MM position nucleotide.

In certain exemplary embodiments, the SNP position nucleotide is present from position 2 to position 6 from the 5' end. In certain exemplary embodiments, the MM position nucleotide is located 2-11 nucleotides from the SNP position nucleotide. In certain exemplary embodiments, the MM position nucleotide is located 2-6 nucleotides from the SNP position nucleotide.

In certain exemplary embodiments, X and Y are the same.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 1 discloses SEQ ID NOS 265-268, respectively, in order of appearance.

FIG. 12A-FIG. 12C depict the SNP2, SNP4 and SNP6 hsiRNA libraries, respectively. Antisense strands are depicted 5' to 3', with the SNP site in red and the mismatch in blue. FIG. 12A discloses SEQ ID NOS 269-284, respectively, in order of appearance. FIG. 12B discloses SEQ ID NOS 285-300, respectively, in order of appearance. FIG. 12C discloses SEQ ID NOS 301-316, respectively, in order of appearance.

FIG. 13 depicts antisense and sense strand sequences and modification patterns for various hsiRNA constructs according to certain embodiments. mm4-7 and mm6-11 demonstrated superior SNP discrimination, and were selected for further screening. FIG. 13 discloses SEQ ID NOS 317, 291-292, 299, 305, 308, 311, 314, 316, 318, 319, 319, 319, 320, 320, 320, 320 and 320, respectively, in order of columns.

FIG. 14 depicts an exemplary SNP-selective compound designed as a di-siRNA. FIG. 14 discloses SEQ ID NOS 321-322 and 321-322, respectively, in order of appearance.

FIG. 15 depicts backbone linkages according to certain exemplary embodiments. Oligonucleotide backbones may comprise one or any combination of phosphates, phosphorothioates (a racemic mixture or stereospecific), diphosphorothioates, phosphoramidates, peptide nucleic acids (PNAs), boranophosphates, 2'-5'-phosphodiesters, amides, phosphonoacetates, morpholinos and the like FIG. 16 depicts sugar modifications according to certain exemplary embodiments. Sugar modifications include one or any combination of 2'-O-methyl, 2'-fluoro, 2'-ribo, 2'-deoxyribo, 2'-F-ANA, MOE, 4'-S-RNA, LNA, 4'-S—F-ANA, 2'-O-allyl, 2'-O-ethylamine, CNet-RNA, tricyclo-DNA, CeNA, ANA, HNA and the like.

FIG. 18 depicts 5' stabilization modifications according to certain exemplary embodiments. A suitable 5' stabilization modification can be a phosphate, no phosphate, a vinyl phosphonate, a C5-methyl (R or S or racemic), a C5-methyl on vinyl, reduced vinyl (e.g., three carbon alkyl) or the like.

FIG. 19 depicts conjugates moieties according to certain exemplary embodiments. A suitable conjugated moiety can be any length alkyl chain, a vitamin, a ligand, a peptide or a bioactive conjugate, e.g., a glycosphingolipid, a polyunsaturated fatty acid, a secosteroid, a steroid hormone, a steroid lipid, or the like.

FIG. 23 is a pictorial representation of a VP-modified RNA according to certain exemplary embodiments.

FIG. 24 illustrates the sequences of VP-modified oligonucleotides synthesized according to certain exemplary embodiments. FIG. 24 discloses SEQ ID NOS 323-342, respectively, in order of appearance.

FIG. 27A discloses SEQ ID NOS 343-346, 234, 347-348, 235, 349-350, 236, 351-352, 237, 353 and 238, respectively, in order of appearance.

FIGS. 28A and 28B depict VP-modified sequences prepared by a synthesizer. FIG. 28A discloses SEQ ID NOS 354-360, respectively, in order of appearance. FIG. 28B discloses SEQ ID NOS 361-364, 355-360, respectively, in order of appearance.

FIG. 34 discloses SEQ ID NOS 343-346, 234, 348, 235, 349-350, 236, 351-352, 237, 353, 238, respectively, in order of appearance.

FIG. 35 illustrates a number of exemplary oligonucleotide backbone modifications. FIG. discloses SEQ ID NOS 365, 386 and 366-373, respectively, in order of columns.

FIG. 47 discloses SEQ ID NOS 374-385, respectively, in order of appearance.

DETAILED DESCRIPTION

Figure 1:
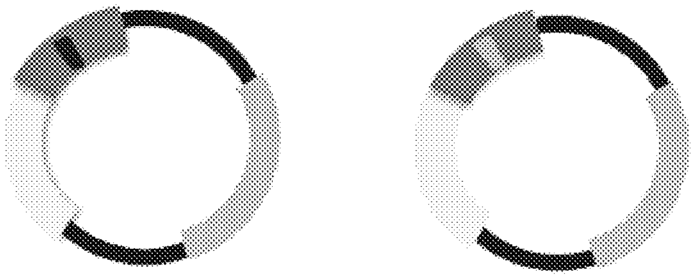
FIG. 1 depicts psiCHECK reporter plasmids containing either a wild-type region of htt or the same region of htt with the SNP, rs362273.

The present disclosure relates to compositions comprising oligonucleotide, e.g., RNA, silencing agents, e.g., RNAs such as double-stranded RNAs ("dsRNAs"), antisense oligonucleotides ("ASOs") and the like, that are useful for silencing allelic polymorphisms located within a gene encoding a mutant protein. In a particular aspect, an oligonucleotide, e.g., an RNA, silencing agent is a dsRNA agent provided herein, that destroys a corresponding mutant mRNA (e.g., a SNP-containing mRNA) with nucleotide specificity and selectivity. Oligonucleotide, e.g., RNA, silencing agents, e.g., dsRNA agents disclosed herein target mRNA corresponding to polymorphic regions of a mutant gene, resulting in cleavage of mutant mRNA, and preventing synthesis of the corresponding mutant protein e.g., a gain of function mutant protein such as the huntingtin protein.

Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

As used herein in the context of oligonucleotide sequences, "A" represents a nucleoside comprising the base adenine (e.g., adenosine or a chemically-modified derivative thereof), "G" represents a nucleoside comprising the base guanine (e.g., guanosine or a chemically-modified derivative thereof), "U" represents a nucleoside comprising the base uracil (e.g., uridine or a chemically-modified derivative thereof), and "C" represents a nucleoside comprising the base adenine (e.g., cytidine or a chemically-modified derivative thereof), As used herein, the term "capping group" refers to a chemical moiety that replaces a hydrogen atom in a functional group such as an alcohol (ROH), a carboxylic acid ($RCO_2H$), or an amine ($RNH_2$). Non-limiting examples of capping groups include: alkyl (e.g., methyl, tertiary-butyl); alkenyl (e.g., vinyl, allyl); carboxyl (e.g., acetyl, benzoyl); carbamoyl; phosphate; and phosphonate (e.g., vinylphosphonate). Other suitable capping groups are known to those of skill in the art.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, and the like; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. In particular embodiments, RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, exemplary oligonucleotides include, but are not limited to, siRNAs, miRNAs, shRNAs, CRISPR guides, DNA oligonucleotides, antisense oligonucleotides, AAV oligonucleotides, gapmers, mixmers, miRNA inhibitors, SSOs, PMOs, PNAs and the like.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

As used herein, the term "hsiRNA" refers to an embodiment of the double-stranded RNAs provided herein, wherein the RNA molecule is fully chemically modified, including one or more hydrophobic modifications, as described herein.

An RNAi agent, e.g., an RNA silencing agent, having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, translational repression and the like) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence, e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g., promoter or enhancer elements) of a target gene. In other embodiments, the target polynucleotide sequence is a target mRNA encoded by a target gene.

A gene "involved" in a disease or disorder includes a gene, the normal or aberrant expression or function of which effects or causes the disease or disorder or at least one symptom of said disease or disorder.

As used herein, the term "target gene" (e.g., the mutant allele of a heterozygous polymorphism, e.g., a heterozygous SNP) is a gene whose expression is to be substantially inhibited or "silenced." This silencing can be achieved by RNA silencing, e.g., by cleaving the mRNA of the target gene or translational repression of the target gene. The term "non-target gene" (e.g., the wild-type allele) is a gene whose expression is not to be substantially silenced. In one embodiment, the polynucleotide sequences of the target and non-target gene (e.g., mRNA encoded by the target and non-target genes) can differ by one or more nucleotides. In another embodiment, the target and non-target genes can differ by one or more polymorphisms (e.g., single nucleotide polymorphisms or SNPs). In another embodiment, the target and non-target genes can share less than 100% sequence identity. In another embodiment, the non-target gene may be a homolog (e.g., an ortholog or paralog) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is an allele (e.g., the corresponding wild-type allele) whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism," as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared.

In particular embodiments, the polymorphism is a single nucleotide polymorphism (SNP). A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP, also referred to herein as a heterozygous SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In particular embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g. a SNP allele) is at least 10% (e.g., at least 15%, 20%, 25%, 30%, 35%, 40% or more) in a sample population.

The term "gain-of-function mutation," as used herein, refers to any mutation in a gene in which the protein encoded by said gene (i.e., the mutant protein) acquires a function not normally associated with the protein (i.e., the wild-type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "gain-of-function disorder" refers to a disorder characterized by a gain-of-function mutation. In one embodiment, the gain-of-function disorder is a neurodegenerative disease caused by a gain-of-function mutation, e.g., polyglutamine disorders and/or trinucleotide repeat diseases, for example, Huntington's disease. In another embodiment, the gain-of-function disorder is caused by a gain-of-function in an oncogene, the mutated gene product being a gain-of-function mutant, e.g., cancers caused by a mutation in the ret oncogene (e.g., ret-1), for example, endocrine tumors, medullary thyroid tumors, parathyroid hormone tumors, multiple endocrine neoplasia type2, and the like. Additional exemplary gain-of-function disorders include, but are not limited to, Alzheimer's disease, amyotrophic lateral sclerosis (ALS), human immunodeficiency disorder (HIV), and slow channel congenital myasthenic syndrome (SCCMS).

The term "trinucleotide repeat diseases," as used herein, refers to any disease or disorder characterized by an expanded trinucleotide repeat region located within a gene, the expanded trinucleotide repeat region being causative of the disease or disorder. Examples of trinucleotide repeat diseases include, but are not limited to, spino-cerebellar ataxia type 12 spino-cerebellar ataxia type 8, fragile X syndrome, fragile XE Mental Retardation, Friedreich's ataxia and myotonic dystrophy. Preferred trinucleotide repeat diseases for treatment according to the present invention are those characterized or caused by an expanded trinucleotide repeat region at the 5' end of the coding region of a gene, the gene encoding a mutant protein which causes or is causative of the disease or disorder. Certain trinucleotide diseases, for example, fragile X syndrome, where the mutation is not associated with a coding region may not be suitable for treatment according to the methodologies of the present invention, as there is no suitable mRNA to be targeted by RNAi. By contrast, disease such as Friedreich's ataxia may be suitable for treatment according to the methodologies of the invention because, although the causative mutation is not within a coding region (i.e., lies within an intron), the mutation may be within, for example, an mRNA precursor (e.g., a pre-spliced mRNA precursor).

The term "polyglutamine disorder," as used herein, refers to any disease or disorder characterized by an expanded of a $(CAG)_n$ repeats at the 5' end of the coding region (thus encoding an expanded polyglutamine region in the encoded protein). In one embodiment, polyglutamine disorders are characterized by a progressive degeneration of nerve cells. Examples of polyglutamine disorders include, but are not limited to, Huntington's disease, spino-cerebellar ataxia type 1, spino-cerebellar ataxia type 2, spino-cerebellar ataxia type 3 (also known as Machado-Joseph disease), and spino-cerebellar ataxia type 6, spino-cerebellar ataxia type 7, dentatorubral-pallidoluysian atrophy and the like.

The term "single nucleotide polymorphism disorder" or "SNP disorder" refers to a disorder characterized by a the presence of an SNP, e.g., a heterozygous SNP. SNP disorders include, but are not limited to, phenylketonuria, cystic fibrosis, sickle-cell anemia, albinism, Huntington's disease, myotonic dystrophy type 1, hypercholesterolemia (autosomal dominant, type B), neurofibromatosis (type 1), polycystic kidney disease (1 and 2), hemophilia A, Duchenne's muscular dystrophy, X-linked hypophosphatemic rickets, Rett's syndrome, non-obstructive spermatogenic failure and the like. An exemplary heterozygous SNP disorder is Huntington's disease.

In certain aspects, a double-stranded RNA (dsRNA) is provided comprising a first strand of about 15-35 nucleotides that is complementary to a region of a gene comprising an allelic polymorphism, and a second strand of about 15-35 nucleotides that is complementary to at least a portion of the first strand, wherein the first strand comprises a single nucleotide polymorphism (SNP) position nucleotide at a position 2 to 7 from the 5' end that is complementary to the allelic polymorphism; and a mismatch (MM) position nucleotide located 2-11 nucleotides from the SNP position nucleotide that is a mismatch with a nucleotide in the gene. In some cases, the MM position is located 2 to 10 nucleotides from the SNP position. In some cases, the SNP position nucleotide is any one of positions 2 to 6 from the 5' end. In exemplary embodiments, the SNP position nucleotide is at a position 2, 4 or 6 from the 5' end and the mismatch (MM) position nucleotide is located 2-6 nucleotides from the SNP position nucleotide. In some cases, the SNP position nucleotide is any one of positions 2 to 6 from the 5' end and the nucleotide is located 2-6 nucleotides from the SNP position nucleotide.

As used herein, a "single nucleotide polymorphism position nucleotide" or a "SNP position nucleotide" refers to the position of an RNA described herein (e.g., the first strand of a dsRNA) that corresponds to the polymorphic position of a target nucleic acid sequence (i.e., either the mutant nucleotide corresponding to the SNP allele or the wild-type nucleotide corresponding to the wild-type allele). For example, a strand may be labeled "SNP2," "SNP3," or "SNP3" to denote the position of the SNP as being 2, 3, or 4 nucleotides from the 5' end of the strand.

In certain exemplary embodiments, a SNP position nucleotide is within a seed region. In certain exemplary embodiments, a SNP position nucleotide is located from position 2 to position 7 from the 5' end, from position 2 to position 6 from the 5' end, or from position 2 to position 5 from the 5' end. In certain exemplary embodiments, a SNP position nucleotide is located at position 2 from the 5' end, at position 3 from the 5' end, at position 4 from the 5' end, at position from the 5' end, at position 6 from the 5' end, or at position 7 from the 5' end of an RNA described herein (e.g., the first strand of a dsRNA). In certain exemplary embodiments, a SNP position nucleotide is located at a position set forth in Tables 5-7.

As used herein, the term "seed region" refers to a six-nucleotide stretch corresponding to positions 2-7 from the 5' end of an RNA strand. siRNA recognition of the target mRNA is believed to be conferred by the seed region of its antisense strand.

As used herein, a "mismatch position nucleotide" or a "MM position nucleotide" refers to the position of an RNA described herein (e.g., the first strand of a dsRNA) that is in a position that does not correspond to the SNP position nucleotide. A MM position nucleotide can be defined by its position from the 5' end or the 3' end of an RNA described herein (e.g., the 5' or the 3' end of first strand of a dsRNA), or defined by its position relative to a SNP position nucleotide of an RNA described herein (e.g., a first strand of a dsRNA).

In certain exemplary embodiments, a MM position nucleotide is located 2-11 nucleotides, 2-10 nucleotides, 2-9 nucleotides, 2-8 nucleotides, 2-7 nucleotides, or 2-6 nucleotides from a SNP position nucleotide. In certain exemplary embodiments, a MM position nucleotide is located 11 nucleotides, 10 nucleotides, 9 nucleotides, 8 nucleotides, 7 nucleotides, 6 nucleotides, 5 nucleotides, 4 nucleotides, 3 nucleotides or 2 nucleotides from a SNP position nucleotide. In certain exemplary embodiments, a MM position nucleotide is located at a position set forth in Tables 5-7.

In one embodiment, an RNA described herein (e.g., the first strand of a dsRNA) is homologous to an allelic polymorphism except for one mismatched oligonucleotide at a particular position relative to the nucleotide corresponding to the allelic polymorphism. In certain embodiments, the mismatch is within about 6 nucleotides of the SNP position nucleotide, within about 5 nucleotides of the SNP position nucleotide, within about 4 nucleotides of the SNP position nucleotide, within about 3 nucleotide of the SNP position nucleotide, within about 2 nucleotide of the SNP position nucleotide, or within about 1 nucleotide of the SNP position nucleotide. In particular embodiments, the mismatch is not adjacent to a SNP position nucleotide.

In another embodiment, a SNP position nucleotide is at position 2, 3, 4, 5, or 6 from the 5' end. In an embodiment, a SNP position nucleotide is at position 2 from the 5' end. In an embodiment, is at position 3 from the 5' end. In an embodiment, a SNP position nucleotide is at position 4 from the 5' end. In an embodiment, a SNP position nucleotide is at position 5 from the 5' end. In an embodiment, a SNP position nucleotide is at position 6 from the 5' end.

In certain exemplary embodiments, an RNA described herein (e.g., the first strand of a dsRNA) comprises a MM position nucleotide at position 5, 7, 8, 11, 14, 15 or 16 from the 5' end. In certain exemplary embodiments, an RNA described herein (e.g., the first strand of a dsRNA) comprises a MM position nucleotide 1, 2, 3, 4, 5, 8, 9, 10 or 11 nucleotides from the SNP position nucleotide.

In certain exemplary embodiments, an RNA described herein (e.g., the first strand of a dsRNA) comprises a SNP position nucleotide (referenced from the 5' end)—MM position nucleotide (referenced from the 5' end) combination selected from the group consisting of 2-7, 4-7, 4-8, 4-15, 6-5, 6-8, 6-11, 6-14, 6-16, 3-5, 3-7 and 3-8.

In a particularly exemplary embodiment, an RNA described herein (e.g., the first strand of a dsRNA) comprises an SNP position nucleotide at position 6 from the 5' end and a MM position nucleotide at position 11 from the 5' end. In another particularly exemplary embodiment, an RNA described herein (e.g., the first strand of a dsRNA) comprises an SNP position nucleotide at position 4 from the 5' end and a mismatch at position 7 from the 5' end.

In one aspect, the double-stranded RNAs provided herein selectively silence a mutant allele having an allelic polymorphism. In an embodiment, the double-stranded RNAs provided herein silence a mutant allele having an allelic polymorphism and do not affect the wild-type allele of the same gene. In another embodiment, the double-stranded RNAs provided herein silence a mutant allele having an allelic polymorphism and silence the wild-type allele of the same gene to a lesser extent than the mutant allele.

Accordingly, in one aspect, the present invention provides a method of treating a subject having or at risk of having a disease characterized or caused by a mutant protein associated with an allelic polymorphism by administering to the subject an effective amount of an RNAi agent targeting an allelic polymorphism within a gene encoding a mutant protein (e.g., huntingtin protein), such that sequence-specific interference of a gene occurs resulting in an effective treatment for the disease.

In one aspect, RNA silencing agents disclosed herein preferentially silence a mutant allele comprising a polymorphism more efficiently than the corresponding wild-type allele. In certain exemplary embodiments, dsRNAs disclosed herein silence the allele comprising a polymorphism about 20%, about 30%, about 40%, about 50%, about 60%, about 70%, about 80%, or about 90% more than the corresponding wild-type allele. In an embodiment, RNA silencing agents disclosed herein silence the allele comprising a polymorphism at least about 50% more than the corresponding wild-type allele. In certain exemplary embodiments, dsRNAs disclosed herein silence the allele comprising a polymorphism at least about 5 times, about 10 times, about 15 times, about 20 times, about 25 times, about 30 times, about 35 times, about 40 times, about 45 times, about 50 times, about 55 times, about 60 times, about 65 times, about 70 times, about 75 times, about 80 times, about 85 times, about 90 times, about 95 times, about 100 times, about 110 times, about 120 times, about 130 times, about 140 times, about 150 times, about 160 times, about 170 times, about 180 times, about 190 times, about 200 times, about 250 times, about 300 times, about 350 times, about 400 times, about 450 times, or up to about 500 times the level of silencing of the corresponding wild-type allele.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "antisense oligonucleotide" or "ASO" refers to a nucleic acid (e.g., an RNA), having sufficient sequence complementarity to a target an RNA (e.g., a SNP-containing mRNA or a SNP-containing pre-mRNA) in order to block a region of a target RNA in an effective manner, e.g., in a manner effective to inhibit translation of a target mRNA and/or splicing of a target pre-mRNA. An antisense oligonucleotide having a "sequence sufficiently complementary to a target RNA" means that the antisense agent has a sequence sufficient to mask a binding site for a protein that would otherwise modulate splicing and/or that the antisense agent has a sequence sufficient to mask a binding site for a ribosome and/or that the antisense agent has a sequence sufficient to alter the three-dimensional structure of the targeted RNA to prevent splicing and/or translation.

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, Van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

Linkers useful in conjugated compounds of the invention include glycol chains (e.g., polyethylene glycol), alkyl chains, peptides, RNA, DNA, and combinations thereof. As used herein, the abbreviation "TEG" refers to triethylene glycol.

Design of Oligonucleotides

In certain embodiments, an oligonucleotide, e.g., an siRNA, of the invention is a duplex consisting of a sense strand and complementary antisense strand, the antisense strand having sufficient complementary to an target mRNA containing an allelic polymorphism to mediate RNAi. In exemplary embodiments, the siRNA molecule has a length from about 10-50 or more nucleotides, i.e., each strand comprises 10-50 nucleotides (or nucleotide analogs). In particularly exemplary embodiments, the siRNA molecule has a length from about 15-35, e.g., about 15, about 16, about 17, about 18, about 19, about 20, about 21, about 22, about 23, about 24, about 25, about 26, about 27, about 28, about 29, about 30, about 31, about 32, about 33, about 34 or about 35 nucleotides in each strand, wherein one of the strands is sufficiently complementary to a target region. In exemplary embodiments, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. In exemplary embodiments, the siRNA molecule has a length from about 10-50 or more nucleotides, i.e., each strand comprises 10-50 nucleotides (or nucleotide analogs). In particularly exemplary embodiments, the siRNA molecule has a length from about 15-35, e.g., about 15, about 16, about 17, about 18, about 19, about 20, about 21, about 22, about 23, about 24, about 25, about 26, about 27, about 28, about 29, about 30, about 31, about 32, about 33, about 34 or about 35 nucleotides in each strand, wherein one of the strands is substantially complementary to a target sequence containing an allelic polymorphism, and the other strand is complementary or substantially complementary to the first strand. In an embodiment, the siRNA molecule in fully complementary to a target sequence containing an allelic polymorphism except for one additional mismatch, also known as secondary mismatch.

Generally, siRNAs can be designed by using any method known in the art, for instance, by using the following protocol:

1. The siRNA may be specific for a target sequence which contains an allelic polymorphism. In exemplary embodiments, the first strand is substantially complementary to the target sequence containing an allelic polymorphism having one mismatch to the target sequence containing an allelic polymorphism, and the other strand is substantially complementary to the first strand. In an embodiment, the target sequence is outside a coding region of the target gene. Exemplary target sequences are selected from the 5' untranslated region (5'-UTR) or an intronic region of a target gene. Cleavage of mRNA at these sites should eliminate translation of corresponding mutant protein. Target sequences from other regions of the htt gene are also suitable for targeting. A sense strand is designed based on the target sequence. Further, siRNAs with lower G/C content (35-55%) may be more active than those with G/C content higher than 55%. Thus in one embodiment, the invention includes nucleic acid molecules having 35-55% G/C content.
2. The sense strand of the siRNA is designed based on the sequence of the selected target site and the position of the allelic polymorphism. In exemplary embodiments, the RNA silencing agents of the invention do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently identical to a target sequence portion of the target gene to effect RISC-mediated cleavage of the target gene are used. Accordingly, in an exemplary embodiment, the sense strand of the siRNA is designed have to have a sequence sufficiently identical to a portion of the target which contains an allelic polymorphism. The invention has the advantage of being able to tolerate certain sequence variations to enhance efficiency and specificity of RNAi. In an aspect, the sense strand has 1 mismatched nucleotide with a target region containing an allelic polymorphism, such as a target region that differs by at least one base pair between a wild-type and mutant allele, e.g., a target region comprising the gain-of-function mutation, and the other strand is identical or substantially identical to the first strand. In some embodiments, the mismatch is 4 nucleotides upstream, 3 nucleotides upstream nucleotide corresponding to the allelic polymorphism, 2 nucleotides upstream nucleotide corresponding to the allelic polymorphism, 1 nucleotide upstream, 1 nucleotide downstream nucleotide corresponding to the allelic polymorphism, 2 nucleotides downstream nucleotide corresponding to the allelic polymorphism, 3 nucleotides downstream nucleotide corresponding to the allelic polymorphism, 4 nucleotides downstream nucleotide corresponding to the allelic polymorphism, or 5 nucleotides downstream nucleotide corresponding to the allelic polymorphism. In certain embodiments, the mismatch is not adjacent to the nucleotide corresponding to the allelic polymorphism. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., percent (%) homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). An exemplary, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). An exemplary, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA. As noted above, it is desirable to choose a target region wherein the mutant:wild-type mismatch is a purine:purine mismatch.
4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.
5. Select one or more sequences that meet the criteria for evaluation.

Further general information about the design and use of siRNA may be found in "The siRNA User Guide," available at The Max-Plank-Institut fur Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional exemplary hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference in its entirety for all purposes.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant huntingtin mRNA), the siRNA may be incubated with target cDNA (e.g., huntingtin cDNA) in a *Drosophila*-based in vitro mRNA expression system. Radiolabeled with $^{32}P$, newly synthesized target mRNAs (e.g., huntingtin mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

Sites of siRNA-mRNA complementation are selected, which result in optimal mRNA specificity and maximal mRNA cleavage.

siRNA-Like Molecules siRNA-like molecules of the invention have a sequence (i.e., have a strand having a sequence) that is "sufficiently complementary" to a target sequence of an mRNA (e.g. an htt mRNA) to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g., within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further exemplary embodiment, the "bulge" is centered at nucleotide positions 12 and 13 from the 5' end of the miRNA molecule.

Modified RNA Silencing Agents

In certain aspects of the invention, an RNA silencing agent (or any portion thereof) of the invention as described supra may be modified such that the activity of the agent is further improved. For example, the RNA silencing agents described in above may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In certain exemplary embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is typically utilized because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly exemplary embodiments, the universal nucleotide is an inosine residue or a naturally occurring analog thereof.

In certain embodiments, the RNA silencing agents of the invention are modified by the introduction of at least one destabilizing nucleotide within 11 nucleotides from a specificity-determining nucleotide (e.g., within 11 nucleotides from the nucleotide which recognizes the disease-related polymorphism (e.g., a SNP position nucleotide)). For example, the destabilizing nucleotide may be introduced at a position that is within 11, 10, 9, 8, 7, 6, 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destabilizing nucleotide and the specificity-determining nucleotide). In RNA silencing agents having two strands or strand portions (e.g., siRNAs and shRNAs), the destabilizing nucleotide may be introduced in the strand or strand portion that does not contain the specificity-determining nucleotide. In particular exemplary embodiments, the destabilizing nucleotide is introduced in the same strand or strand portion that contains the specificity-determining nucleotide.

In certain embodiments, the RNA silencing agents of the invention are modified by the introduction of a modified intersubunit linkage of Formula 1:

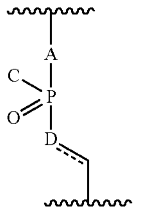

(1)

wherein:

D is selected from the group consisting of O, $OCH_2$, OCH, $CH_2$, and CH;

C is selected from the group consisting of $O^-$, OH, $OR^1$, $NH^-$, $NH_2$, $S^-$, and SH;

A is selected from the group consisting of 0 and $CH_2$;

$R^1$ is a protecting group;

⎓ an optional double bond; and the intersubunit is bridging two optionally modified nucleosides.

In an embodiment, when C is $O^-$, either A or D is not O.

In an embodiment, D is CH2. In another embodiment, the modified intersubunit linkage of Formula VIII is a modified intersubunit linkage of Formula 2:

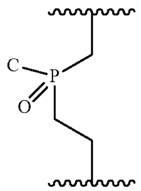

(2)

In an embodiment, D is O. In another embodiment, the modified intersubunit linkage of Formula VIII is a modified intersubunit linkage of Formula 3:

(3)

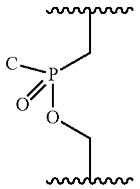

In an embodiment, D is $CH_2$. In another embodiment, the modified intersubunit linkage of Formula VIII is a modified intersubunit linkage of Formula 4:

(4)

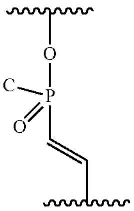

In another embodiment, the modified intersubunit linkage is a modified intersubunit linkage of Formula 5:

(5)

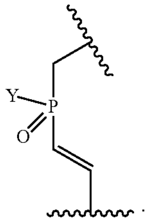

In an embodiment, D is $OCH_2$. In another embodiment, the modified intersubunit linkage is a modified intersubunit linkage of Formula 6:

(6)

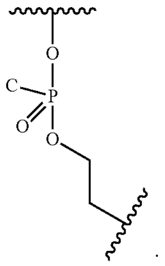

In another embodiment, the modified intersubunit linkage of Formula VII is a modified intersubunit linkage of Formula 7:

(7)

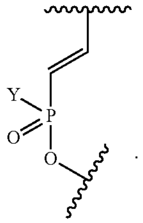

Figure 43:
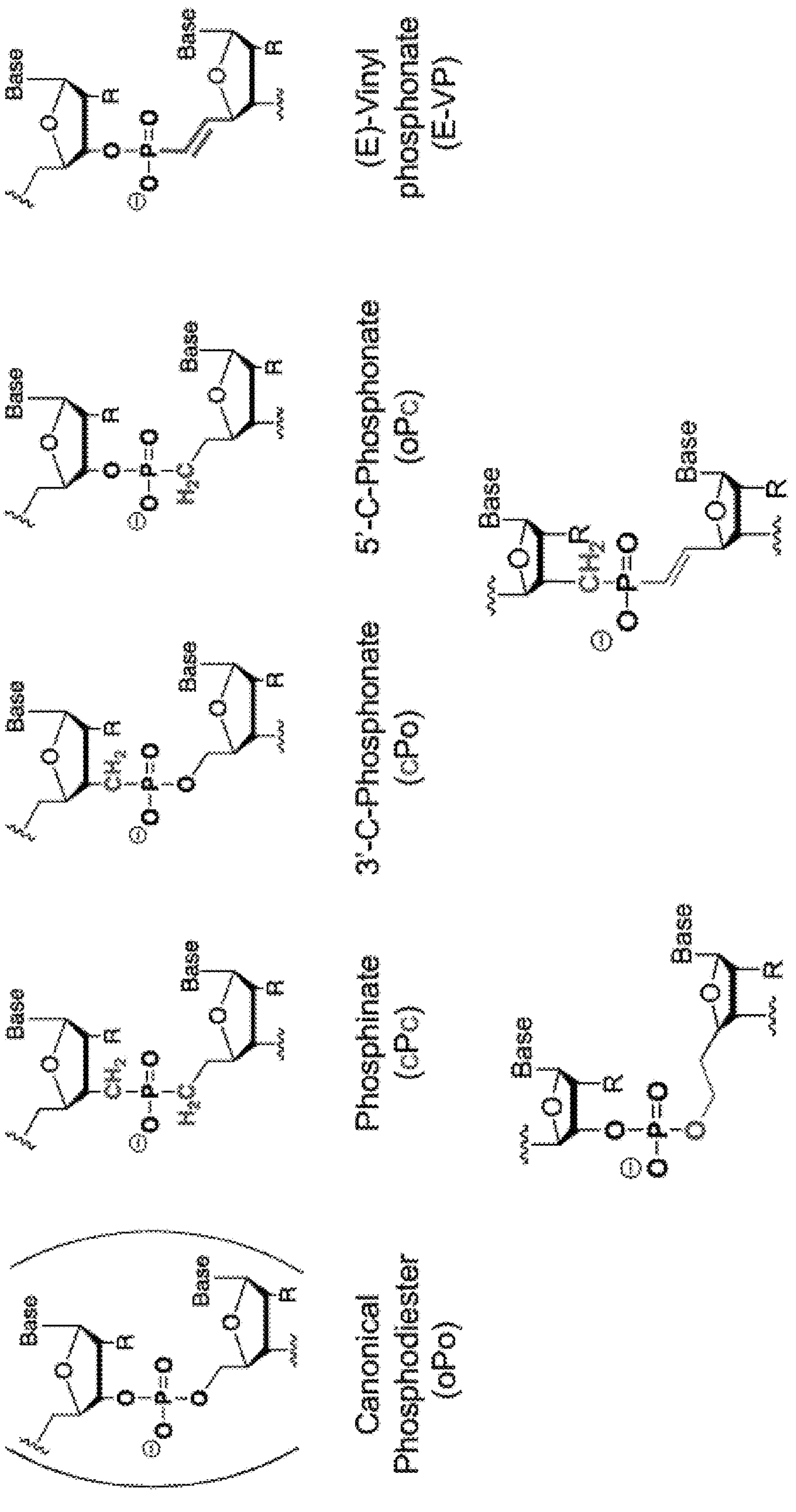
FIG. 43 illustrates example modified intersubunit linkers.

In certain embodiments, the RNA silencing agents of the invention are modified by the introduction of one or more of the intersubunit linkers of FIG. 43. In an exemplary embodiment, an intersubunit linker of FIG. 43 is inserted between the SNP position nucleotide and a nucleotide at a position directly adjacent to and on either side of the SNP position nucleotide of the antisense strand.

In certain embodiments, the RNA silencing agents of the invention are modified by the introduction of one or more vinyl phosphonate (VP) motifs in the intersubunit linker having the following formula:

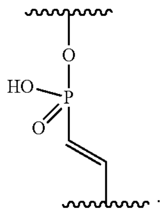 [SMILES: */C=C/P(=O)(O)O*]

In certain embodiments, a VP motif is inserted at any position(s) of an oligonucleotide, e.g., an RNA. For example, for an oligonucleotide having a length of 20 nucleotides, a VP motif can be inserted at position 1-2, 2-3, 3-4, 4-5, 5-6, 6-7, 7-8, 8-9, 9-10, 10-11, 11-12, 12-13, 13-14, 14-15, 15-16, 16-17, 17-18, 18-19 or 19-20 and at any combinations of these.

In certain exemplary embodiments, a VP motif is inserted at one or more of positions 1-2, 5-6, 6-7, 10-11, 18-19 and/or 19-20 of the antisense strand.

In other exemplary embodiments, a VP motif is inserted at one or more of positions 1-2, 6-7, 10-11 and/or 19-20 of the antisense strand.

In an exemplary embodiment, a VP motif is inserted next to (i.e., between a SNP position nucleotide and a nucleotide at a position directly adjacent to and on either side of) the SNP position nucleotide of the antisense strand. In another exemplary embodiment, a VP motif is inserted next to (i.e., between a MM position nucleotide and a nucleotide at a position directly adjacent to and on either side of) the MM position nucleotide of the antisense strand.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. In exemplary embodiments, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S'5) of said RNA silencing agent.

In one embodiment, the asymmetry of an RNA silencing agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. In an exemplary embodiment, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). In exemplary embodiments, the base pair is selected from the group consisting of an I:A, I:U and I:C. In yet another embodiment, the asymmetry of an RNA silencing agent of the invention may be enhanced such that there is at least one base pair comprising a modified nucleotide. In particular embodiments, the modified nucleotide is selected from the group consisting of 2-amino-G, 2-amino-A, 2,6-diamino-G, and 2,6-diamino-A.

In certain embodiments, the RNA silencing agents of the invention are altered at one or more intersubunit linkages in an oligonucleotide by the introduction of a vinyl phosphonate (VP) motif having the following formula:

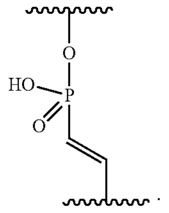

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a particular aspect, the invention features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an “internal” nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a particular embodiment of the present invention, the RNA silencing agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

In certain embodiments, the RNA silencing agents of the invention are altered at one or more intersubunit linkages in an oligonucleotide by the introduction of a vinyl phosphonate (VP) motif having the following formula:

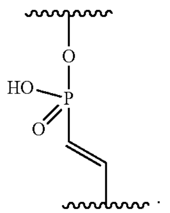 [SMILES: */C=C/P(=O)(O)O*]

A variety of oligonucleotide types (e.g., gapmers, mixmers, miRNA inhibitors, splice-switching oligonucleotides (“SSOs”), phosphorodiamidate morpholino oligonucleotides (“PMOs”), peptide nucleic acids (“PNAs”) and the like) can be used in the oligonucleotides described herein, optionally utilizing various combinations of modifications (e.g., chemical modifications) and/or conjugations described herein and in, e.g., U.S. Ser. No. 15/089,423; U.S. Ser. No. 15/236,051; U.S. Ser. No. 15/419,593; U.S. Ser. No. 15/697,120 and U.S. Pat. No. 9,809,817; and U.S. Ser. No. 15/814,350 and U.S. Pat. No. 9,862,350, each of which is incorporated herein by reference in its entirety for all purposes.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is C1-C6 alkyl, alkenyl or alkynyl and halo is F, Cl, Br or I.

In particular embodiments, the modifications are 2'-fluoro, 2'-amino and/or 2'-thio modifications. Particularly exemplary modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moieties of the instant invention. Additional modified residues include, deoxy-abasic, inosine, N3-methyl-uridine, N6,N6-dimethyl-adenosine, pseudouridine, purine ribonucleoside and ribavirin. In a particularly exemplary embodiment, the 2' moiety is a methyl group such that the linking moiety is a 2'-O-methyl oligonucleotide.

In an exemplary embodiment, the RNA silencing agent of the invention comprises locked nucleic acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the invention comprises peptide nucleic acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

In certain exemplary embodiments nucleobase-modified ribonucleotides, i.e., ribonucleotides, containing at least one non-naturally occurring nucleobase instead of a naturally occurring nucleobase, are used. Bases may be modified to block the activity of adenosine deaminase. Exemplary modified nucleobases include, but are not limited to, uridine and/or cytidine modified at the 5-position, e.g., 5-(2-amino) propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (in most cases, sequence changes are located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents may be modified with chemical moieties, for example, to enhance cellular uptake by target cells (e.g., neuronal cells). Thus, the invention includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, a modification to the RNA silencing agents of the invention comprise a vinyl phosphonate (VP) motif in one or more intersubunit linkers of an oligonucleotide, wherein the VP motif has the following formula:

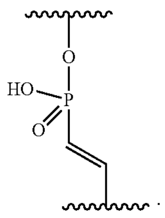

In a particular embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. In certain exemplary embodiments, these are located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, typically covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecogenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycosides, artificial endonucleases (e.g. EDTA), lipophilic molecules, e.g., cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octadecyl) glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, $Eu^{3+}$ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, jasplakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon.

In one aspect, the ligand is a lipid or lipid-based molecule. Such a lipid or lipid-based molecule typically binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. In a particular embodiment, the lipid based ligand binds HSA. However, it is desired that the affinity not be so strong that the HSA-ligand binding cannot be reversed. In another exemplary embodiment, the lipid based ligand binds HSA weakly or not at all.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, typically a helical cell-permeation agent. In certain exemplary embodiments, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is typically an alpha-helical agent, which typically has a lipophilic face and a lipophobic face.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

6) Hydrophobic Moieties

In certain embodiments of the double-stranded RNAs provided herein, the RNA molecule is conjugated to one or more hydrophobic moieties (see PCT Pub. No. WO 2018/031933, which is incorporated herein by reference). In an embodiment, the hydrophobic moiety has an affinity for low density lipoprotein and/or intermediate density lipoprotein. In a related embodiment, the hydrophobic moiety is a saturated or unsaturated moiety having fewer than three double bonds.

In another embodiment, the hydrophobic moiety has an affinity for high density lipoprotein. In a related embodiment, the hydrophobic moiety is a polyunsaturated moiety having at three or more double bonds (e.g., having three, four, five, six, seven, eight, nine or ten double bonds). In a particular embodiment, the hydrophobic moiety is a polyunsaturated moiety having three double bonds. In a particular embodiment, the hydrophobic moiety is a polyunsaturated moiety having four double bonds. In a particular embodiment, the hydrophobic moiety is a polyunsaturated moiety having five double bonds. In a particular embodiment, the hydrophobic moiety is a polyunsaturated moiety having six double bonds.

In another embodiment, the hydrophobic moiety is selected from the group consisting of fatty acids, steroids, secosteroids, lipids, gangliosides and nucleoside analogs, and endocannabinoids.

In another embodiment, the hydrophobic moiety is a neuromodulatory lipid, e.g., an endocannabinoid. Non-limiting examples of endocannabinoids include: anandamide, arachidonoylethanolamine, 2-Arachidonoyl glyceryl ether (noladin ether), 2-Arachidonoyl glyceryl ether (noladin ether), 2-Arachidonylglycerol, and N-Arachidonoyl dopamine.

In another embodiment, the hydrophobic moiety is an omega-3 fatty acid. Non-limiting examples of omega-3 fatty acids include, but are not limited to: hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, Timnodonic acid), heneicosapentaenoic acid (HPA), docosapentaenoic acid (DPA, clupadonic acid), docosahexaenoic acid (DHA, cervonic acid), tetracosapentaenoic acid, and tetracosahexaenoic acid (nisinic acid).

In another embodiment, the hydrophobic moiety is an omega-6 fatty acid. Non-limiting examples of omega-6 fatty acids include, but are not limited to: linoleic acid, gamma-linolenic acid (GLA), eicosadienoic acid, dihomo-gamma-linolenic acid (DGLA), arachidonic acid (AA), docosadienoic acid, adrenic acid, docosapentaenoic acid (osbond acid), tetracosatetraenoic acid, and tetracosapentaenoic acid.

In another embodiment, the hydrophobic moiety is an omega-9 fatty acid. Non-limiting examples of omega-9 fatty acids include, but are not limited to: oleic acid, eicosenoic acid, Mead acid, erucic acid, and nervonic acid.

In another embodiment, the hydrophobic moiety is a conjugated linolenic acid. Non-limiting examples of conjugated linolenic acids include, but are not limited to: α-calendic acid, β-calendic acid, jacaric acid, α-eleostearic acid, β-eleostearic acid, catalpic acid, and punicic acid.

In another embodiment, the hydrophobic moiety is a saturated fatty acid. Non-limiting examples of saturated fatty acids include, but are not limited to: caprylic acid, capric acid, docosanoic acid, lauric acid, myristic acid, palmitic acid, stearic acid, arachidic acid, behenic acid, lignoceric acid, and cerotic acid.

In another embodiment, the hydrophobic moiety is an acid selected from the group consisting of: rumelenic acid, α-parinaric acid, β-parinaric acid, bosseopentaenoic acid, pinolenic acid, and podocarpic acid.

In another embodiment, the hydrophobic moiety is selected from the group consisting of: docosanoic acid (DCA), docosahexaenoic acid (DHA), and eicosapentaenoic acid (EPA). In a particular embodiment, the hydrophobic moiety is docosanoic acid (DCA). In another particular embodiment, the hydrophobic moiety is DHA. In another particular embodiment, the hydrophobic moiety is EPA.

In another embodiment, the hydrophobic moiety is a secosteroid. In a particular embodiment, the hydrophobic moiety is calciferol. In another embodiment, the hydrophobic moiety is a steroid other than cholesterol.

In a particular embodiment, the hydrophobic moiety is not cholesterol.

In another embodiment, the hydrophobic moiety is an alkyl chain, a vitamin, a peptide, or a bioactive conjugate, including but not limited to: glycosphingolipids, polyunsaturated fatty acids, secosteroids, steroid hormones, or sterol lipids.

In an embodiment, a double-stranded RNA provided herein comprises one or more chemically-modified nucleotides. In a particular embodiment, the double-stranded RNA comprises alternating 2'-methoxy-nucleotides and 2'-fluoro-nucleotides. In another particular embodiment, one or more nucleotides of the double-stranded RNA are connected to adjacent nucleotides via phosphorothioate linkages. In certain embodiments of the dsRNAs disclosed herein, the mismatch nucleotide and the nucleotide(s) adjacent to the mismatch nucleotide are 2'-methoxy-ribonucleotides.

In another particular embodiment, the nucleotides at positions 1 and 2 from the 3' end of the double-stranded RNAs provided herein are connected to adjacent nucleotides via phosphorothioate linkages. In yet another particular embodiment, the nucleotides at positions 1 and 2 from the 3' end of the double-stranded RNAs and the nucleotides at positions 1 and 2 from the 5' end of the double-stranded RNAs are connected to adjacent nucleotides via phosphorothioate linkages.

In one embodiment of a double-stranded RNA, the first oligonucleotide comprises at least 16 contiguous nucleotides, a 5' end, a 3' end, and has complementarity to a target, wherein:

(1) the first oligonucleotide comprises alternating 2'-methoxy-nucleotides and 2'-fluoro-nucleotides;
(2) the nucleotides at positions 2 and 14 from the 5' end are not 2'-methoxy-nucleotides;
(3) the nucleotides are connected via phosphodiester or phosphorothioate linkages; and
(4) the nucleotides at positions 1-6 from the 3' end, or positions 1-7 from the 3' end, are connected to adjacent nucleotides via phosphorothioate linkages.

7) Advanced Stabilization Pattern

In one embodiment of the double-stranded RNAs provided herein:

(1) the first oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the first oligonucleotide are not 2'-methoxy-ribonucleotides;
(2) the second oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the second oligonucleotide are 2'-methoxy-ribonucleotides;
(3) the nucleotides of the first oligonucleotide are connected to adjacent nucleotides via phosphodiester or phosphorothioate linkages, wherein the nucleotides at positions 1-6 from the 3' end, or positions 1-7 from the 3' end are connected to adjacent nucleotides via phosphorothioate linkages; and
(4) the nucleotides of the second oligonucleotide are connected to adjacent nucleotides via phosphodiester or phosphorothioate linkages, wherein the nucleotides at positions 1 and 2 from the 3' end are connected to adjacent nucleotides via phosphorothioate linkages.

In one embodiment of the double-stranded RNAs, the first oligonucleotide has 3-7 more ribonucleotides than the second oligonucleotide.

In one embodiment, the double-stranded RNA comprises 11-16 base pair duplexes, wherein the nucleotides of each base pair duplex have different chemical modifications (e.g., one nucleotide has a 2'-fluoro modification and the other nucleotide has a 2'-methoxy).

In one embodiment of the double-stranded RNAs, the first oligonucleotide has 3-7 more ribonucleotides than the second oligonucleotide. In another embodiment.

In one embodiment, the first oligonucleotide is the antisense strand and the second oligonucleotide is the sense strand. See PCT Pub. No. WO 2016/161388, which is incorporated herein by reference.

In one embodiment, the first or second oligonucleotide comprises one or more VP intersubunit modifications having the following formula:

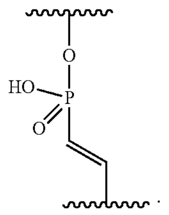

8) Branched Oligonucleotides

Figure 31:
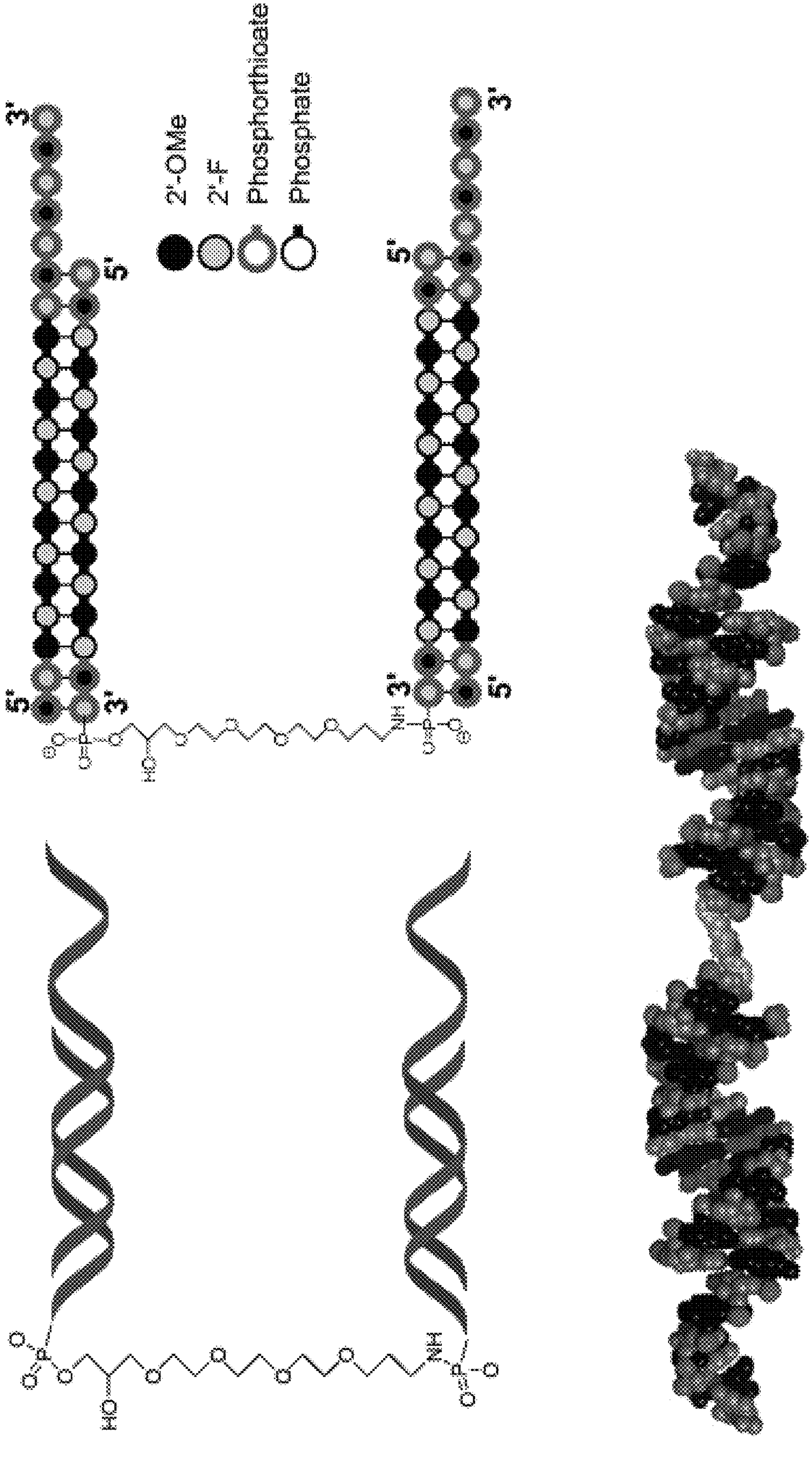
FIG. 31 illustrates an example di-branched siRNA chemical scaffold.

Two or more RNA silencing agents as disclosed above, for example oligonucleotide constructs such as siRNAs, may be connected to one another by one or more moieties independently selected from a linker, a spacer and a branching point, forming a branched oligonucleotide containing two or more RNA silencing agents. FIG. 31 illustrates an exemplary di-siRNA di-branched scaffolding for delivering two siRNAs. In representative embodiments, the nucleic acids of the branched oligonucleotide each comprise an antisense strand (or portions thereof), wherein the antisense strand has sufficient complementary to a heterozygous single nucleotide polymorphism to mediate an RNA-mediated silencing mechanism (e.g. RNAi). In other embodiments, there is provided a second type of branched oligonucleotides featuring nucleic acids that comprise a sense strand (or portions thereof) for silencing antisense transcripts, where the sense strand has sufficient complementarity to an antisense transcript to mediate an RNA-mediated silencing mechanism. In further embodiments, there is provided a third type of branched oligonucleotides including nucleic acids of both types, that is, a nucleic acid comprising an antisense strand (or portions thereof) and an oligonucleotide comprising a sense strand (or portions thereof).

In exemplary embodiments, the branched oligonucleotides may have two to eight RNA silencing agents attached through a linker. The linker may be hydrophobic. In a particular embodiment, branched oligonucleotides of the present application have two to three oligonucleotides. In one embodiment, the oligonucleotides independently have substantial chemical stabilization (e.g., at least 40% of the constituent bases are chemically-modified). In a particular embodiment, the oligonucleotides have full chemical stabilization (i.e., all of the constituent bases are chemically-modified). In some embodiments, branched oligonucleotides comprise one or more single-stranded phosphorothioated tails, each independently having two to twenty nucleotides. In a particular embodiment, each single-stranded tail has eight to ten nucleotides.

In certain embodiments, branched oligonucleotides are characterized by three properties: (1) a branched structure, (2) full metabolic stabilization, and (3) the presence of a single-stranded tail comprising phosphorothioate linkers. In a specific embodiment, branched oligonucleotides have 2 or 3 branches. It is believed that the increased overall size of the branched structures promotes increased uptake. Also, without being bound by a particular theory of activity, multiple adjacent branches (e.g., 2 or 3) are believed to allow each branch to act cooperatively and thus dramatically enhance rates of internalization, trafficking and release.

Figure 36:
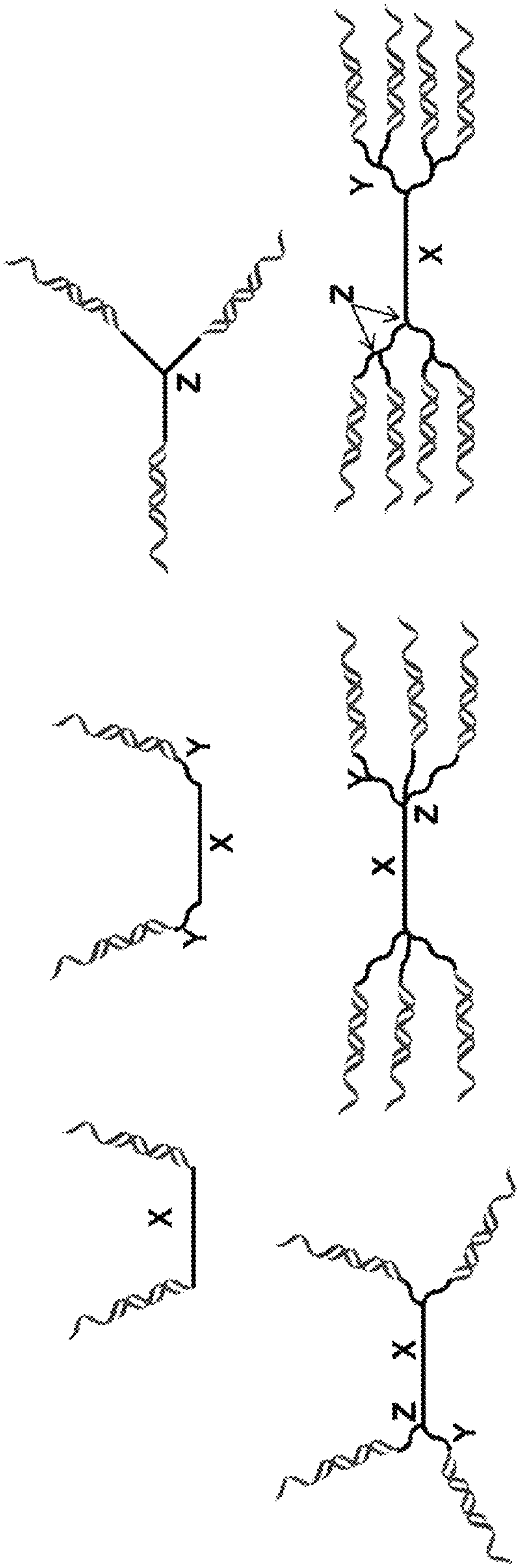
FIG. 36 shows oligonucleotide branching motifs according to certain exemplary embodiments. The double-helices represent oligonucleotides. The combination of different linkers, spacer(s) and branching points allows generation of a wide diversity of branched hsiRNA structures.

Branched oligonucleotides are provided in various structurally diverse embodiments. As shown in FIG. 36, for example, in some embodiments nucleic acids attached at the branching points are single stranded and consist of miRNA inhibitors, gapmers, mixmers, SSOs, PMOs, or PNAs. These single strands can be attached at their 3' or 5' end. Combinations of siRNA and single stranded oligonucleotides could also be used for dual function. In another embodiment, short nucleic acids complementary to the gapmers, mixmers, miRNA inhibitors, SSOs, PMOs, and PNAs are used to carry these active single-stranded nucleic acids and enhance distribution and cellular internalization. The short duplex region has a low melting temperature ($T_m$~37° C.) for fast dissociation upon internalization of the branched structure into the cell.

Figure 37:
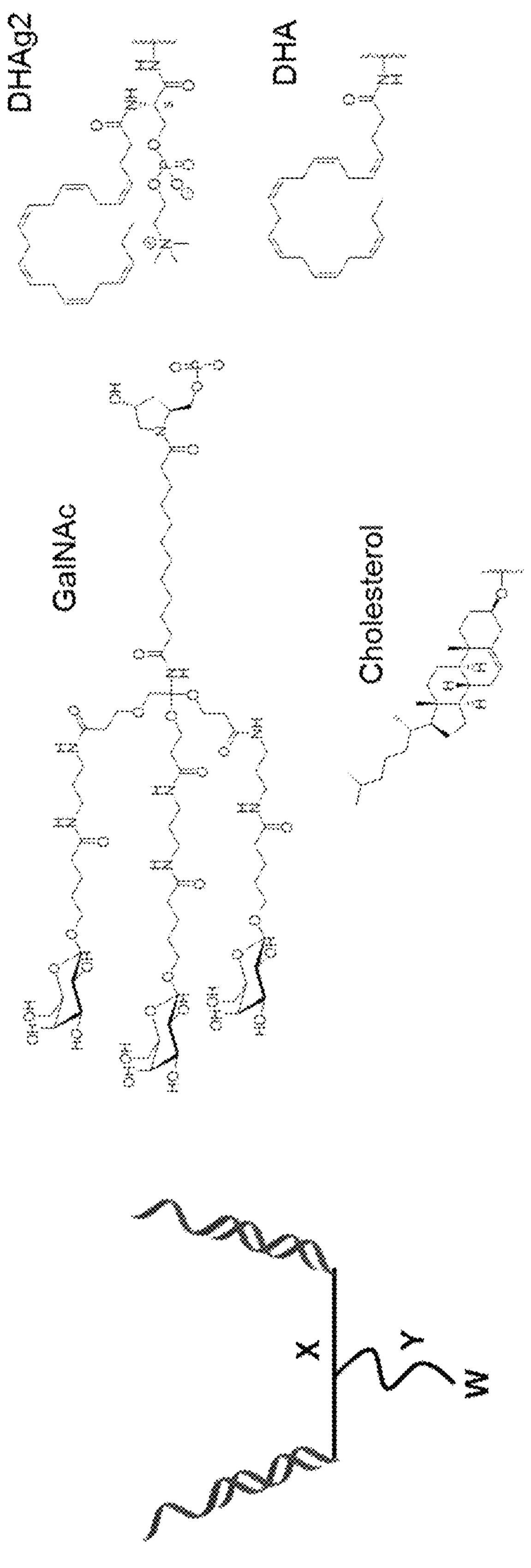
FIG. 37 shows branched oligonucleotides of the invention with conjugated bioactive moieties.

As shown in FIG. 37, Di-siRNA branched oligonucleotides may comprise chemically diverse conjugates. Conjugated bioactive ligands may be used to enhance cellular specificity and to promote membrane association, internalization, and serum protein binding. Examples of bioactive moieties to be used for conjugation include DHAg2, DHA, GalNAc, and cholesterol. These moieties can be attached to Di-siRNA either through the connecting linker or spacer, or added via an additional linker or spacer attached to another free siRNA end.

The presence of a branched structure improves the level of tissue retention in the brain more than 100-fold compared to non-branched compounds of identical chemical composition, suggesting a new mechanism of cellular retention and distribution. Branched oligonucleotides have unexpectedly uniform distribution throughout the spinal cord and brain. Moreover, branched oligonucleotides exhibit unexpectedly efficient systemic delivery to a variety of tissues, and very high levels of tissue accumulation.

Branched oligonucleotides comprise a variety of therapeutic nucleic acids, including ASOs, miRNAs, miRNA inhibitors, splice switching, PMOs, PNAs. In some embodiments, branched oligonucleotides further comprise conjugated hydrophobic moieties and exhibit unprecedented silencing and efficacy in vitro and in vivo.

Linkers

In an embodiment of the branched oligonucleotide, each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment, each linker is an ethylene glycol chain. In another embodiment, each linker is an alkyl chain. In another embodiment, each linker is a peptide. In another embodiment, each linker is RNA. In another embodiment, each linker is DNA. In another embodiment, each linker is a phosphate. In another embodiment, each linker is a phosphonate. In another embodiment, each linker is a phosphoramidate. In another embodiment, each linker is an ester. In another embodiment, each linker is an amide. In another embodiment, each linker is a triazole. In another embodiment, each linker is a structure selected from the formulas of FIG. 37.

9) Compound of Formula (I)

In another aspect, provided herein is a branched oligonucleotide compound of formula (I):

$$L\text{-}(N)_n \qquad \text{(I)}$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (I) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; N is an RNA duplex comprising a sense strand and an antisense strand, wherein the antisense strand comprises a region of complementarity which is substantially complementary to a region of a gene comprising an allelic polymorphism, wherein the antisense strand comprises: a single nucleotide polymorphism (SNP) position nucleotide at a position 2 to 7 from the 5' end that is complementary to the allelic polymorphism; and a mismatch (MM) position nucleotide located 2-11 nucleotides from the SNP position nucleotide that is a mismatch with a nucleotide in the gene. In exemplary embodiments, the SNP position nucleotide is at a position 2, 4 or 6 from the 5' end and the mismatch (MM) position nucleotide is located 2-6 nucleotides from the SNP position nucleotide.

The sense strand and antisense strand each independently comprise one or more chemical modifications; and n is 2, 3, 4, 5, 6, 7 or 8.

In an embodiment, the compound of formula (I) has a structure selected from formulas (I-1)-(I-9) of Table 1.

TABLE 1

N—L—N (I-1)

N—S—L—S—N (I-2)

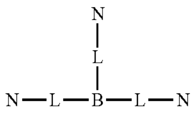

(I-3)

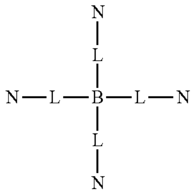

(I-4)

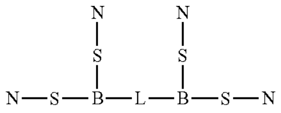

(I-5)

TABLE 1-continued

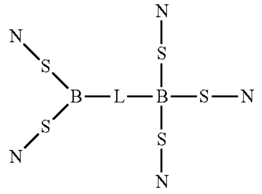

(I-6)

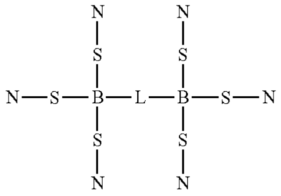

(I-7)

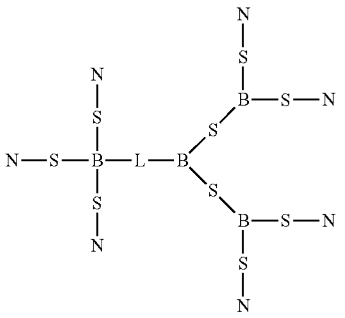

(I-8)

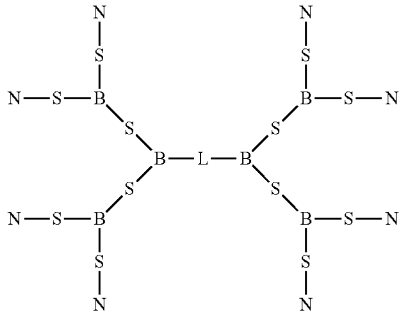

(I-9)

In one embodiment, the compound of formula (I) is formula (I-1). In another embodiment, the compound of formula (I) is formula (I-2). In another embodiment, the compound of formula (I) is formula (I-3). In another embodiment, the compound of formula (I) is formula (I-4). In another embodiment, the compound of formula (I) is formula (I-5). In another embodiment, the compound of formula (I) is formula (I-6). In another embodiment, the compound of formula (I) is formula (I-7). In another embodiment, the compound of formula (I) is formula (I-8). In another embodiment, the compound of formula (I) is formula (I-9).

In an embodiment of the compound of formula (I), each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment of the compound of formula (I), each linker is an ethylene glycol chain. In another embodiment, each linker is an alkyl chain. In another embodiment of the compound of formula (I), each linker is a peptide. In another embodiment of the compound of formula (I), each linker is RNA. In another embodiment of the compound of formula (I), each linker is DNA. In another embodiment of the compound of formula (I), each linker is a phosphate. In another embodiment, each linker is a phosphonate. In another embodiment of the compound of formula (I), each linker is a phosphoramidate. In another embodiment of the compound of formula (I), each linker is an ester. In another embodiment of the compound of formula (I), each linker is an amide. In another embodiment of the compound of formula (I), each linker is a triazole. In another embodiment of the compound of formula (I), each linker is a structure selected from the formulas of FIG. 36.

Figure 38:
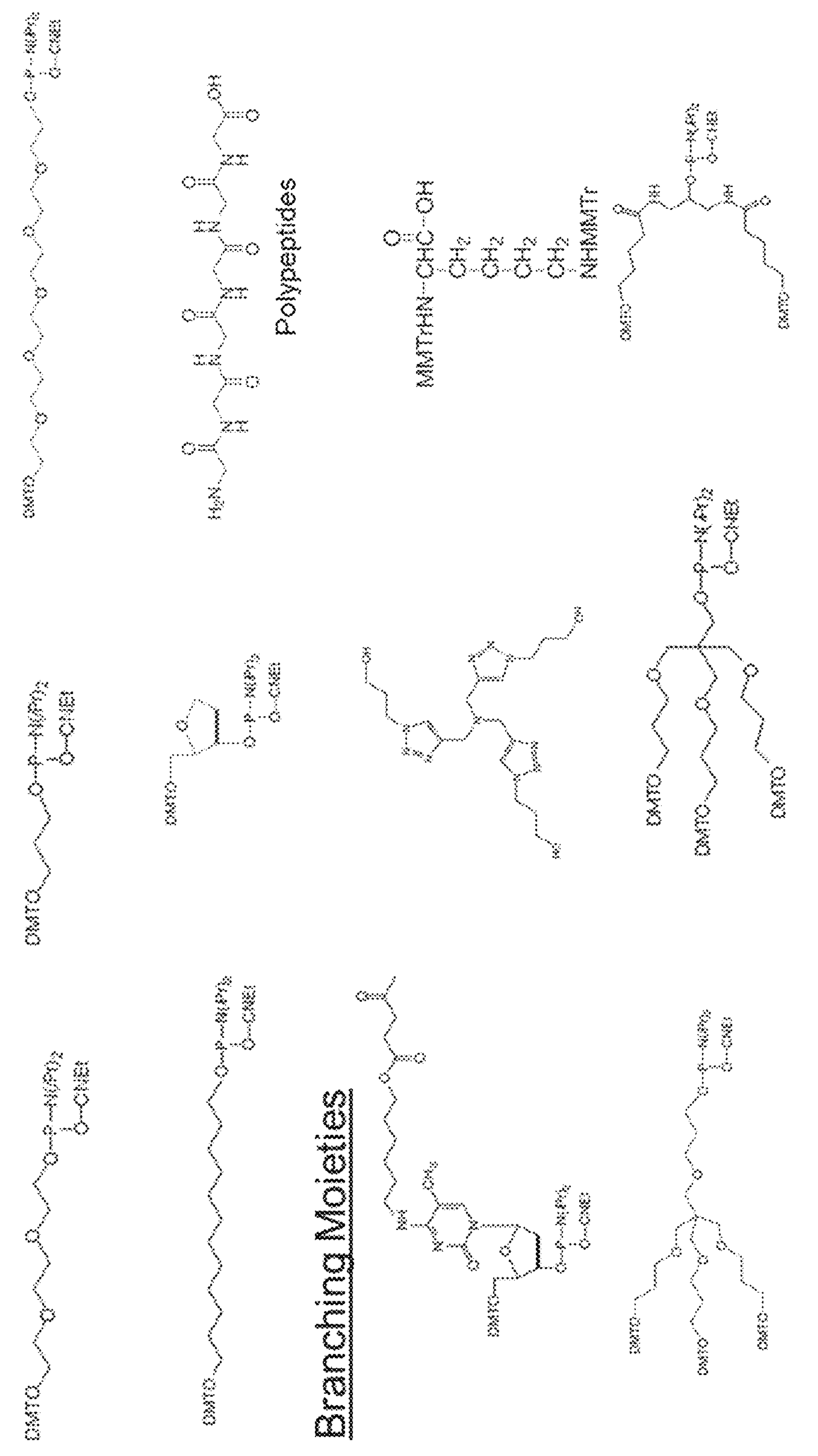
FIG. 38 shows exemplary amidite linkers, spacers and branching moieties.

In one embodiment of the compound of formula (I), B is a polyvalent organic species. In another embodiment of the compound of formula (I), B is a derivative of a polyvalent organic species. In one embodiment of the compound of formula (I), B is a triol or tetrol derivative. In another embodiment, B is a tri- or tetra-carboxylic acid derivative. In another embodiment, B is an amine derivative. In another embodiment, B is a tri- or tetra-amine derivative. In another embodiment, B is an amino acid derivative. In another embodiment of the compound of formula (I), B is selected from the formulas of FIG. 38.

Polyvalent organic species are moieties comprising carbon and three or more valencies (i.e., points of attachment with moieties such as S, L or N, as defined above). Non-limiting examples of polyvalent organic species include triols (e.g., glycerol, phloroglucinol, and the like), tetrols (e.g., ribose, pentaerythritol, 1,2,3,5-tetrahydroxybenzene, and the like), tri-carboxylic acids (e.g., citric acid, 1,3,5-cyclohexanetricarboxylic acid, trimesic acid, and the like), tetra-carboxylic acids (e.g., ethylenediaminetetraacetic acid, pyromellitic acid, and the like), tertiary amines (e.g., tripropargylamine, triethanolamine, and the like), triamines (e.g., diethylenetriamine and the like), tetramines, and species comprising a combination of hydroxyl, thiol, amino, and/or carboxyl moieties (e.g., amino acids such as lysine, serine, cysteine, and the like).

In an embodiment of the compound of formula (I), each nucleic acid comprises one or more chemically-modified nucleotides. In an embodiment of the compound of formula (I), each nucleic acid consists of chemically-modified nucleotides. In certain embodiments of the compound of formula (I), >95%, >90%, >85%, >80%, >75%, >70%, >65%, >60%, >55% or >50% of each nucleic acid comprises chemically-modified nucleotides.

In an embodiment, each antisense strand independently comprises a 5' terminal group R selected from the groups of Table 2:

TABLE 2

| | |
|---|---|
| 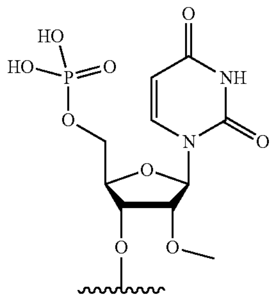 | $R^1$ |
| 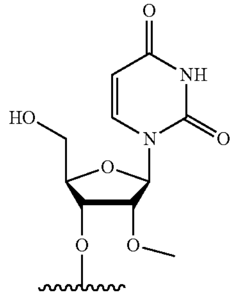 | $R^2$ |
| 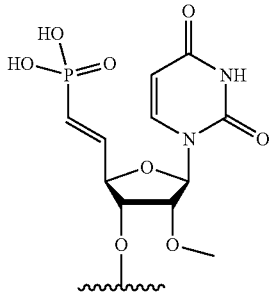 | $R^3$ |

TABLE 2-continued

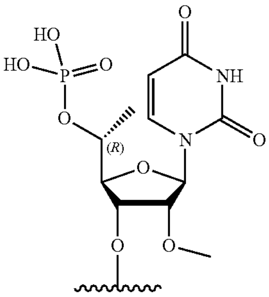

$R^4$

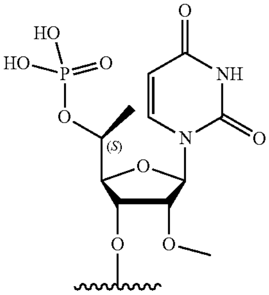

$R^5$

TABLE 2-continued

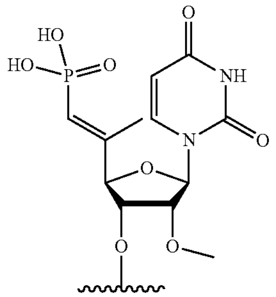

$R^8$

In one embodiment, R is $R_1$. In another embodiment, R is $R_2$. In another embodiment, R is $R_3$. In another embodiment, R is $R_4$. In another embodiment, R is $R_5$. In another embodiment, R is $R_6$. In another embodiment, R is $R_7$. In another embodiment, R is $R_5$.

Structure of Formula (II)

In an embodiment, the compound of formula (I) the structure of formula (II):

(II)

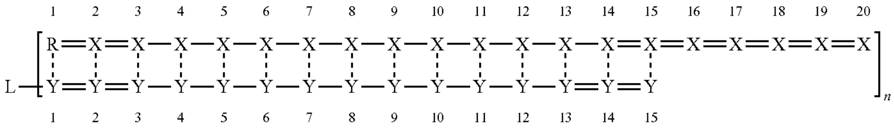

TABLE 2-continued

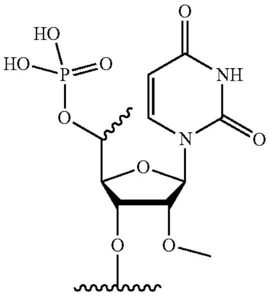

$R^6$

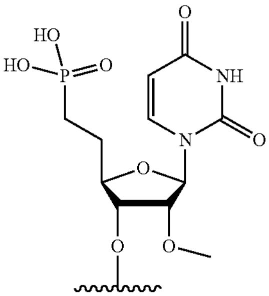

$R^7$ wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; — represents a phosphodiester internucleoside linkage; = represents a phosphorothioate internucleoside linkage; and - - - represents, individually for each occurrence, a base-pairing interaction or a mismatch.

In certain embodiments, the structure of formula (II) does not contain mismatches. In one embodiment, the structure of formula (II) contains 1 mismatch. In another embodiment, the compound of formula (II) contains 2 mismatches. In another embodiment, the compound of formula (II) contains 3 mismatches. In another embodiment, the compound of formula (II) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (II) are chemically-modified nucleotides. In other embodiments, >95%, >90%, >85%, >80%, >75%, >70%, >65%, >60%, >55% or >50% of X's of the structure of formula (II) are chemically-modified nucleotides.

Structure of Formula (III)

In an embodiment, the compound of formula (I) has the structure of formula (III):

(III)

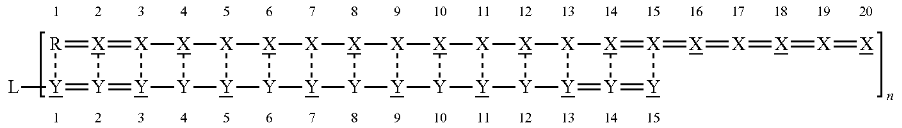

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In an embodiment, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (III) does not contain mismatches. In one embodiment, the structure of formula (III) contains 1 mismatch. In another embodiment, the compound of formula (III) contains 2 mismatches. In another embodiment, the compound of formula (III) contains 3 mismatches. In another embodiment, the compound of formula (III) contains 4 mismatches.

Structure of Formula (IV)

In an embodiment, the compound of formula (I) has the structure of formula (IV):

(IV)

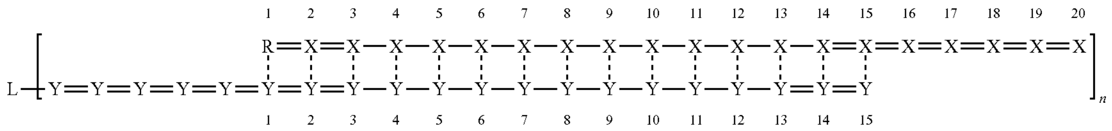

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; — represents a phosphodiester internucleoside linkage; = represents a phosphorothioate internucleoside linkage; and - - - represents, individually for each occurrence, a base-pairing interaction or a mismatch.

In certain embodiments, the structure of formula (IV) does not contain mismatches. In one embodiment, the structure of formula (IV) contains 1 mismatch. In another embodiment, the compound of formula (IV) contains 2 mismatches. In another embodiment, the compound of formula (IV) contains 3 mismatches. In another embodiment, the compound of formula (IV) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (II) are chemically-modified nucleotides. In other embodiments, >95%, >90%, >85%, >80%, >75%, >70%, >65%, >60%, >55% or >50% of X's of the structure of formula (II) are chemically-modified nucleotides.

Structure of Formula (V)

In an embodiment, the compound of formula (I) has the structure of formula (V):

(V)

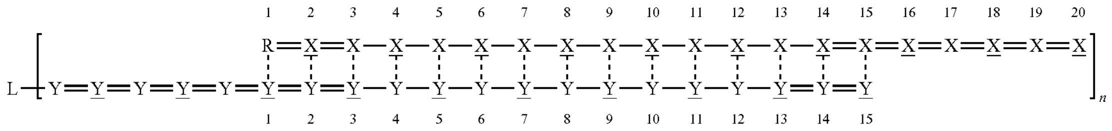

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In certain embodiments, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (V) does not contain mismatches. In one embodiment, the structure of formula (V) contains 1 mismatch. In another embodiment, the compound of formula (V) contains 2 mismatches. In another embodiment, the compound of formula (V) contains 3 mismatches. In another embodiment, the compound of formula (V) contains 4 mismatches.

Variable Linkers

In an embodiment of the compound of formula (I), L has the structure of L1:

(L1)

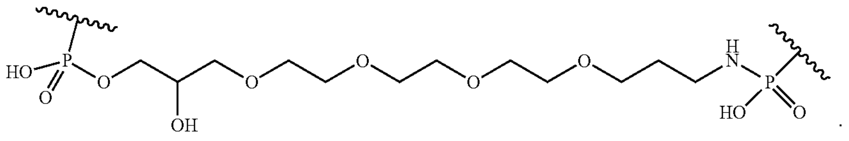

In an embodiment of L1, R is $R^3$ and n is 2.

In an embodiment of the structure of formula (II), L has the structure of L1. In an embodiment of the structure of formula (III), L has the structure of L1. In an embodiment of the structure of formula (IV), L has the structure of L1. In an embodiment of the structure of formula (V), L has the structure of L1. In an embodiment of the structure of formula (VI), L has the structure of L1. In an embodiment of the structure of formula (VI), L has the structure of L1. In an embodiment of the compound of formula (I), L has the structure of L2:

(L2)

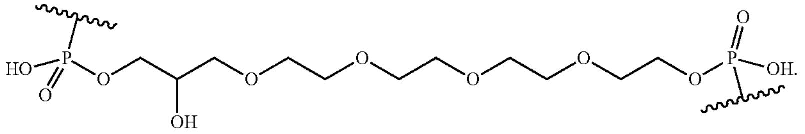

In an embodiment of L2, R is $R^3$ and n is 2. In an embodiment of the structure of formula (II), L has the structure of L2. In an embodiment of the structure of formula (III), L has the structure of L2. In an embodiment of the structure of formula (IV), L has the structure of L2. In an embodiment of the structure of formula (V), L has the structure of L2. In an embodiment of the structure of formula (VI), L has the structure of L2. In an embodiment of the structure of formula (VI), L has the structure of L2.

10) Delivery System

In a further aspect, provided herein is a delivery system for therapeutic nucleic acids having the structure of formula (VI):

$$L\text{-}(cNA)_n \qquad (VI)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (VI) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; each cNA, independently, is a carrier nucleic acid comprising one or more chemical modifications; and n is 2, 3, 4, 5, 6, 7 or 8.

In one embodiment of the delivery system, L is an ethylene glycol chain. In another embodiment of the delivery system, L is an alkyl chain. In another embodiment of the delivery system, L is a peptide. In another embodiment of the delivery system, L is RNA. In another embodiment of the delivery system, L is DNA. In another embodiment of the delivery system, L is a phosphate. In another embodiment of the delivery system, L is a phosphonate. In another embodiment of the delivery system, L is a phosphoramidate. In another embodiment of the delivery system, L is an ester. In another embodiment of the delivery system, L is an amide. In another embodiment of the delivery system, L is a triazole.

In one embodiment of the delivery system, S is an ethylene glycol chain. In another embodiment, S is an alkyl chain. In another embodiment of the delivery system, S is a peptide. In another embodiment, S is RNA. In another embodiment of the delivery system, S is DNA. In another embodiment of the delivery system, S is a phosphate. In another embodiment of the delivery system, S is a phosphonate. In another embodiment of the delivery system, S is a phosphoramidate. In another embodiment of the delivery system, S is an ester. In another embodiment, S is an amide. In another embodiment, S is a triazole.

In one embodiment of the delivery system, n is 2. In another embodiment of the delivery system, n is 3. In another embodiment of the delivery system, n is 4. In another embodiment of the delivery system, n is 5. In another embodiment of the delivery system, n is 6. In another embodiment of the delivery system, n is 7. In another embodiment of the delivery system, n is 8.

In certain embodiments, each cNA comprises >95%, >90%, >85%, >80%, >75%, >70%, >65%, >60%, >55% or >50% chemically-modified nucleotides.

In an embodiment, the compound of formula (VI) has a structure selected from formulas (VI-1)-(VI-9) of Table 3:

TABLE 3

ANc—L—cNA (VI-1)

ANc—S—L—S—cNA (VI-2)

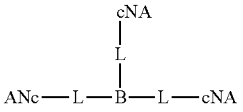
(VI-3)

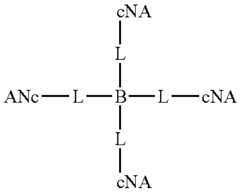
(VI-4)

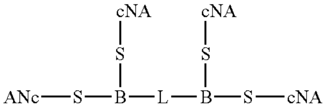
(VI-5)

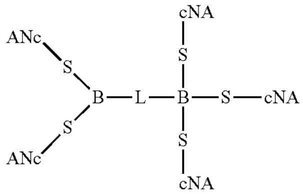
(VI-6)

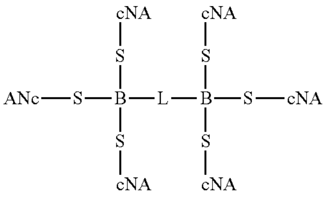
(VI-7)

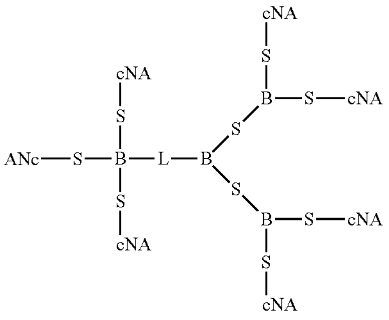
(VI-8)

TABLE 3-continued

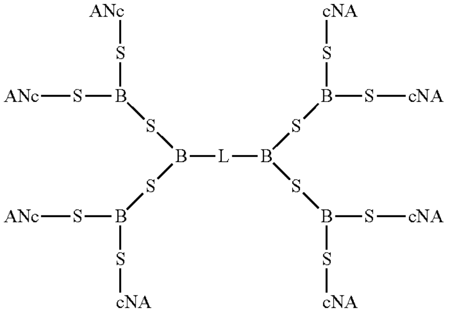
(VI-9)

In an embodiment, the compound of formula (VI) is the structure of formula (VI-1). In an embodiment, the compound of formula (VI) is the structure of formula (VI-2). In an embodiment, the compound of formula (VI) is the structure of formula (VI-3). In an embodiment, the compound of formula (VI) is the structure of formula (VI-4). In an embodiment, the compound of formula (VI) is the structure of formula (VI-5). In an embodiment, the compound of formula (VI) is the structure of formula (VI-6). In an embodiment, the compound of formula (VI) is the structure of formula (VI-7). In an embodiment, the compound of formula (VI) is the structure of formula (VI-8). In an embodiment, the compound of formula (VI) is the structure of formula (VI-9). In an embodiment, the compound of formulas (VI) (including, e.g., formulas (VI-1)-(VI-9), each cNA independently comprises at least 15 contiguous nucleotides. In an embodiment, each cNA independently consists of chemically-modified nucleotides.

In an embodiment, the delivery system further comprises n therapeutic nucleic acids (NA), wherein each NA comprises a region of complementarity which is substantially complementary to a region of a gene comprising an allelic polymorphism, wherein the antisense strand comprises: a single nucleotide polymorphism (SNP) position nucleotide at a position 2 to 7 from the 5' end that is complementary to the allelic polymorphism; and a mismatch (MM) position nucleotide located 2-11 nucleotide from the SNP position nucleotide that is a mismatch with a nucleotide in the gene. In exemplary embodiments, the SNP position nucleotide is at a position 2, 4 or 6 from the 5' end and the mismatch (MM) position nucleotide is located 2-6 nucleotides from the SNP position nucleotide. Also, each NA is hybridized to at least one cNA. In one embodiment, the delivery system is comprised of 2 NAs. In another embodiment, the delivery system is comprised of 3 NAs. In another embodiment, the delivery system is comprised of 4 NAs. In another embodiment, the delivery system is comprised of 5 NAs. In another embodiment, the delivery system is comprised of 6 NAs. In another embodiment, the delivery system is comprised of 7 NAs. In another embodiment, the delivery system is comprised of 8 NAs.

In an embodiment, each NA independently comprises at least 16 contiguous nucleotides. In an embodiment, each NA independently comprises 16-20 contiguous nucleotides. In an embodiment, each NA independently comprises 16 contiguous nucleotides. In another embodiment, each NA independently comprises 17 contiguous nucleotides. In another embodiment, each NA independently comprises 18 contiguous nucleotides. In another embodiment, each NA independently comprises 19 contiguous nucleotides. In another embodiment, each NA independently comprises 20 contiguous nucleotides.

In an embodiment, each NA comprises an unpaired overhang of at least 2 nucleotides. In another embodiment, each NA comprises an unpaired overhang of at least 3 nucleotides. In another embodiment, each NA comprises an unpaired overhang of at least 4 nucleotides. In another embodiment, each NA comprises an unpaired overhang of at least 5 nucleotides. In another embodiment, each NA comprises an unpaired overhang of at least 6 nucleotides. In an embodiment, the nucleotides of the overhang are connected via phosphorothioate linkages.

In an embodiment, each NA, independently, is selected from the group consisting of: DNA, siRNAs, antagomiRs, miRNAs, gapmers, mixmers, or guide RNAs. In one embodiment, each NA, independently, is a DNA. In another embodiment, each NA, independently, is a siRNA. In another embodiment, each NA, independently, is an antagomiR. In another embodiment, each NA, independently, is a miRNA. In another embodiment, each NA, independently, is a gapmer. In another embodiment, each NA, independently, is a mixmer. In another embodiment, each NA, independently, is a guide RNA. In an embodiment, each NA is the same. In an embodiment, each NA is not the same.

In an embodiment, the delivery system further comprising n therapeutic nucleic acids (NA) has a structure selected from formulas (I), (II), (III), (IV), (V), (VI), and embodiments thereof described herein. In one embodiment, the delivery system has a structure selected from formulas (I), (II), (III), (IV), (V), (VI), and embodiments thereof described herein further comprising 2 therapeutic nucleic acids (NA). In another embodiment, the delivery system has a structure selected from formulas (I), (II), (III), (IV), (V), (VI), and embodiments thereof described herein further comprising 3 therapeutic nucleic acids (NA). In one embodiment, the delivery system has a structure selected from formulas (I), (II), (III), (IV), (V), (VI), and embodiments thereof described herein further comprising 4 therapeutic nucleic acids (NA). In one embodiment, the delivery system has a structure selected from formulas (I), (II), (III), (IV), (V), (VI), and embodiments thereof described herein further comprising 5 therapeutic nucleic acids (NA). In one embodiment, the delivery system has a structure selected from formulas (I), (II), (III), (IV), (V), (VI), and embodiments thereof described herein further comprising 6 therapeutic nucleic acids (NA). In one embodiment, the delivery system has a structure selected from formulas (I), (II), (III), (IV), (V), (VI), and embodiments thereof described herein further comprising 7 therapeutic nucleic acids (NA). In one embodiment, the delivery system has a structure selected from formulas (I), (II), (III), (IV), (V), (VI), and embodiments thereof described herein further comprising 8 therapeutic nucleic acids (NA).

In one embodiment, the delivery system has a structure selected from formulas (I), (II), (III), (IV), (V), (VI), further comprising a linker of structure L1 or L2 wherein R is R3 and n is 2. In another embodiment, the delivery system has a structure selected from formulas (I), (II), (III), (IV), (V), (VI), further comprising a linker of structure L1 wherein R is R3 and n is 2. In another embodiment, the delivery system has a structure selected from formulas (I), (II), (III), (IV), (V), (VI), further comprising a linker of structure L2 wherein R is R3 and n is 2.

Pharmaceutical Compositions and Methods of Administration

In one aspect, provided herein is a pharmaceutical composition comprising a therapeutically effective amount of one or more compound, oligonucleotide, or nucleic acid as described herein, and a pharmaceutically acceptable carrier.

In one embodiment, the pharmaceutical composition comprises one or more double-stranded, chemically-modified nucleic acid as described herein, and a pharmaceutically acceptable carrier. In a particular embodiment, the pharmaceutical composition comprises one double-stranded, chemically-modified nucleic acid as described herein, and a pharmaceutically acceptable carrier. In another particular embodiment, the pharmaceutical composition comprises two double-stranded, chemically-modified nucleic acids as described herein, and a pharmaceutically acceptable carrier.

In a particular embodiment, the pharmaceutical composition comprises a double-stranded RNA molecule comprising about 15-35 nucleotides complementary to a region of a gene encoding a heterozygous SNP mutant protein, said region comprising an allelic polymorphism, and a second strand comprising about 15-35 nucleotides complementary to the first strand, wherein the dsRNA molecule comprises a mismatch that is not in the position of the allelic polymorphism; and the mismatch and the nucleotide corresponding to the polymorphism are not in the center of the dsRNA molecule.

In an embodiment, the mismatch is 4 nucleotides upstream, 3 nucleotides upstream nucleotide corresponding to the allelic polymorphism, 2 nucleotides upstream nucleotide corresponding to the allelic polymorphism, 1 nucleotide upstream, 1 nucleotide downstream nucleotide corresponding to the allelic polymorphism, 2 nucleotides downstream nucleotide corresponding to the allelic polymorphism, 3 nucleotides downstream nucleotide corresponding to the allelic polymorphism, 4 nucleotides downstream nucleotide corresponding to the allelic polymorphism, or 5 nucleotides downstream nucleotide corresponding to the allelic polymorphism. In certain embodiments, the mismatch is not adjacent to the nucleotide corresponding to the allelic polymorphism.

In another embodiment of the pharmaceutical composition, the double-stranded RNA comprises a nucleotide corresponding to the allelic polymorphism which is in position 2, 3, 4, 5, or 6 from the 5' end. In an embodiment, the nucleotide corresponding to the allelic polymorphism is in position 2 from the 5' end. In an embodiment, the nucleotide corresponding to the allelic polymorphism is in position 3 from the 5' end. In an embodiment, the nucleotide corresponding to the allelic polymorphism is in position 4 from the 5' end. In an embodiment, the nucleotide corresponding to the allelic polymorphism is in position 5 from the 5' end. In an embodiment, the nucleotide corresponding to the allelic polymorphism is in position 6 from the 5' end.

In an embodiment of the pharmaceutical composition, the double-stranded RNA selectively silences a mutant allele having an allelic polymorphism, e.g., a heterozygous SNP. In an embodiment of the pharmaceutical composition, the double-stranded RNA silences a mutant allele having an allelic polymorphism and does not affect the wild-type allele of the same gene. In another embodiment of the pharmaceutical composition, the double-stranded RNA provided herein silences a mutant allele having an allelic polymorphism and silences the wild-type allele of the same gene to a lesser extent than the mutant allele.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desired to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, typical methods of preparation are vacuum drying and freeze-drying which yields a powder of the active ingredient plus any additional desired ingredient from a previously sterile-filtered solution thereof.

The data obtained from the cell culture assays and animal studies can be used in formulating a range of dosage for use in humans. The dosage of such compounds should typically lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

Methods of Treatment

The present invention provides for both prophylactic and therapeutic methods of treating a subject at risk of (or susceptible to) a disease or disorder caused, in whole or in part, by an allelic polymorphism (e.g., a heterozygous SNP). In one embodiment, the disease or disorder is a trinucleotide repeat disease or disorder. In another embodiment, the disease or disorder is a polyglutamine disorder. In an embodiment, the methods comprise administering a therapeutically effective amount of a double-stranded RNA molecule provided herein. In an embodiment, the disease or disorder is a disorder associated with the expression of huntingtin and in which alteration of huntingtin, especially the amplification of CAG repeat copy number, leads to a defect in the huntingtin gene (structure or function) or huntingtin protein (structure or function or expression), such that clinical manifestations include those seen in Huntington's disease patients.

In embodiments of the methods, the double-stranded RNAs disclosed herein are homologous to an allelic polymorphism except for one mismatched oligonucleotide at a particular position relative to the nucleotide corresponding to the allelic polymorphism. In certain embodiments, the mismatch is within about 6 nucleotides of the nucleotide corresponding to the allelic polymorphism, within about 5 nucleotides of the nucleotide corresponding to the allelic polymorphism, within about 4 nucleotides of the nucleotide corresponding to the allelic polymorphism within about 3 nucleotide of the nucleotide corresponding to the allelic polymorphism, within about 2 nucleotide of the nucleotide corresponding to the allelic polymorphism, or within about 1 nucleotides of the nucleotide corresponding to the allelic polymorphism. In particularly exemplary embodiments, the mismatch is not adjacent to the nucleotide corresponding to the allelic polymorphism.

In another embodiment of the methods, the double-stranded RNA comprises a nucleotide corresponding to the allelic polymorphism which is in position 2, 3, 4, 5, or 6 from the 5' end. In an embodiment, the nucleotide corresponding to the allelic polymorphism is in position 2 from the 5' end. In an embodiment, the nucleotide corresponding to the allelic polymorphism is in position 3 from the 5' end. In an embodiment, the nucleotide corresponding to the allelic polymorphism is in position 4 from the 5' end. In an embodiment, the nucleotide corresponding to the allelic polymorphism is in position 5 from the 5' end. In an embodiment, the nucleotide corresponding to the allelic polymorphism is in position 6 from the 5' end.

In an embodiment of the methods, the dsRNA comprises a nucleotide corresponding to a polymorphism at position 6 from the 5' end and a mismatch at position 11 from the 5' end. In an embodiment of the methods, the dsRNA comprises a nucleotide corresponding to a polymorphism at position 4 from the 5' end and a mismatch at position 7 from the 5' end.

In another embodiment of the methods, the double-stranded RNA selectively silences a mutant allele having an allelic polymorphism. In an embodiment, the double-stranded RNA silences a mutant allele having an allelic polymorphism and does not affect the wild-type allele of the same gene. In another embodiment, the double-stranded RNA silences a mutant allele having an allelic polymorphism and silences the wild-type allele of the same gene to a lesser extent than the mutant allele.

In an embodiment of the methods, the dsRNA comprises one or more VP intersubunit linkage modifications wherein the intersubunit linkage has the following formula:

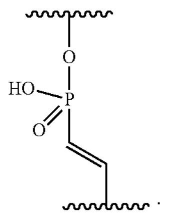

In additional embodiments, the dsRNA comprises one or more of the intersubunit linkage modifications depicted in FIG. 43.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNAi agent or vector or transgene encoding same) that is specific for one or more target sequences within the gene, such that sequence specific interference with the gene is achieved. These methods can be performed in vitro (e.g., by culturing the cell with the agent) or, alternatively, in vivo (e.g., by administering the agent to a subject).

An RNA silencing agent modified for enhanced uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4\times10^{16}$ copies) per kg of bodyweight, or less than 1500, 750, 300, 150, 75, 15, 7.5, 1.5, 0.75, 0.15, 0.075, 0.015, 0.0075, 0.0015, 0.00075 or 0.00015 nmole of RNA silencing agent per kg of bodyweight. The unit dose, for example, can be administered by injection (e.g., intravenous or intramuscular, intrathecally, or directly into the brain), an inhaled dose, or a topical application. In exemplary embodiments, dosages are less than 2, 1 or 0.1 mg/kg of body weight.

Delivery of an RNA silencing agent directly to an organ (e.g., directly to the brain) can be at a dosage on the order of about 0.00001 mg to about 3 mg per organ, or about 0.0001-0.001 mg per organ, about 0.03-3.0 mg per organ, about 0.1-3.0 mg per organ or about 0.3-3.0 mg per organ. The dosage can be an amount effective to treat or prevent a neurological disease or disorder (e.g., Huntington's disease). In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 μg to 1.4 mg/kg of body weight per day, e.g., 10, 1, 0.1, 0.01, 0.001, or 0.00001 mg per kg of bodyweight per day. The maintenance doses are typically administered no more than once every 5, 10, or 30 days. Further, the treatment regimen may last for a period of time which will vary depending upon the nature of the particular disease, its severity and the overall condition of the patient. In particular embodiments, the dosage may be delivered no more than once per day, e.g., no more than once per 24, 36, 48 or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

Huntington's Disease

In certain aspects of the invention, RNA silencing agents are designed to target polymorphisms (e.g., heterozygous single nucleotide polymorphisms) in the mutant human huntingtin protein (htt) for the treatment of Huntington's disease. Accordingly, in another aspect, provided herein is a method of treating or managing Huntington's disease comprising administering to a patient in need of such treatment or management a therapeutically effective amount of a compound, oligonucleotide, or nucleic acid as described herein, or a pharmaceutical composition comprising said compound, oligonucleotide, or nucleic acid.

Huntington's disease, inherited as an autosomal dominant disease, causes impaired cognition and motor disease. Patients can live more than a decade with severe debilitation, before premature death from starvation or infection. The disease begins in the fourth or fifth decade for most cases, but a subset of patients manifest disease in teenage years. The genetic mutation for Huntington's disease is a lengthened CAG repeat in the huntingtin gene. The CAG repeat varies in number from 8 to 35 copies in normal individuals (Kremer et al., 1994). The genetic mutation (e.g., an increase in length of the CAG repeats from less than 36 in the normal huntingtin gene to greater than 36 in the disease) is associated with the synthesis of a mutant huntingtin protein, which has greater than 36 consecutive polyglutamine residues (Aronin et al., 1995). In general, individuals with 36 or more CAG repeats will get Huntington's disease. Prototypic for as many as twenty other diseases with a lengthened CAG as the underlying mutation, Huntington's disease still has no effective therapy. A variety of interventions—such as interruption of apoptotic pathways, addition of reagents to boost mitochondrial efficiency, and blockade of NMDA receptors—have shown promise in cell cultures and mouse model of Huntington's disease. However, at best these approaches reveal a short prolongation of cell or animal survival.

The disease gene linked to Huntington's disease is termed Huntingtin or (htt). The huntingtin locus is large, spanning 180 kb and consisting of 67 exons. The huntingtin gene is widely expressed and is required for normal development. It is expressed as 2 alternatively polyadenylated forms displaying different relative abundance in various fetal and adult tissues. The larger transcript is approximately 13.7 kb and is expressed predominantly in adult and fetal brain whereas the smaller transcript of approximately 10.3 kb is more widely expressed. The two transcripts differ with respect to their 3' untranslated regions (Lin et al., 1993). Both messages are predicted to encode a 348 kilodalton protein containing 3144 amino acids. The genetic defect leading to Huntington's disease is believed to confer a new property on the mRNA or alter the function of the protein.

Huntington's disease complies with the central dogma of genetics: a mutant gene serves as a template for production of a mutant mRNA; the mutant mRNA then directs synthesis of a mutant protein (Aronin et al., 1995; DiFiglia et al., 1997). Mutant huntingtin (protein) likely accumulates in selective neurons in the striatum and cortex, disrupts as yet determined cellular activities, and causes neuronal dysfunction and death (Aronin et al., 1999; Laforet et al., 2001). Because a single copy of a mutant gene suffices to cause Huntington's disease, the most parsimonious treatment would render the mutant gene ineffective. Theoretical approaches might include stopping gene transcription of mutant huntingtin, destroying mutant mRNA, and blocking translation. Each has the same outcome—loss of mutant huntingtin.

Huntington SNPs

Exemplary SNPs in the huntingtin gene sequence suitable for targeting according to certain exemplary embodiments are disclosed in Table 4 below. Genomic sequence for each SNP site can be found in, for example, the publicly available "SNP Entrez" database maintained by the NCBI. The frequency of heterozygosity for each SNP site for HD patient and control DNA is further illustrated in Table 4. Targeting combinations of frequently heterozygous SNPs allows the treatment of a large percentage of the individuals in a HD population using a relatively small number of allele-specific RNA silencing agents.

TABLE 4 htt SNPs.

| | | | |
|---|---|---|---|
| rs363125 | ORF, exon 39 | 11.00% | GTTAAGAGATGGGGACAGT A[A/C]TTCAACGCTAGAA GAACACA (SEQ ID NO: 1) |
| rs362273 | ORF, exon 57 | 35.20% | AGCCACGAGAAGCTGCTGC T[A/G]CAGATCAACCCCG AGCGGGA (SEQ ID NO: 2) |
| rs362307 | 3' UTR, exon 67 | 48.60% | CCGGAGCCTTTGGAAGTCT G[C/T]GCCCTTGTGCCCT GCCTCCA (SEQ ID NO: 3) |
| rs362336 | ORF, exon 48 | 37.40% | CAGCCCGAGCTGCCTGCAG A[A/G]CCGGCGGCCTACT GGAGCAA (SEQ ID NO: 4) |
| rs362331 | ORF, exon 50 | 39.40% | CCCACGCCTGCTCCCTCAT C[C/T]ACTGTGTGCACTT CATCCTG (SEQ ID NO: 5) |
| rs362272 | ORF, exon 61 | 36.10% | GGGTTGGAGCCCTGCACGG C[A/G]TCCTCTATGTGCT GGAGTGC (SEQ ID NO: 6) |
| rs362306 | 3' UTR, exon 67 | 35.80% | CTGCTGGTTGTTGCCAGGT T[A/G]CAGCTGCTCTTGC ATCTGGG (SEQ ID NO: 7) |
| rs362268 | 3' UTR, exon 67 | 35.80% | TCCTCCCTCCTGCAGGCTG G[C/G]TGTTGGCCCCTST GCTGTCC (SEQ ID NO: 8) |
| rs362267 | 3' UTR, exon 67 | 35.50% | GATTTGGGAGCTCTGCTTG C[C/T]GACTGGCTGTGAG ACGAGGC (SEQ ID NO: 9) |
| rs363099 | ORF, exon 29 | 35.80% | GAAAAGTTTGGAGGGTTTC T[C/T]CGCTCAGCCTTGG ATGTTCT (SEQ ID NO: 10) |

In one embodiment, RNA silencing agents of the invention are capable of targeting one or more of the SNP sites listed in Table 4. In one embodiment, RNA silencing agents of the invention are capable of targeting rs363125 SNP site of the Huntingtin mRNA. In another embodiment, RNA silencing agents of the invention are capable of targeting rs362273 SNP site of the Huntingtin mRNA. In another embodiment, RNA silencing agents of the invention are capable of targeting rs362307 SNP site of the Huntingtin mRNA. In another embodiment, RNA silencing agents of the invention are capable of targeting rs362336 SNP site of the Huntingtin mRNA. In another embodiment, RNA silencing agents of the invention are capable of targeting rs362331 SNP site of the Huntingtin mRNA. In another embodiment, RNA silencing agents of the invention are capable of targeting rs362272 SNP site of the Huntingtin mRNA. In another embodiment, RNA silencing agents of the invention are capable of targeting rs362306 SNP site of the Huntingtin mRNA. In another embodiment, RNA silencing agents of the invention are capable of targeting rs362268 SNP site of the Huntingtin mRNA. In another embodiment, RNA silencing agents of the invention are capable of targeting rs362267 SNP site of the Huntingtin mRNA. In another embodiment, RNA silencing agents of the invention are capable of targeting rs363099 SNP site of the Huntingtin mRNA. In some embodiments, SNP sites targeted by RNA silencing agents are associated with Huntington's Disease. In particularly exemplary embodiments, SNP sites targeted by RNA silencing agents are significantly associated with Huntington's Disease.

In additional exemplary embodiments, the RNA silencing agents include one or more of the sequences of Tables 5-7:

TABLE 5

| HTT SNP | compound name | snp position | additional mismatch position | sequence: antisense strand | SEQ ID NO: | sense strand | SEQ ID NO: |
|---|---|---|---|---|---|---|---|
| rs362273 | SNP2-7 | 2 | 7 | UUAGCAUCAGCUUCUCGUGG | 230 | AGAAGCUGCUGCUAA | 242 |
| rs362273 | SNP4-7 | 4 | 7 | UUGUAGUAGCAGCUUCUCGU | 231 | AAGCUGCUGCUACAA | 243 |
| rs362273 | SNP4-8 | 4 | 8 | UUGUAGCUGCAGCUUCUCGU | 232 | AAGCUGCUGCUACAA | 243 |
| rs362273 | SNP4-15 | 4 | 15 | UUGUAGCAGCAGCUACUCGU | 233 | AAGCUGCUGCUACAA | 243 |
| rs362273 | SNP6-5A | 6 | 5 | UUCUAUAGCAGCAGCUUCUC | 234 | GCUGCUGCUACAGAA | 244 |
| rs362273 | SNP6-8 | 6 | 8 | UUCUGUAUCAGCAGCUUCUC | 235 | GCUGCUGCUACAGAA | 244 |
| rs362273 | SNP6-11 | 6 | 11 | UUCUGUAGCAUCAGCUUCUC | 236 | GCUGCUGCUACAGAA | 244 |
| rs362273 | SNP6-14 | 6 | 14 | UUCUGUAGCAGCAUCUUCUC | 237 | GCUGCUGCUACAGAA | 244 |
| rs362273 | SNP6-16 | 6 | 16 | UUCUGUAGCAGCAGCAUCUC | 238 | GCUGCUGCUACAGAA | 244 |
| rs362307 | SNP3-5G | 3 | 5 | UCGCGGACUUCCAAAGGCUC | 239 | UUUGGAAGUCCGCGA | 245 |
| rs362307 | SNP3-7G | 3 | 7 | UCGCAGGCUUCCAAAGGCUC | 240 | UUUGGAAGCCUGCGA | 246 |
| rs362307 | SNP3-8 | 3 | 8 | UCGCAGAUUUCCAAAGGCUC | 241 | UUUGGAAAUCUGCGA | 247 |

In DNA molecules, U can be replaced with T

TABLE 6

| SNP of interest SNP | compound name | description of siRNA sequence flanking snp site: snp position | additional mismatch position | sequence: antisense strand | SEQ ID NO: | sense strand | SEQ ID NO: |
|---|---|---|---|---|---|---|---|
| rs362273 (A) | SNP2-7 | 2 | 7 | UUAGCAUCAGCUUCUCGUGG | 230 | AGAAGCUGCUGCUAA | 242 |
| rs362273 (A) | SNP4-7 | 4 | 7 | UUGUAGUAGCAGCUUCUCGU | 231 | AAGCUGCUGCUACAA | 243 |
| rs362273 (A) | SNP4-8 | 4 | 8 | UUGUAGCUGCAGCUUCUCGU | 232 | AAGCUGCUGCUACAA | 243 |
| rs362273 (A) | SNP4-15 | 4 | 15 | UUGUAGCAGCAGCUACUCGU | 233 | AAGCUGCUGCUACAA | 243 |
| rs362273 (A) | SNP6-5A | 6 | 5 | UUCUAUAGCAGCAGCUUCUC | 234 | GCUGCUGCUACAGAA | 244 |
| rs362273 (A) | SNP6-8 | 6 | 8 | UUCUGUAUCAGCAGCUUCUC | 235 | GCUGCUGCUACAGAA | 244 |
| rs362273 (A) | SNP6-11 | 6 | 11 | UUCUGUAGCAUCAGCUUCUC | 236 | GCUGCUGCUACAGAA | 244 |
| rs362273 (A) | SNP6-14 | 6 | 14 | UUCUGUAGCAGCAUCUUCUC | 237 | GCUGCUGCUACAGAA | 244 |
| rs362273 (A) | SNP6-16 | 6 | 16 | UUCUGUAGCAGCAGCAUCUC | 238 | GCUGCUGCUACAGAA | 244 |
| rs362307 (C') | SNP3-5G | 3 | 5 | UCGCGGACUUCCAAAGGCUC | 239 | UUUGGAAGUCCGCGA | 245 |
| rs362307 (C') | SNP3-7G | 3 | 7 | UCGCAGGCUUCCAAAGGCUC | 240 | UUUGGAAGCCUGCGA | 246 |
| rs362307 (C') | SNP3-8 | 3 | 8 | UCGCAGAUUUCCAAAGGCUC | 241 | UUUGGAAAUCUGCGA | 247 |

TABLE 7

| | | description of siRNA sequence flanking snp | | sequence | | | |
|---|---|---|---|---|---|---|---|
| SNP of interest SNP | compound name | snp position | additional mismatch position | antisense strand | SEQ ID NO: | sense strand | SEQ ID NO: |
| rs362273 (G) | SNP2-7 | 2 | 7 | UCAGCAUCAGCUUCUCGUGG | 248 | AGAAGCUGCUGCUGA | 259 |
| rs362273 (G) | SNP4-7 | 4 | 7 | UUGCAGUAGCAGCUUCUCGU | 249 | AAGCUGCUGCUGCAA | 260 |
| rs362273 (G) | SNP4-8 | 4 | 8 | UUGCAGCUGCAGCUUCUCGU | 250 | AAGCUGCUGCUGCAA | 260 |
| rs362273 (G) | SNP4-15 | 4 | 15 | UUGCAGCAGCAGCUACUCGU | 251 | AAGCUGCUGCUGCAA | 260 |
| rs362273 (G) | SNP6-5A | 6 | 5 | UUCUACAGCAGCAGCUUCUC | 252 | GCUGCUGCUGCAGAA | 261 |
| rs362273 (G) | SNP6-8 | 6 | 8 | UUCUGCAUCAGCAGCUUCUC | 253 | GCUGCUGCUGCAGAA | 261 |
| rs362273 (G) | SNP6-11 | 6 | 11 | UUCUGCAGCAUCAGCUUCUC | 254 | GCUGCUGCUGCAGAA | 261 |
| rs362273 (G) | SNP6-14 | 6 | 14 | UUCUGCAGCAGCAUCUUCUC | 255 | GCUGCUGCUGCAGAA | 261 |
| rs362307 (T) | SNP3-5G | 3 | 5 | UCACGGACUUCCAAAGGCUC | 256 | UUUGGAAGUCCGUGA | 262 |
| rs362307 (T) | SNP3-7G | 3 | 7 | UCACAGGCUUCCAAAGGCUC | 257 | UUUGGAAGCCUGUGA | 263 |
| rs362307 (T) | SNP3-8 | 3 | 8 | UCACAGAUUUCCAAAGGCUC | 258 | UUUGGAAAUCUGUGA | 264 |

Methods of Delivering Nucleic Acids

RNA silencing agents of the invention may be directly introduced into a cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-IS mediated transport, such as calcium phosphate, and the like. Thus, the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly), or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double-stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, fluorescence activated cell analysis (FACS) and the like.

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell. mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In a particular aspect, the efficacy of an RNAi agent of the invention (e.g., an siRNA targeting a polymorphism in a mutant gene) is tested for its ability to specifically degrade mutant mRNA (e.g., mutant htt mRNA and/or the production of mutant huntingtin protein) in cells, in particular, in neurons (e.g., striatal or cortical neuronal clonal lines and/or primary neurons). Also suitable for cell-based validation assays are other readily transfectable cells, for example, HeLa cells or COS cells. Cells are transfected with human wild-type or mutant cDNAs (e.g., human wild-type or mutant huntingtin cDNA). Standard siRNA, modified siRNA or vectors able to produce siRNA from U-looped mRNA are co-transfected. Selective reduction in mutant mRNA (e.g., mutant huntingtin mRNA) and/or mutant protein (e.g., mutant huntingtin) is measured. Reduction of mutant mRNA or protein can be compared to levels of normal mRNA or protein. Exogenously-introduced normal mRNA or protein (or endogenous normal mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

In certain exemplary embodiments, a composition that includes an RNA agent, e.g., a dsRNA agent, of the invention can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the RNA agents, e.g., dsRNA agents, to peripheral neurons. An exemplary route of delivery is directly to the brain, e.g., into the ventricles or the hypothalamus of the brain, or into the lateral or dorsal areas of the brain. The RNA agents, e.g., dsRNA agents, for neural cell delivery can be incorporated into pharmaceutical compositions suitable for administration.

For example, compositions can include one or more species of an RNA agent, e.g., a dsRNA agent, and a pharmaceutically acceptable carrier. The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the invention is delivered across the Blood-Brain-Barrier (BBB) suing a variety of suitable compositions and methods described herein.

The route of delivery can be dependent on the disorder of the patient. For example, a subject diagnosed with Huntington's disease can be administered an anti-htt RNA agent, e.g., a dsRNA agent, of the invention directly into the brain (e.g., into the globus pallidus or the corpus striatum of the basal ganglia, and near the medium spiny neurons of the corpus striatum). In addition to an RNA silencing agent of the invention, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). For the treatment of Huntington's disease, for example, symptomatic therapies can include the drugs haloperidol, carbamazepine, or valproate. Other therapies can include psychotherapy, physiotherapy, speech therapy, communicative and memory aids, social support services, and dietary advice.

An RNA agent, e.g., a dsRNA agent, can be delivered to neural cells of the brain. Delivery methods that do not require passage of the composition across the blood-brain barrier can be utilized. For example, a pharmaceutical composition containing an RNA agent, e.g., a dsRNA agent, can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA agent, e.g., a dsRNA agent, can be delivered into multiple regions of the central nervous system (e.g., into multiple regions of the brain, and/or into the spinal cord). The RNA agent, e.g., a dsRNA agent, can be delivered into diffuse regions of the brain (e.g., diffuse delivery to the cortex of the brain).

In one embodiment, the RNA agent, e.g., a dsRNA agent, can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA agent, e.g., dsRNA agent. The flow or delivery can be mediated by a pump, e.g., an osmotic pump or minipump, such as an Alzet pump (Durect, Cupertino, CA). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

An RNA agent, e.g., a dsRNA agent, of the invention can be further modified such that it is capable of traversing the blood brain barrier. For example, the RNA agent, e.g., a dsRNA agent, can be conjugated to a molecule that enables the agent to traverse the barrier. Such modified RNA agents, e.g., dsRNA agents, can be administered by any desired method, such as by intraventricular or intramuscular injection, or by pulmonary delivery, for example.

In certain embodiments, exosomes are used to deliver an RNA agent, e.g., a dsRNA agent, of the invention. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood M J. (2011). Delivery of siRNA to the mouse brain by systemic injection of targeted exosomes. Nat Biotechnol. 2011 April; 29(4): 341-5. doi: 10.1038/nbt.1807; El-Andaloussi S, Lee Y, Lakhal-Littleton S, Li J, Seow Y, Gardiner C, Alvarez-Erviti L, Sargent I L, Wood M J. (2011). Exosome-mediated delivery of siRNA in vitro and in vivo. Nat Protoc. 2012 December; 7(12):2112-26. doi: 10.1038/nprot.2012.131; EL Andaloussi S, Mager I, Breakefield X O, Wood M J. (2013). Extracellular vesicles: biology and emerging therapeutic opportunities. Nat Rev Drug Discov. 2013 May; 12(5):347-57. doi: 10.1038/nrd3978; El Andaloussi S, Lakhal S, Mager I, Wood M J. (2013). Exosomes for targeted siRNA delivery across biological barriers. Adv. Drug Deliv Rev. 2013 March; 65(3):391-7. doi: 10.1016/j.addr.2012.08.008).

In certain embodiments, one or more lipophilic molecules are used to allow delivery of an RNA agent, e.g., a dsRNA agent, of the invention past the BBB (Alvarez-Ervit (2011)). The RNA silencing agent would then be activated, e.g., by enzyme degradation of the lipophilic disguise to release the drug into its active form.

In certain embodiments, one or more receptor-mediated permeabilizing compounds can be used to increase the permeability of the BBB to allow delivery of an RNA silencing agent of the invention. These drugs increase the permeability of the BBB temporarily by increasing the osmotic pressure in the blood which loosens the tight junctions between the endothelial cells ((El-Andaloussi (2012)). By loosening the tight junctions normal intravenous injection of an RNA silencing agent can be performed.

In certain embodiments, nanoparticle-based delivery systems are used to deliver an RNA agent, e.g., a dsRNA agent, of the invention across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide) (PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tae-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi:10.1155/2013/782041 (incorporated by reference in its entirety.)

An RNA agent, e.g., a dsRNA agent, of the invention can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agent can also be applied via an ocular patch.

In general, an RNA agent, e.g., a dsRNA agent, of the invention can be administered by any suitable method. As used herein, topical delivery can refer to the direct application of an RNA agent, e.g., a dsRNA agent, to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA agent, e.g., a dsRNA agent, to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration typically do not include a transfection reagent or an additional lipophilic moiety besides, for example, the lipophilic moiety attached to the RNA agent, e.g., a dsRNA agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An RNA agent, e.g., a dsRNA agent, of the invention can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an RNA agent, e.g., a dsRNA agent, administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are exemplary. One of the benefits of using an atomizer or inhaler is that the potential for contamination is minimized because the devices are self-contained. Dry powder dispersion devices, for example, deliver drugs that may be readily formulated as dry powders. An RNA silencing agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. An exemplary group of carbohydrates includes lactose, trehalose, raffinose maltodextrins, and mannitol. Suitable polypeptides include aspartame. Amino acids include alanine and glycine, with glycine being exemplary.

Suitable pH adjusters or buffers include organic salts prepared from organic acids and bases, such as sodium citrate, sodium ascorbate, and the like; sodium citrate is exemplary.

An RNA agent, e.g., a dsRNA agent, of the invention can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier.

In one embodiment, unit doses or measured doses of a composition that include RNA agents, e.g., dsRNA agents, are dispensed by an implanted device. The device can include a sensor that monitors a parameter within a subject. For example, the device can include a pump, such as an osmotic pump and, optionally, associated electronics.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Figure 46:
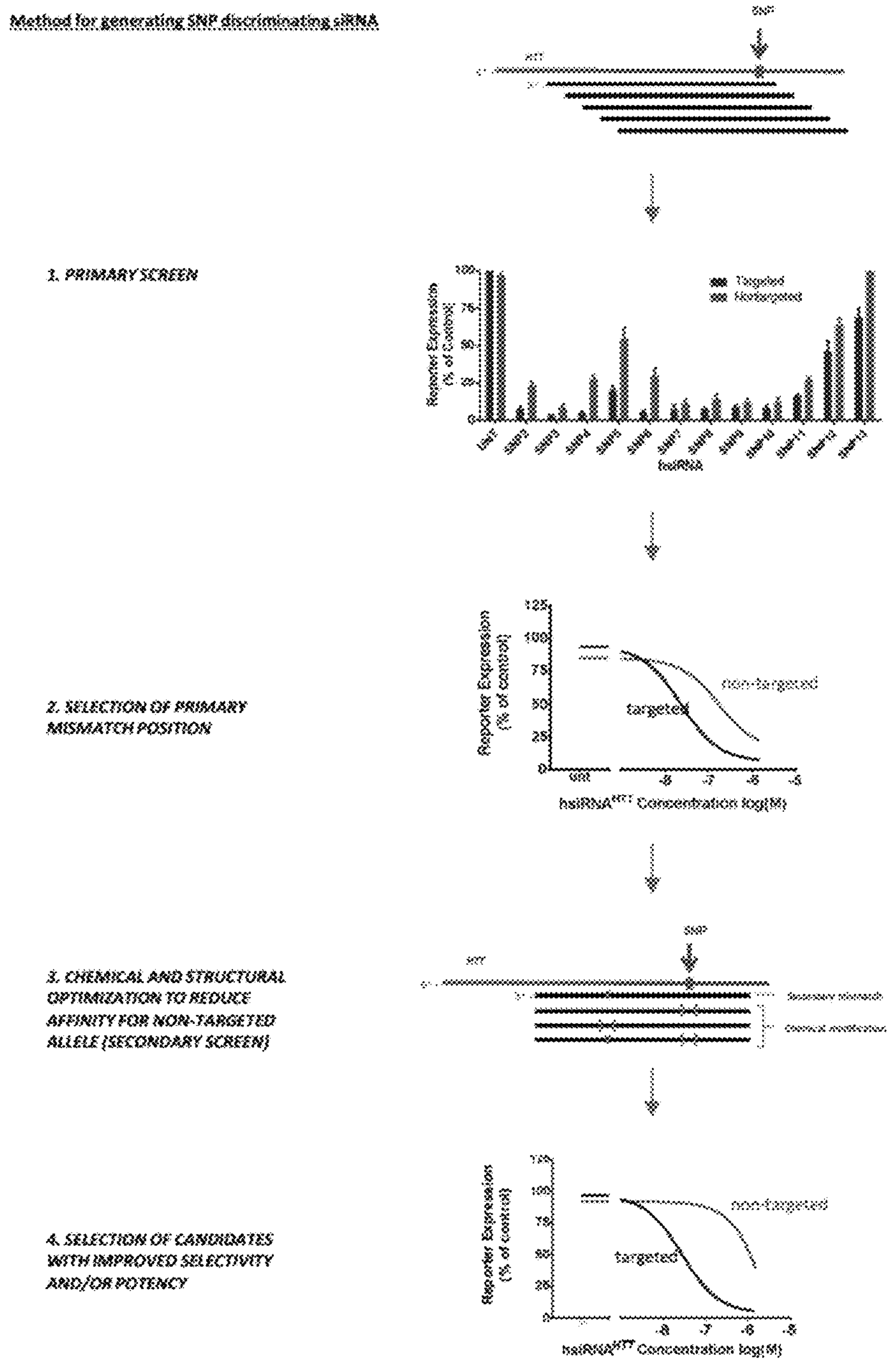
FIG. 46 is a flow chart illustrating a methodology for generating and selecting SNP-discriminating siRNAs.

Example 1: SNP Discrimination Varies According to the Position of the Mismatch FIG. 46 is a flow chart illustrating a methodology for generating and selecting SNP-discriminating siRNAs that was implemented in the instance of HTT, but is also applicable to SNPs in other genes. A primary screen is conducted to determine which position the SNP is placed at causes the greatest discrimination. Then, the mismatch position(s) yielding best results are selected, and affinity for non-target alleles is further reduced in a secondary screening where chemical and structural optimizations to the siRNA molecule with improved selectivity and/or potency are selected.

Figure 45:
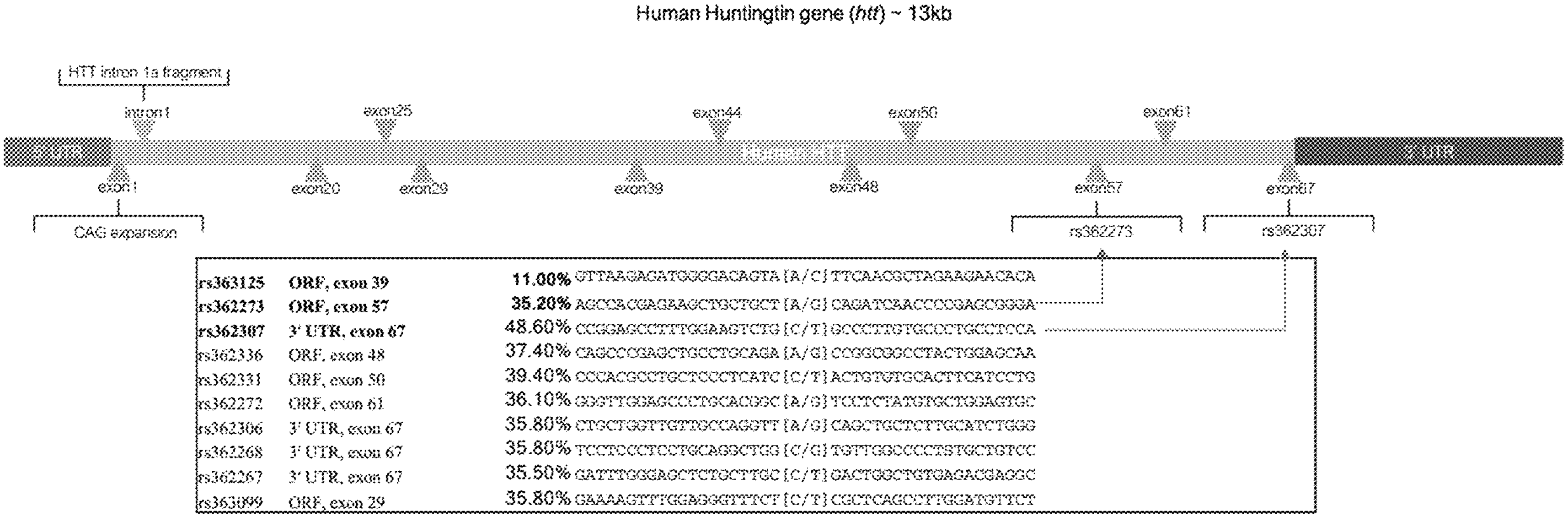
FIG. 45 illustrates exemplary SNPs within the HTT gene (SEQ ID NOs: 1-10 (numbered from top to bottom)).

There are several SNPs within the HTT gene that have high rates of heterozygosity in HD patients (FIG. 45). For optimization of SNP-specific RNAi-mediated silencing of huntingtin, SNP rs362273 in exon 57 of HTT mRNA was used as model target for optimization of SNP selective silencing. This SNP heterozygosity occurs in 35% of the HD patient population.

The psiCHECK reporter plasmid described herein contains SNP rs362273 and a partial flanking region from exon 57 of htt, within a Rluc 3' UTR. The wild-type psiCHECK reporter plasmid contains the same region of htt without the SNP (FIG. 1).

Figure 2:
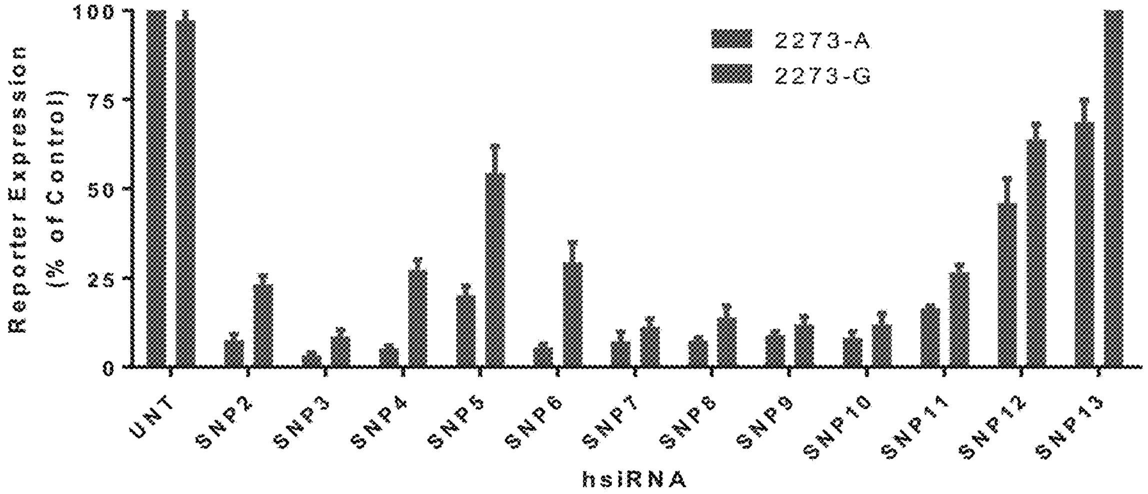
FIG. 2 depicts a bar graph showing luciferase activity following a psiCHECK reporter plasmid assay in HeLa cells transfected with hsiRNAs with the SNP nucleotide at varying positions. This primary screen yielded multiple efficacious hydrophobically modified siRNA (hsiRNA) sequences.
Figure 47:
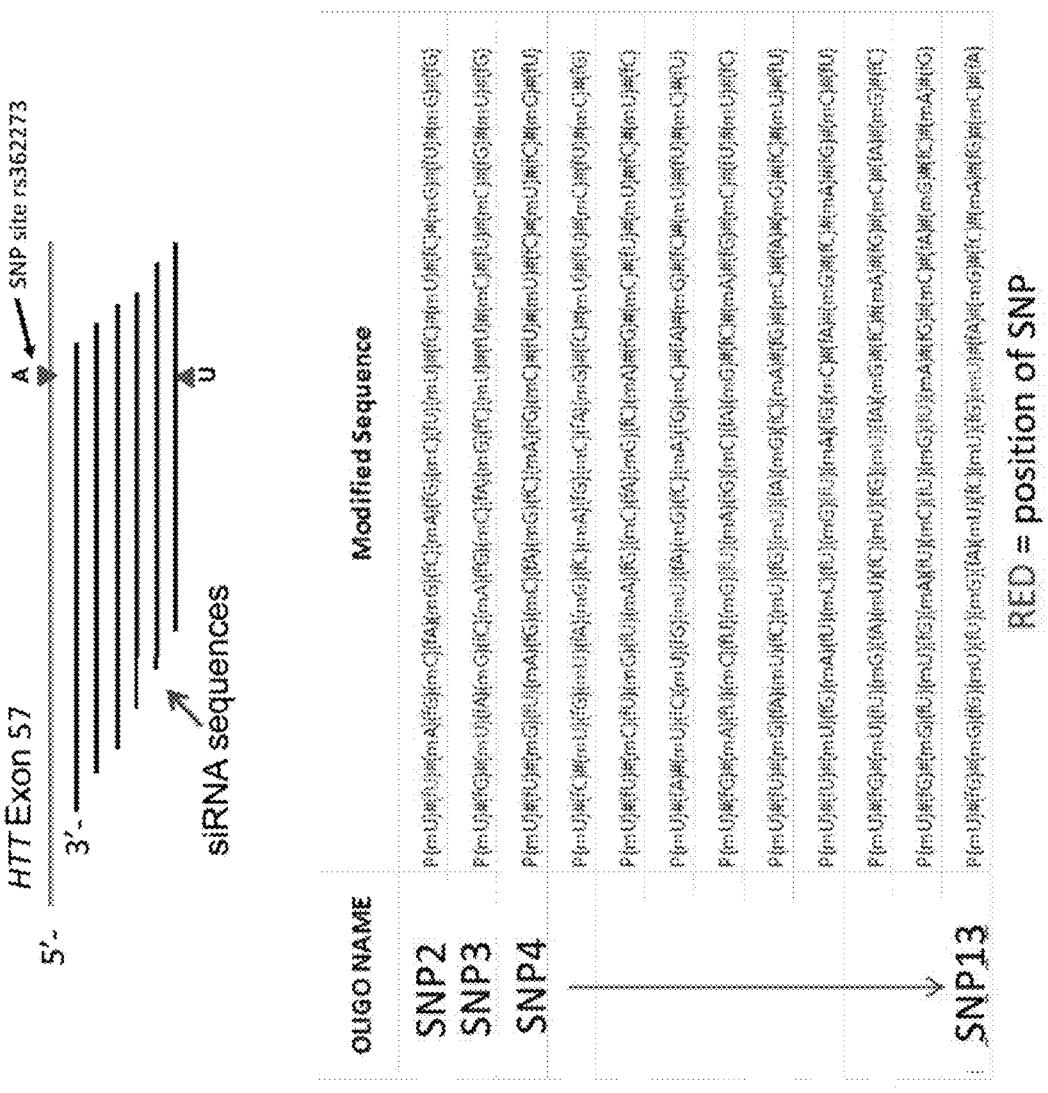
FIG. 47 illustrates a naming convention denoting the position of an SNP within an siRNA.

Hydrophobically modified RNAs (hsiRNAs) designed to be complimentary to the Huntingtin (htt) mRNA containing the mutant SNP (2273-1 (A)) were screened for efficacy with the psiCheck reporter plasmid system. The number following SNP represents the position of the SNP in the siRNA (FIG. 47). FIG. 2 shows that placing the SNP in position 2, 4 or 6 provided the greatest SNP discrimination, without losing efficacy against the mutant allele. HeLa cells transfected with one of two reporter plasmids were reverse transfected with 1.5 μM hsiRNAs by passive uptake, and treated for 72 hours. Luciferase activity was measured at 72 hours post transfection (FIG. 2).

Figure 3:
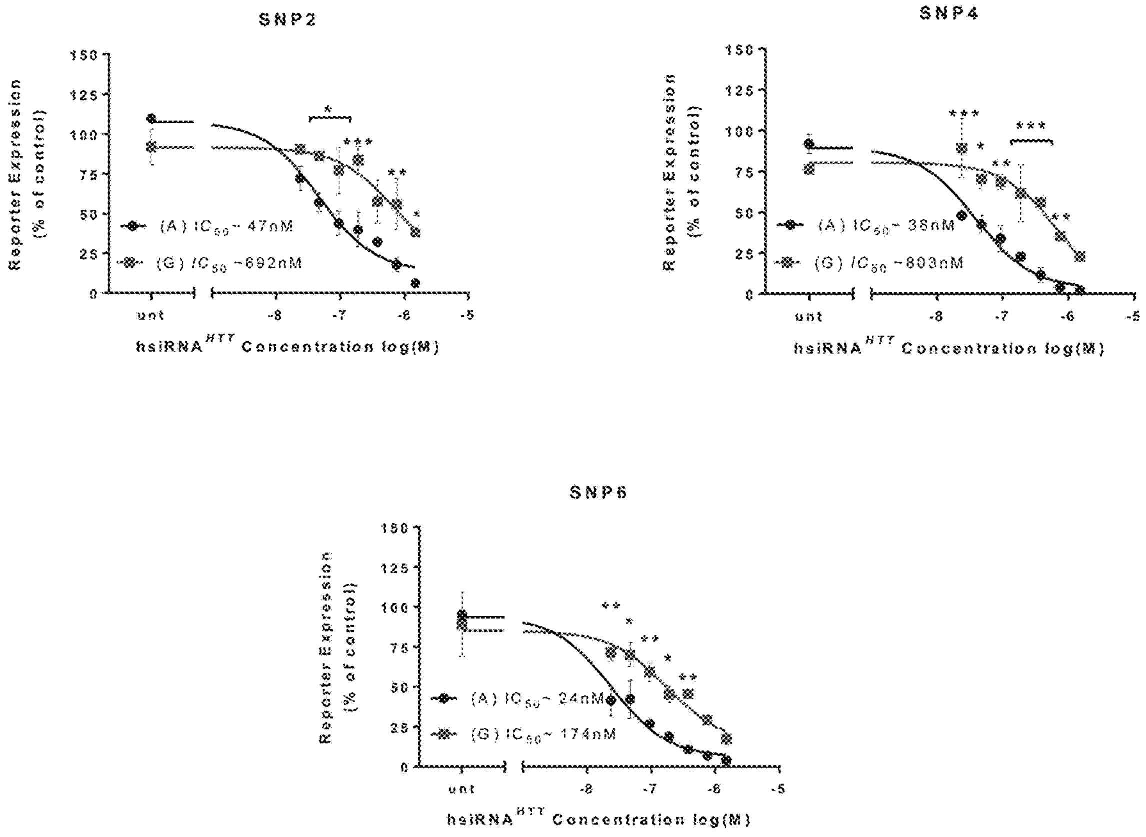
FIG. 3 depicts dose response curves showing the silencing effects of three exemplary hsiRNAs of the invention on psiCHECK reporter plasmids.

The hsiRNAs were further tested for allelic discrimination in a dose response dual luciferase assay in HeLa cells (FIG. 3). Multiple hsiRNAs preferentially silenced the reporter plasmid containing the mutant SNP as compared to the wild-type reporter plasmid. HeLa cells transfected with one of two reporter plasmids were reverse transfected with 1.5 μM hsiRNAs by passive uptake, and treated for 72 hours. Reporter plasmid expression was measured at 72 hours post transfection (FIG. 3).

Example 2: SNP Discrimination in the Endogenous Htt mRNA

Figure 4:
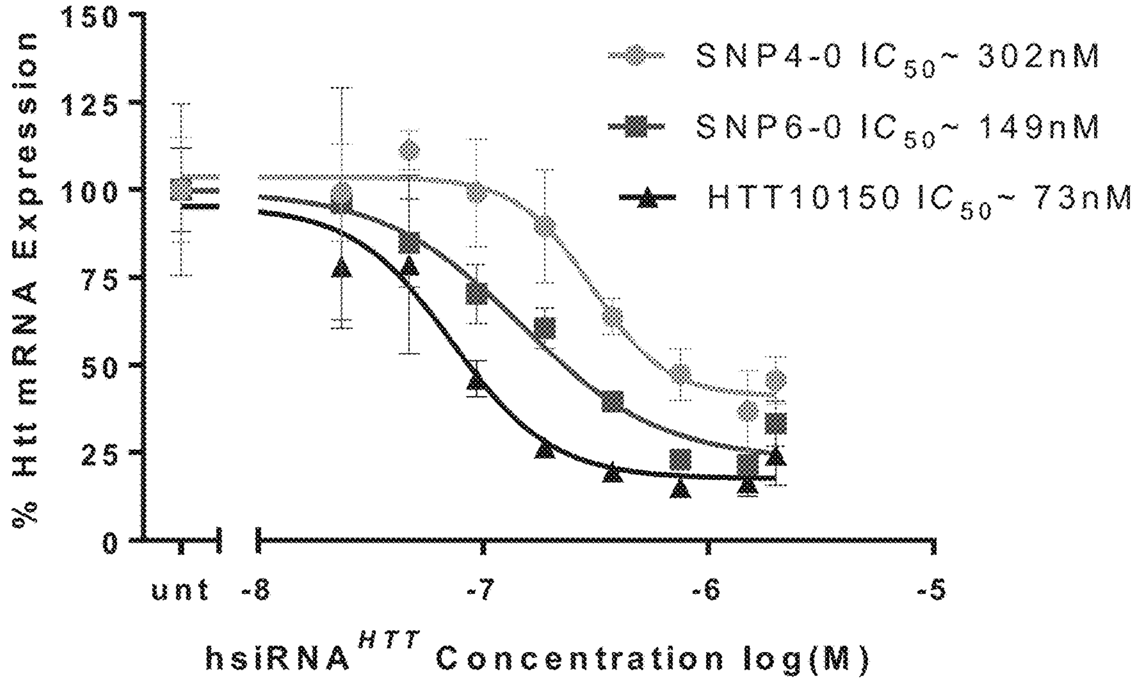
FIG. 4 depicts a dose response curve showing the efficacy of two hsiRNAs on silencing htt mRNA.

The hsiRNAs were tested for efficacy against the endogenous Huntingtin mRNA containing a homozygous rs362273 SNP. As HeLa cells are homozygous at rs362273, with an A on each allele, allelic discrimination was not assessed with this assay. Instead, FIG. 4 shows that two hsiRNAs, SNP4-0 and SNP6-0, were highly effective at silencing the htt mRNA containing the correct SNP. The mRNA levels were measured using Quantigene 2.0 bDNA assay after treating HeLa cells with hsiRNAs via passive uptake for 72 hours. Human htt mRNA levels were normalized to human HPRT.

Figure 34:
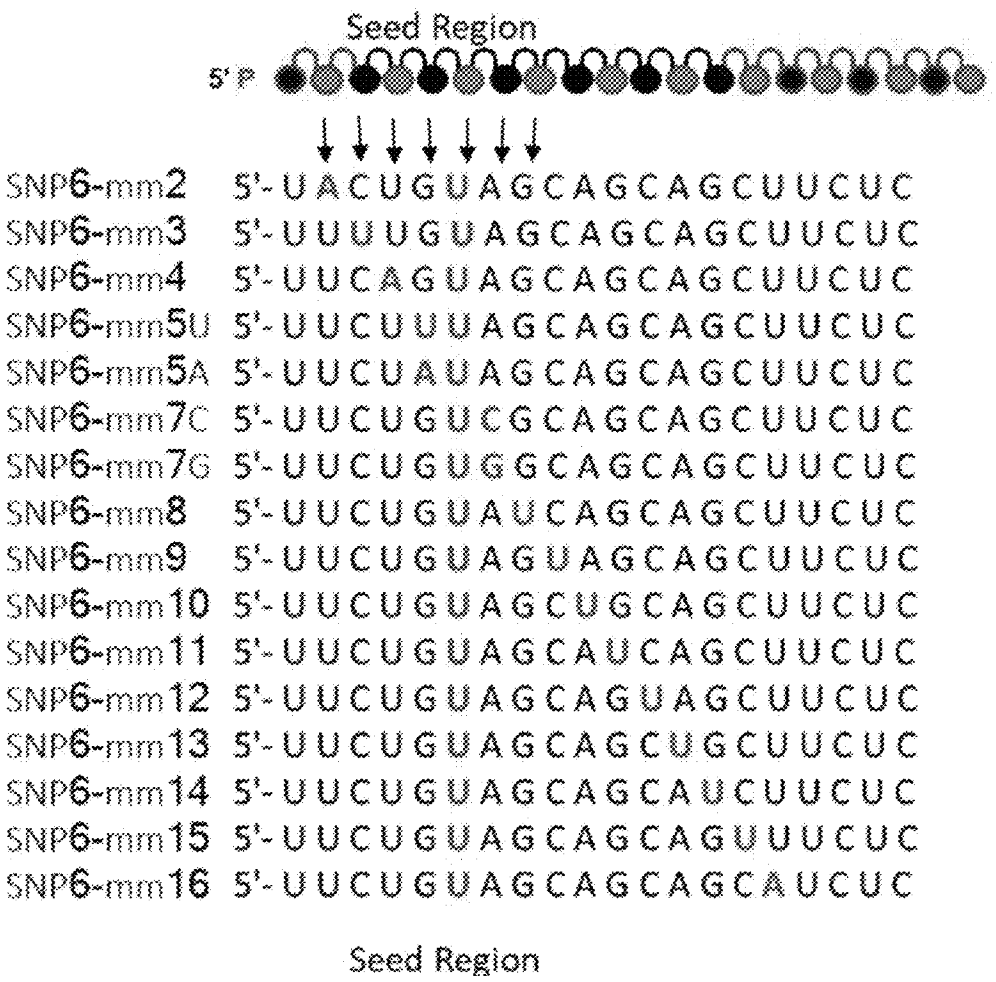
FIG. 34 illustrates example sequences introducing single mismatches in sequences previously chosen for dose response.

Example 3: Designing hsiRNAs with a Second Mismatch for Greater Allelic Discrimination For each of the three hsiRNAs (SNP2-0, SNP4-0, and SNP6-0, also named mm2, mm4, and mm6, respectively) previously chosen for dose response, 16 new hsiRNAs were designed and synthesized with slight sequence modifications (FIG. 34). These sequences introduced a single mismatch at every possible position along the original sequence, in order to test if the second mismatch impairs silencing of the off-target SNP more significantly than before, with little effect on silencing the target SNP. Antisense strand sequences shown 5' to 3', with the SNP site in red, and the new mismatch in blue (FIG. 12).

Figure 5:
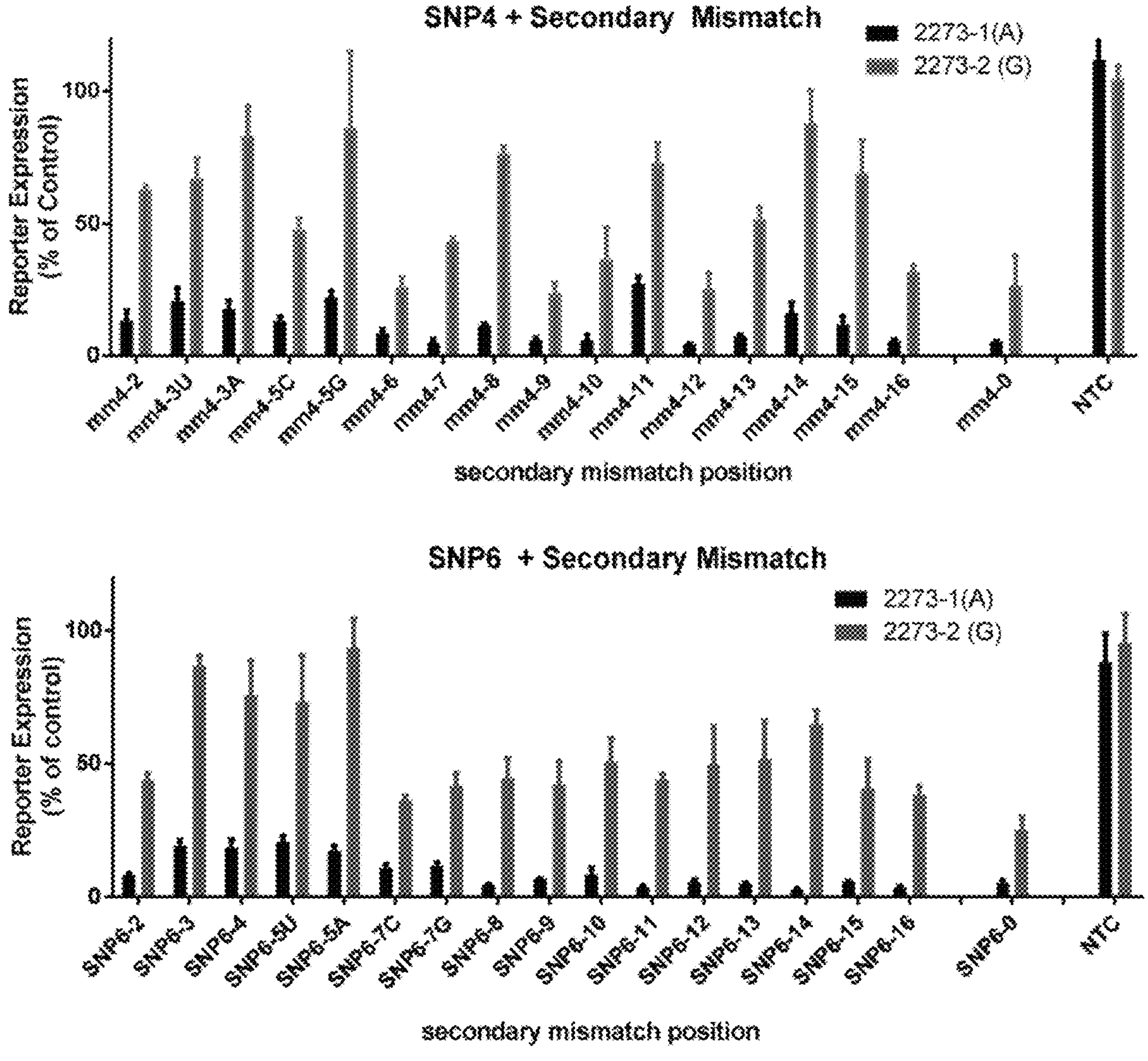
FIG. 5 depicts bar graphs showing luciferase activity following a psiCHECK reporter plasmid assay in HeLa cells transfected with hsiRNAs having a second mismatch at varying positions.

A primary screen of the efficacy of the hsiRNAs in FIG. 12 showed that the position of the second mismatch, relative to the position of the nucleotide corresponding to the SNP, resulted in varying levels of SNP discrimination in HeLa cells. HeLa cells transfected with one of two psiCHECK reporter plasmids were reverse transfected with 1.5 μM hsiRNAs by passive uptake, and treated for 72 hours. Luciferase activity was measured at 72 hours post transfection. FIG. 5 shows that multiple hsiRNAs discriminately silenced the reporter plasmid containing the SNP mutation as compared to the wild-type reporter plasmid.

Figure 6:
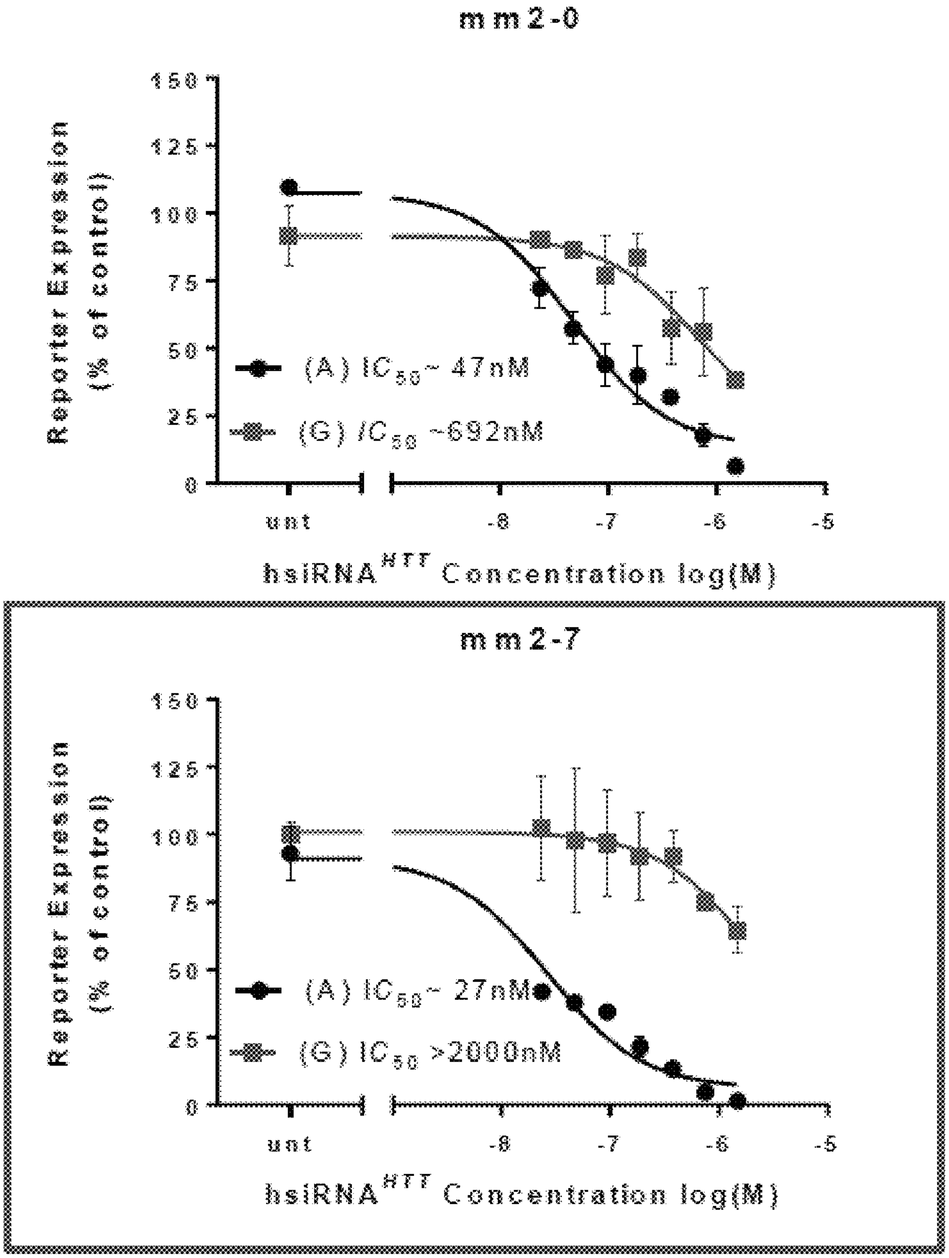
FIG. 6 depicts dose response curves comparing silencing effects of SNP2 hsiRNA with (mm2-7) or without (mm2-0) an additional mismatch.
Figure 7:
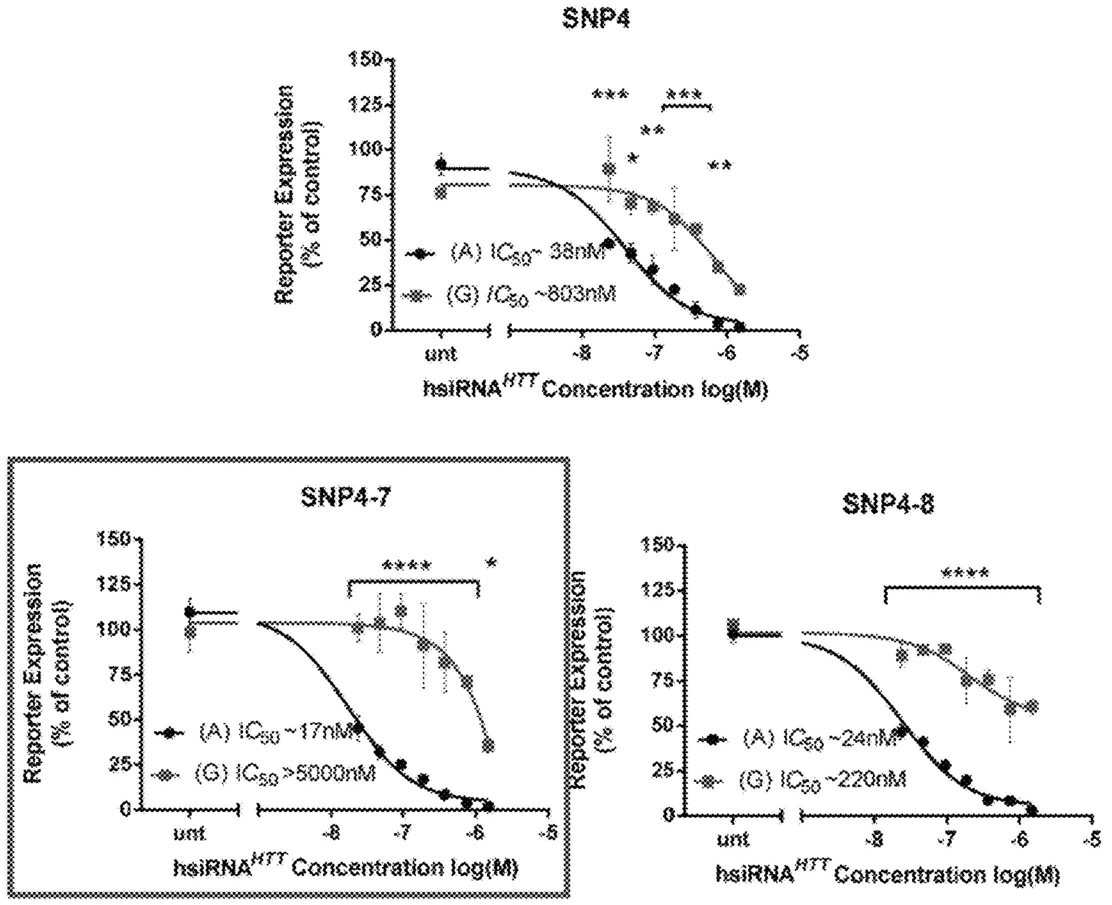
FIG. 7 depicts dose response curves comparing silencing effects of SNP4 hsiRNAs with or without an additional mismatch.
Figure 8:
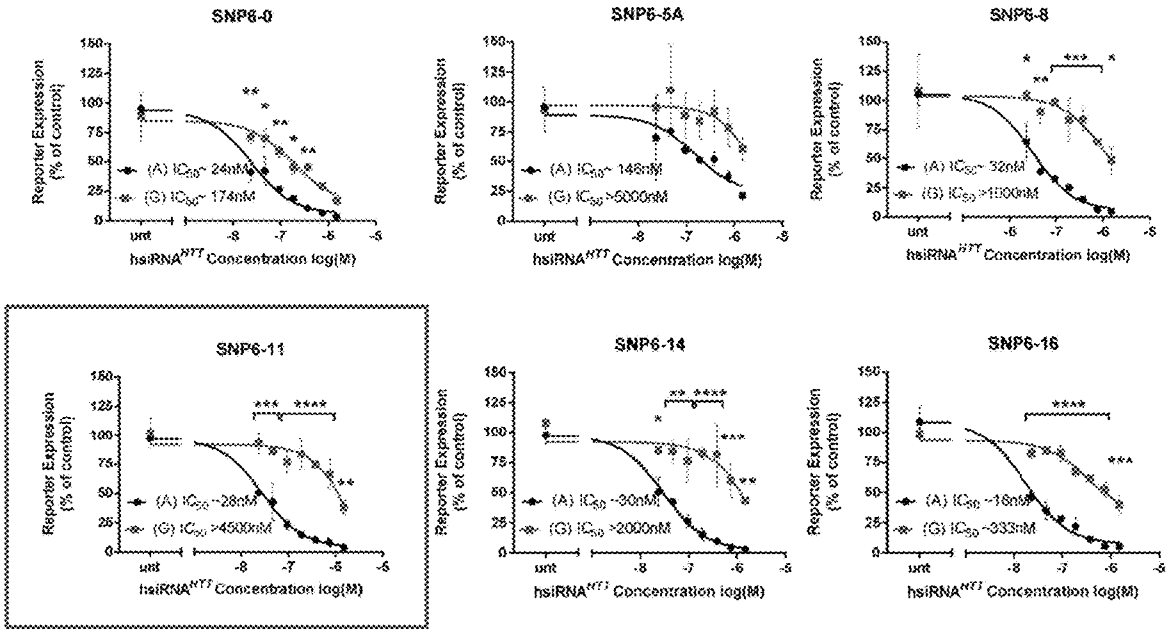
FIG. 8 depicts dose response curves comparing silencing effects of SNP6 hsiRNAs with or without an additional mismatch.
Figure 9:
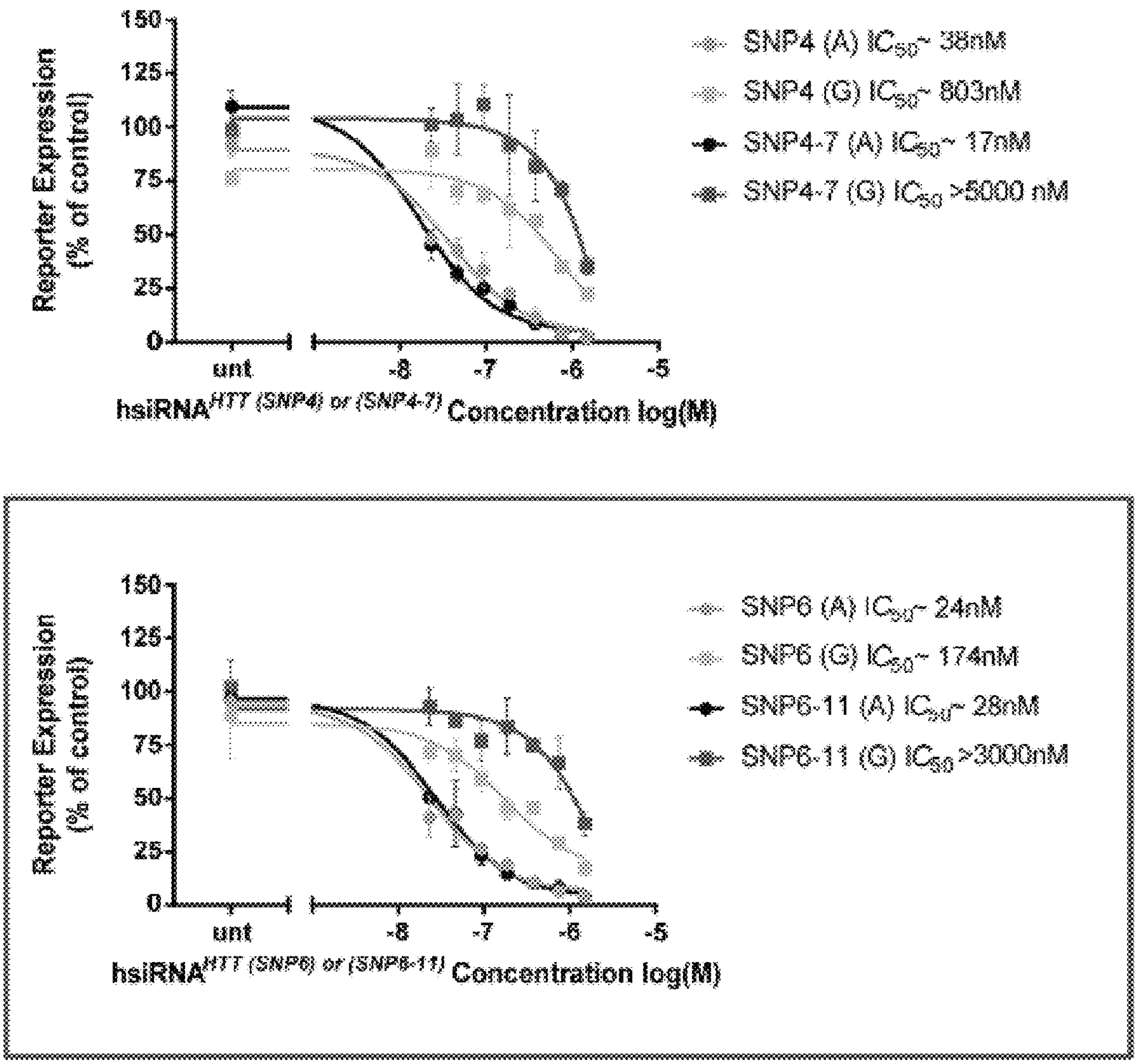
FIG. 9 depicts dose response curves comparing silencing effects of SNP4 or SNP6 hsiRNAs with an additional mismatch (SNP4-7 and SNP6-11, respectively), compared to the same hsiRNAs without an additional mismatch (SNP4-0 and SNP4-11). HeLa cells transfected with one of two reporter plasmids were revers transfected with hsiRNAs by passive uptake, and treated for 72 hours. reporter expression was measured with a dual luciferase assay.
Figure 10:
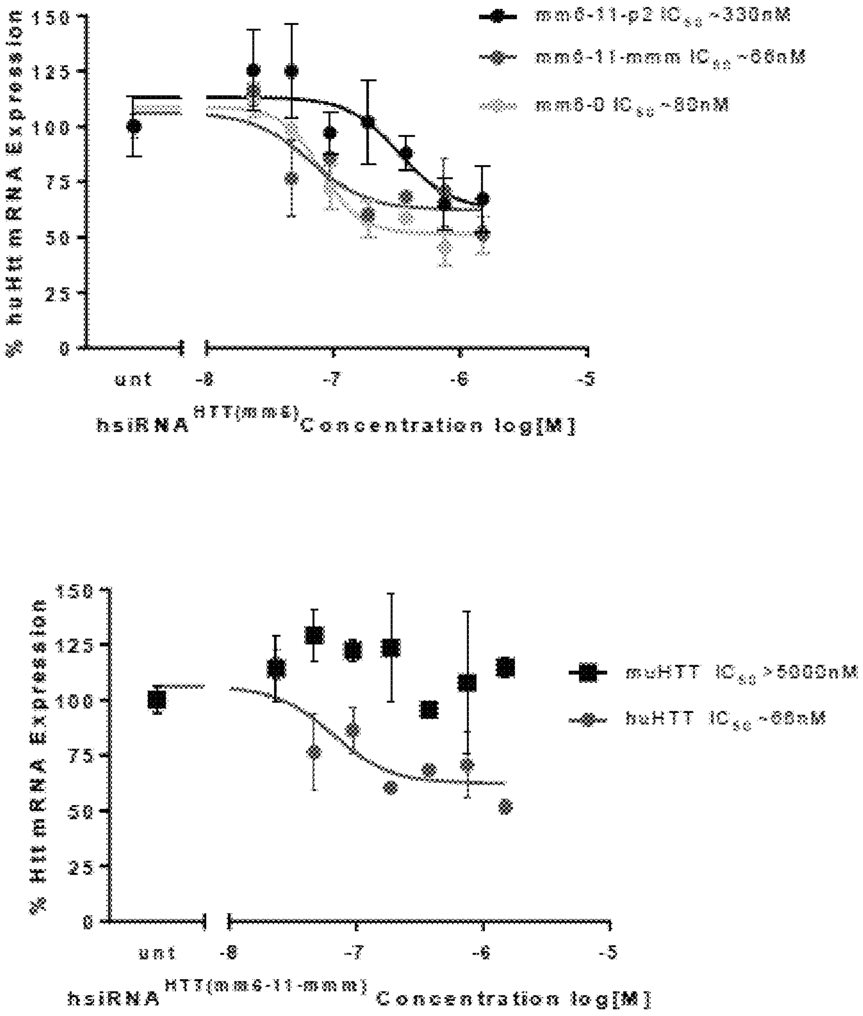
FIG. 10 depicts dose response curves of htt mRNA expression that measures silencing efficacy of hsiRNAs with additional mismatches.
Figure 11:
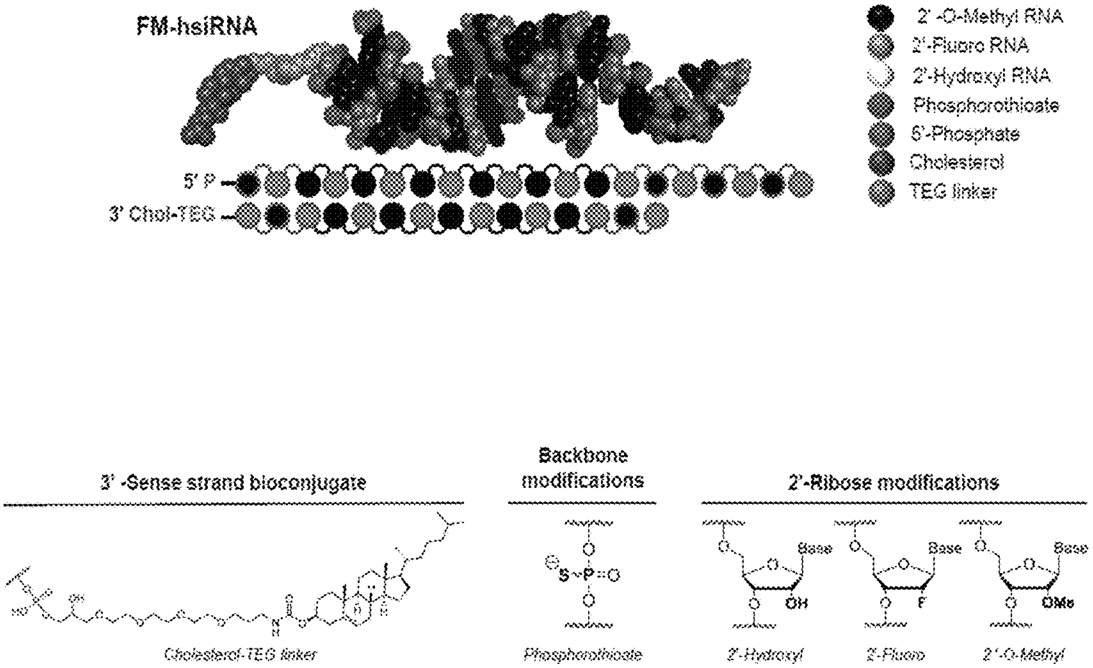
FIG. 11 schematically depicts an hsiRNA and exemplary modifications according to certain embodiments of the invention.

The most efficacious hsiRNAs, containing the second mismatch, were further tested in a dose response curve to verify improved SNP discrimination. HeLa cells transfected with one of two reporter plasmids were reverse transfected with hsiRNAs by passive uptake, and treated for 72 hours. Reporter expression measured with a dual-luciferase assay. FIGS. 6-8 show the IC50 values of the hsiRNAs with two mismatches for silencing the reporter plasmid containing the SNP mutation versus the wild-type reporter plasmid. The SNP6-11 hsiRNA (hsiRNA molecule with the nucleotide corresponding to the polymorphism at position 6 from the 5' end and the mismatch at position 11 from the 5' end) and the SNP4-7 hsiRNA (hsiRNA molecule with the nucleotide corresponding to the polymorphism at position 4 from the 5' end and the mismatch at position 7 from the 5' end) were shown to be the most efficacious (see FIGS. 7-9). Surprisingly, altering the modification pattern around the SNP rescues efficacy lost by introducing the second mismatch without impairing discrimination. The SNP6-11 hsiRNA was altered so that it had 2'O-methyl modifications flanking the mismatch nucleotide (as well as the mismatch nucleotide itself having the 2'O-methyl modification) (see FIG. 10).

Example 4: Additional Modifications

A variety of oligonucleotide types (e.g., gapmers, mixmers, miRNA inhibitors, splice-switching oligonucleotides ("SSOs"), phosphorodiamidate morpholino oligonucleotides ("PMOs"), peptide nucleic acids ("PNAs") and the like) can be used in the oligonucleotides described herein, optionally utilizing various combinations of modifications (e.g., chemical modifications) and/or conjugations described herein and in, e.g., U.S. Ser. No. 15/089,423; U.S. Ser. No. 15/236,051; U.S. Ser. No. 15/419,593; U.S. Ser. No. 15/697,120 and U.S. Pat. No. 9,809,817; and U.S. Ser. No. 15/814,350 and U.S. Pat. No. 9,862,350, each of which is incorporated herein by reference in its entirety for all purposes.

Figure 15:
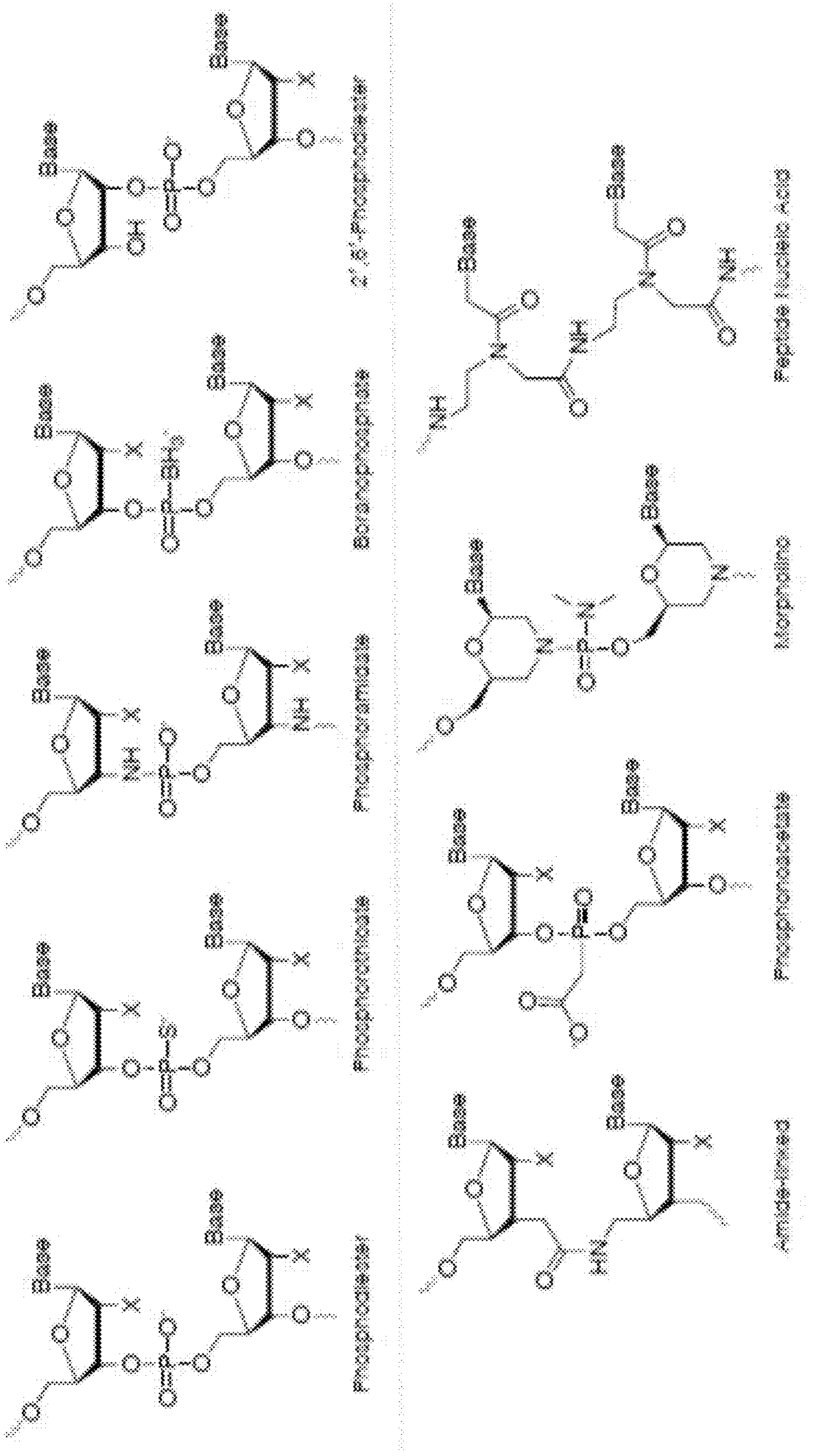
Figure 16:
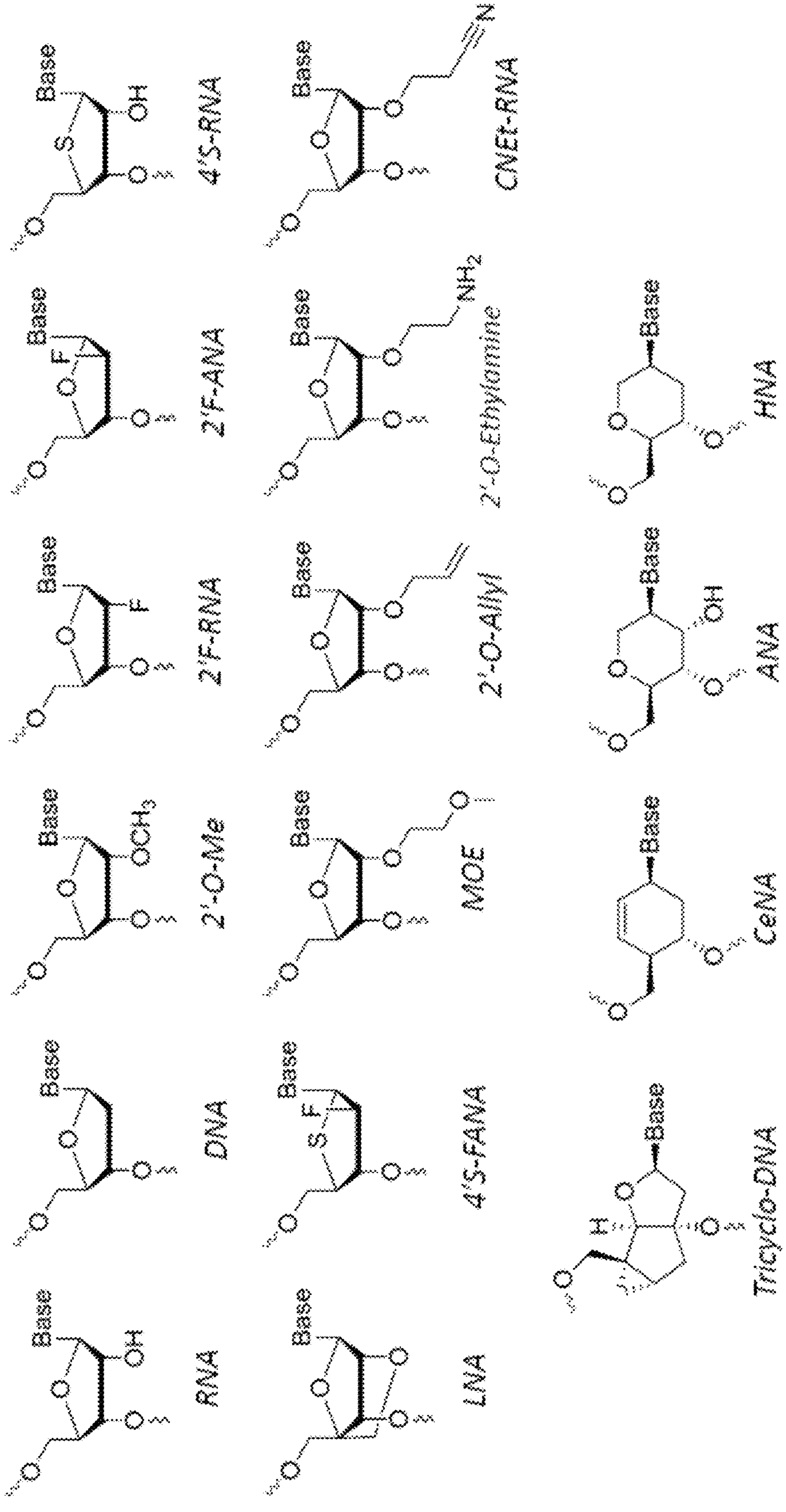
Figure 17:
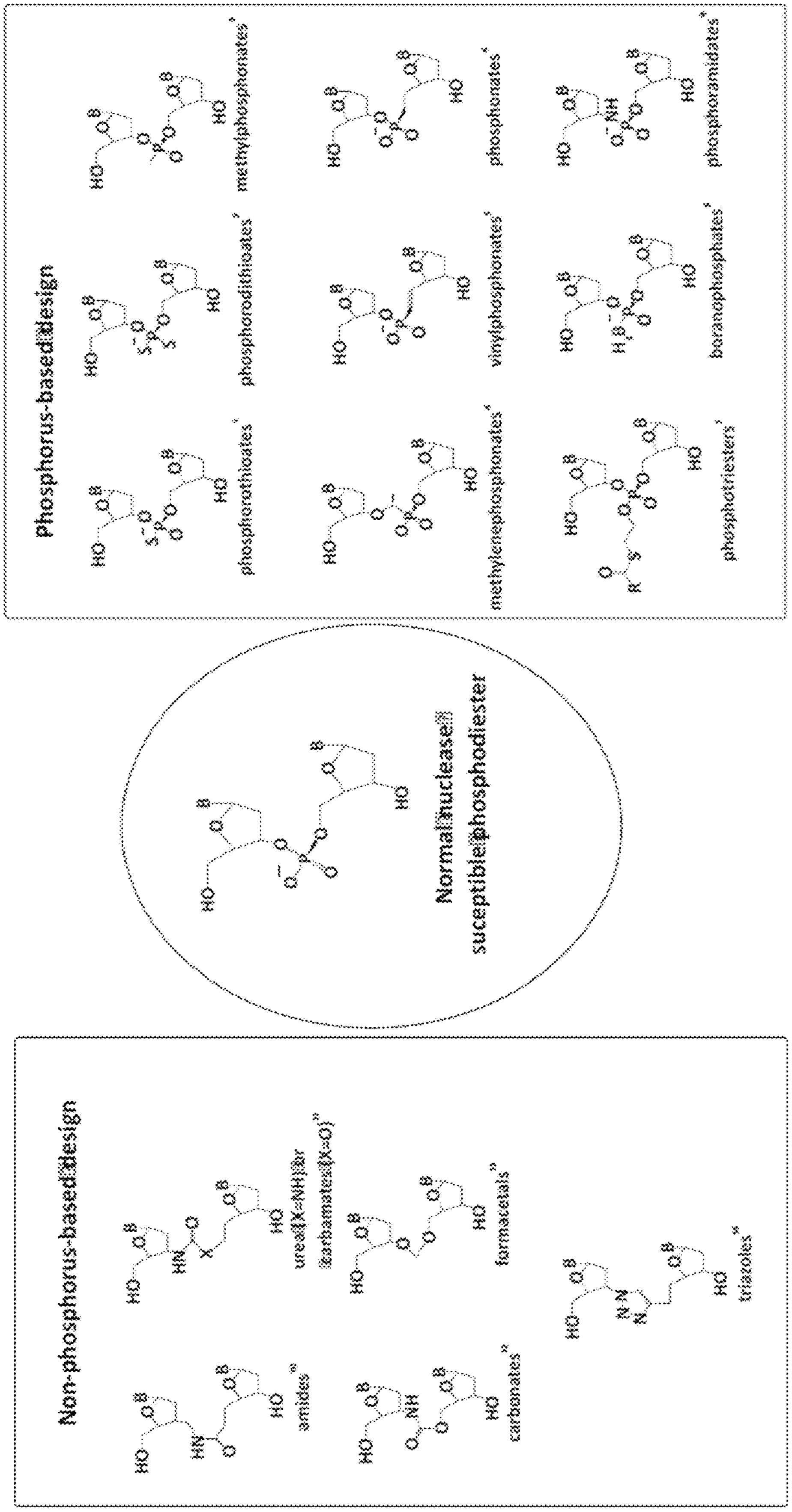
FIG. 17 depicts internucleotide bonds according to certain exemplary embodiments. Potential internucleotide bonds can be between the first two nucleotides at the 5' or 3' ends of any given oligonucleotide strand can be stabilized with any of the moieties depicted.
Figure 18:
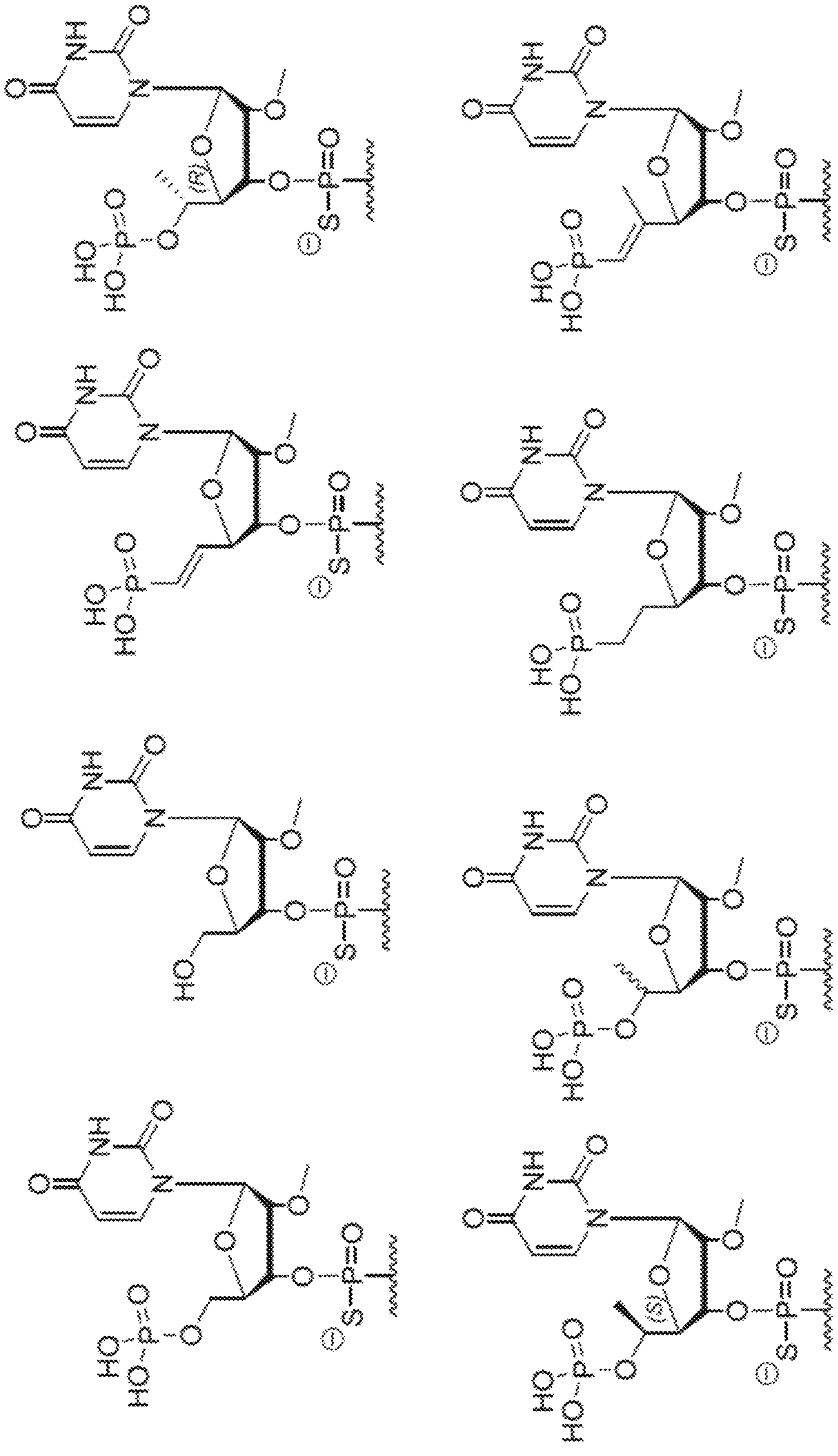
Figure 19:
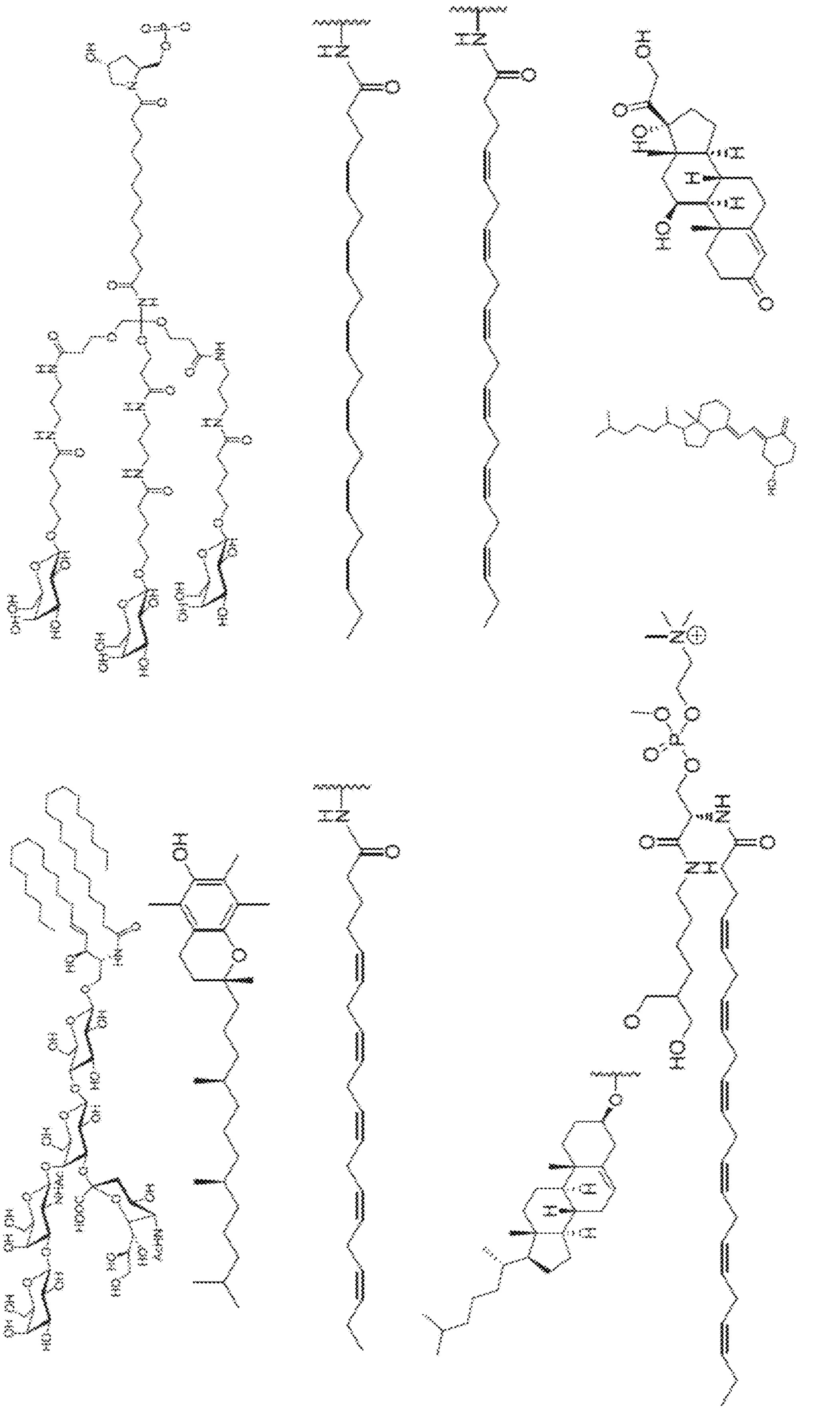

For example, an oligonucleotide described herein may be designed as a di-siRNA (see, e.g., FIG. 14). An oligonucleotide described herein may include one or more different backbone linkages (see, e.g., FIG. 15). An oligonucleotide described herein may include a variety of sugar modifications (see, e.g., FIG. 16). An oligonucleotide described herein may include a variety of internucleotide bonds (see, e.g., FIG. 17). An oligonucleotide described herein may include one or more 5' stabilization modifications (see, e.g., FIG. 18). An oligonucleotide described herein may include one or more conjugated moieties (see, e.g., FIG. 19). Illustrated in FIG. 35 are a number of exemplary oligonucleotide backbone modifications.

Figure 33:
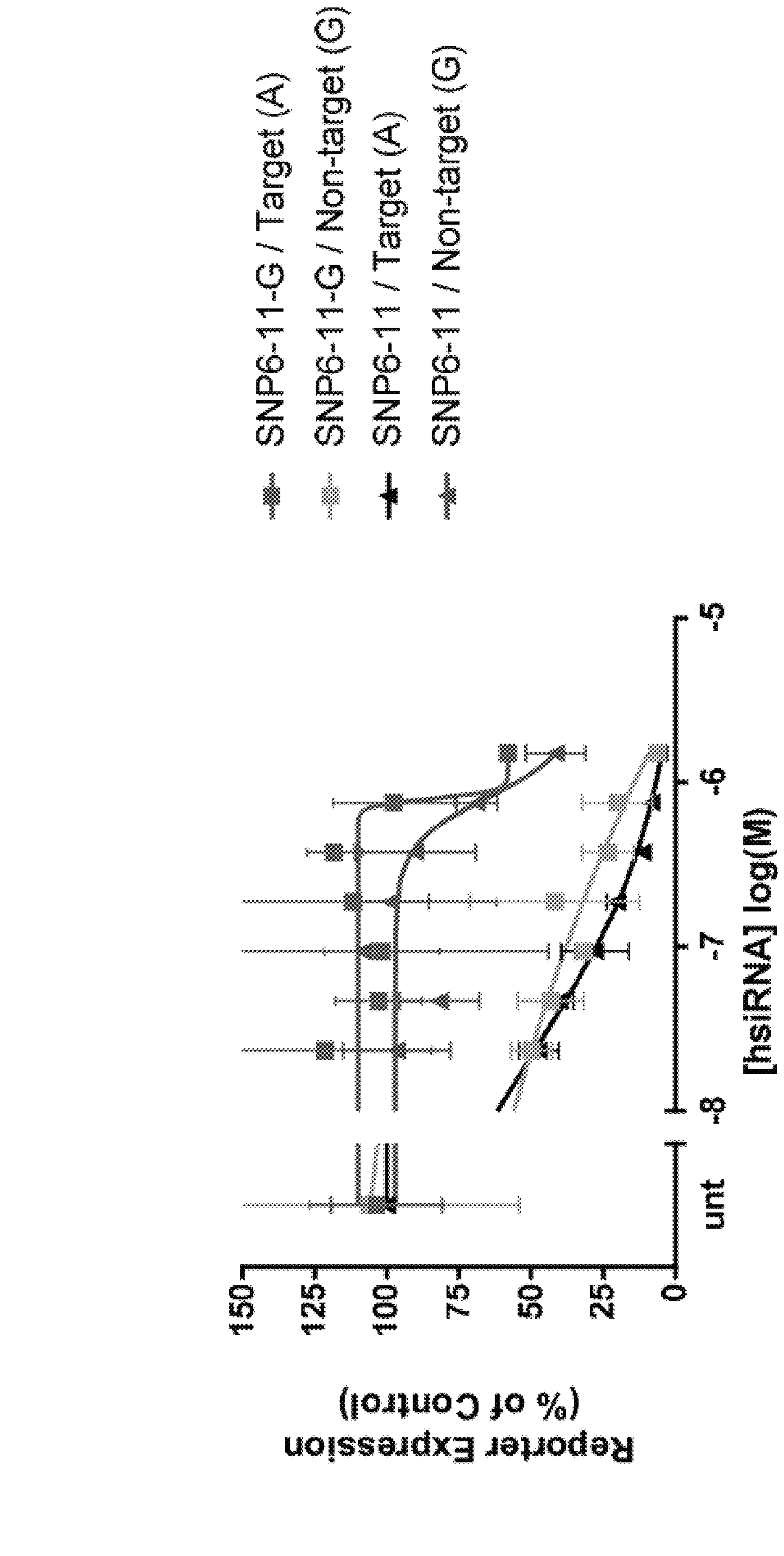
FIG. 33 depicts dose response curves comparing silencing effects for oligonucleotides targeting G at the SNP site instead of A.

An oligonucleotide described herein can effectively be used to target a G at the SNP site simply by changing the base at the SNP position. As seen in FIG. 33, compound SNP6-11 was synthesized a second time, this time to target a G at the SNP site instead of an A. This allowed for selectively silencing either allele, a strategy that is very useful for patients with different heterozygosities at the same SNP site.

In certain exemplary embodiments, one or more abasic nucleotides are utilized at an SNP position nucleotide, at a MM position nucleotide, at the 5' end, at the 3' end, or any combination of these.

In certain exemplary embodiments, hsiRNAs are synthesized with varying sugar modifications around the mismatch to improve allele specificity, e.g., 2'FANA instead of 2'F; triple 2'F or triple 2' OMe around SNP/mismatch position.

Example 5: HTT Mouse Model

BAC97-HD refer to a transgenic mouse comprising a human bacterial artificial chromosome (BAC) transgenic insert containing the entire pathogenic 170 kb human Huntingtin (htt) genomic locus that was modified by replacing the human htt exon 1 with a loxP-flanked human mutant htt exon 1 sequence containing 97 mixed CAA-CAG repeats encoding a continuous polyglutamine (polyQ) stretch.

Lead compound (SNP6-11) was synthesized into the di-branched chemical scaffold having the structure illustrated in FIG. 31 and subsequently tested in vivo via 40 nmol bilateral intracerebroventricular (ICV) injection (20 nmols to each side) in BAC97-HD female mice at 8 weeks of age. The mice had two copies of normal mouse htt gene with a G at SNP rs362273 and a transgenic insert of pathogenic human htt gene with an A at SNP rs362273A. A nonsense sequence with no target matches in the RNA transcriptome was also synthesized into the same di-branched scaffold and injected in the mice as a negative control (NTC).

Figure 32A:
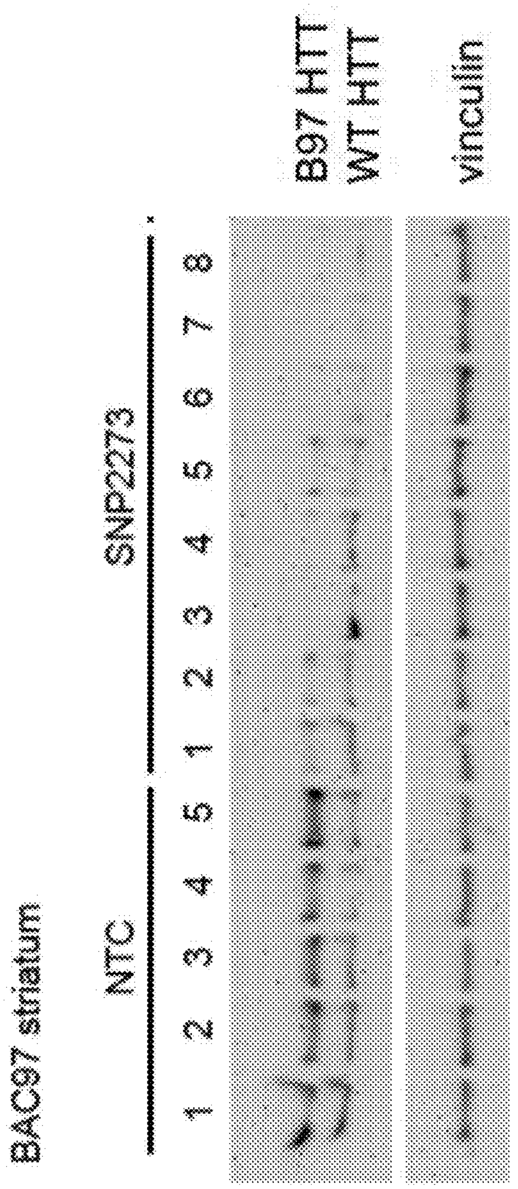
FIG. 32A is a western blot performed to measure HTT protein levels.
Figure 32B:
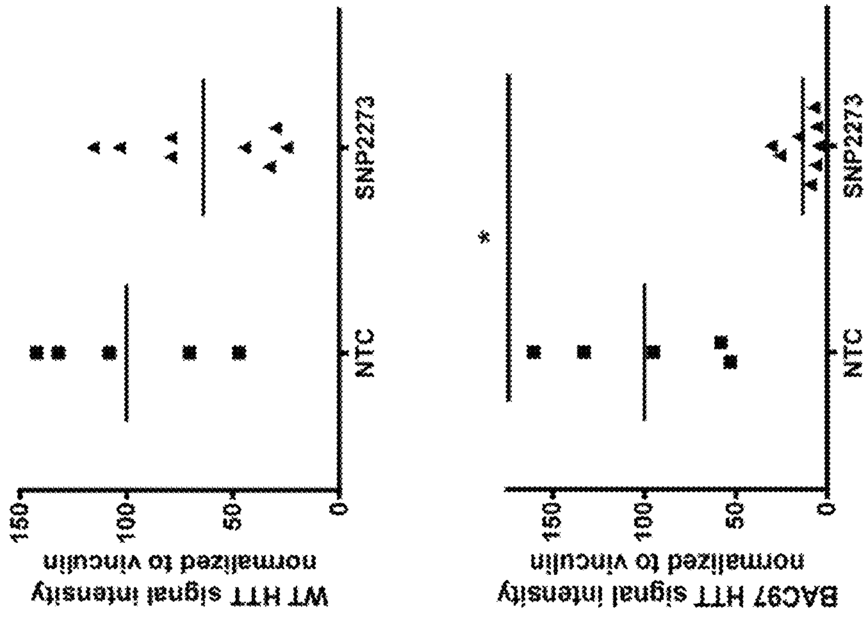
FIG. 32B shows protein levels normalized to vinculin.

Several brain regions were collected from the mice for RNA and protein analysis 1 month post injection, and HTT protein levels were measured by western blot using Ab1 antibody. FIG. 32A is a western blot performed on collected striatum tissue, and protein levels normalized to vinculin are presented in FIG. 32B.

Example 6: SNP Targeting is Sequence-Independent

Figure 20:
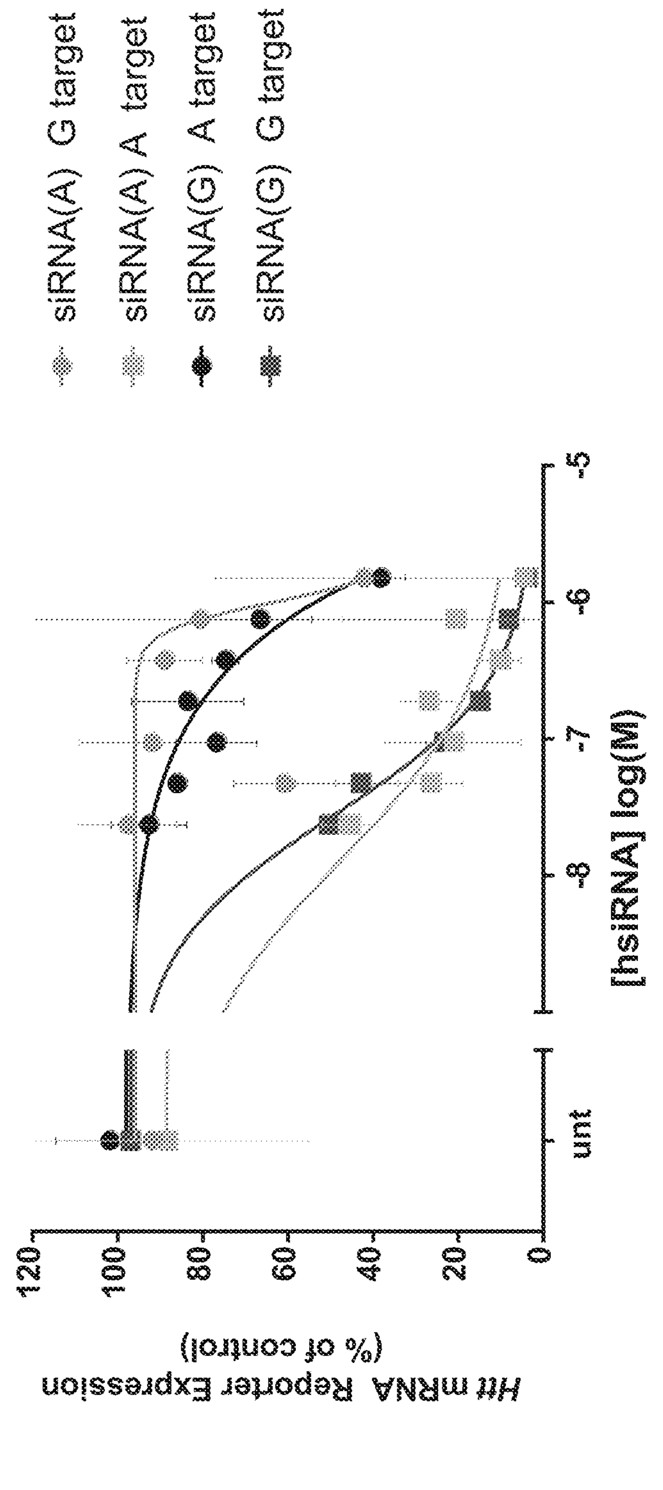
FIG. 20 graphically depicts that the activity of a SNP discriminating scaffold that comprises a SNP position nucleotide at position 6 from the 5' end, and a mismatch position nucleotide located at position 11 from the 5' end, is sequence-independent.

Whether SNP discrimination of lead compounds was sequence-dependent was assessed. Hydrophobically modified RNAs (hsiRNAs) designed to be complimentary to the Huntingtin (htt) mRNA containing a U to G mismatch or a C to A mismatch in rs362273 were used. Both the 6-11 hsiRNA complementary to a U to G mismatch and the 6-11 hsiRNA complementary to a C to A mismatch preferentially cleaved the target SNP (FIG. 20).

Example 7: Synthesis of Vinyl Phosphonate Modified Intersubunit Linkages

Figure 21:
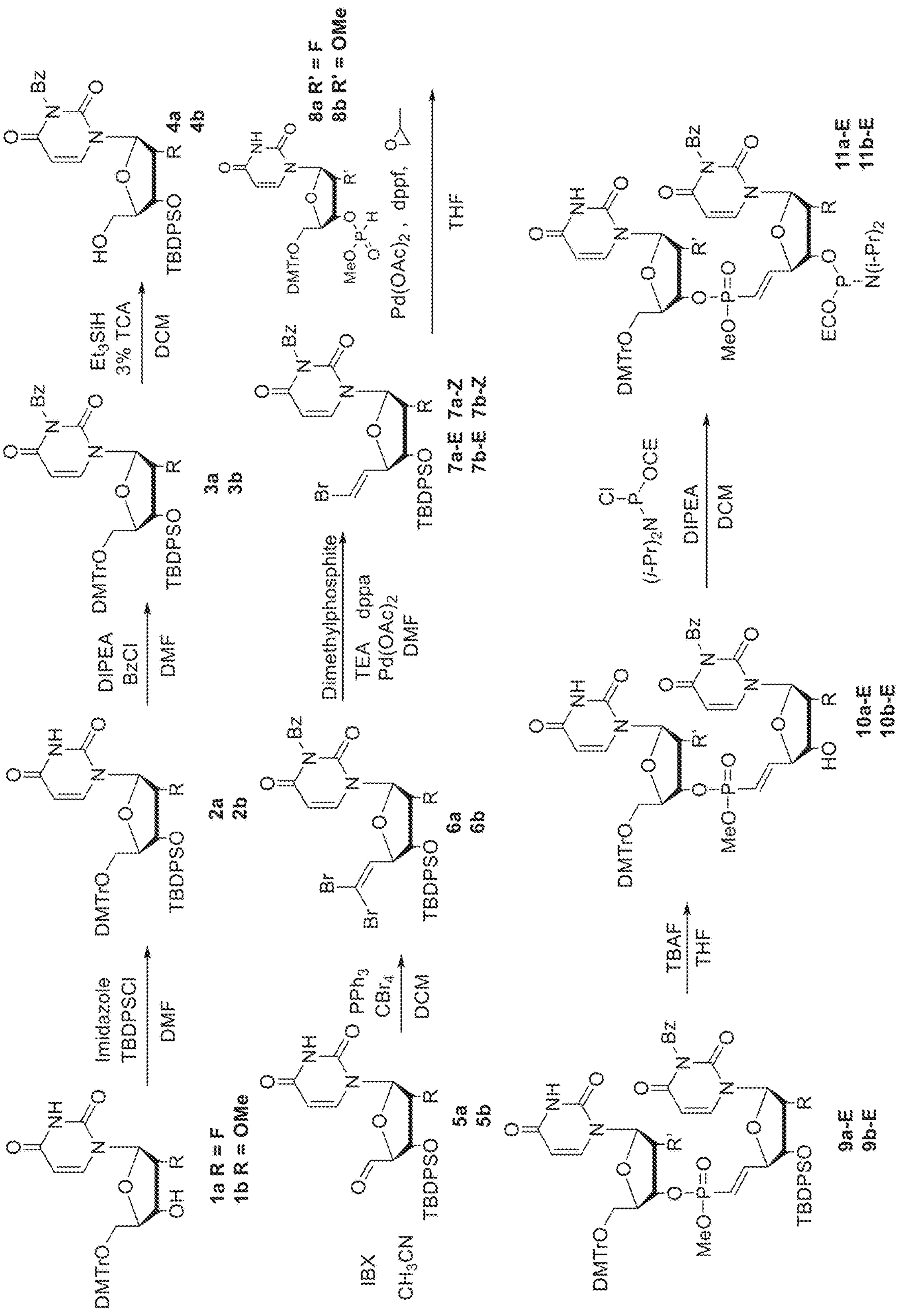
FIG. 21 illustrates a representative synthesis of the vinyl phosphonate (VP)-modified intersubunit linkage described herein.
Figure 29:
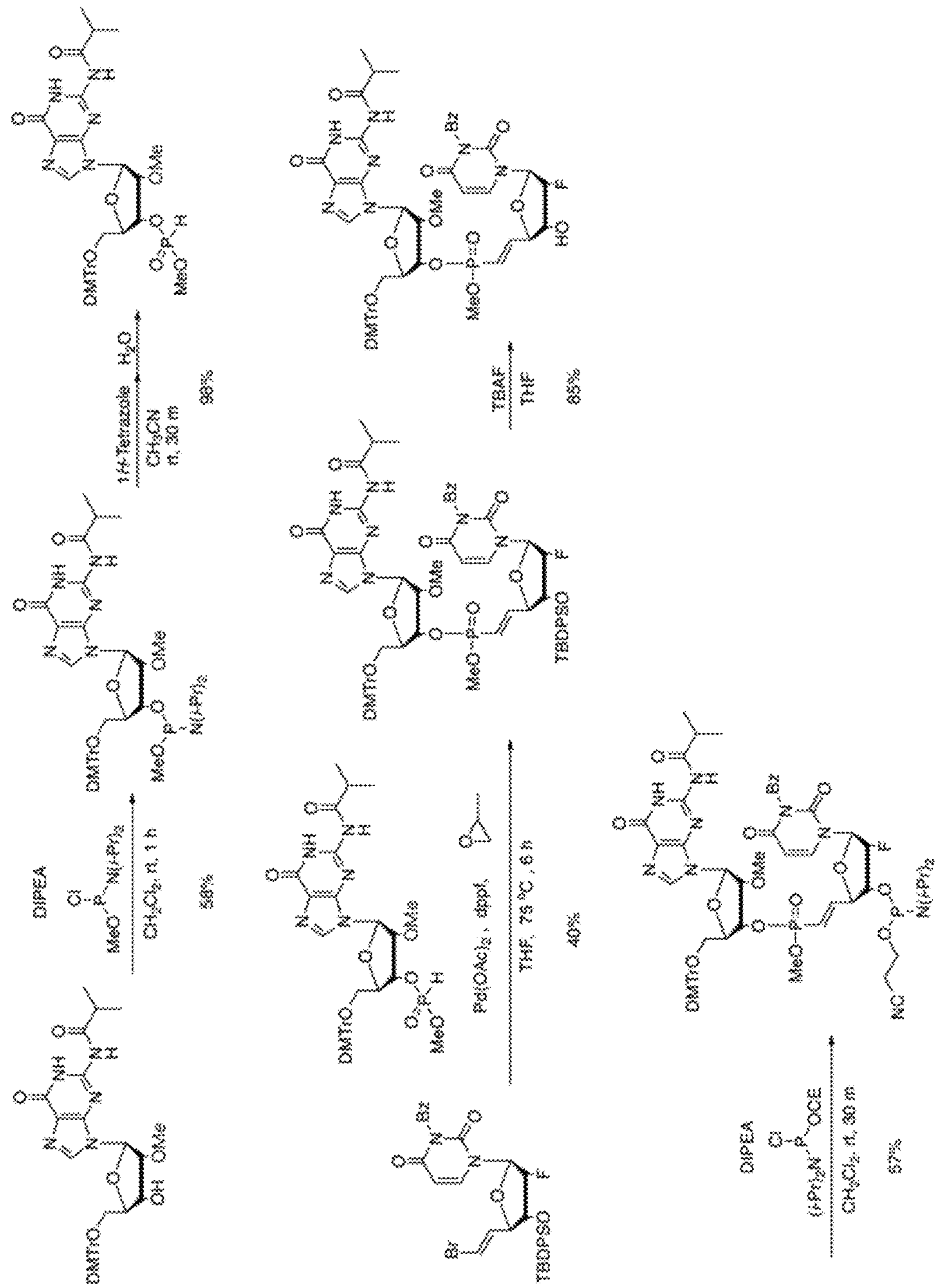
FIG. 29 demonstrates another method for preparing the VP-modified oligonucleotides provided herein.

Representative syntheses of the vinyl phosphinate modified intersubunit linkages discussed herein are illustrated in FIGS. 21 and 29. The synthetic procedure of FIG. 21 is detailed below.

Synthesis of Compound 3a

Anhydrous solution of compound 2a (16.6 g, 20.8 mmol) in pyridine (100 mL) was added anhydrous DIPEA (6.5 mL, 37.4 mmol) and benzoyl chloride (3.6 mL, 31.2 mmol). After the mixture was stirred for 4 hours at room temperature, excess pyridine was evaporated and diluted with $CH_2Cl_2$. The organic solution was washed by sat. aq. $NaHCO_3$. The organic layer was collected, dried over $MgSO_4$, filtered and evaporated. Obtained crude material was purified by silica gel column chromatography (hexane-ethyl acetate, 4:1 to 1:1) yielding compound 3a as a slightly yellow foam (14.5 g, 78%); $^1$H NMR (500 MHz, $CDCl_3$) δ 7.88-7.87 (m, 2H), 7.84 (d, 1H, J=8.3 Hz), 7.67-7.58 (m, 5H), 7.48-7.45 (m, 4H), 7.39-7.32 (m, 4H), 7.25-7.23 (m, 3H), 7.18-7.17 (m, 2H), 7.12-7.07 (m, 4H), 6.80-6.75 (m, 4H), 6.08 (dd, 1H, $J_{HH}$=1.5 Hz, $J_{HF}$=15.2 Hz), 5.14, (d, 1H, $J_{HH}$=8.3 Hz), 4.59 (ddd, 1H, $J_{HH}$=3.7, 1.5 Hz, $J_{HF}$=51.9 Hz), 4.43 (ddd, 1H, $J_{HH}$=7.4, 4.0 Hz, $J_{HF}$=19.1 Hz), 4.24-4.23 (m, 1H), 3.79 (s, 6H), 3.62 (dd, 1H, $J_{HH}$=11.2, 2.0 Hz), 3.35 (dd, 1H, $J_{HH}$=11.1, 2.0 Hz), 1.00 (s, 9H); $^{13}$C NMR (126 Hz, $CDCl_3$) δ 168.4, 161.8, 158.72, 158.66, 148.9, 143.9, 139.4, 135.71. 135.70, 135.1, 134.8, 134.7, 132.3, 132.2, 131.3, 130.4, 130.2, 130.1, 129.1, 128.2, 128.0, 127.91, 127.89, 127.2, 113.19, 113.16, 102.2, 92.5 (d, $J_{CF}$=194.4 Hz), 87.7 (d, $J_{CF}$=34.5 Hz), 87.2, 82.4, 70.0 (d, $J_{CF}$=15.4 Hz), 60.7, 60.4, 55.2, 26.6.

Synthesis of Compound 4a

Compound 3a (14.5 g, 16.3 mmol) was dissolved into 3% trichloroacetic acid/$CH_2Cl_2$ solution (200 mL) containing triethylsilane (8.0 mL, 50.1 mmol) and stirred for 1 hour at room temperature. After the solution was washed by sat. aq. $NaHCO_3$ three times, collected organic layer was dried over $MgSO_4$, filtered, and evaporated. Obtained crude material was purified by silica gel column chromatography (hexane/ethyl acetate, 4:1 to 3:7) yielding compound 4a as a white foam (8.67 g, 91%); $^1$H NMR (500 MHz, $CDCl_3$) δ 7.89-7.88 (m, 2H), 7.68-7.64 (6H, m), 7.51-7.45 (m, 4H), 7.42-7.38 (4H, m), 5.93 (dd, 1H, $J_{HH}$=2.9 Hz, $J_{HF}$=15.1 Hz), 5.73 (d, 1H, $J_{HH}$=8.2 Hz), 4.74 (ddd, 1H, $J_{HH}$=4.1, 3.2 Hz, $J_{HF}$=52.2 Hz), 4.31 (ddd, 1H, $J_{HH}$=5.8, 4.7, $J_{HF}$=15.4 Hz), 4.11-4.09 (m, 1H), 3.82-3.79 (m, 1H), 3.39 (ddd, 1H, $J_{HH}$=12.1, 5.6, 1.5 Hz), 1.64 (br, 1H), 1.11 (s, 9H); $^{13}$C NMR (126 Hz, $CDCl_3$) δ 168.3, 161.8, 149.0, 140.5, 135.7, 135.2, 132.8, 132.3, 131.3, 130.5, 130.4, 130.3, 129.2, 128.02, 127.96, 102.4, 91.8 (d, $J_{CF}$=91.8 Hz), 89.5 (d, $J_{CF}$=33.6 Hz), 69.5 (d, $J_{CF}$=69.5 Hz), 60.3, 26.8.

Synthesis of Compound 6a

Anhydrous solution of compound 4a (6.5 g, 11.0 mmol) was added IBX (7.7 g, 27.6 mmol) and stirred for 2 hours at 85° C. After cooling the mixture in an ice bath, the precipitate in the solution was filtered off through celite. Collected eluent was evaporated, co-evaporated with anhydrous $CH_3CN$ three times under argon atmosphere, and obtained compound 5a as a white foam was used without further purification. In a separate flask, anhydrous $CH_2Cl_2$ (25 mL) solution containing $CBr_4$ (7.3 g, 22.1 mmol) was added $PPh_3$ (11.6 g, 44.2 mmol) at 0° C. and stirred for 0.5 h at 0° C. To this solution, anhydrous $CH_2Cl_2$ solution (25 mL) of compound 5a was added dropwise (10 min) at 0° C. and stirred for 2 h at 0° C. After diluting with $CH_2Cl_2$, the organic solution was washed by aq. sat. $NH_4C_1$, dried over $MgSO_4$, filtered, and evaporated. Obtained material was dissolved into minimum amount of diethyl ether and added dropwise to excess diethyl ether solution under vigorously stirring at 0° C. Precipitate in solution was filtered off through celite and eluents was evaporated. Obtained crude material was purified by silica gel column chromatography (hexane/ethyl acetate, 9:1 to 1:1) yielding compound 6a as a white foam (4.3 g, 52%). 1H NMR (500 MHz, $CDCl_3$) δ 7.68-7.84 (m, 2H), 7.70-7.65 (m, 3H), 7.60-7.58 (m, 2H), 7.52-7.49 (m, 2H), 7.42-7.36 (m, 4H), 7.31-7.28 (m, 2H), 7.09 (d, 1H, J=8.2 Hz), 6.25 (d, 1H, J=8.9 Hz), 5.75 (dd, 1H, $J_{HF}$=8.24 Hz), 5.49 (dd, 1H, $J_{HF}$=21.4 Hz), 4.77 (t, 1H, $J_{HH}$=8.5 Hz, $J_{HF}$=8.5 Hz), 4.38 (dd, 1H, $J_{HH}$=4.1 Hz, $J_{HF}$=52.1 Hz), 4.25 (ddd, 1H, $J_{HH}$=8.1, 4.9 Hz, $J_{HF}$=19.4 Hz), 1.10 (s, 9H); $^{13}$C NMR (126 Hz, $CDCl_3$) δ 167.9, 161.6, 148.3, 141.4, 135.8, 134.7 (d, $J_{C-Br}$=139.0 Hz), 132.5, 132.2, 131.1, 130.5, 130.3, 130.2, 129.2, 127.9, 102.7, 97.3, 93.3 (d, $J_{CF}$=39.1 Hz), 91.5 (d, $J_{CF}$=190.7 Hz), 82.4, 73.9 (d, $J_{CF}$=16.4 Hz), 26.7.

Synthesis of Compound 7a-E and 7a-Z

Anhydrous solution of compound 6a (4.2 g, 5.66 mmol) in DMF (25 mL) was added dimethylphosphite (2.09 mL, 22.6 mmol) and triethylamine (1.58 mL, 11.3 mmol) at 0° C., and then stirred overnight at room temperature. After the solution was diluted with ethyl acetate, the organic solution was washed with aq. sat. $NH_4Cl$ and brine. Then the organic solution was dried over $MgSO_4$, filtered and evaporated. Obtained crude material was purified repeatedly by silica gel column chromatography (hexane/ethyl acetate, 9:1 to 1:1) until all pure isomeric compound were collected separately, giving compound 7a-E (1.95 g, 52%); $^1$H NMR (500 MHz, $CDCl_3$) δ 7.87-7.85 (m, 2H), 7.89-7.85 (m, 3H), 7.61-7.59 (m, 2H), 7.52-7.48 (m, 2H), 7.45-7.32 (m, 6H), 7.08 (d, 1H, $J_{HH}$=8.2), 6.49 (d, 1H, $J_{HH}$=13.7), 5.99 (dd, 1H, $J_{HH}$=13.7 Hz, 8.1 Hz), 5.75 (d, 1H, $J_{HH}$=8.2), 5.63 (d, 1H, $J_{HF}$=19.8 Hz), 4.43 (dd, 1H, $J_{HH}$=52.6 Hz, $J_{HF}$=4.3 Hz), 4.42 (t, 1H, $J_{HH}$=8.0 Hz), 4.07 (ddd, $J_{HH}$=7.8, 4.7 Hz, $J_{HF}$=19.5 Hz), 1.08 (s, 9H); $^{13}$C NMR (126 Hz, $CDCl_3$) δ 148.4, 140.4, 135.8, 135.7, 135.3, 133.3, 132.3, 132.4, 132.1, 131.1, 130.5, 130.4, 130.3, 129.2, 127.95, 127.93, 112.4, 102.7, 91.7 (d, $J_{CF}$=36.3 Hz), 91.6 (d, $J_{CF}$=191.6 Hz), 82.8, 73.9 (d, $J_{CF}$=16.4 Hz), 26.7, 19.1; and 7a-Z (0.58 g, 15%); $^1$H NMR (500 MHz, $CDCl_3$) δ 7.87-7.85 (m, 2H), 7.68-7.65 (m, 3H), 7.61-7.59 (m, 2H), 7.52-7.48 (m, 2H), 7.42-7.39 (m, 2H), 7.34-7.29 (m, 4H), 7.12 (d, 1H, $J_{HH}$=8.2 Hz), 6.51 (d, 1H, $J_{HH}$=7.4 Hz), 5.96 (dd, 1H, $J_{HH}$=8.4 Hz, 7.4 Hz), 5.75 (d, 1H, =8.2 Hz), 5.57 (dd, 1H, =1.2 Hz, $J_{HF}$=20.6 Hz), 5.04 (dd, 1H, =8.2 Hz), 4.48 ($J_{HH}$=3.5 Hz, $J_{HF}$=53.1 Hz), 4.24 (ddd, 1H, $J_{HH}$=7.8, 4.9 Hz, $J_{HF}$=18.6 Hz), 1.09 (s, 9H); $^{13}$C NMR (126 Hz, $CDCl_3$) δ 168.0, 161.7, 148.4, 141.4, 135.9, 135.8, 135.2, 132.6, 132.5, 131.2, 130.6, 130.5, 130.2, 130.1, 129.2, 127.8, 127.7, 114.5, 102.6, 93.0 (d, $J_{CF}$=37.2 Hz), 91.6 (d, $J_{CF}$=191.6 Hz), 80.3, 74.3 (d, $J_{CF}$=16.4 Hz), 26.7, 19.1.

Synthesis of Compound 9a

Anhydrous compound 7a-E (1.95 g, 2.94 mmol) and $Pd(OAc)_2$ (125 mg, 0.59 mmol) and [1,1'-Bis(diphenylphosphino)ferrocene]dichloropalladium (II) (652 mg, 1.18 mmol) were purged with argon, and then dissolved into anhydrous THF (50 mL). After adding propylene oxide (2.06 mL, 29.4 mmol), compound 8a (2.07 g, 3.24 mmol) was added in one portion and stirred at for 4 h at 70° C. After removing solvent under reduced pressure, the crude mixture was purified by silica gel column chromatography (hexane/ethyl acetate, 50:50 to 0:100) and obtained fractions containing compound 9a were further purified by silica gel column chromatography ($CH_2Cl_2$-MeOH, 0% to 5%) yielding compound 9a as a mixture of diastereo-isomers (2.04 g, 57%); $^{31}P$ NMR (202 MHz, $CDCl_3$) δ 18.3.

Synthesis of Compound 10a

Compound 9a (2.0 g, 1.64 mmol) in anhydrous THF (22.5 mL) was added 1.0 M TBAF-THF (2.5 mL, 2.5 mmol) and stirred at ambient temperature for 30 minutes. After diluting with $CH_2Cl_2$ (120 mL), the organic layer was washed with brine, dried over $MgSO_4$, filtered, and then evaporated. Obtained crude material was purified by silica gel column chromatography (1% TEA-$CH_2Cl_2$/MeOH, 0% to 6%) yielding compound 10a (1.52 g, 94%); $^{31}P$ NMR (202 MHz, $CDCl_3$) δ 19.0, 18.7.

Synthesis of Compound 11a

Compound 10a (589.7 mg, 0.6 mmol) was rendered anhydrous by repeated co-evaporation with anhydrous $CH_3CN$ and then dissolved into anhydrous $CH_2Cl_2$ (6.0 mL). To this solution N,N-diisopropylethylamine (0.31 mL, 1.8 mmol) and 2-cyanoethyl N,N-diisopropylchlorophosphoramidite (0.16 mL, 0.72 mmol) were added at 0° C. After stirring for 30 min at 0° C., the reaction mixture was diluted with excess $CH_2Cl_2$. The organic layer was repeatedly washed with aq. sat. $NaHCO_3$, dried over $MgSO_4$, filtered, and evaporated. The obtained crude material was purified by silica gel column chromatography (1% TEA-$CH_2Cl_2$/MeOH, from 100% to 4%) yielding compound 11a as a white foam (570 mg, 80%); $^{31}P$ NMR (202 MHz, $CDCl_3$) δ 150.3, 151.2, 151.1, 151.0, 18.72, 18.65, 18.55, 18.3.

Synthesis of Compound 4b

Anhydrous solution of compound 3b (1.35 g, 2.0 mmol) in pyridine (10 mL) was added DIPEA (0.63 mL, 3.6 nnol) and benzoyl chloride (0.35 mL, 3.0 mmol), and stirred for 3 hours at room temperature. After diluting with excess $CH_2Cl_2$, the organic solution was washed with aq. sat. $NaHCO_3$ and brine. After drying over $MgSO_4$, filtered and evaporating, obtained crude material was used for the next reaction without further purification. Obtained crude material containing compound 3b was added 3% trichloroacetic acid in $CH_2Cl_2$ (25 mL) and triethylsilane (1 mL, 6.26 mmol), and stirred for 1 hour at room temperature. After the reaction mixture was diluted with $CH_2Cl_2$, the solution was washed with sat. $NaHCO_3$ aq. three times, dried over $MgSO_4$, filtered, then evaporated. Obtained crude material was purified by silica gel column chromatography (hexane/ethyl acetate, 4:1 to 1:4) yielding pure compound 4b (596.7 mg, 63% in 2 steps); $^1H$ NMR (500 MHz, DMSO-d6) δ 8.13 (d, 1H, $J_{HH}$=8.2 Hz), 7.95 (d, 2H, $J_{HH}$=7.3 Hz), 7.81 (t, 1H, $J_{HH}$=7.5 Hz), 7.69-7.68 (m, 2H), 7.64-7.59 (m, 4H), 7.49-7.42 (m, 6H), 5.93 (d, 1H, $J_{HH}$=4.6 Hz), 5.26 (t, 1H, $J_{HH}$=4.6 Hz), 4.36 (dd, 1H, $J_{HH}$=4.6, 4.6 Hz), 4.02-4.00 (m, 1H), 3.65-3.61 (m, 1H), 3.54 (dd, 1H, $J_{HH}$=4.6, 4.6 Hz), 3.09 (s, 3H), 1.03 (s, 9H); $^{13}C$ NMR (126 Hz, DMSO-d6) 169.8, 162.1, 149.5, 141.3, 136.1, 135.9, 135.8, 133.4, 133.2, 131.5, 130.7, 130.52, 130.48, 130.0, 128.4, 128.3, 102.1, 86.7, 85.6, 82.8, 79.7, 70.8, 60.2, 57.8, 27.2, 19.4; HRMS (ESI) m/z calcd for $C_{33}H_{35}N_2O_7Si^-$ $[M-H]^-$ m/z 599.2219, found m/z 599.2258.

Synthesis of Compound 6b

Anhydrous solution of compound 4b (300.4 mg, 0.5 mmol) in $CH_3CN$ (5 mL) was added IBX (350 mg, 1.3 mmol) and stirred for 2 hours at 85° C. After cooling the solution at 0° C., the precipitate was filtered off by celite-filtration. Obtained eluent containing compound 5b was evaporated, rendered anhydrous by repeated co-evaporation with anhydrous $CH_3CN$, and used for the next reaction without further purification. Separatory prepared anhydrous solution of $CBr_4$ (331.6 mg, 1.0 mmol) in $CH_2Cl_2$ (5.0 mL) was added triphenylphosphine (524.6 mg, 2.0 mmol) at 0° C. in one portion and stirred at 0° C. for 30 minutes. To this solution, compound 5b in anhydrous $CH_2Cl_2$ (1.5 mL) was added dropwise (10 min) at 0° C. and stirred for 2 h at 0° C. The solution was then diluted with $CH_2Cl_2$ and washed with sat. $NaHCO_3$ aq. and brine. After the organic solution was dried over $MgSO_4$, filtered and evaporated, obtained crude material was purified by silica gel column chromatography (hexane/ethyl acetate, 9:1 to 4:6) yielding compound 6b (210.9 mg, 56%); $^1H$ NMR (500 MHz, $CDCl_3$) δ 7.88 (d, 2H, $J_{HH}$=7.3 Hz), 7.70-7.62 (5H, m), 7.51-7.38 (m, 9H), 7.08 (d, 1H, $J_{HH}$=8.2 Hz), 6.26 (d, 1H, $J_{HH}$=8.6 Hz), 5.75 (d, 1H, $J_{HH}$=8.2 Hz), 5.68 (d, 1H, $J_{HH}$=0.8 Hz), 4.84 (dd, 1H, $J_{HH}$=8.6 Hz, 8.6 Hz), 3.86 (dd, 1H, $J_{HH}$=7.5 Hz, 5.0 Hz), 3.30 (s, 3H), 3.18 (br, 1H), 1.11 (s, 9H); $^{13}C$ NMR (126 Hz, $CDCl_3$) 168.3, 161.7, 148.6, 138.9, 135.9, 135.8, 134.3, 132.6, 132.4, 131.2, 130.5, 130.4, 130.3, 129.2, 128.0, 127.9, 102.4, 97.5, 90.0, 82.44, 82.39, 74.4, 58.2, 26.7, 19.1; HRMS (ESI) m/z calcd for $C_{34}H_{33}Br_2N_2O_6Si^-$ $[M-H]^-$ m/z 751.0480 $[M-H]^-$, found m/z 753.6495.

Synthesis of 7b-E and 7b-Z

Anhydrous Solution of Compound 6b (6.11 g, 8.1 Mmol) in DMF (35 mL) was Added dimethylphosphite (2.97 mL, 34.0 mmol) and triethylamine (2.26 mL, 17.0 mmol) at 0° C., and then stirred overnight at room temperature. After the solution was diluted with ethyl acetate, the organic solution was washed with sat. $NH_4Cl$ aq. and brine. Then the organic solution was dried over $MgSO_4$, filtered and evaporated, and obtained crude material was purified repeatedly by silica gel column chromatography (hexane/ethyl acetate, 9:1 to 1:1) until all pure isomeric compound were collected separately, giving compound 7b-E (3.0 g, 55%); $^1H$ NMR (500 MHz, $CDCl_3$) δ 7.89-7.87 (m, 2H), 7.70-7.62 (m, 5H), 7.51-7.39 (m, 8H), 7.10 (d, 1H, $J_{HH}$=8.3 Hz), 6.47 (dd, 1H, $J_{HH}$=13.6, 0.8 Hz), 6.01 (dd, 1H, $J_{HH}$=13.6, 7.9 Hz), 5.76-5.74 (m, 2H), 4.51 (dd, 1H, $J_{HH}$=7.8, 7.8 Hz), 7.36 (dd, 1H, $J_{HH}$=7.8 Hz, 4.9 Hz), 3.34 (s, 3H), 3.17 (dd, 1H, $J_{HH}$=4.7, 1.2 Hz), 1.09 (s, 9H); $^{13}C$ NMR (126 Hz, $CDCl_3$) δ 168.3, 161.7, 148.7, 138.4, 135.9, 135.8, 135.3, 133.8, 132.6, 132.4, 131.2, 130.5, 130.4, 130.3, 129.2, 128.0, 127.9, 112.1, 102.3, 88.9, 82.8, 82.6, 77.2, 74.2, 58.1, 26.8, 19.1; and 7b-Z (1.23 g, 22%); 1H NMR (500 MHz, $CDCl_3$) δ 7.89-7.87 (m, 2H), 7.72-7.70 (m, 2H), 7.68-7.63 (m, 3H), 7.51-7.44 (m, 4H), 7.41-7.37 (m, 4H), 7.16 (d, 1H, J–8.2 Hz), 6.53 (dd, 1H, $J_{HH}$=7.4, 0.6 Hz), 6.03 (dd, 1H, $J_{HH}$=8.5, 7.4 Hz), 5.75-5.73 (m, 2H), 5.12 (t, 1H, $J_{HH}$=8.1 Hz), 3.93 (dd, 1H, $J_{HH}$=6.9, 5.0 Hz), 3.32 (br, 1H), 3.26 (s, 3H), 1.10 (s, 9H); $^{13}C$ NMR (126 Hz, $CDCl_3$) δ 168.3, 161.8, 148.7, 139.3, 135.91, 135.85, 135.22, 132.74, 132.71, 131.2, 130.8, 130.5, 130.23, 130.16, 129.2, 127.78, 127.75, 114.6, 102.2, 90.1, 82.4, 80.6, 77.2, 74.8, 58.1, 26.8, 19.2.

Synthesis of Compound 8b

Anhydrous 5'-O-DMTr-2'-deoxy-2'-fluoro-3'-[methyl-N, N-(diisopropyl)amino]phosphoramidite (4.26 g, 6.0 mmol) was dissolved in 0.45 M 1H-tetrazole/$CH_3CN$ solution (27 mL, 12 mmol) and stirred for 30 minutes at room temperature. To this solution, $H_2O$ (3.6 mL) was added and stirred for 30 minutes at room temperature. After diluting with ethyl acetate, the organic solution was washed with brine six times, dried over $MgSO_4$, filtered and then evaporated. Obtained compound 8b with a slight amount of impurity was used for the next reaction without further purification; $^{31}P$ NMR ($CDCl_3$, 202 MHz) δ 8.92, 8.28.

Synthesis of Compound 9b

Anhydrous compound 7b-E (2.84 g, 4.20 mmol) and $Pd(OAc)_2$ (188.6 mg, 0.84 mmol) and [1,1'-Bis(diphenylphosphino)ferrocene]dichloropalladium (II) (931.4 mg, 1.68 mmol) were purged with argon, and then dissolved into anhydrous THF (50 mL). After adding propylene oxide (2.94 mL, 42.0 mmol), compound 9b (3.16 g, 5.04 mmol) was added in one portion and stirred at for 4 hours at 70° C. After removing solvent under reduced pressure, the crude mixture was purified by silica gel column chromatography (hexane-ethyl acetate, 50:50 to 0:100) and obtained fractions containing compound 9b were further purified by silica gel column chromatography (1% TEA-$CH_2Cl_2$/MeOH, 0% to 5%) yielding compound 9b as a mixture of diastereoisomers (3.3 g, 64%); $^{31}P$ NMR (202 MHz, $CDCl_3$) δ 19.31, 18.72.

Synthesis of Compound 10b

Compound 9b (3.3 g, 2.70 mmol) in anhydrous THF (36.5 mL) was added 1.0 M TBAF-THF (4.05 mL, 4.05 mmol) and stirred at ambient temperature for 30 minutes. After diluting with $CH_2Cl_2$ (150 mL), the organic layer was washed with brine, dried over $MgSO_4$, filtered, and then evaporated. Obtained crude material was purified by silica gel column chromatography (1% TEA-$CH_2Cl_2$/MeOH, 0% to 8%) yielding compound 10b (1.25 g, 47%); $^{31}P$ NMR (202 MHz, $CDCl_3$) δ 19.8, 19.1.

Synthesis of Compound 11b

Compound 10b (393.2 mg, 0.4 mmol) was rendered anhydrous by repeated co-evaporation with anhydrous $CH_3CN$ and then dissolved into anhydrous $CH_2Cl_2$ (4.0 mL). To this solution N,N-diisopropylethylamine (0.21 mL, 1.2 mmol) and 2-cyanoethyl N,N-diisopropylchlorophosphoramidite (0.11 mL, 0.48 mmol) were added at 0° C. After stirring for 30 min at 0° C., the reaction mixture was diluted with excess $CH_2Cl_2$. The organic layer was repeatedly washed with aq. sat. $NaHCO_3$, dried over $MgSO_4$, filtered, and evaporated. The obtained crude material was purified by silica gel column chromatography (1% TEA-$CH_2Cl_2$/MeOH, from 100% to 4%) yielding compound 11b as a white foam (319.6 mg, 68%); $^{31}P$ NMR (202 MHz, $CDCl_3$) δ 150.7, 150.4, 150.3, 19.9, 19.5, 19.4, 18.8.

Figure 22:
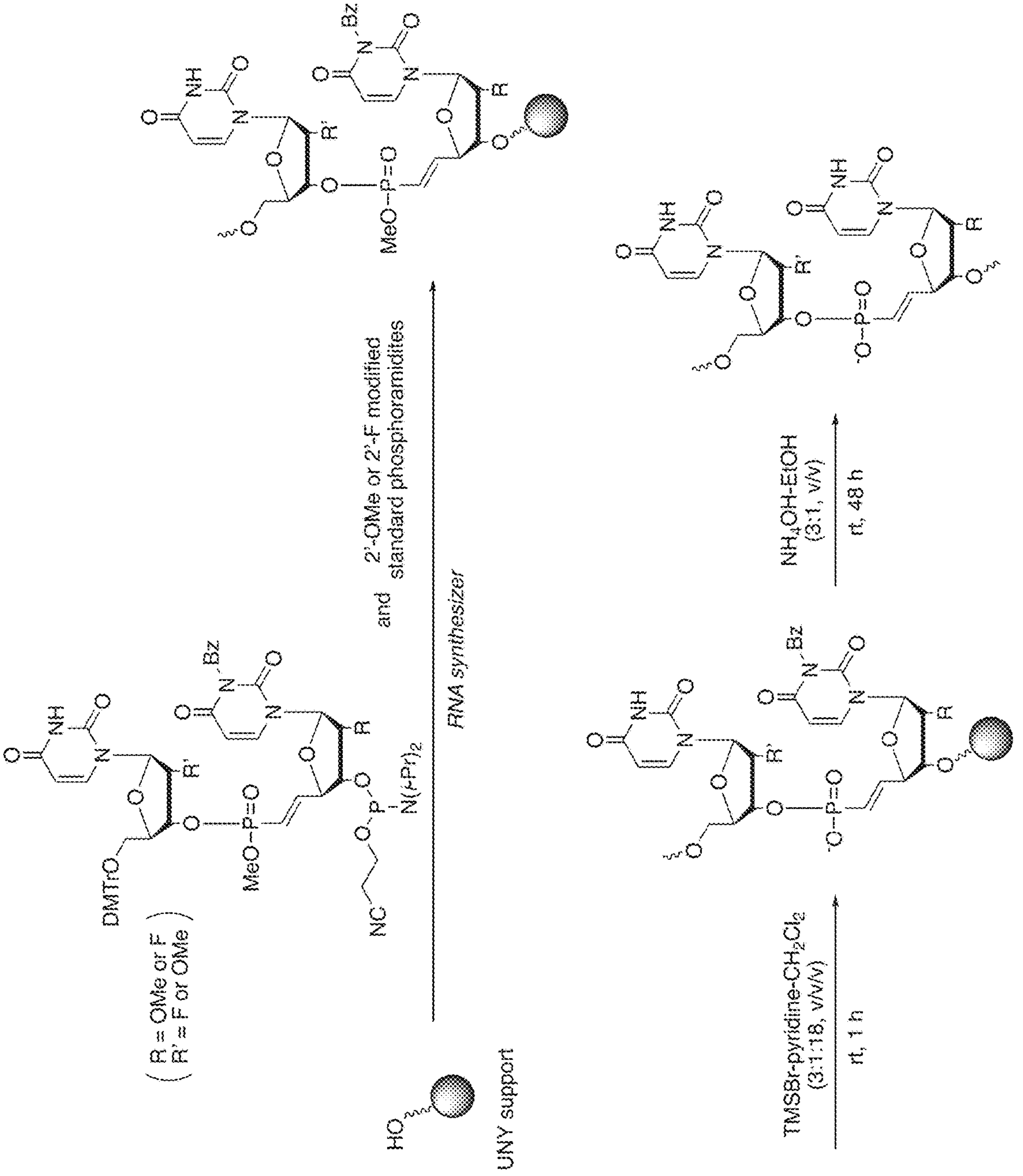
FIG. 22 depicts a method for preparing oligonucleotides having a VP-modified intersubunit linkage.

Example 8: Solid Support-Mediated Synthesis of Vinyl Phosphonate-Modified Oligonucleotides A representative synthesis of an oligonucleotide having a vinyl phosphinate modified intersubunit linkages is illustrated in FIG. 22. Examples of VP-modified sequences that were synthesized can be found in FIGS. 28A and 28B.

Synthesis of Inter-Nucleotide (E)-Vinyl Phosphonate Modified RNA Oligonucleotides The synthesis RNA oligonucleotides having one vinyl phosphonate linkage was performed on MerMade 12 automated RNA synthesizer (BioAutomation) using 0.1 M anhydrous $CH_3CN$ solution of 2'-modified (2'-fluoro, 2'-O-methyl) phosphoramidites and vinylphosphonate-linked dimer phosphoramidites. For the solid support, UnyLinker support (ChemGenes) was used. The synthesis was conducted by standard 1.0 μmol scale RNA phosphoramidite synthesis cycle, which consists of (i) detritylation, (ii) coupling, (iii) capping, and (iv) iodine oxidation. 5-(Benzylthio)-1H-tetrazole in anhydrous $CH_3CN$ was used for phosphoramidite activating reagent, and 3% dichloroacetic acid in $CH_2Cl_2$ was used for detritylation. 16% N-methylimidazole in tetrahydrofurane (Cap A) and 80:10:10 (v/v/v) tetrhydrofurane-$Ac_2O$-2,6-lutidine (Cap B) were used for capping reaction. 0.02 M 12 in THF-pyridine-$H_2O$ (7:2:1, v/v/v) was used for oxidation and 0.1 M 3-[(Dimethylamino-methylidene)amino]-3H-1,2,4-dithiazole3-thione in pyridine:$CH_3CN$ (9:1, v/v) was used for sulfurizing. For 5'-terminal phosphorylation, bis(2-cyanoethyl)-N,N-diisopropyl phosphoramidite was used. For the 3'-cholesterol modified RNA oligonucleotide synthesis, cholesterol 3'-lcaa CPG 500 Å (ChemGenes) was used, and RNA synthesis was conducted in the same condition as the condition used for VP-modified RNAs. After the chemical chain elongation, deprotection and cleavage from the solid support were conducted by $NH_4OH$-EtOH (3:1, v/v) for 48 hours at 26° C. In the case of vinyl phosphonate modified RNA, RNA on solid support was first treated with TMSBr-pyridine-$CH_2Cl_2$ (3:1:18, v/v/v) for 1 h at ambient temperature in RNA synthesis column. Solid support was then washed by water (1 mL×3), $CH_3CN$ (1 mL×3) and $CH_2Cl_2$ (1 mL×3) by flowing solution thorough synthesis column, and then dried under vacuum. After transferring the solid support to screw-capped sample tube, base treatment by $NH_4OH$-EtOH (3:1, v/v) for 48 h at 26° C. was conducted. Crude RNA oligonucleotide without cholesterol conjugate was purified by standard anion exchange HPLC, whereas RNAs with cholesterol-conjugate were purified by reversed-phase HPLC. Obtained all purified RNAs were desalted by Sephadex G-25 (GE Healthcare) and characterized by electrospray ionization mass spectrometry (ESI-MS) analysis.

Example 9: Silencing Efficacy

Figure 25:
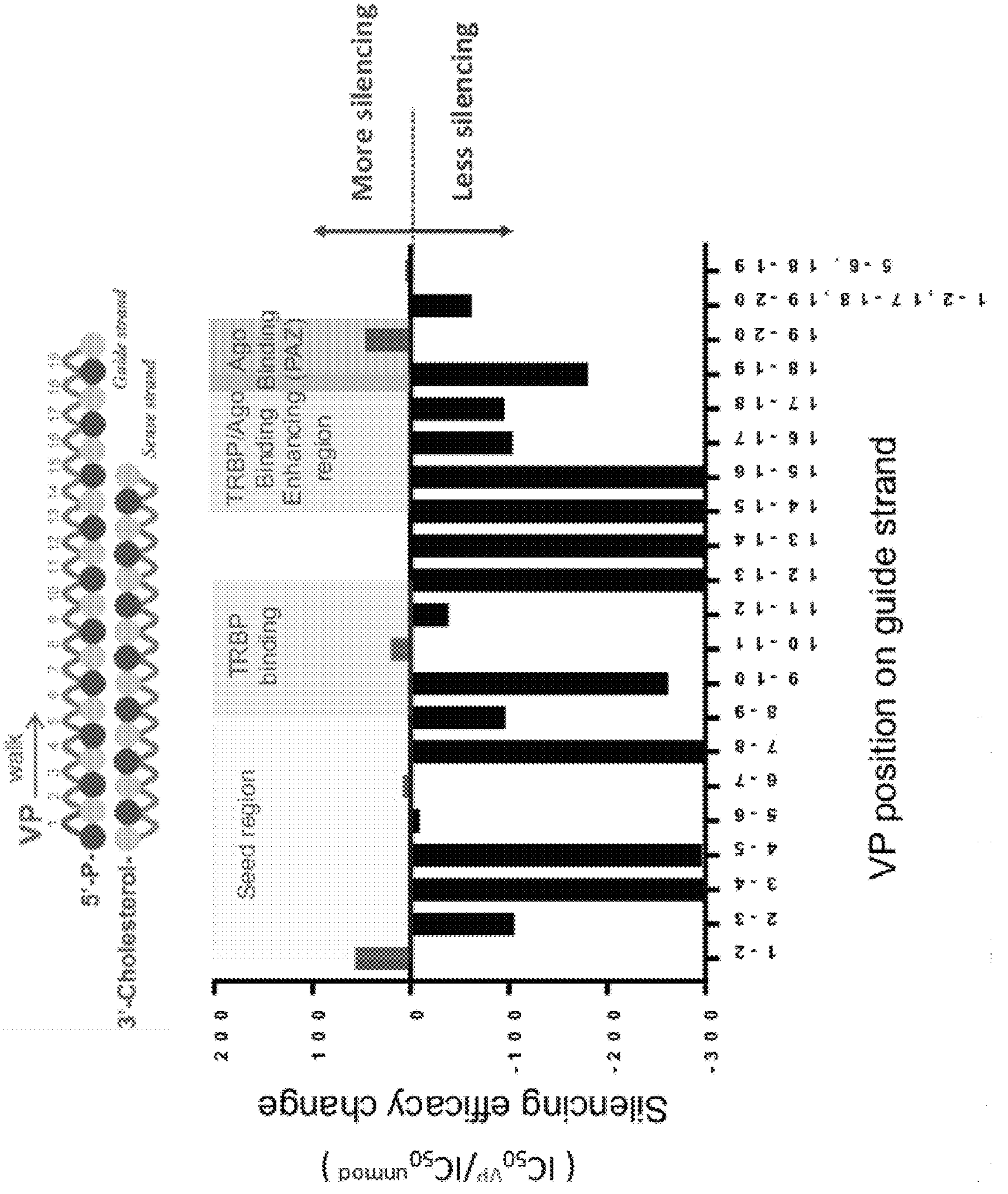
FIG. 25 is a summary of a comparative study of siRNA efficacy.

FIGS. 23 and 24 provide visual representations of the VP-modified siRNA studied herein. FIG. 25 exemplifies the effect that one or more vinyl phosphonate modifications in an intersubunit linkage at varying positions on the guide strand has on silencing. As can be seen from the data in FIG. 25, RISC is very sensitive to VP modification, and having a mismatch base pair at various positions can disrupt siRNA potency.

Figure 26:
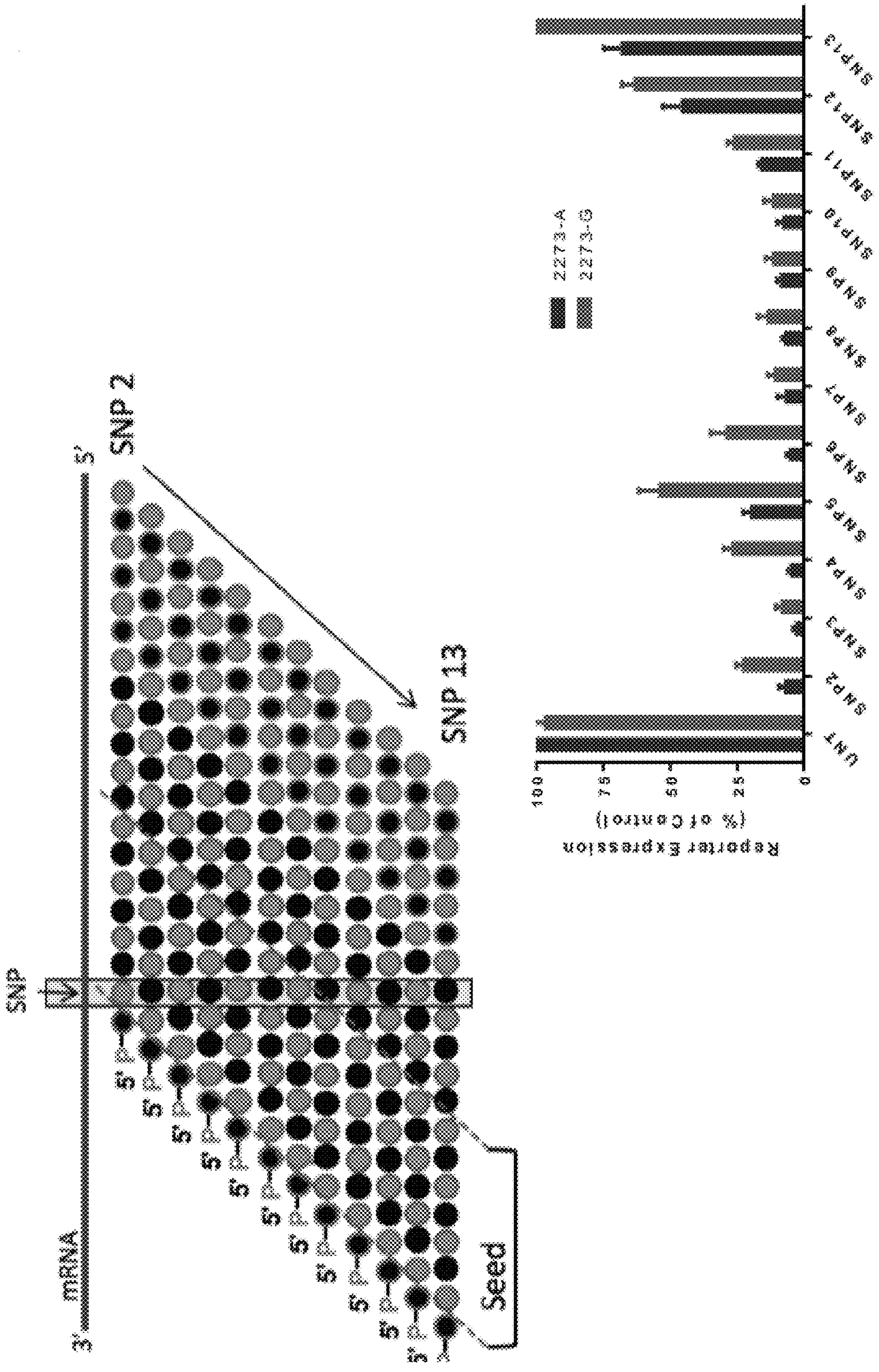
FIG. 26 is a schematic of hsiRNA antisense scaffolds aligned to HTT sequence surrounding SNP site rs362273 wherein the green box depicts the position of the SNP site.
Figure 27A:
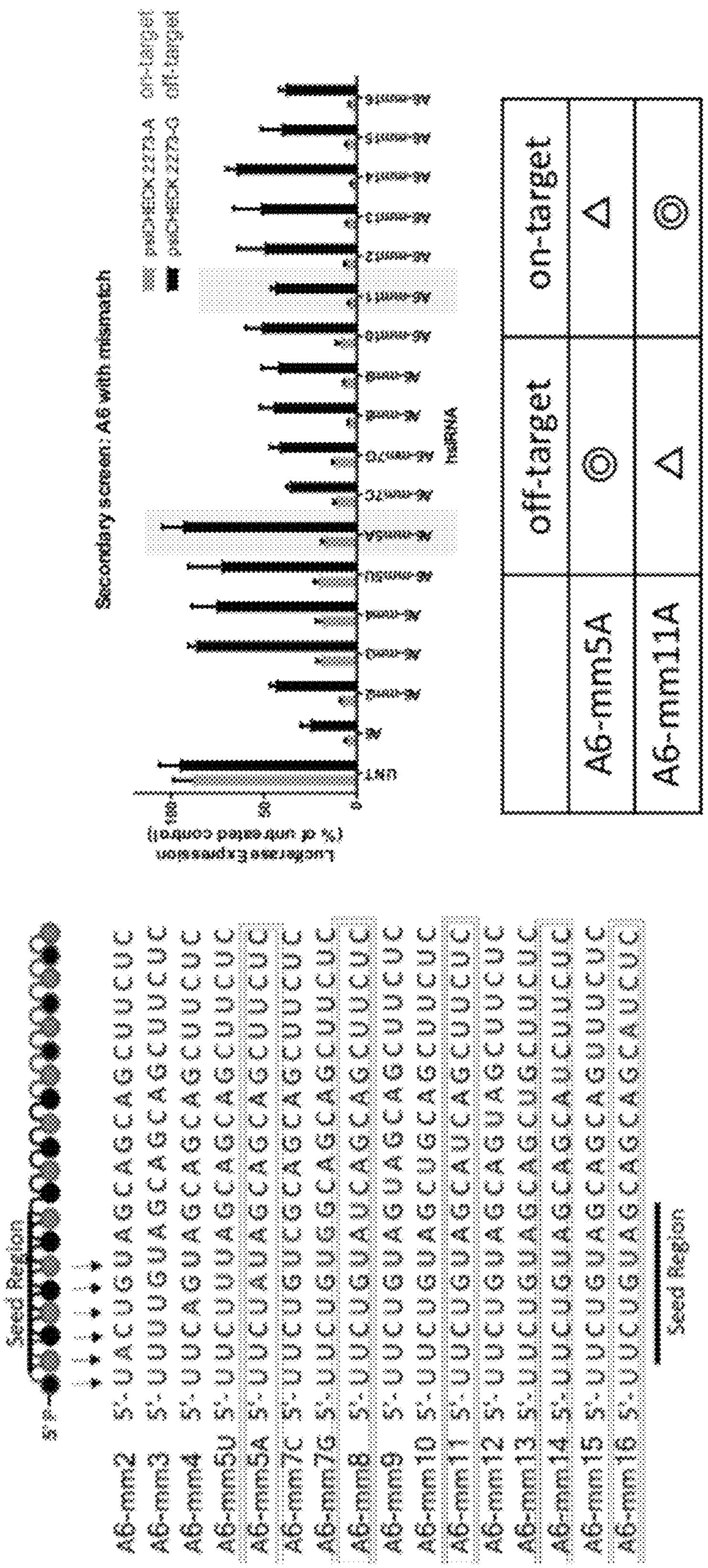
FIGS. 27A and 27B illustrate the effect of adding a mismatch in the siRNA sequence improves allelic discrimination without impairing the silencing of the mutant allele.
Figure 27B:
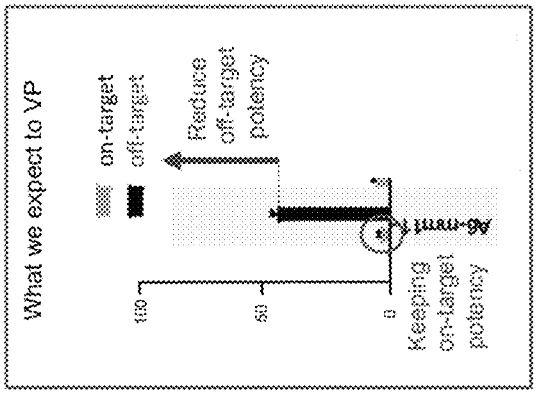
Figure 30:
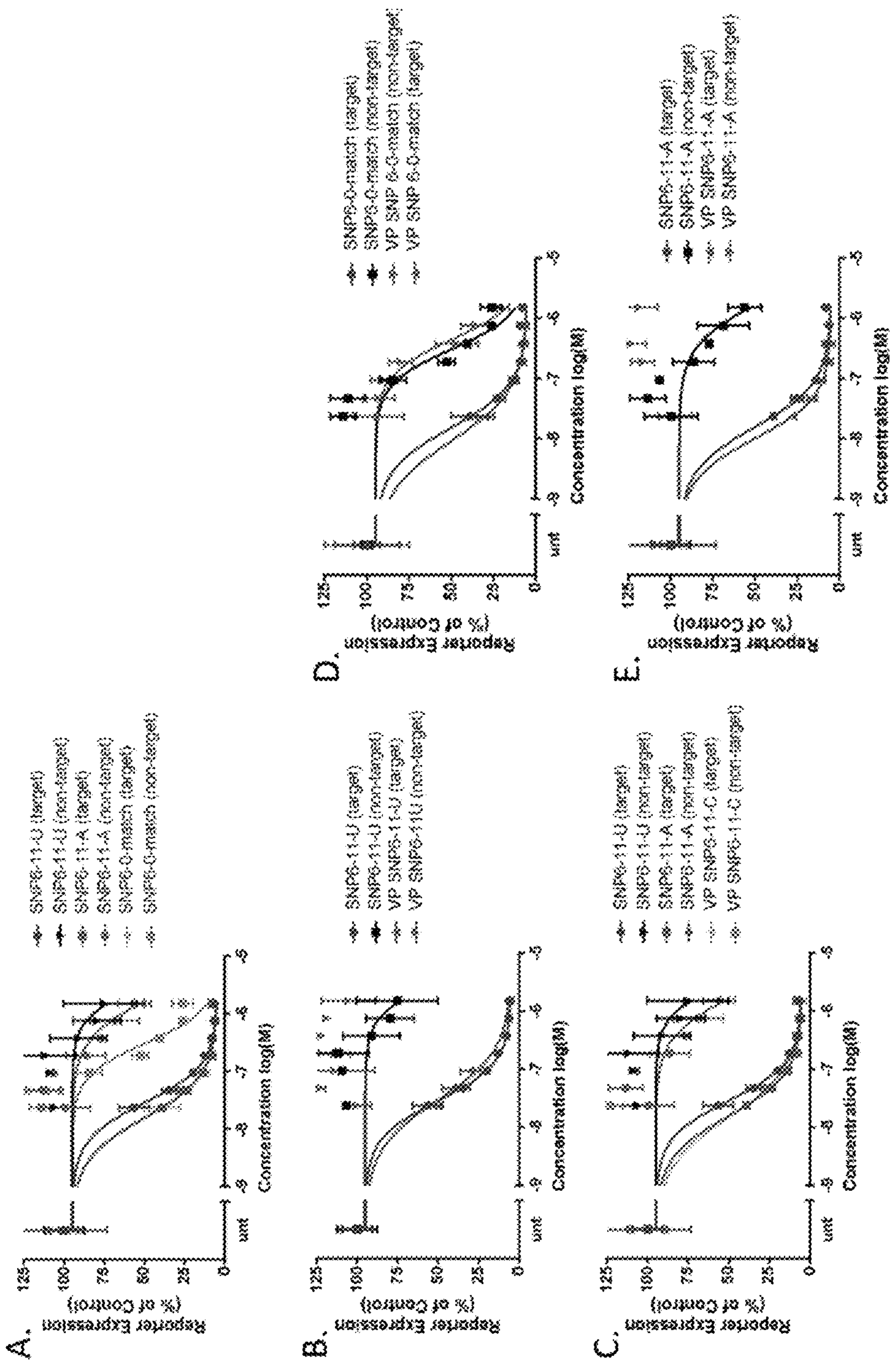
FIG. 30 demonstrates the effect a VP-modified linkage has on target/non-target discrimination of SNP-selective siRNAs.

FIGS. 26, 27A, and 27B also illustrate the ability of VP-modified siRNA to silence the mutant allele. As can be seen by FIGS. 27A and 27B, adding a mismatch in the siRNA sequence could improve allelic discrimination without affecting mutant allele silencing. FIG. 30 demonstrates that the introduction of a VP-modified linkage next to the SNP site significantly enhanced target/non-target discrimination of SNP-selective siRNAs. Compounds containing primary (position 6) and secondary (position 11) SNPs were synthesized with or without a VP-modification between positions 5 and 6. As can be seen in FIG. 30, the presence of a VP-modification had no impact on "on target" activity, but fully eliminated any detectable silencing for non-target mRNAs. The method for generating the data in FIGS. 25, 26, 27A, and 27B is described below.

hsiRNA Passive Delivery.

Cells were plated in Dulbecco's Modified Eagle's Medium containing 6% FBS at 8,000 cells per well in 96-well cell culture plates. hsiRNAs were diluted to twice the final concentration in OptiMEM (Carlsbad, CA: 31985-088), and 50 μL diluted hsiRNAs were added to 50 μL of cells, resulting in 3% FBS final. Cells were incubated for 72 hours at 37° C. and 5% $CO_2$. The maximal dose in the in vitro dose response assays was 1.5 μM compound.

Method for Quantitative Analysis of Target mRNA.

mRNA was quantified from cells using the QuantiGene 2.0 assay kit (Affymetrix, QS0011). Cells were lysed in 250 μL diluted lysis mixture composed of one part lysis mixture (Affymetrix, 13228), two parts $H_2O$ and 0.167 μg/μL proteinase K (Affymetrix, QS0103) for min at 55° C. Cell lysates were mixed thoroughly, and 40 μL of each lysate was added per well of a capture plate with 20 μL diluted lysis mixture without proteinase K. Probe sets for human HTT and HPRT (Affymetrix; #SA-50339, SA-10030) were diluted and used according to the manufacturer's recommended protocol. Datasets were normalized to HPRT.

Method for Creating Bar Graph.

Data were analyzed using GraphPad Prism 7 software (GraphPad Software, Inc., San Diego, CA). Concentration-dependent $IC_{50}$ curves were fitted using a log(inhibitor) versus response—variable slope (four parameters). For each cell treatment plate, the level of knockdown at each dose was normalized to the mean of the control group (untreated group). The lower limit of the curve was set to less than 5, and the upper limit of the curve was set to greater than 95. To create the bar graph, the percent difference was calculated by subtracting the $IC_{50}$ value for each compound from the $IC_{50}$ value for each corresponding control compound, dividing by the $IC_{50}$ value for the control compound, and multiplying by 100. If the percent difference was less than −500%, the percent difference was artificially set to −500%. The lower limit of the graph was cut at −0.300%.

The contents of all cited references (including literature references, patents, patent applications, and websites) that may be cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

Figure 39:
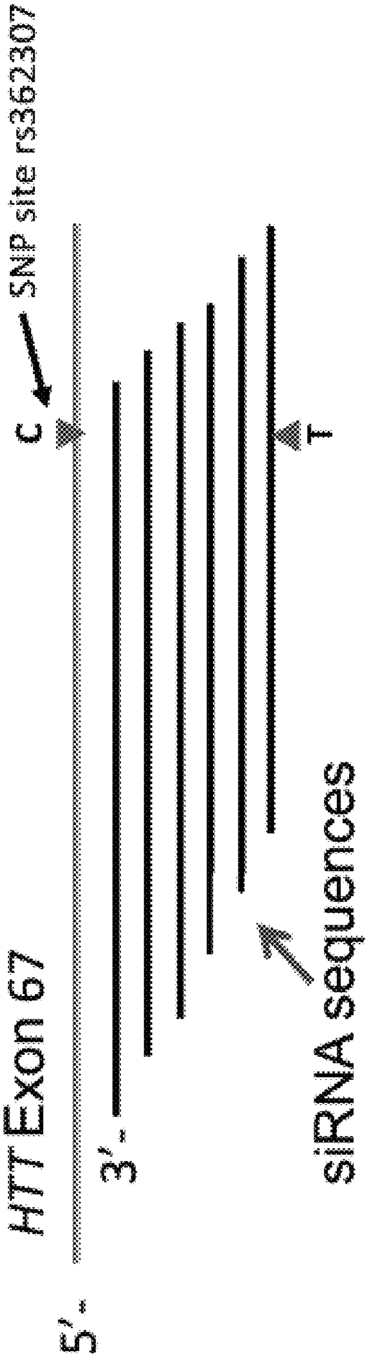
FIG. 39 is a schematic of hsiRNA antisense scaffolds aligned to HTT sequence surrounding alternative SNP site rs362273.
Figure 40:
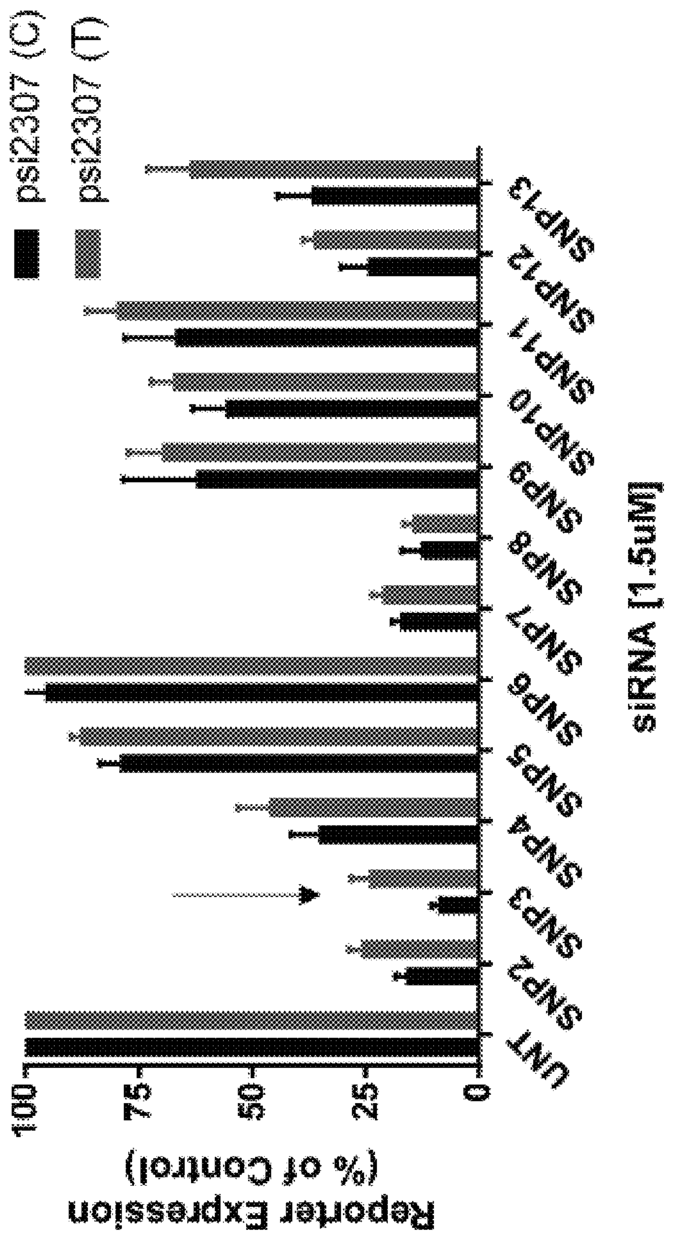
FIG. 40 depicts bar graphs showing luciferase activity following a psiCHECK reporter plasmid assay in HeLa cells transfected with the hsiRNAs of FIG. 39. The number following "SNP" represents the position of the SNP in the siRNA.
Figure 41:
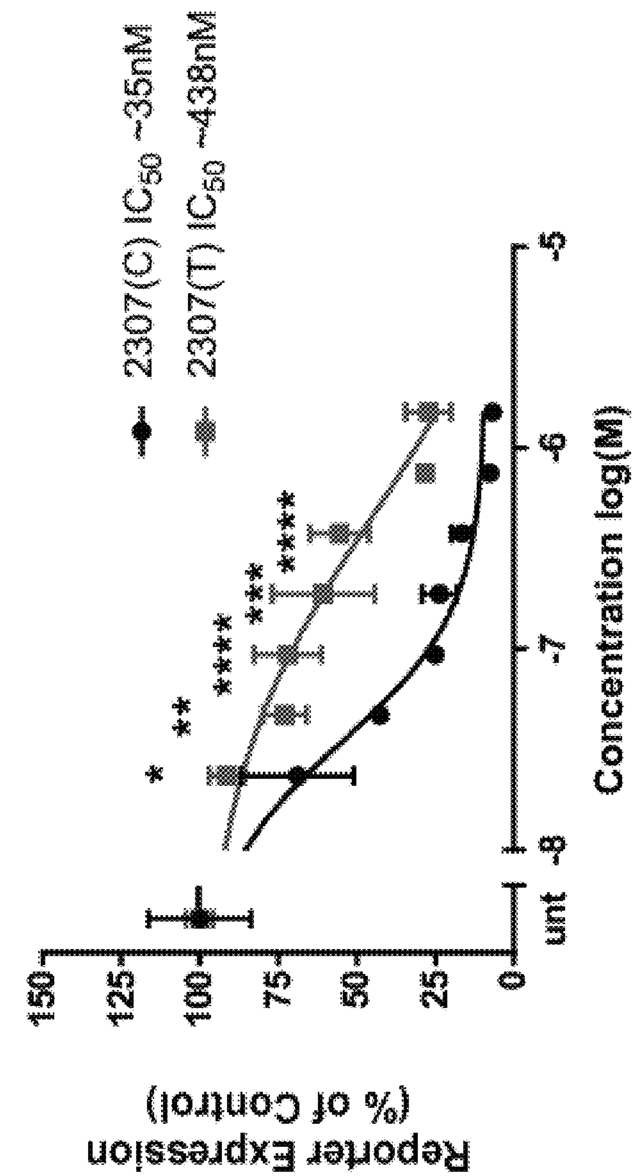
FIG. 41 depicts dose response curves comparing silencing effects for oligonucleotides of FIG. 39 targeting C or T at the SNP3 site.

Example 10: Primary Screen Yields Multiple Efficacious siRNA Sequences for SNP Rs362307 Heterozygosity siRNAs designed to be complimentary the HTT mRNA containing an alternative mutant SNP (rs362307) (FIG. 39) were all screened with reporter plasmids containing the target region for the SNP of interest (FIG. 40). HeLa cells transfected with one of two reporter plasmids were reverse transfected with 1.5 uM hsiRNAs by passive uptake, and treated for 72 hours. The number following SNP represents the position of the SNP in the siRNA. It was expected that this SNP would be more difficult to target based on the high G/C content of the region around it. It appears that placing the SNP in position 3 provided the most SNP discrimination, without losing efficacy against the mutant allele, showing that the best SNP position is sequence-specific (FIG. 41). This primary screening process may thus be carried out for selecting the best SNP position for any SNP.

Figure 42:
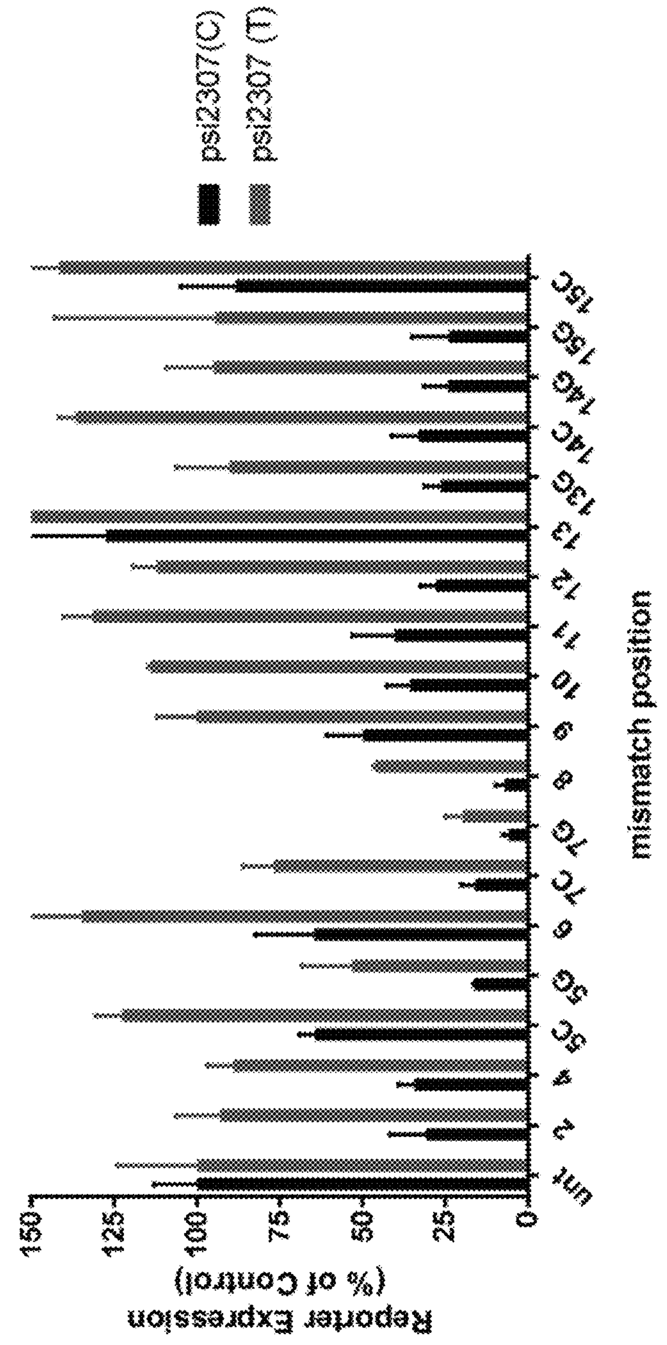
FIG. 42 depicts bar graphs showing luciferase activity following a psiCHECK reporter plasmid assay in HeLa cells transfected with hsiRNAs of FIG. 39 which were modified to feature a second mismatch at varying positions.

Example 11: When Applied to SNP Rs362307, a Secondary Mismatch Continues to Improve Allelic Discrimination As reported in FIG. 42, primary screen of new sequences with mismatches introduced into all possible positions yields multiple efficacious hsiRNAs with increased SNP discrimination at position rs362307 as well. Introducing a mismatch at position 7 and 8 appeared to increase selectivity while preserving target silencing efficacy. Other secondary mismatches provided excellent discrimination, but less activity overall.

Example 12: Measuring SNP Discrimination in Sequences Including an SNP

To measure SNP discrimination by each of the sequences disclosed in Tables 5-7 (i.e., each hsiRNA having a particular SNP position nucleotide and mismatch (MM) position nucleotide combination), psiCHECK reporter plasmids containing either a wild-type region of htt or the same region of htt with the SNP of the sequence are prepared and tested using a dual-luciferase. HeLa cells transfected with one of two reporter plasmids are reverse transfected with hsiRNAs by passive uptake, and treated for 72 hours. Luciferase activities are measured in the assays with or without the additional mismatch, and are then plotted in dose response curves and compared to reveal sequences yielding the best results in terms of discrimination and efficacy of silencing.

Example 13: Synthesis of a Phosphinate-Modified Intersubunit Linkage

Figure 44A:
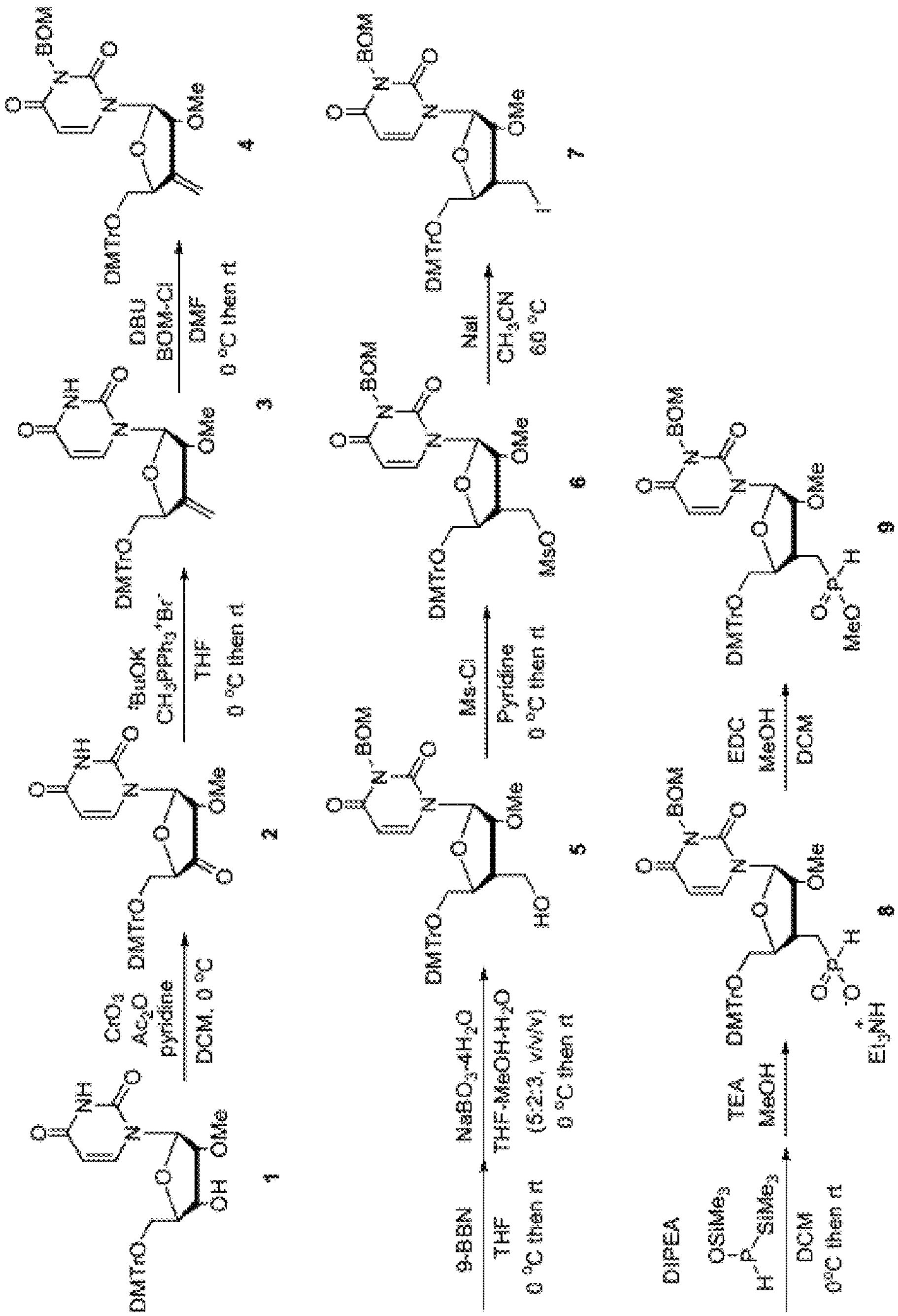
FIG. 44A shows a representative example for preparing a monomer for the modified phosphinate-containing oligonucleotides provided herein.
Figure 44B:
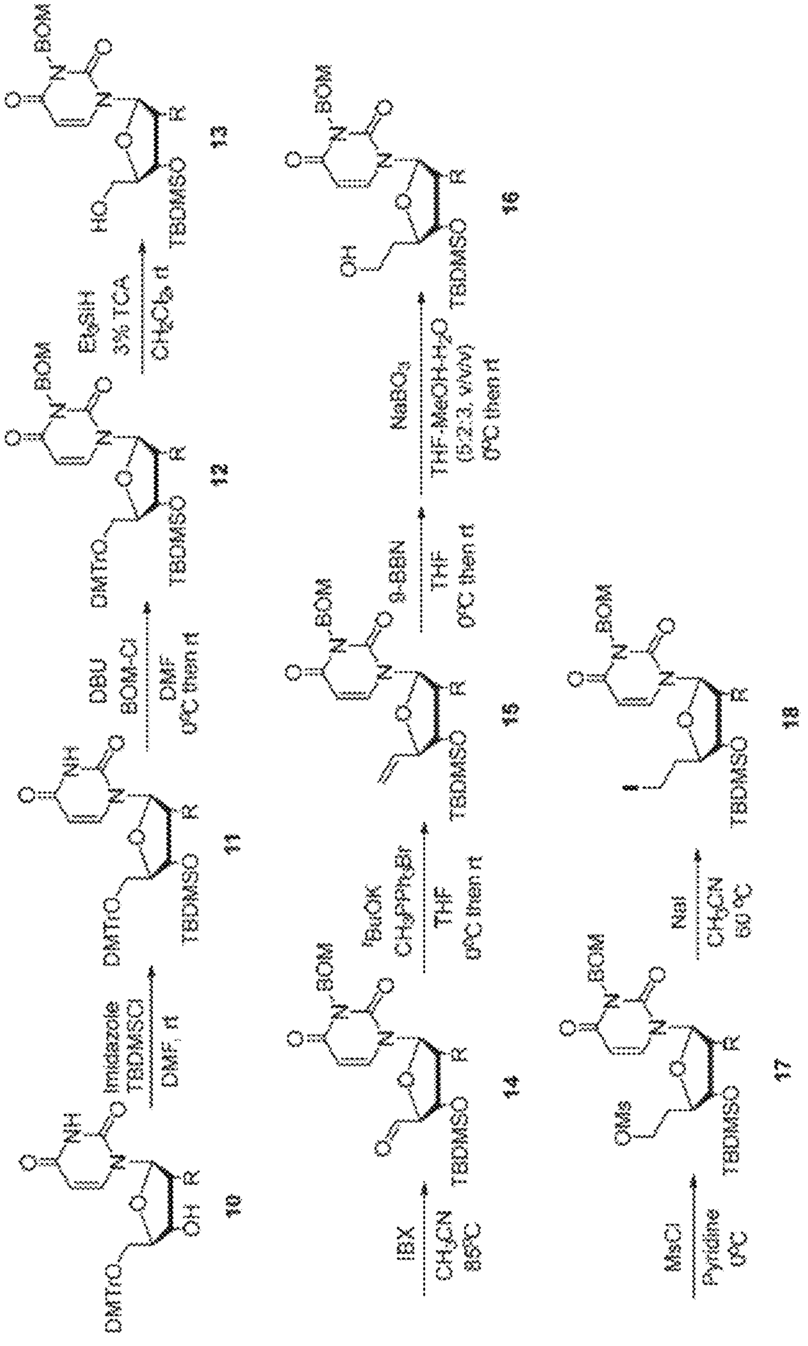
FIG. 44B shows a representative example for preparing another monomer for the modified phosphinate-containing oligonucleotides provided herein.
Figure 44C:
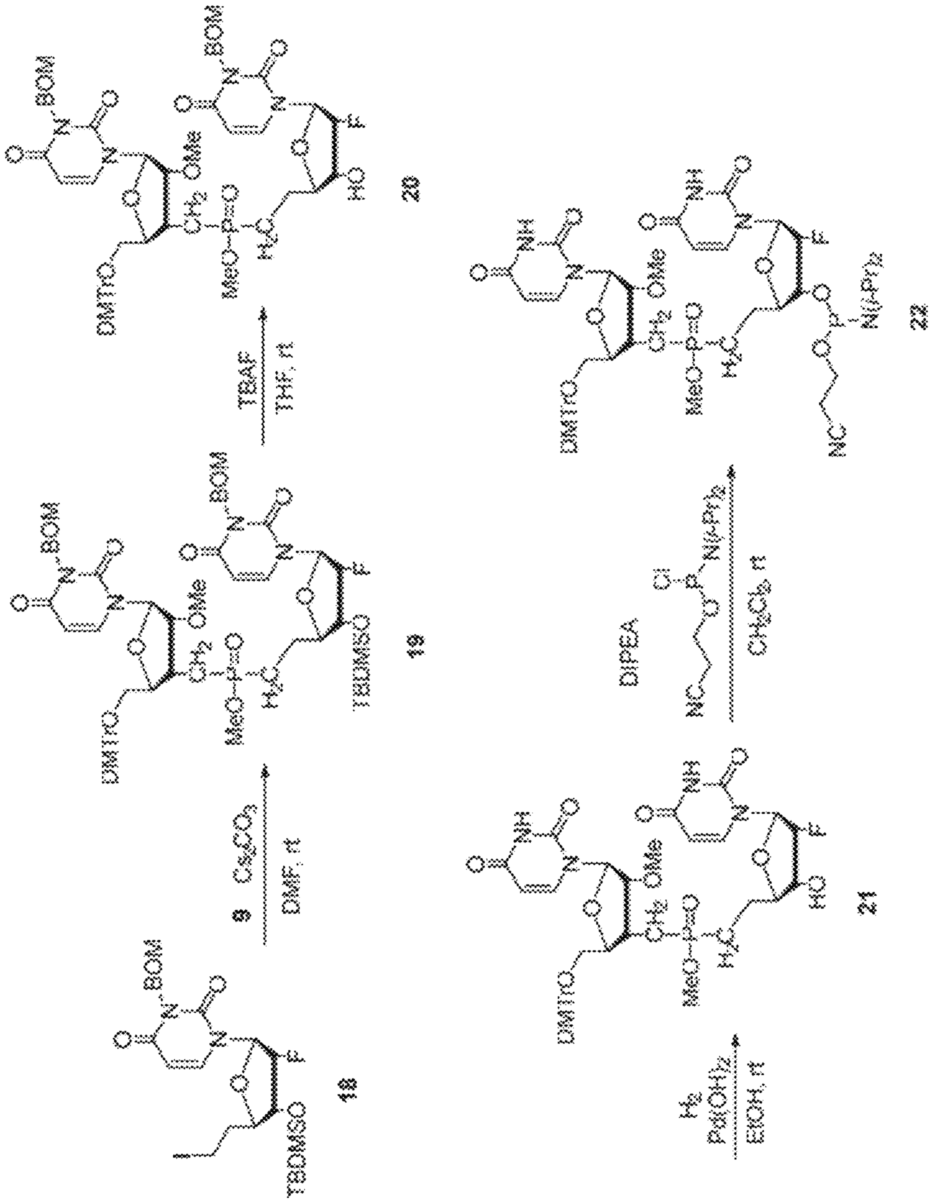
FIG. 44C shows a representative example for preparing a modified phosphinate-containing oligonucleotides provided herein.

A method for preparing a phosphinate-modified intersubunit linkage of the invention is summarized in FIGS. 44A-44C. This method involves Jones oxidation from a free alcohol to the corresponding ketone followed by a Wittig olefination to achieve the exomethylene moiety shown in intermediate compound 3. Protecting of the amide with BOM followed by hydroboration-oxidation results in the free alcohol intermediate 5. Mesylation followed by a modified Finkelstein reaction produces the iodinated intermediate 7, which then undergoes further functionalization to achieve the methyl phosphinate monomer 9.

To achieve monomer 18, various protection and deprotection steps are employed to achieve intermediate 13. IBX oxidation produces the corresponding ketone followed by Wittig olefination to access the methylene. Once again, hydroboration-oxidation followed by mesylation and Finkelstein reaction results in monomer 18.

Combining monomers 9 and 18 under basic conditions produces phosphinate-linked dimer 19. Acid-mediated and Pearlman's catalyzed deprotection followed by further phosphanamine functionalization results in dimer 22.

The invention claimed is:

1. A double-stranded RNA (dsRNA) comprising a first strand having 15-35 nucleotides in length, a 5' end, a 3' end, and a seed region, wherein the first strand is complementary to a region of a gene comprising an allelic polymorphism, and wherein the first strand comprises:
   a single nucleotide polymorphism (SNP) position nucleotide at a position within the seed region, wherein the SNP position nucleotide is complementary to the allelic polymorphism; and a mismatch (MM) position nucleotide located 2-11 nucleotides from the SNP position nucleotide that is a mismatch with a nucleotide in the gene.

2. An oligonucleotide having 15-35 nucleotides in length, a 5' end, a 3' end and a seed region, wherein the oligonucleotide is complementary to a region of a gene comprising an allelic polymorphism, and wherein the oligonucleotide comprises:
   a single nucleotide polymorphism (SNP) position nucleotide at a position within the seed region, wherein the SNP position nucleotide is complementary to the allelic polymorphism; and
   a mismatch (MM) position nucleotide located 2-11 nucleotides from the SNP position nucleotide that is a mismatch with a nucleotide in the gene.

3. The oligonucleotide of claim 2, wherein said oligonucleotide is an ASO.

4. The dsRNA of claim 1, wherein the dsRNA further comprises:
   a second strand of 15-35 nucleotides that is complementary to a portion of the first strand,
   wherein the first strand comprises the SNP position nucleotide at position 2-6 from the 5' end that is complementary to the allelic polymorphism, and
   wherein the first strand comprises the MM position nucleotide located 2-6 nucleotides from the SNP position nucleotide that is a mismatch with a nucleotide in the gene.

5. The dsRNA of claim 1, further comprising at least one modified nucleotide.

6. A double-stranded RNA (dsRNA) comprising:
   a first strand of 15-35 nucleotides that is complementary to a region of a gene comprising an allelic polymorphism; and
   a second strand of 15-35 nucleotides that is complementary a portion of the first strand,
   wherein the first strand comprises a single nucleotide polymorphism (SNP) position nucleotide at position 4 from the 5' end that is complementary to the allelic polymorphism, and
   wherein the first strand comprises a mismatch (MM) position nucleotide located at position 7 from the 5' end is a mismatch with a nucleotide in the gene.

7. A double-stranded RNA (dsRNA) comprising:
   a first strand of 15-35 nucleotides that is complementary to a region of a gene comprising an allelic polymorphism; and
   a second strand of 15-35 nucleotides that is complementary to a portion of the first strand,
   wherein the first strand comprises a single nucleotide polymorphism (SNP) position nucleotide at a position 6 from the 5' end that is complementary to the allelic polymorphism, and
   wherein the first strand comprises a mismatch (MM) position nucleotide located at position 11 from the 5' end is a mismatch with a nucleotide in the gene.

8. The oligonucleotide of claim 2, further comprising a 5' stabilizing moiety selected from the group consisting of phosphate, vinyl phosphonate, C5-methyl (R or S or racemic), C5-methyl on vinyl, and reduced vinyl.

9. The oligonucleotide of claim 2, further comprising a conjugate moiety selected from the group consisting of alkyl chain, vitamin, peptide, glycosphingolipid, polyunsaturated fatty acid, secosteroid, steroid hormone, and steroid lipid.

10. A nucleic acid having 15-35 nucleotides in length, a 5' end, a 3' end, and a seed region, that is complementary to a region of a gene comprising an allelic polymorphism, wherein the nucleic acid comprises:

a single nucleotide polymorphism (SNP) position nucleotide at a position within the seed region, wherein the SNP position nucleotide is complementary to the allelic polymorphism;

a mismatch (MM) position that is a mismatch with a nucleotide in the gene; and at least one modified nucleotide (X) on either side of the SNP position nucleotide, wherein each X is located within four, three or two nucleotides from the SNP position nucleotide.

11. A nucleic acid having 15-35 nucleotides in length, a 5' end, a 3' end and a seed region, that is complementary to a region of a gene comprising an allelic polymorphism, wherein the nucleic acid comprises:

a single nucleotide polymorphism (SNP) position nucleotide at a position within the seed region, wherein the SNP position nucleotide is complementary to the allelic polymorphism;

a mismatch (MM) position that is a mismatch with a nucleotide in the gene; and at least one modified nucleotide (Y) on either side of the MM position nucleotide, wherein each Y is located within four, three or two nucleotides from the MM position nucleotide.

12. A nucleic acid having 15-35 nucleotides in length, a 5' end, a 3' end, and a seed region, that is complementary to a region of a gene comprising an allelic polymorphism, wherein the nucleic acid comprises:

a single nucleotide polymorphism (SNP) position nucleotide at a position within the seed region, wherein the SNP position nucleotide is complementary to the allelic polymorphism;

a mismatch (MM) position that is a mismatch with a nucleotide in the gene; and at least one modified nucleotide (X) on either side of the SNP position nucleotide, wherein each X is located within four, three or two nucleotides from the SNP position nucleotide; and at least one modified nucleotide (Y) on either side of the MM position nucleotide, wherein each Y is located within four, three or two nucleotides from the MM position nucleotide.

* * * * *